United States Patent
Grice et al.

(10) Patent No.: US 11,142,517 B2
(45) Date of Patent: Oct. 12, 2021

(54) CRYSTALLINE FORMS OF A MAGL INHIBITOR

(71) Applicant: H. Lundbeck A/S, Valby (DK)

(72) Inventors: Cheryl A. Grice, San Diego, CA (US); Todd K. Jones, San Diego, CA (US); Kurt G. Grimm, San Diego, CA (US); Jacqueline Lorayne Blankman, San Diego, CA (US); Channing Rodney Beals, San Diego, CA (US)

(73) Assignee: H. LUNDBECK A/S, Valby (DK)

( * ) Notice: Subject to any disclaimer, the term of this patent is extended or adjusted under 35 U.S.C. 154(b) by 0 days.

(21) Appl. No.: 16/349,142

(22) PCT Filed: Nov. 15, 2017

(86) PCT No.: PCT/US2017/061875
§ 371 (c)(1),
(2) Date: May 10, 2019

(87) PCT Pub. No.: WO2018/093953
PCT Pub. Date: May 24, 2018

(65) Prior Publication Data
US 2020/0190063 A1 Jun. 18, 2020

Related U.S. Application Data

(60) Provisional application No. 62/423,126, filed on Nov. 16, 2016.

(51) Int. Cl.
*C07D 403/10* (2006.01)

(52) U.S. Cl.
CPC ........ *C07D 403/10* (2013.01); *C07B 2200/13* (2013.01)

(58) Field of Classification Search
None
See application file for complete search history.

(56) References Cited

U.S. PATENT DOCUMENTS

| | | |
|---|---|---|
| 4,327,725 A | 5/1982 | Cortese et al. |
| 4,624,848 A | 11/1986 | Lee |
| 4,968,509 A | 11/1990 | Radebaugh et al. |
| 5,323,907 A | 6/1994 | Kalvelage |
| 5,456,923 A | 10/1995 | Nakamichi et al. |
| 5,461,140 A | 10/1995 | Heller et al. |
| 5,516,527 A | 5/1996 | Curatolo |
| 5,622,721 A | 4/1997 | Dansereau et al. |
| 5,686,105 A | 11/1997 | Kelm et al. |
| 5,700,410 A | 12/1997 | Nakamichi et al. |
| 5,977,175 A | 11/1999 | Lin |
| 6,465,014 B1 | 10/2002 | Moroni et al. |
| 6,932,983 B1 | 8/2005 | Straub et al. |
| 9,133,148 B2 * | 9/2015 | Cisar .................. A61P 25/28 |
| 9,487,495 B2 | 11/2016 | Cisar et al. |
| 10,450,302 B2 | 10/2019 | Blankman et al. |
| 10,463,753 B2 * | 11/2019 | Grice .................. A61K 51/0459 |
| 2008/0214524 A1 | 9/2008 | Lee et al. |
| 2010/0015225 A1 | 1/2010 | Diederich et al. |
| 2014/0163068 A1 | 6/2014 | Verwijs et al. |
| 2014/0357693 A1 | 12/2014 | Shaul et al. |
| 2015/0018335 A1 | 1/2015 | Cisar et al. |
| 2015/0148330 A1 | 5/2015 | Cisar et al. |
| 2015/0313843 A1 | 11/2015 | Shaw et al. |
| 2020/0055841 A1 | 2/2020 | Blankman et al. |
| 2020/0188393 A1 | 6/2020 | Grice et al. |

FOREIGN PATENT DOCUMENTS

| | | |
|---|---|---|
| CN | 101530399 A | 9/2009 |
| JP | 2006505494 A | 2/2006 |
| RU | 2292206 C2 | 1/2007 |
| WO | WO-2010063802 A1 | 6/2010 |
| WO | WO-2013103973 A1 | 7/2013 |
| WO | WO-2013159095 A1 | 10/2013 |
| WO | WO-2015179559 A2 | 11/2015 |
| WO | WO-2016149401 A2 | 9/2016 |
| WO | WO-2016183097 A1 | 11/2016 |
| WO | WO-2018093946 A1 | 5/2018 |
| WO | WO-2018093947 A1 | 5/2018 |
| WO | WO-2018093949 A1 | 5/2018 |
| WO | WO-2018093950 A1 | 5/2018 |
| WO | WO-2018093953 A1 | 5/2018 |

OTHER PUBLICATIONS

Berge et al., Pharmaceutical Salts. Journal of Pharmaceutical Sciences, 1977, 66, 1-19.*
Aitipamula et al., Polymorphs, Salts, and Cocrystals: What's in a Name?, 2012, 12, 2147-2152.*
Pellkofer et al. The major brain endocannabinoid 2-AG controls neuropathic pain and mechanical hyperalgesia in patients with neuromyelitis optical. PLoS One 8(8):e71500 (2013).
Alhouayek et al. Increasing endogenous 2-arachidonoylglycerol levels counteracts colitis and related systemic inflammation. FASEB 25(8):2711-2721 (2011).
Ameloot et al. Endocannabinoid control of gastric sensorimotor function in man. Aliment Pharmacol Ther 31(10):1123-1131 (2010).
Anderson et al. Actions of the dual FAAH/MAGL inhibitor JZL195 in a murine inflammatory pain model. Neuropharmacology 81:224-230 (2013).
Berge et al. Pharmaceutical Salts. Journal of Pharmaceutical Sciences 66(1):1-19 (Jan. 1977).
Bernstein. Crystal Structure Prediction and Polymorphism. ACA Transactions 39:14-23 (2004).

(Continued)

*Primary Examiner* — Po-Chih Chen
(74) *Attorney, Agent, or Firm* — Wilson Sonsini Goodrich & Rosati

(57) ABSTRACT

Described herein is the MAGL inhibitor 1,1,1,3,3,3-hexafluoropropan-2-yl 4-(2-(pyrrolidin-1-yl)-4-(trifluoromethyl)benzyl)piperazine-1-carboxylate, including crystalline forms and pharmaceutically acceptable salts and solvates thereof.

15 Claims, 60 Drawing Sheets

(56) References Cited

OTHER PUBLICATIONS

Blake et al. Preliminary assessment of the efficacy, tolerability and safety of a cannabis-based medicine (Sativex) in the treatment of pain caused by rheumatoid arthritis. Rheumatology (Oxford) 45(1):50-52 (2006).
Blankman et al. A comprehensive profile of brain enzymes that hydrolyze the endocannabinoid 2-arachidonoylglycerol. Chem. Biol. 14:1347-1356 (2007).
Braga et al. Making crystals from crystals: a green route to crystal engineering and polymorphism. Chemical Communications (29):3635-45 (2005).
Burckhardt et al. The fibromyalgia impact questionnaire: development and validation. J Rheumatol 18(5):728-733 (1991).
Chang et al. Highly Selective Inhibitors of Monoacylglycerol Lipase Bearing a Reactive Group that is Bioisosteric with Endocannabinoid Substrates. ChemBiol 19(5):579-588 (2012).
Chang et al. Proteome-wide reactivity profiling identifies diverse carbamate chemotypes tuned for serine hydrolase inhibition. ACS Chem Biol 8:1590-1599 (2013).
Chen et al. Monoacylglycerol lipase is a therapeutic target for Alzheimer's disease. Cell Rep. 2(5):1329-1339 (2012).
Collin et al. A double-blind, randomized, placebo-controlled, parallel-group study of Sativex, in subjects with symptoms of spasticity due to multiple sclerosis. Neurol Res 32(5):451-459 (2010).
Collin et al. Randomized controlled trial of cannabis-based medicine in spasticity caused by multiple sclerosis. Eur J Neurol 14(3):290-296 (2007).
Fiz et al. Cannabis use in patients with fibromyalgia: effect on symptoms relief and health-related quality of life. PLoS One 6(4):e18440 (2011).
Fleisher et al. Improved oral drug delivery: solubility limitations overcome by the use of prodrugs. Advanced Drug Delivery Reviews 19:115-130 (1996).
Foster et al. Deuterium isotope effects in the metabolism of drugs and xenobiotics: implications for drug design. Adv Drug Res 14:1-36 (1985).
Fowler. Monoacylglycerol lipase—a target for drug development? Br Pharmacol. 166:1568-1585 (2012).
Gately et al. Deuterioglucose: alteration of biodistribution by an isotope effect. J Nucl Med 27:388-394 (1986).
Gordon et al. The metabolism of the abortifacient terpene, (R)-(+)-pulegone, to a proximate toxin, menthofuran. Drug Metab Dispos 15:589-594(1987).
Guindon et al. Alterations in endocannabinoid tone following chemotherapy-induced peripheral neuropathy: effects of endocannabinoid deactivation inhibitors targeting fatty-acid amide hydrolase and monoacylglycerol lipase in comparison to reference analgesics following cisplatin treatment. Pharmacol Res 67(1):94-109 (2013).
Hanlon et al. Circadian rhythm of circulating levels of the endocannabinoid 2-arachidonoylglycerol. J Clin Endocrinol Metab 100:220-226 (2015).
Hill. Medical Marijuana for Treatment of Chronic Pain and Other Medical and Psychiatric Problems: A Clinical Review. JAMA 313(24):2474-2483 (2015).
Howard et al. Cannabis use in sickle cell disease: a questionnaire study. Br J Haematol 131(1):123-128 (2005).
Hruba et al. Simultaneous Inhibition of Fatty Acid Amide Hydrolase and Monoacylglycerol Lipase Shares Discriminative Stimulus Effects with delta9-Tetarhydrocannbinol in Mice. The Journal of Pharmacology and Experimental Therapeutics 353:261-268 (2015).
Jiang et al. (+)-Borneol alleviates mechanical hyperalgesia in models of chronic inflammatory and neuropathic pain in mice. EurJ Pharmacol 757:53-58 (2015).
Jones et al. Pharmaceutical Cocrystals: An Emerging Approach to Physical Property Enhancement. MRS Bulletin 31:875-879 (2006).
Khasabova et al. Increasing 2-arachidonoyl glycerol signaling in the periphery attenuates mechanical hyperalgesia in a model of bone cancer pain. Pharmacol Res 64(1):60-67 (2011).
King et al. URB602 inhibits monoacylglycerol lipase and selectively blocks 2-arachidonoylglycerol degradation in intact brain slices. Chem Biol 14(12):1357-1365 (2007).
Kinsey et al. Blockade of Endocannabinoid-Degrading Enzymes Attenuates Neuropathic Pain. J Pharmacol Exp Ther 330(3):902-910 (2009).
Kohli et al. Pain-related behaviors and neurochemical alterations in mice expressing sickle hemoglobin: modulation by cannabinoids. Blood 116(3):456-465 (2010).
Korhonen et al. Piperazine and piperidine carboxamides and carbamates as inhibitors of fatty acid amide hydrolase (FAAH) and monoacylglycerol lipase (MAGL). Bioorg Med Chem 22(23):6694-6705 (2014).
Kushner et al. Pharmacological uses and perspectives of heavy water and deuterated compounds. Can J Physiol Pharmacol 77:79-88 (1999).
Labar et al. A review on the monoacylglycerol lipase: at the interface between fat and endocannabinoid signalling. Curr Med Chem 17(24):2588-2607 (2010).
Langford et al. A double-blind, randomized, placebo-controlled, parallel-group study of THC/CBD oromucosal spray in combination with the existing treatment regimen, in the relief of central neuropathic pain in patients with multiple sclerosis. J Neurol 260(4):984-997 (2013).
Liberman et al. Pharmaceutical Dosage Forms. 2nd Ed. 1:209-214 (1990).
Lijinsky et al. Dose-response studies in carcinogenesis by nitroso-N-methyl-N-(2-phenyl)ethylamine in rats and the effects of deuterium substitution. Food Chem Toxicol 20:393-399 (1982).
Lijinsky et al. Dose-response studies with nitrosoheptamethyleneimine and its alpha-deuterium-labeled derivative in F344 rats. J Nat Cancer Inst 69:1127-1133 (1982).
Long et al. Characterization of tunable piperidine and piperazine carbamates as inhibitors of endocannabinoid hydrolases. J Med chem 53(4):1830-1842 (2010).
Long et al. Selective blockade of 2-arachidonoylglycerol hydrolysis produces cannabinoid behavioral effects. Nat Chem Biol. 5(1):37-44 (2009).
Ly et al. Increased cerebral cannabinoid-1 receptor availability is a stable feature of functional dyspepsia: a [F]MK-9470 PET study. Psychother Psychosom 84(3):149-158 (2015).
Malik et al. Dronabinol increases pain threshold in patients with functional chest pain: a pilot double-blind placebo-controlled trial. Dis Esophagus 30(2):1-8 (2017).
Mangold et al. Effects of deuterium labeling on azido amino acid mutagenicity in *Salmonella typhimurium*. Mutat Res 308:33-42 (1994).
Meanwell et al. Synopsis of some recent tactical application of bioisosteres in drug design. J Med Chem 54(8):2529-2591 (2011).
Mease et al. A randomized, double-blind, placebo-controlled, phase III trial of pregabalin in the treatment of patients with fibromyalgia. J Rheumatol 35(3):502-514 (2008).
Mukhamadieva et al. Search for New Drugs Synthesis and Biological Activity of O-Carbamoylated 1,1,1,3,3,3-Hexafluoroisopropanols as New Specific Inhibitors of Carboxylesterase. Pharmaceutical Chemistry Journal 46(8):461-464 (2012).
Muller-Vahl et al. Treatment of Tourette Syndrome with Delta-9-Tetrahydrocannbinol (delta9-THC): No Influence on Neuropsychological Performance. Neuropsychopharmacology 28:384-388 (2003).
Müller-Vahl et al. Treatment of Tourette's syndrome with Delta 9-tetrahydrocannabinol (THC): a randomized crossover trial. Pharmacopsychiatry 35(2):57-61 (2002).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Nomura et al. Endocannabinoid hydrolysis generates brain prostaglandins that promote neuroinflammation. Science 334(6057):809-813 (2011).
Patani et al. Bioisosterism: A Rational Approach in Drug Design. Chem. Rev. 96:3147-3176 (1996).
PCT/US2016/031668 International Search Report and Written Opinion dated Aug. 11, 2016.

(56) References Cited

OTHER PUBLICATIONS

PCT/US2017/061867 Invitation to Pay Additional Fees dated Jan. 22, 2018.
PCT/US2017/061871 International Search Report and Written Opinion dated Feb. 7, 2018.
PCT/US2017/061875 International Search Report and Written Opinion dated Feb. 7, 2018.
Piro et al. A dysregulated endocannabinoid-eicosanoid network supports pathogenesis in a mouse model of Alzheimer's disease. Cell Rep. 1(6):617-623 (2012).
Porsteinsson et al. Effect of citalopram on agitation in Alzheimer disease: the CitAD randomized clinical trial. JAMA 311(7):682-691 (2014).
Price. The computational prediction of pharmaceutical crystal structures and polymorphism. Advanced Drug Delivery Reviews 56:301-319 (2004).
PubChem CID 17217128 http://pubchem.ncbi.nlm.nih.gov/summary/summary.cgi?cid=17217128 Retrieved Apr. 30, 2013 Create Date: Nov. 13, 2007 (3 pgs.).
PubChem CID 3469875. Compound Summary downloaded at https://pubchem.ncbi.nlm.nih.gov/compound/3469875 on Jun. 5, 2019,pp. 1-8 (2019).
PubChem CID 3469875. http://pubchem.ncbi.nlm.nih.gov/summary/summary.cgi?cid=3469875Retrieved Mar. 4, 2013 Create Date: Sep. 8, 2005 (11 pgs.).
PubChem CID 669902 http://pubchem.ncbi.nlm.nih.gov/summary/summary.cgi?cid=669902 Retrieved May 1, 2013 Create Date: Jul. 8, 2005 (4 pgs.).
PubChem CID 71657619 Create date: Aug. 19, 2013 (12 pgs).
Rautio et al. Prodrugs: design and clinical applications. Nat Rev Drug Discov 7(3):255-270 (2008).
Rhyne et al. Effects of Medical Marijuana on Migraine Headache Frequency in an Adult Population. Pharmacotherapy 36:505-510 (2016).
Richardson et al. Characterisation of the cannabinoid receptor system in synovial tissue and fluid in patients with osteoarthritis and rheumatoid arthritis. Arthritis Res Ther 10(2):R43 (2008).
Rog et al. Randomized, controlled trial of cannabis-based medicine in central pain in multiple sclerosis. Neurology 65(6):812-819 (2005).
Sarchielli et al. Endocannabinoids in chronic migraine: CSF findings suggest a system failure. Neuropsychopharmacology 32(6):1384-1390 (2007).
Science IP Report dated Dec. 11, 2014 (126 pgs.).
Silverman. The Organic Chemistry of Drug Design and Drug Action. Academic Press (pp. 15-22) (1992).
Singh et al. Encyclopedia of Pharmaceutical Technology 2nd Ed. pp. 751-753 (2002).
Skrabek et al. Nabilone for the treatment of pain in fibromyalgia. J Pain 9(2):164-173 (2008).
South. Synthesis and Reactions of Halogenated Thiazole Isocyanates. Journal of Heterocyclic Chemistry 28:1003-1011 (1991).
Studnev et al. Synthesis, Antibacterial and Immunotropic Activity of Poly(fluoroalkyl-N-arylcarbamates. Pharmaceutical Chemistry Journal 36(12):654-657 (2002).
Thornber. Isosterism and molecular modification in drug design. Chem Soc Rev 8:563-580 (1979).
Turcotte et al. Nabilone as an adjunctive to gabapentin for multiple sclerosis-induced neuropathic pain: a randomized controlled trial. Pain Med 16(1):149-159 (2015).
U.S. Appl. No. 15/573,272 Office Action dated Dec. 14, 2018.
Urry et al. Free-radical chain addition reactions of aldehydes with perfluoro ketones and chloro perfluoro ketones. J Org Chem 32(2):347-352 (1967).
Volicer et al. Effects of dronabinol on anorexia and disturbed behavior in patients with Alzheimer's disease. Int J Geriatr Psychiatry 12(9):913-919 (1997).
Wade. Deuterium isotope effects on noncovalent interactions between molecules. Chem Biol Interact 117:191-217 (1999).
Walther et al. Randomized, controlled crossover trial of dronabinol, 2.5 mg, for agitation in 2 patients with dementia. J Clin Psychopharmacol 31(2):256-258 (2011).
Ware et al. The effects of nabilone on sleep in fibromyalgia: results of a randomized controlled trial. Anesth Analg 110(2):604-610 (2010).
Whiting et al. Cannabinoids for Medical Use: A Systematic Review and Meta-analysis. JAMA 313(24):2456-2473 (2015).
Zajicek et al. Cannabinoids for treatment of spasticity and other symptoms related to multiple sclerosis (CAMS study): multicentre randomised placebo-controlled trial. Lancet 362(9395):1517-1526 (2003).
Zello et al. Plasma and urine enrichments following infusion of L-[1-13C]phenylalanine and L-[ring-2H5]phenylalanine in humans: evidence for an isotope effect in renal tubular reabsorption. Metabolism 43:487-491 (1994).
Brittain. Polymorphism in Pharmaceutical Solids. 192:1-241 (2009).
Guindon et al. Peripheral Antinociceptive Effects of Inhibitors of Monoacylglycerol Lipase in a Rat Model of Inflammatory Pain. Br J Pharmacol 163(7):1464-1478 (2011).
Long et al. Dual blockade of FAAH and MAGL identifies behavioral processes regulated by endocannabinoid crosstalk in vivo. PNAS USA 106(48):20270-20275 (2009).
Caira. Crystalline Polymorphism of Organic Compounds. Topics in Current Chemistry. 198:163-208 (Jan. 1998).
Morissette et al. High-throughput crystallization: polymorphs. salts. co-crystals and solvates of pharmaceutical solids. Advanced Drug Delivery Reviews 56:275-300 (2004).

* cited by examiner

CRYSTALLINE FORMS OF A MAGL INHIBITOR

CROSS-REFERENCE

This application is a U.S. National Stage entry of PCT application PCT/US2017/061875 filed Nov. 15, 2017, which claims the benefit of U.S. Provisional Application No. 62/423,126, filed on Nov. 16, 2016, which are herein incorporated by reference in their entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system. The serine hydrolase α-β-hydrolase domain 6 (ABHD6) is another lipid mediator.

SUMMARY OF THE INVENTION

Described herein is the MAGL inhibitor 1,1,1,3,3,3-hexafluoropropan-2-yl 4-(2-(pyrrolidin-1-yl)-4-(trifluoromethyl)benzyl)piperazine-1-carboxylate, including pharmaceutically acceptable solvates (including hydrates), polymorphs, and amorphous phases, and methods of uses thereof.

Also described are pharmaceutically acceptable salts of the MAGL inhibitor 1,1,1,3,3,3-hexafluoropropan-2-yl 4-(2-(pyrrolidin-1-yl)-4-(trifluoromethyl)benzyl)piperazine-1-carboxylate, including pharmaceutically acceptable solvates (including hydrates), polymorphs, and amorphous phases, and methods of uses thereof. 1,1,1,3,3,3-Hexafluoropropan-2-yl 4-(2-(pyrrolidin-1-yl)-4-(trifluoromethyl)benzyl)piperazine-1-carboxylate, as well as the pharmaceutically acceptable salts thereof, are used in the manufacture of medicaments for the treatment of diseases or conditions that are associated with MAGL activity.

Also described herein are methods for preparing crystalline forms of 1,1,1,3,3,3-hexafluoropropan-2-yl 4-(2-(pyrrolidin-1-yl)-4-(trifluoromethyl)benzyl)piperazine-1-carboxylate. Further described are pharmaceutical compositions that include the crystalline forms and methods of using the MAGL inhibitor in the treatment of diseases or conditions (including diseases or conditions wherein irreversible inhibition of MAGL provides therapeutic benefit to a mammal having the disease or condition).

In one embodiment is a crystalline form of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt, including solvate thereof.

In another embodiment, the crystalline form of 1,1,1,3,3,3-hexafluoropropan-2-yl 4-(2-(pyrrolidin-1-yl)-4-(trifluoromethyl)benzyl)piperazine-1-carboxylate is a free base.

In another aspect, described herein is a crystalline form of 1,1,1,3,3,3-hexafluoropropan-2-yl 4-(2-(pyrrolidin-1-yl)-4-(trifluoromethyl)benzyl)piperazine-1-carboxylate free base that has at least one of the following properties:
  (a) an X-ray powder diffraction (XRPD) pattern substantially the same as shown in FIG. 1;
  (b) an X-ray powder diffraction (XRPD) pattern with characteristic peaks at 7.8° 2-Theta, 12.0° 2-Theta, 18.5° 2-Theta, 19.0° 2-Theta, 19.6° 2-Theta and 21.2° 2-Theta;
  (c) a thermo-gravimetric analysis (TGA) substantially similar to the one set forth in FIG. 2;
  (d) a DSC thermogram substantially similar to the one set forth in FIG. 3;
  (e) a DSC thermogram with an endotherm having an onset at about 80° C.;
  (f) infrared (IR) spectrum substantially similar to the one set forth in FIG. 6;
  (g) infrared (IR) spectrum with peaks at about 1735 cm-1, 1427 cm-1, 1102 cm-1, 982 cm-1, and 888 cm-1;
  (h) non-hygroscopicity; or
  (i) combinations thereof.

In some embodiments, the crystalline free base has an X-ray powder diffraction (XRPD) pattern substantially the same as shown in FIG. 1. In some embodiments, the crystalline free base has an X-ray powder diffraction (XRPD) pattern with characteristic peaks at 7.8° 2-Theta, 12.0° 2-Theta, 18.5° 2-Theta, 19.0° 2-Theta, 19.6° 2-Theta and 21.2° 2-Theta. In some embodiments, the crystalline free base has a thermo-gravimetric analysis (TGA) thermogram substantially similar to the one set forth in FIG. 2. In some embodiments, the crystalline free base has a DSC thermogram substantially similar to the one set forth in FIG. 3. In some embodiments, the crystalline free base has a DSC thermogram with an endotherm having an onset at about 80° C. In some embodiments, the crystalline free base has a DSC thermogram with an endotherm having an onset at about 80° C. and a peak at about 83° C. In some embodiments, the crystalline free base has an infrared (IR) spectrum substantially similar to the one set forth in FIG. 6. In some embodiments, the crystalline free base has an infrared (IR) spectrum weak peaks at about 1735 $cm^{-1}$, 1427 $cm^{-1}$, 1102 $cm^{-1}$, 982 $cm^{-1}$, and 888 $cm^{-1}$. In some embodiments, the crystalline free base is non-hygroscopic. In some embodiments, the crystalline free base is characterized as having properties (a), (b), (c), (d), (e), (f), (g), and (h). In some embodiments, the crystalline free base is obtained from acetone, acetone/water, acetonitrile, anisole, dichloromethane, diisopropyl ether, dimethylacetamide, dimethylformamide, dimethylsulfoxide, 1,4-dioxane, ethanol, ethyl acetate, isopropyl acetate, methanol, methanol/water, methyethyl ketone, methyl isobutyl ketone, N-methyl-2-pyrrolidone, 2-propanol, 2-propanol/water, tert-butyl methyl ketone, tetrahydrofuran, toluene, water, 1-butanol, 2-ethoxyethanol, 2-methyl tetrahydrofuran, benzonitrile, chlorobenzene, heptane, hexane, or tert-amyl alcohol. In some embodiments, the crystalline free base is solvated. In some embodiments, the crystalline free base is unsolvated. In some embodiments, the crystalline free base is anhydrous.

In another embodiment, the crystalline form of 1,1,1,3,3,3-hexafluoropropan-2-yl 4-(2-(pyrrolidin-1-yl)-4-(trifluoromethyl)benzyl)piperazine-1-carboxylate is a 1,1,1,3,3,3-hexafluoropropan-2-yl 4-(2-(pyrrolidin-1-yl)-4-(trifluoromethyl)benzyl)piperazine-1-carboxylate salt. In some embodiments, the 1,1,1,3,3,3-hexafluoropropan-2-yl 4-(2-(pyrrolidin-1-yl)-4-(trifluoromethyl)benzyl)piperazine-1-carboxylate is a mono-hydrochloride salt, bis-hydrochloride salt, fumarate salt, besylate salt, or mesylate salt; or solvate thereof.

In another embodiment, the crystalline form of 1,1,1,3,3,3-hexafluoropropan-2-yl 4-(2-(pyrrolidin-1-yl)-4-(trifluoromethyl)benzyl)piperazine-1-carboxylate is a 1,1,1,3,3,3-hexafluoropropan-2-yl 4-(2-(pyrrolidin-1-yl)-4-(trifluoromethyl)benzyl)piperazine-1-carboxylate mono-hydrochloride salt; or solvate thereof.

In another embodiment, described herein is a crystalline Form 1 of 1,1,1,3,3,3-hexafluoropropan-2-yl 4-(2-(pyrrolidin-1-yl)-4-(trifluoromethyl)benzyl)piperazine-1-carboxylate mono-hydrochloride salt that has at least one of the following properties:
- (a) an X-ray powder diffraction (XRPD) pattern substantially the same as shown in FIG. 9;
- (b) an X-ray powder diffraction (XRPD) pattern with characteristic peaks at 6.4° 2-Theta, 14.9° 2-Theta, 16.9° 2-Theta, 18.4° 2-Theta, and 20.9° 2-Theta;
- (c) a thermo-gravimetric analysis (TGA) thermogram substantially similar to the one set forth in FIG. 10;
- (d) a DSC thermogram substantially similar to the one set forth in FIG. 11;
- (e) a DSC thermogram with an endotherm having an onset at about 182° C.;
- (f) non-hygroscopicity; or
- (g) combinations thereof.

In some embodiments, the crystalline mono-hydrochloride salt, Form 1, has an X-ray powder diffraction (XRPD) pattern substantially the same as shown in FIG. 9. In some embodiments, the crystalline mono-hydrochloride salt, Form 1, has an X-ray powder diffraction (XRPD) pattern with characteristic peaks at 6.4° 2-Theta, 14.9° 2-Theta, 16.9° 2-Theta, 18.4° 2-Theta, and 20.9° 2-Theta. In some embodiments, the crystalline mono-hydrochloride salt, Form 1, has a thermo-gravimetric analysis (TGA) thermogram substantially similar to the one set forth in FIG. 10. In some embodiments, the crystalline mono-hydrochloride salt, Form 1, has a DSC thermogram substantially similar to the one set forth in FIG. 11. In some embodiments, the crystalline mono-hydrochloride salt, Form 1, has a DSC thermogram with an endotherm having an onset at about 182° C. In some embodiments, the crystalline mono-hydrochloride salt, Form 1, has a DSC thermogram with an endotherm having an onset at about 182° C. and a peak at about 187° C. In some embodiments, the crystalline mono-hydrochloride salt, Form 1, is non-hygroscopic. In some embodiments, the crystalline mono-hydrochloride salt, Form 1, is characterized as having properties (a), (b), (c), (d), (e), and (f). In some embodiments, the crystalline mono-hydrochloride salt, Form 1, is obtained from acetonitrile, 1,4-dioxane, ethyl acetate, methanol, tert-butylmethyl ether, or 2-propanol. In some embodiments, the crystalline mono-hydrochloride salt, Form 1, is solvated. In some embodiments, the crystalline mono-hydrochloride salt, Form 1, is unsolvated. In some embodiments, the crystalline mono-hydrochloride salt, Form 1, is anhydrous.

In another embodiment, described herein is a crystalline Form 2 of 1,1,1,3,3,3-hexafluoropropan-2-yl 4-(2-(pyrrolidin-1-yl)-4-(trifluoromethyl)benzyl)piperazine-1-carboxylate mono-hydrochloride salt that has at least one of the following properties:
- (a) an X-ray powder diffraction (XRPD) pattern substantially the same as shown in FIG. 28;
- (b) an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta;
- (c) a thermo-gravimetric analysis (TGA) thermogram substantially similar to the one set forth in FIG. 26;
- (d) a DSC thermogram substantially similar to the one set forth in FIG. 27;
- (e) a DSC thermogram with an endotherm having an onset at about 201° C.;
- (f) an infrared (IR) spectrum substantially similar to the one set forth in FIG. 29;
- (g) infrared (IR) spectrum with peaks at about 1729 cm$^{-1}$, 1426 cm$^{-1}$, 1102 cm$^{-1}$, 984 cm$^{-1}$, and 907 cm$^{-1}$;
- (h) non-hygroscopicity; or
- (i) combinations thereof.

In some embodiments, the crystalline mono-hydrochloride salt, Form 2, has an X-ray powder diffraction (XRPD) pattern substantially the same as shown in FIG. 28. In some embodiments, the crystalline mono-hydrochloride salt, Form 2, has an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta. In some embodiments, the crystalline mono-hydrochloride salt, Form 2, has a thermo-gravimetric analysis (TGA) thermogram substantially similar to the one set forth in FIG. 26. In some embodiments, the crystalline mono-hydrochloride salt, Form 2, has a DSC thermogram substantially similar to the one set forth in FIG. 27. In some embodiments, the crystalline mono-hydrochloride salt, Form 2, has a DSC thermogram with an endotherm having an onset at about 201° C. In some embodiments, the crystalline mono-hydrochloride salt, Form 2, has a DSC thermogram with an endotherm having an onset at about 201° C. and a peak at about 205° C. In some embodiments, the crystalline mono-hydrochloride salt, Form 2, has an infrared (IR) spectrum substantially similar to the one set forth in FIG. 29. In some embodiments, the crystalline mono-hydrochloride salt, Form 2, has an infrared (IR) spectrum with peaks at about 1729 cm$^{-1}$, 1426 cm$^{-1}$, 1102 cm$^{-1}$, 984 cm$^{-1}$, and 907 cm$^{-1}$. In some embodiments, the crystalline mono-hydrochloride salt, Form 2, is non-hygroscopic. In some embodiments, the crystalline mono-hydrochloride salt, Form 2, is characterized as having properties (a), (b), (c), (d), (e), (f), (g), and (h). In some embodiments, the crystalline mono-hydrochloride salt, Form 2, is obtained from acetone, acetonitrile, anisole, dichloromethane, diisopropyl ether, ethanol, ethyl acetate, isopropyl acetate, methanol, methylethyl ketone, methyl isobutyl ketone, tert-butylmethyl ether, 2-propanol, tetrahydrofuran, toluene, 2-ethoxyethanol, 2-methyl tetrahydrofuran, or tert-amyl alcohol. In some embodiments, the crystalline mono-hydrochloride salt, Form 2, is solvated. In some embodiments, the crystalline mono-hydrochloride salt, Form 2, is unsolvated. In some embodiments, the crystalline mono-hydrochloride salt, Form 2, is anhydrous.

In another embodiment, the crystalline form of 1,1,1,3,3,3-hexafluoropropan-2-yl 4-(2-(pyrrolidin-1-yl)-4-(trifluoromethyl)benzyl)piperazine-1-carboxylate is a 1,1,1,3,3,3-hexafluoropropan-2-yl 4-(2-(pyrrolidin-1-yl)-4-(trifluoromethyl)benzyl)piperazine-1-carboxylate bis-hydrochloride salt; or solvate thereof.

In another embodiment, described herein is a crystalline form of 1,1,1,3,3,3-hexafluoropropan-2-yl 4-(2-(pyrrolidin-1-yl)-4-(trifluoromethyl)benzyl)piperazine-1-carboxylate bis-hydrochloride salt that has at least one of the following properties:
- (a) an X-ray powder diffraction (XRPD) pattern substantially the same as shown in FIG. 17;
- (b) an X-ray powder diffraction (XRPD) pattern with characteristic peaks at 6.4° 2-Theta, 12.0° 2-Theta, 12.5° 2-Theta, 14.3° 2-Theta, 18.5° 2-Theta, and 22.8° 2-Theta;
- (c) a thermo-gravimetric analysis (TGA) thermogram substantially similar to the one set forth in FIG. 18;
- (d) a DSC thermogram substantially similar to the one set forth in FIG. 19;
- (e) a DSC thermogram with an endotherm having an onset at about 154° C.; or
- (f) combinations thereof.

In some embodiments, the crystalline bis-hydrochloride salt has an X-ray powder diffraction (XRPD) pattern substantially the same as shown in FIG. 17. In some embodiments, the crystalline bis-hydrochloride salt has an X-ray powder diffraction (XRPD) pattern with characteristic peaks at 6.4° 2-Theta, 12.0° 2-Theta, 12.5° 2-Theta, 14.3° 2-Theta, 18.5° 2-Theta, and 22.8° 2-Theta. In some embodiments, the crystalline bis-hydrochloride salt has a thermo-gravimetric analysis (TGA) thermogram substantially similar to the one set forth in FIG. 18. In some embodiments, the crystalline bis-hydrochloride salt has a DSC thermogram substantially similar to the one set forth in FIG. 19. In some embodiments, the crystalline bis-hydrochloride salt has a DSC thermogram with an endotherm having an onset at about 154° C. In some embodiments, the crystalline bis-hydrochloride salt has a DSC thermogram with an endotherm having an onset at about 154° C. and a peak at about 164° C. In some embodiments, the crystalline bis-hydrochloride salt that is characterized as having properties (a), (b), (c), (d), and (e). In some embodiments, the crystalline bis-hydrochloride salt is obtained from tert-butylmethyl ether and 5 equivalents of HCl. In some embodiments, the crystalline bis-hydrochloride salt is solvated. In some embodiments, the crystalline bis-hydrochloride salt is unsolvated. In some embodiments, the crystalline bis-hydrochloride salt is anhydrous.

In another embodiment, the crystalline form of 1,1,1,3,3,3-hexafluoropropan-2-yl 4-(2-(pyrrolidin-1-yl)-4-(trifluoromethyl)benzyl)piperazine-1-carboxylate is a 1,1,1,3,3,3-hexafluoropropan-2-yl 4-(2-(pyrrolidin-1-yl)-4-(trifluoromethyl)benzyl)piperazine-1-carboxylate fumarate salt; or solvate thereof.

In another embodiment, described herein is a crystalline Form 1 of 1,1,1,3,3,3-hexafluoropropan-2-yl 4-(2-(pyrrolidin-1-yl)-4-(trifluoromethyl)benzyl)piperazine-1-carboxylate fumarate salt that has at least one of the following properties:
 (a) an X-ray powder diffraction (XRPD) pattern substantially the same as shown in FIG. 42;
 (b) an X-ray powder diffraction (XRPD) pattern with characteristic peaks at 13.6° 2-Theta, 14.1° 2-Theta, 14.3° 2-Theta, 20.0° 2-Theta, and 21.9° 2-Theta;
 (c) a thermo-gravimetric analysis (TGA) thermogram substantially similar to the one set forth in FIG. 44;
 (d) a DSC thermogram substantially similar to the one set forth in FIG. 45;
 (e) a DSC thermogram with an endotherm having an onset at about 126° C.;
 (f) non-hygroscopicity; or
 (g) combinations thereof.

In some embodiments, the crystalline fumarate salt, Form 1, has an X-ray powder diffraction (XRPD) pattern substantially the same as shown in FIG. 42. In some embodiments, the crystalline fumarate salt, Form 1, has an X-ray powder diffraction (XRPD) pattern with characteristic peaks at 13.6° 2-Theta, 14.1° 2-Theta, 14.3° 2-Theta, 20.0° 2-Theta, and 21.9° 2-Theta. In some embodiments, the crystalline fumarate salt, Form 1, has a thermo-gravimetric analysis (TGA) thermogram substantially similar to the one set forth in FIG. 44. In some embodiments, the crystalline fumarate salt, Form 1, has a DSC thermogram substantially similar to the one set forth in FIG. 45. In some embodiments, the crystalline fumarate salt, Form 1, has a DSC thermogram with an endotherm having an onset at about 126° C. In some embodiments, the crystalline fumarate salt, Form 1, has a DSC thermogram with an endotherm having an onset at about 126° C. and a peak at about 132° C. In some embodiments, the crystalline fumarate salt, Form 1, is non-hygroscopic. In some embodiments, the crystalline fumarate salt, Form 1, is characterized as having properties (a), (b), (c), (d), (e) and (f). In some embodiments, the crystalline fumarate salt, Form 1, is obtained from 1-butanol, 1-propanol, 2-propanol, acetone/water mixtures, acetonitrile/water mixtures, ethanol, methyl acetate/water, methyl ethyl ketone/water, methanol/acetonitrile and 2-methoxyethanol/acetonitrile. In some embodiments, the crystalline fumarate salt, Form 1, is solvated. In some embodiments, the crystalline fumarate salt, Form 1, is unsolvated. In some embodiments, the crystalline fumarate salt, Form 1, is anhydrous.

In another embodiment, described herein is a crystalline Form 2 of 1,1,1,3,3,3-hexafluoropropan-2-yl 4-(2-(pyrrolidin-1-yl)-4-(trifluoromethyl)benzyl)piperazine-1-carboxylate fumarate salt that has at least one of the following properties:
 (a) an X-ray powder diffraction (XRPD) pattern substantially the same as shown in FIG. 46;
 (b) an X-ray powder diffraction (XRPD) pattern with characteristic peaks at 9.2° 2-Theta, 12.1° 2-Theta, 15.2° 2-Theta, 17.4° 2-Theta, 18.2° 2-Theta, 19.1° 2-Theta, and 19.7° 2-Theta;
 (c) a thermo-gravimetric analysis (TGA) thermogram substantially similar to the one set forth in FIG. 48; or
 (d) combinations thereof.

In some embodiments, the crystalline fumarate salt, Form 2, has an X-ray powder diffraction (XRPD) pattern substantially the same as shown in FIG. 46. In some embodiments, the crystalline fumarate salt, Form 2, has an X-ray powder diffraction (XRPD) pattern with characteristic peaks at 9.2° 2-Theta, 12.1° 2-Theta, 15.2° 2-Theta, 17.4° 2-Theta, 18.2° 2-Theta, 19.1° 2-Theta, and 19.7° 2-Theta. In some embodiments, the crystalline fumarate salt, Form 2, has a thermo-gravimetric analysis (TGA) thermogram substantially similar to the one set forth in FIG. 48. In some embodiments, the crystalline fumarate salt, Form 2, is characterized as having properties (a), (b), and (c). In some embodiments, the crystalline fumarate salt, Form 2, is obtained from acetone/water.

In another embodiment, described herein is a crystalline Form 3 of 1,1,1,3,3,3-hexafluoropropan-2-yl 4-(2-(pyrrolidin-1-yl)-4-(trifluoromethyl)benzyl)piperazine-1-carboxylate fumarate salt that has at least one of the following properties:
 (a) an X-ray powder diffraction (XRPD) pattern substantially the same as shown in FIG. 49;
 (b) an X-ray powder diffraction (XRPD) pattern with characteristic peaks at 6.7° 2-Theta, 9.5° 2-Theta, 12.0° 2-Theta, 13.9° 2-Theta, 14.6° 2-Theta, 17.6° 2-Theta, 19.4° 2-Theta, and 20.3° 2-Theta;
 (c) a thermo-gravimetric analysis (TGA) thermogram substantially similar to the one set forth in FIG. 51;
 (d) a DSC thermogram substantially similar to the one set forth in FIG. 52;
 (e) a DSC thermogram with an endotherm having an onset at about 107° C.; or
 (f) combinations thereof.

In some embodiments, the crystalline fumarate salt, Form 3, has an X-ray powder diffraction (XRPD) pattern substantially the same as shown in FIG. 49. In some embodiments, the crystalline fumarate salt, Form 3, has an X-ray powder diffraction (XRPD) pattern with characteristic peaks at 6.7° 2-Theta, 9.5° 2-Theta, 12.0° 2-Theta, 13.9° 2-Theta, 14.6° 2-Theta, 17.6° 2-Theta, 19.4° 2-Theta, and 20.3° 2-Theta. In some embodiments, the crystalline fumarate salt, Form 3, has a thermo-gravimetric analysis (TGA) thermogram substantially similar to the one set forth in FIG. 51. In some embodiments, the crystalline fumarate salt, Form 3, has a DSC thermogram substantially similar to the one set forth in FIG. 52. In some embodiments, the crystalline fumarate salt, Form 3, has a DSC thermogram with an endotherm having an onset at about 107° C. In some embodiments, the crystalline fumarate salt, Form 3, has a DSC thermogram with an endotherm having an onset at about 107° C. and a peak at about 115° C. In some embodiments, the crystalline fumarate salt, Form 3, is characterized as having properties (a), (b), (c), (d), and (e). In some embodiments, the crystalline fumarate salt, Form 3, is obtained from dioxane/water.

In another embodiment, the crystalline form of 1,1,1,3,3,3-hexafluoropropan-2-yl 4-(2-(pyrrolidin-1-yl)-4-(trifluoromethyl)benzyl)piperazine-1-carboxylate is a 1,1,1,3,3,3-hexafluoropropan-2-yl 4-(2-(pyrrolidin-1-yl)-4-(trifluoromethyl)benzyl)piperazine-1-carboxylate mesylate salt; or solvate thereof.

In another embodiment, described herein is a crystalline form of 1,1,1,3,3,3-hexafluoropropan-2-yl 4-(2-(pyrrolidin-1-yl)-4-(trifluoromethyl)benzyl)piperazine-1-carboxylate mesylate salt that has at least one of the following properties:
  (a) an X-ray powder diffraction (XRPD) pattern substantially the same as shown in FIG. 38;
  (b) an X-ray powder diffraction (XRPD) pattern with characteristic peaks at 8.6° 2-Theta, 12.4° 2-Theta, 14.6° 2-Theta, 16.5° 2-Theta, 17.7° 2-Theta, and 19.7° 2-Theta;
  (c) a thermo-gravimetric analysis (TGA) thermogram substantially similar to the one set forth in FIG. 40;
  (d) a DSC thermogram substantially similar to the one set forth in FIG. 41;
  (e) a DSC thermogram with an endotherm having an onset at about 179° C.; or
  (f) combinations thereof.

In some embodiments, crystalline mesylate salt has an X-ray powder diffraction (XRPD) pattern substantially the same as shown in FIG. 38. In some embodiments, crystalline mesylate salt has an X-ray powder diffraction (XRPD) pattern with characteristic peaks at 8.6° 2-Theta, 12.4° 2-Theta, 14.6° 2-Theta, 16.5° 2-Theta, 17.7° 2-Theta, and 19.7° 2-Theta. In some embodiments, the crystalline mesylate salt has a thermo-gravimetric analysis (TGA) thermogram substantially similar to the one set forth in FIG. 40. In some embodiments, the crystalline mesylate salt has a DSC thermogram substantially similar to the one set forth in FIG. 41. In some embodiments, the crystalline mesylate salt has a DSC thermogram with an endotherm having an onset at about 179° C. In some embodiments, the crystalline mesylate salt has a DSC thermogram with an endotherm having an onset at about 179° C. and a peak at about 182° C. In some embodiments, the crystalline mesylate salt that is characterized as having properties (a), (b), (c), (d), and (e). In some embodiments, the crystalline mesylate salt is obtained from tert-butylmethyl ether, ethyl acetate, tetrahydrofuran, water/acetone, water/acetonitrile, or water/2-propanol. In some embodiments, the crystalline mesylate salt is solvated. In some embodiments, the crystalline mesylate salt is unsolvated. In some embodiments, the crystalline mesylate salt is anhydrous.

In another embodiment, the crystalline form of 1,1,1,3,3,3-hexafluoropropan-2-yl 4-(2-(pyrrolidin-1-yl)-4-(trifluoromethyl)benzyl)piperazine-1-carboxylate is a 1,1,1,3,3,3-hexafluoropropan-2-yl 4-(2-(pyrrolidin-1-yl)-4-(trifluoromethyl)benzyl)piperazine-1-carboxylate besylate salt; or solvate thereof.

In some embodiments, crystalline besylate salt, Form 1, has an X-ray powder diffraction (XRPD) pattern substantially the same as shown in FIG. 30. In some embodiments, crystalline besylate salt, Form 1, has an X-ray powder diffraction (XRPD) pattern with characteristic peaks at 13.2° 2-Theta, 15.2° 2-Theta, 18.2° 2-Theta, 19.3° 2-Theta, and 21.6° 2-Theta. In some embodiments, the crystalline besylate salt is obtained from acetone, acetonitrile, ethyl acetate, 2-propanol, and THF. In some embodiments, the crystalline besylate salt, Form 1, is solvated. In some embodiments, the crystalline besylate salt, Form 1, is unsolvated. In some embodiments, the crystalline besylate salt, Form 1, is anhydrous.

In another embodiment, described herein is a crystalline Form 2 of 1,1,1,3,3,3-hexafluoropropan-2-yl 4-(2-(pyrrolidin-1-yl)-4-(trifluoromethyl)benzyl)piperazine-1-carboxylate besylate salt that has at least one of the following properties:
  (a) an X-ray powder diffraction (XRPD) pattern substantially the same as shown in FIG. 31;
  (b) an X-ray powder diffraction (XRPD) pattern with characteristic peaks at 6.4° 2-Theta, 15.9° 2-Theta, 17.8° 2-Theta, 18.8° 2-Theta, and 19.9° 2-Theta;
  (c) a thermo-gravimetric analysis (TGA) thermogram substantially similar to the one set forth in FIG. 33; or
  (d) combinations thereof.

In some embodiments, crystalline besylate salt, Form 2, has an X-ray powder diffraction (XRPD) pattern substantially the same as shown in FIG. 31. In some embodiments, crystalline besylate salt, Form 2, has an X-ray powder diffraction (XRPD) pattern with characteristic peaks at 6.4° 2-Theta, 15.9° 2-Theta, 17.8° 2-Theta, 18.8° 2-Theta, and 19.9° 2-Theta. In some embodiments, the crystalline besylate salt that is characterized as having properties (a), (b), and (c). In some embodiments, the crystalline besylate salt, Form 2, is obtained from tert-butylmethyl ether. In some embodiments, the crystalline besylate salt, Form 2, is solvated. In some embodiments, the crystalline besylate salt, Form 2, is unsolvated. In some embodiments, the crystalline besylate salt, Form 2, is anhydrous.

In a further aspect are provided pharmaceutical compositions, which include 1,1,1,3,3,3-hexafluoropropan-2-yl 4-(2-(pyrrolidin-1-yl)-4-(trifluoromethyl)benzyl)piperazine-1-carboxylate as described herein, and at least one additional ingredient selected from pharmaceutically acceptable carriers, diluents and excipients. In some embodiments, the pharmaceutical composition comprises crystalline 1,1,1,3,3,3-hexafluoropropan-2-yl 4-(2-(pyrrolidin-1-yl)-4-(trifluoromethyl)benzyl)piperazine-1-carboxylate free base. In some embodiments, the pharmaceutical composition comprises crystalline 1,1,1,3,3,3-hexafluoropropan-2-yl 4-(2-(pyrrolidin-1-yl)-4-(trifluoromethyl)benzyl)piperazine-1-carboxylate mono-HCl salt Form 1. In some embodiments, the pharmaceutical composition comprises crystalline 1,1,1,3,3,3-hexafluoropropan-2-yl 4-(2-(pyrrolidin-1-yl)-4-(trifluoromethyl)benzyl)piperazine-1-carboxylate mono-HCl salt Form 2. In some embodiments, the pharmaceutical composition comprises crystalline 1,1,1,3,3,3-hexafluoropropan-2-yl 4-(2-(pyrrolidin-1-yl)-4-(trifluoromethyl)benzyl)piperazine-1-carboxylate bis-HCl salt. In some embodiments, the pharmaceutical composition comprises crystalline 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, the pharmaceutical composition comprises crystalline 1,1,1,3,3,3-hexafluoropropan-2-yl 4-(2-(pyrrolidin-1-yl)-4-(trifluoromethyl)benzyl)piperazine-1-carboxylate mesylate salt. In some embodiments, the pharmaceutical composition comprises crystalline 1,1,1,3,3,3-hexafluoropropan-2-yl 4-(2-(pyrrolidin-1-yl)-4-(trifluoromethyl)benzyl)piperazine-1-carboxylate besylate salt Form 1. In some embodiments, the pharmaceutical composition comprises crystalline 1,1,1,3,3,3-hexafluoropropan-2-yl 4-(2-(pyrrolidin-1-yl)-4-(trifluoromethyl)benzyl)piperazine-1-carboxylate besylate salt Form 2. In some embodiments, the pharmaceutical composition is in a form suitable for oral administration to a mammal. In some embodiments, the pharmaceutical composition is an oral solid dosage form. In some embodiments, the pharmaceutical composition comprises about 0.5 mg to about 1000 mg of crystalline 1,1,1,3,3,3-hexafluoropropan-2-yl 4-(2-(pyrrolidin-1-yl)-4-(trifluoromethyl)benzyl)piperazine-1-carboxylate.

In another aspect, provided herein is 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt, or solvate thereof, for use in medicine.

In another aspect, provided herein is a method of treating pain in a patient in need thereof, comprising administering to the patient in need thereof a therapeutically effective amount of a crystalline form of 1,1,1,3,3,3-hexafluoropropan-2-yl 4-(2-(pyrrolidin-1-yl)-4-(trifluoromethyl)benzyl)piperazine-1-carboxylate as described herein. In some embodiments is a method of treating pain in a patient in need thereof, comprising administering to the patient in need thereof a therapeutically effective amount of a pharmaceutical composition of 1,1,1,3,3,3-hexafluoropropan-2-yl 4-(2-(pyrrolidin-1-yl)-4-(trifluoromethyl)benzyl)piperazine-1-carboxylate as described herein. In some embodiments the pain is neuropathic pain. In some embodiments, the pain is inflammatory pain.

In another aspect, provided herein is a method of treating epilepsy/seizure disorder, multiple sclerosis, neuromyelitis optica (NMO), Tourette syndrome, Alzheimer disease, or abdominal pain associated with irritable bowel syndrome in a patient in need thereof, comprising administering to the patient in need thereof a therapeutically effective amount of a crystalline form of 1,1,1,3,3,3-hexafluoropropan-2-yl 4-(2-(pyrrolidin-1-yl)-4-(trifluoromethyl)benzyl)piperazine-1-carboxylate as described herein. In some embodiments is a method of treating epilepsy/seizure disorder, multiple sclerosis, neuromyelitis optica (NMO), Tourette syndrome, Alzheimer disease, or abdominal pain associated with irritable bowel syndrome in a patient in need thereof, comprising administering to the patient in need thereof a therapeutically effective amount of a pharmaceutical composition of 1,1,1,3,3,3-hexafluoropropan-2-yl 4-(2-(pyrrolidin-1-yl)-4-(trifluoromethyl)benzyl)piperazine-1-carboxylate as described herein.

In another aspect, provided herein is a method of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient in need thereof a therapeutically effective amount of a crystalline form of 1,1,1,3,3,3-hexafluoropropan-2-yl 4-(2-(pyrrolidin-1-yl)-4-(trifluoromethyl)benzyl)piperazine-1-carboxylate as described herein. In some embodiments is a method of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient in need thereof a therapeutically effective amount of a pharmaceutical composition of 1,1,1,3,3,3-hexafluoropropan-2-yl 4-(2-(pyrrolidin-1-yl)-4-(trifluoromethyl)benzyl)piperazine-1-carboxylate as described herein.

In another aspect, provided herein is a method of treating dystonia in a patient in need thereof, comprising administering to the patient in need thereof a therapeutically effective amount of a crystalline form of 1,1,1,3,3,3-hexafluoropropan-2-yl 4-(2-(pyrrolidin-1-yl)-4-(trifluoromethyl)benzyl)piperazine-1-carboxylate as described herein. In some embodiments is a method of treating dystonia in a patient in need thereof, comprising administering to the patient in need thereof a therapeutically effective amount of a pharmaceutical composition of 1,1,1,3,3,3-hexafluoropropan-2-yl 4-(2-(pyrrolidin-1-yl)-4-(trifluoromethyl)benzyl)piperazine-1-carboxylate as described herein.

In another aspect, provided herein is a pharmaceutically acceptable salt of 1,1,1,3,3,3-hexafluoropropan-2-yl 4-(2-(pyrrolidin-1-yl)-4-(trifluoromethyl)benzyl)piperazine-1-carboxylate (Compound 1), wherein the pharmaceutically acceptable salt is a mono-hydrochloride salt, bis-hydrochloride salt, fumarate salt, besylate salt, or mesylate salt. In some embodiments, the pharmaceutically acceptable salt of 1,1,1,3,3,3-hexafluoropropan-2-yl 4-(2-(pyrrolidin-1-yl)-4-(trifluoromethyl)benzyl)piperazine-1-carboxylate is a mono-hydrochloride salt (Compound 2). In some embodiments, the pharmaceutically acceptable salt of 1,1,1,3,3,3-hexafluoropropan-2-yl 4-(2-(pyrrolidin-1-yl)-4-(trifluoromethyl)benzyl)piperazine-1-carboxylate is a bis-hydrochloride salt (Compound 3). In some embodiments, the pharmaceutically acceptable salt of 1,1,1,3,3,3-hexafluoropropan-2-yl 4-(2-(pyrrolidin-1-yl)-4-(trifluoromethyl)benzyl)piperazine-1-carboxylate is a fumarate salt (Compound 6). In some embodiments, the pharmaceutically acceptable salt of 1,1,1,3,3,3-hexafluoropropan-2-yl 4-(2-(pyrrolidin-1-yl)-4-(trifluoromethyl)benzyl)piperazine-1-carboxylate is a mesylate salt (Compound 5). In some embodiments, the pharmaceutically acceptable salt of 1,1,1,3,3,3-hexafluoropropan-2-yl 4-(2-(pyrrolidin-1-yl)-4-(trifluoromethyl)benzyl)piperazine-1-carboxylate is a besylate salt (Compound 4).

In another embodiment, the pharmaceutically acceptable salt of 1,1,1,3,3,3-hexafluoropropan-2-yl 4-(2-(pyrrolidin-1-yl)-4-(trifluoromethyl)benzyl)piperazine-1-carboxylate is crystalline. In another embodiment, the pharmaceutically acceptable salt of 1,1,1,3,3,3-hexafluoropropan-2-yl 4-(2-(pyrrolidin-1-yl)-4-(trifluoromethyl)benzyl)piperazine-1-carboxylate is amorphous.

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

INCORPORATION BY REFERENCE

All publications and patent applications mentioned in this specification are herein incorporated by reference to the extent applicable and relevant.

DETAILED DESCRIPTION OF THE INVENTION

Figure 1:
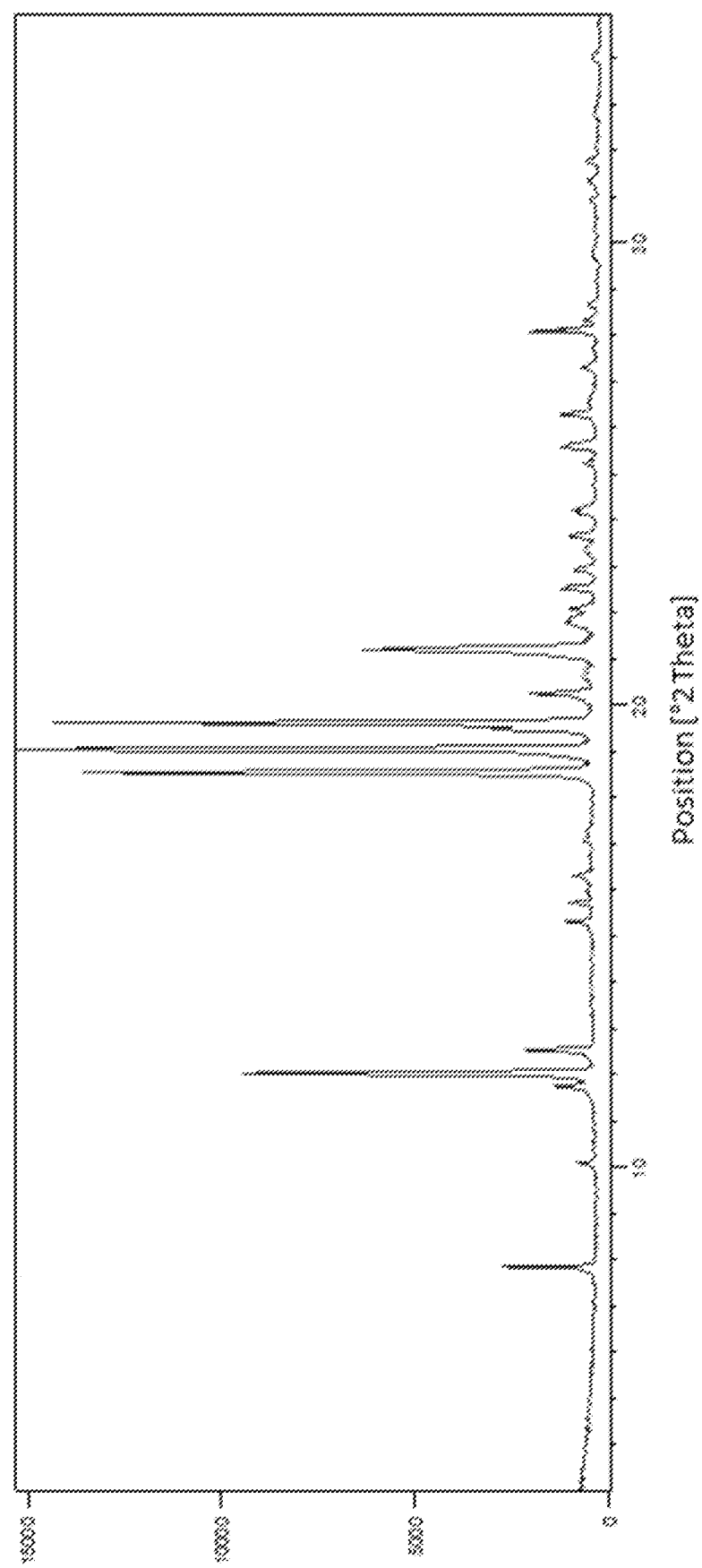
FIG. 1. Illustrates an X-ray powder diffraction (XRPD) pattern of crystalline 1,1,1,3,3,3-hexafluoropropan-2-yl 4-(2-(pyrrolidin-1-yl)-4-(trifluoromethyl)benzyl)piperazine-1-carboxylate free base.

Monoacylglycerol lipase (MAGL) is a primary enzyme responsible for hydrolyzing endocannabinoids such as 2-AG (2-arachidonoylglycerol), an arachidonate based lipid, in the nervous system. The endocannabinoid system regulates a range of physiological processes, including for example, pain sensation, inflammation, and memory. Further, disorders such as obesity, chronic pain, anxiety and depression have been linked to regulation of endocannabinoid system signaling activities.

For example, MAGL modulating compounds may be useful in stimulating 2-AG mediated signaling activities, and disorders associated with such signaling activities, including pain, inflammation, metabolic disorders and the like.

However, MAGL modulating compounds to date have typically lacked the selectivity required for general use as in vivo pharmaceutically acceptable agents, particularly, agents that are selective over fatty acid amide hydrolase (FAAH), a primary N-arachidonoyl ethanolamide (AEA) hydrolyzing enzyme. Genetic or pharmacological disruption of FAAH may result in one or more dependent behavioral effects, for example, inflammation, anxiety, depression, or reduction in pain sensation.

Further, it has recently been discovered that MAGL and its free fatty acid products are upregulated in aggressive cancer cells and in primary tumors, where it regulates a fatty acid network that promotes cancer cell migration and tumor growth. Therefore, new, selective inhibitors of MAGL may be useful in the treatment of cancers.

Compound 1, and Pharmaceutically Acceptable Salts Thereof

The MAGL inhibitor compound described herein, 1,1,1,3,3,3-hexafluoropropan-2-yl 4-(2-(pyrrolidin-1-yl)-4-(trifluoromethyl)benzyl)piperazine-1-carboxylate, is selective for MAGL. Compound 1 is the free base form of 1,1,1,3,3,3-hexafluoropropan-2-yl 4-(2-(pyrrolidin-1-yl)-4-(trifluoromethyl)benzyl)piperazine-1-carboxylate. "Compound 1" or "1,1,1,3,3,3-hexafluoropropan-2-yl 4-(2-(pyrrolidin-1-yl)-4-(trifluoromethyl)benzyl)piperazine-1-carboxylate free base" refers to the compound with the following structure:

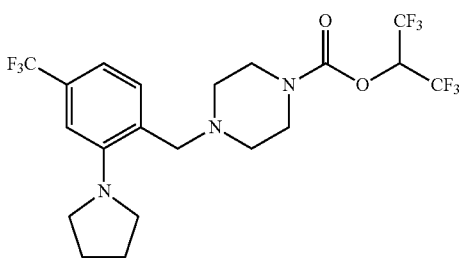 [SMILES: O=C(OC(C(F)(F)F)C(F)(F)F)N1CCN(Cc2ccc(C(F)(F)F)cc2N2CCCC2)CC1]

A wide variety of pharmaceutically acceptable salts are formed from Compound 1 and includes:

acid addition salts formed by reacting Compound 1 with an organic acid, which includes aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, benzenesulfonic acid, p-toluenesulfonic acid, salicylic acid, and the like;

acid addition salts formed by reacting Compound 1 with an inorganic acid, which includes hydrochloric acid, hydrobromic acid, sulfuric acid, nitric acid, phosphoric acid, hydroiodic acid, hydrofluoric acid, phosphorous acid, and the like.

The term "pharmaceutically acceptable salts" in reference to Compound 1 refers to a salt of Compound 1, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C (R3), (November 2005). Hydrates are formed when the solvent is water, or alcoholates are formed when the solvent is alcohol. In some embodiments, solvates of Compound 1, or pharmaceutically acceptable salts thereof, are conveniently prepared or formed during the processes described herein. In some embodiments, solvates of Compound 1 are anhydrous. In some embodiments, Compound 1, or pharmaceutically acceptable salts thereof, exist in unsolvated form. In some embodiments, Compound 1, or pharmaceutically acceptable salts thereof, exist in unsolvated form and are anhydrous.

In yet other embodiments, Compound 1, or a pharmaceutically acceptable salt thereof, is prepared in various forms, including but not limited to, amorphous phase, crystalline forms, milled forms and nano-particulate forms. In some embodiments, Compound 1, or a pharmaceutically acceptable salt thereof, is amorphous. In some embodiments, Compound 1, or a pharmaceutically acceptable salt thereof, is amorphous and anhydrous. In some embodiments, Compound 1, or a pharmaceutically acceptable salt thereof, is crystalline. In some embodiments, Compound 1, or a pharmaceutically acceptable salt thereof, is crystalline and anhydrous.

While not intending to be bound by any particular theory, certain solid forms are characterized by physical properties, e.g., stability, solubility and dissolution rate, appropriate for pharmaceutical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

Amorphous Compound 1

In some embodiments, Compound 1 is amorphous and anhydrous. In some embodiments, Compound 1 is amorphous. In some embodiments, amorphous Compound 1 has an X-ray powder diffraction (XRPD) pattern showing a lack of crystallinity.

Crystalline Forms of MAGL Inhibitors

The identification and selection of a solid form of a pharmaceutical compound are complex, given that a change in solid form may affect a variety of physical and chemical properties, which may provide benefits or drawbacks in processing, formulation, stability, bioavailability, storage, handling (e.g., shipping), among other important pharmaceutical characteristics. Useful pharmaceutical solids include crystalline solids and amorphous solids, depending on the product and its mode of administration. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability.

Whether crystalline or amorphous, solid forms of a pharmaceutical compound include single-component and multiple-component solids. Single-component solids consist essentially of the pharmaceutical compound or active ingredient in the absence of other compounds. Variety among single-component crystalline materials may potentially arise from the phenomenon of polymorphism, wherein multiple three-dimensional arrangements exist for a particular pharmaceutical compound.

Notably, it is not possible to predict a priori if crystalline forms of a compound even exist, let alone how to successfully prepare them (see, e.g., Braga and Grepioni, 2005, "Making crystals from crystals: a green route to crystal engineering and polymorphism," *Chem. Commun.*: 3635-3645 (with respect to crystal engineering, if instructions are not very precise and/or if other external factors affect the process, the result can be unpredictable); Jones et al., 2006, Pharmaceutical Cocrystals: An Emerging Approach to Physical Property Enhancement," *MRS Bulletin* 31:875-879 (At present it is not generally possible to computationally predict the number of observable polymorphs of even the simplest molecules); Price, 2004, "The computational prediction of pharmaceutical crystal structures and polymorphism," *Advanced Drug Delivery Reviews* 56:301-319 ("Price"); and Bernstein, 2004, "Crystal Structure Prediction and Polymorphism," *ACA Transactions* 39:14-23 (a great deal still needs to be learned and done before one can state with any degree of confidence the ability to predict a crystal structure, much less polymorphic forms)).

The variety of possible solid forms creates potential diversity in physical and chemical properties for a given pharmaceutical compound. The discovery and selection of solid forms are of great importance in the development of an effective, stable and marketable pharmaceutical product.

Crystalline Compound 1

Figure 2:
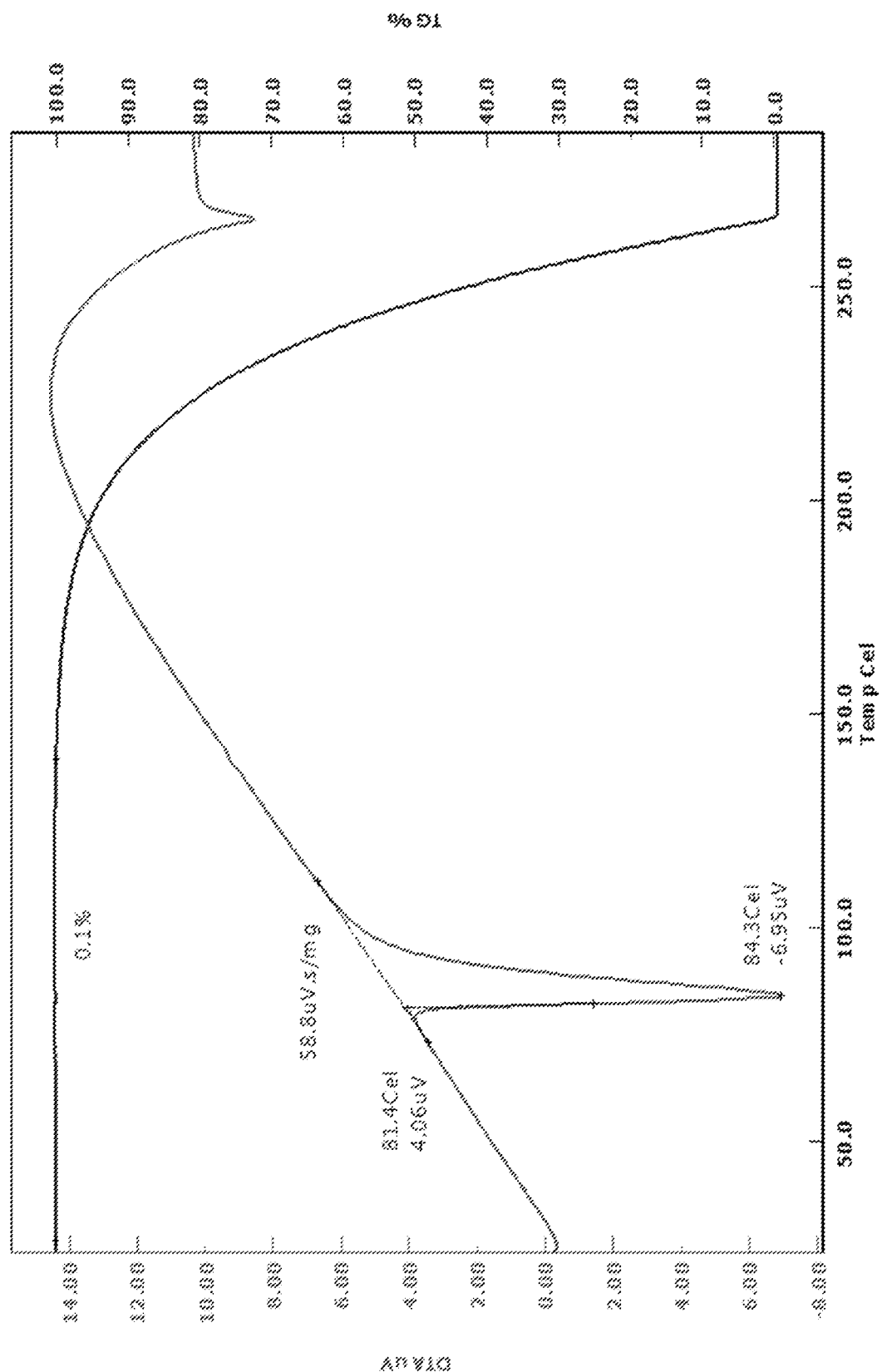
FIG. 2. Illustrates a thermo-gravimetric analysis (TGA) thermogram of crystalline 1,1,1,3,3,3-hexafluoropropan-2-yl 4-(2-(pyrrolidin-1-yl)-4-(trifluoromethyl)benzyl)piperazine-1-carboxylate free base.
Figure 3:
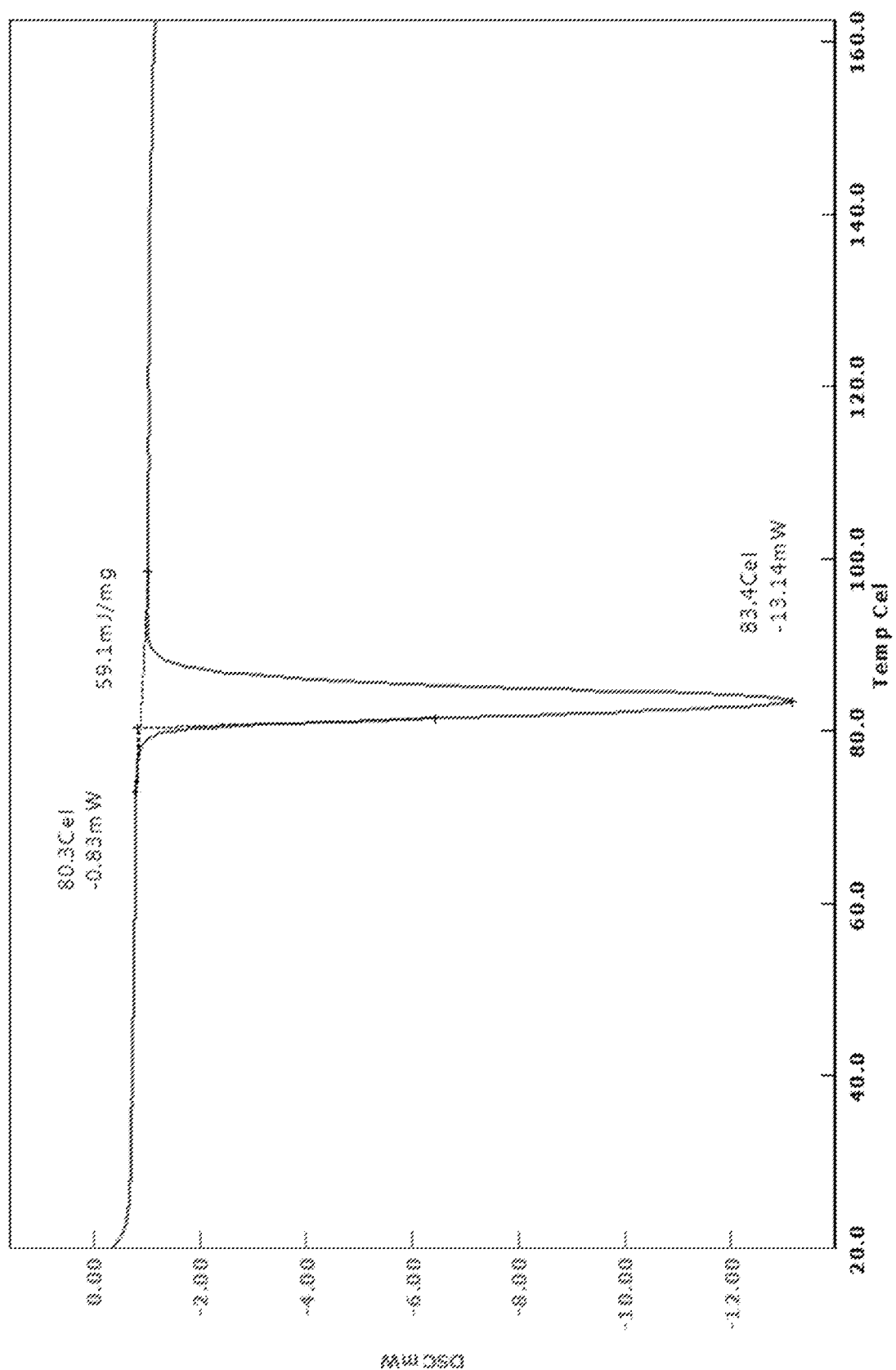
FIG. 3. Illustrates a differential scanning calorimetry (DSC) thermogram of crystalline 1,1,1,3,3,3-hexafluoropropan-2-yl 4-(2-(pyrrolidin-1-yl)-4-(trifluoromethyl)benzyl)piperazine-1-carboxylate free base.

In some embodiments, Compound 1 is crystalline. In some embodiments, crystalline Compound 1 is characterized as having at least one of the following properties:
(a) an X-ray powder diffraction (XRPD) pattern substantially the same as shown in FIG. 1;
(b) an X-ray powder diffraction (XRPD) pattern with characteristic peaks at 7.8° 2-Theta, 12.0° 2-Theta, 18.5° 2-Theta, 19.0° 2-Theta, 19.6° 2-Theta and 21.2° 2-Theta;
(c) a thermo-gravimetric analysis (TGA) substantially similar to the one set forth in FIG. 2;
(d) a DSC thermogram substantially similar to the one set forth in FIG. 3;
(e) a DSC thermogram with an endotherm having an onset at about 80° C.;
(f) infrared (IR) spectrum substantially similar to the one set forth in FIG. 6;
(g) infrared (IR) spectrum weak peaks at about 1735 $cm^{-1}$, 1427 $cm^{-1}$, 1102 $cm^{-1}$, 982 $cm^{-1}$, and 888 $cm^{-1}$;
(h) non-hygroscopicity; or
(i) combinations thereof.

In some embodiments, crystalline Compound 1 is characterized as having at least two of the properties selected from (a) to (h). In some embodiments, crystalline Compound 1 is characterized as having at least three of the properties selected from (a) to (h). In some embodiments, crystalline Compound 1 is characterized as having at least four of the properties selected from (a) to (h). In some embodiments, crystalline Compound 1 is characterized as having at least five of the properties selected from (a) to (h). In some embodiments, crystalline Compound 1 is characterized as having at least six of the properties selected from (a) to (h). In some embodiments, crystalline Compound 1 is characterized as having at least seven of the properties selected from (a) to (h). In some embodiments, crystalline Compound 1 is characterized as having properties (a) to (h).

In some embodiments, crystalline Compound 1 has an X-ray powder diffraction (XRPD) pattern substantially the same as shown in FIG. 1. In some embodiments, crystalline Compound 1 has an X-ray powder diffraction (XRPD) pattern with characteristic peaks at 7.8° 2-Theta, 12.0° 2-Theta, 18.5° 2-Theta, 19.0° 2-Theta, 19.6° 2-Theta and 21.2° 2-Theta. In some embodiments, crystalline Compound 1 has a thermo-gravimetric analysis (TGA) thermogram substantially similar to the one set forth in FIG. 2. In some embodiments, crystalline Compound 1 has a DSC thermogram substantially similar to the one set forth in FIG. 3. In some embodiments, crystalline Compound 1 has a DSC thermogram with an endotherm having an onset at about 80° C. In some embodiments, crystalline Compound 1 has a DSC thermogram with an endotherm having an onset at about 80° C. and a peak at about 83° C. In some embodiments, crystalline Compound 1 has an infrared (IR) spectrum substantially similar to the one set forth in FIG. 6. In some embodiments, crystalline Compound 1 has an infrared (IR) spectrum weak peaks at about 1735 $cm^{-1}$, 1427 $cm^{-1}$, 1102 $cm^{-1}$, 982 $cm^{-1}$, and 888 $cm^{-1}$. In some embodiments, the crystalline Compound 1 is non-hygroscopic. In some embodiments, crystalline Compound 1 is obtained from acetone, acetone/water, acetonitrile, anisole, dichloromethane, diisopropyl ether, dimethylacetamide, dimethylformamide, dimethylsulfoxide, 1,4-dioxane, ethanol, ethyl acetate, isopropyl acetate, methanol, methanol/water, methyethyl ketone, methyl isobutyl ketone, N-methyl-2-pyrrolidone, 2-propanol, 2-propanol/water, tert-butyl methyl ketone, tetrahydrofuran, toluene, water, 1-butanol, 2-ethoxyethanol, 2-methyl tetrahydrofuran, benzonitrile, chlorobenzene, heptane, hexane, or tert-amyl alcohol. In some embodiments, the crystalline free base is solvated. In some embodiments, crystalline Compound 1 is unsolvated. In some embodiments, crystalline Compound 1 is anhydrous.

Compound 2, Mono-HCl Salt

Compound 2 is 1,1,1,3,3,3-hexafluoropropan-2-yl 4-(2-(pyrrolidin-1-yl)-4-(trifluoromethyl)benzyl)piperazine-1-carboxylate mono-HCl salt. In some embodiments, 1,1,1,3,3,3-hexafluoropropan-2-yl 4-(2-(pyrrolidin-1-yl)-4-(trifluoromethyl)benzyl)piperazine-1-carboxylate mono-HCl salt is crystalline Form 1. In some embodiments, 1,1,1,3,3,3-hexafluoropropan-2-yl 4-(2-(pyrrolidin-1-yl)-4-(trifluoromethyl)benzyl)piperazine-1-carboxylate mono-HCl salt is crystalline Form 2.

Compound 2, Form 1

Figure 9:
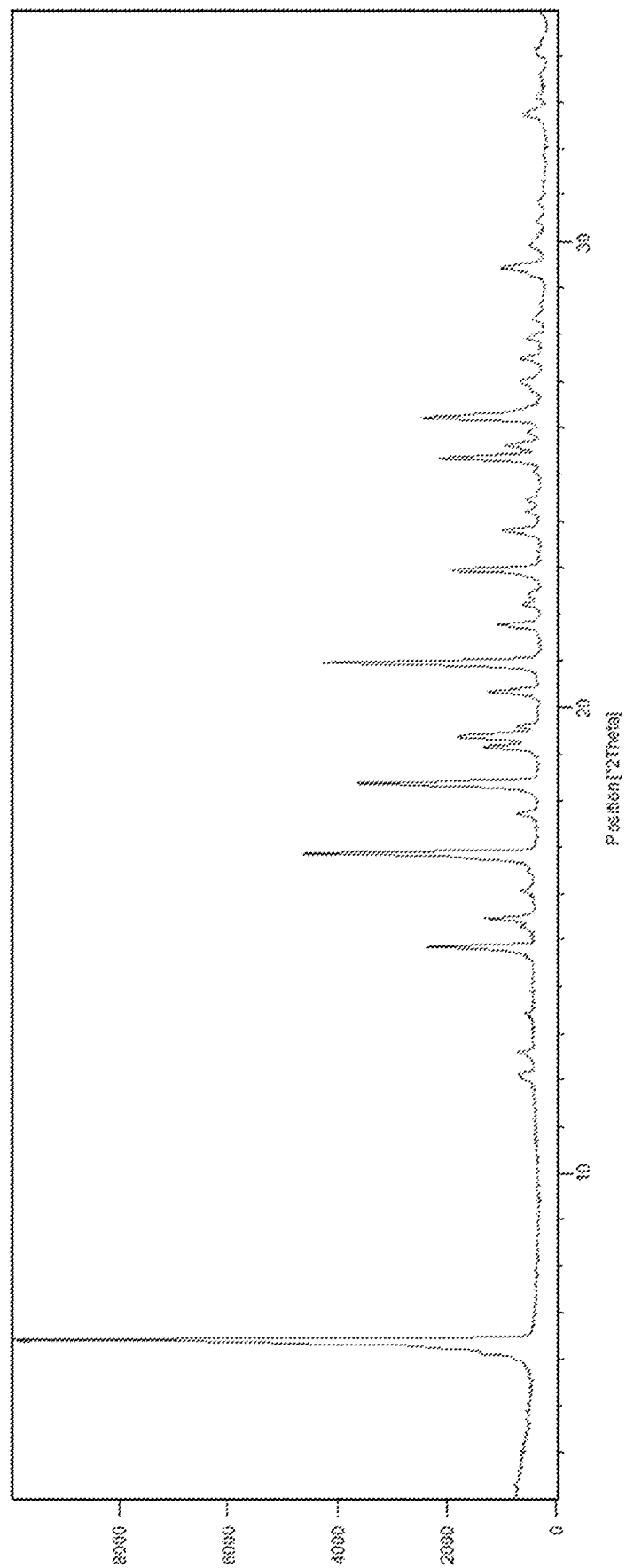
FIG. 9. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 1.
Figure 10:
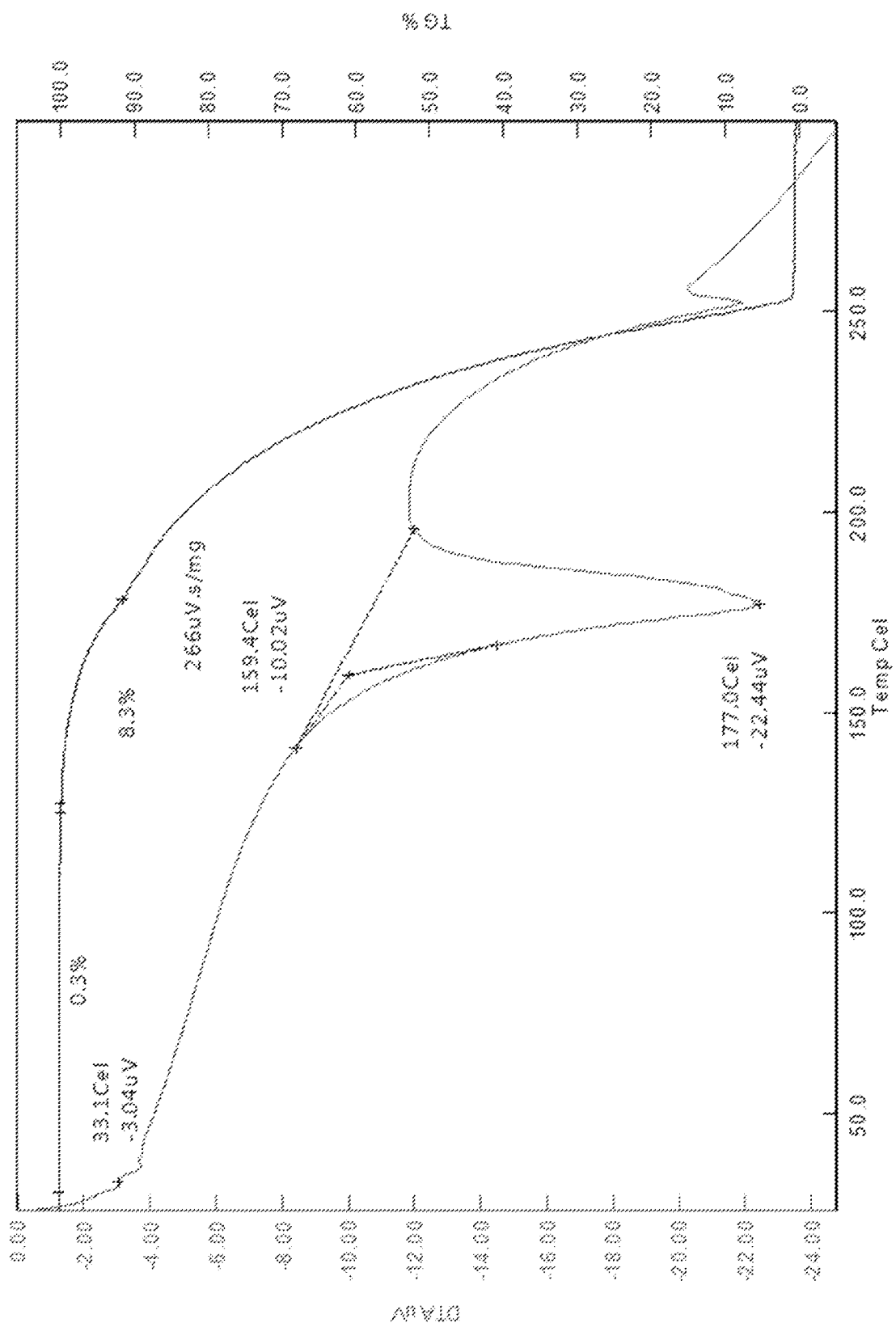
FIG. 10. Illustrates TGA thermogram of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 1.
Figure 11:
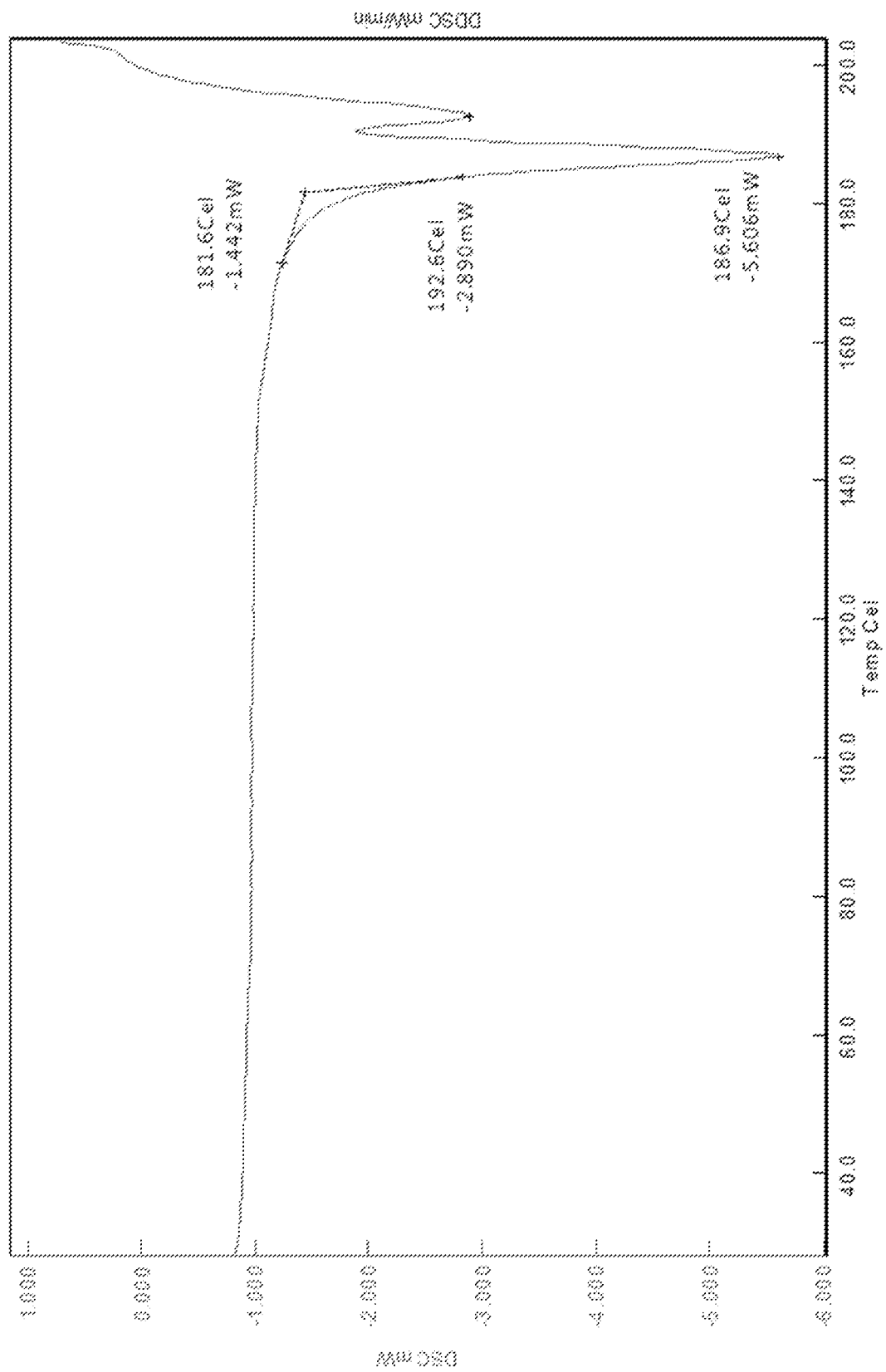
FIG. 11. Illustrates a DSC thermogram of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 1.

In some embodiments, Compound 2 is crystalline. In some embodiments, Compound 2 is crystalline Form 1. Crystalline Form 1 of Compound 2 is characterized as having at least one of the following properties:
(a) an X-ray powder diffraction (XRPD) pattern substantially the same as shown in FIG. 9;
(b) an X-ray powder diffraction (XRPD) pattern with characteristic peaks at 6.4° 2-Theta, 14.9° 2-Theta, 16.9° 2-Theta, 18.4° 2-Theta, and 20.9° 2-Theta;
(c) a thermo-gravimetric analysis (TGA) thermogram substantially similar to the one set forth in FIG. 10;
(d) a DSC thermogram substantially similar to the one set forth in FIG. 11;
(e) a DSC thermogram with an endotherm having an onset at about 182° C.;
(f) non-hygroscopicity; or
(g) combinations thereof.

In some embodiments, Compound 2, Form 1, is characterized as having at least two of the properties selected from (a) to (f). In some embodiments, Compound 2, Form 1, is characterized as having at least three of the properties selected from (a) to (f). In some embodiments, Compound 2, Form 1, is characterized as having at least four of the properties selected from (a) to (f). In some embodiments, Compound 2, Form 1, is characterized as having at least five of the properties selected from (a) to (f). In some embodiments, Compound 2, Form 1, is characterized as having properties (a) to (f).

In some embodiments, Compound 2, Form 1, has an X-ray powder diffraction (XRPD) pattern substantially the same as shown in FIG. 9. In some embodiments, Compound 2, Form 1, has an X-ray powder diffraction (XRPD) pattern with characteristic peaks at 6.4° 2-Theta, 14.9° 2-Theta, 16.9° 2-Theta, 18.4° 2-Theta, and 20.9° 2-Theta. In some embodiments, Compound 2, Form 1, has a thermo-gravimetric analysis (TGA) thermogram substantially similar to the one set forth in FIG. 10. In some embodiments, Compound 2, Form 1, has a DSC thermogram substantially similar to the one set forth in FIG. 11. In some embodiments, Compound 2, Form 1, has a DSC thermogram with an endotherm having an onset at about 182° C. In some embodiments, Compound 2, Form 1, has a DSC thermogram with an endotherm having an onset at about 182° C. and a peak at about 187° C. In some embodiments, Compound 2, Form 1, is non-hygroscopic. In some embodiments, Compound 2, Form 1, is obtained from acetonitrile, 1,4-dioxane, ethyl acetate, methanol, tert-butylmethyl ether, or 2-propanol. In some embodiments, Compound 2, Form 1, is solvated. In some embodiments, Compound 2, Form 1, is unsolvated. In some embodiments, Compound 2, Form 1, is anhydrous.

Compound 2, Form 2

Figure 27:
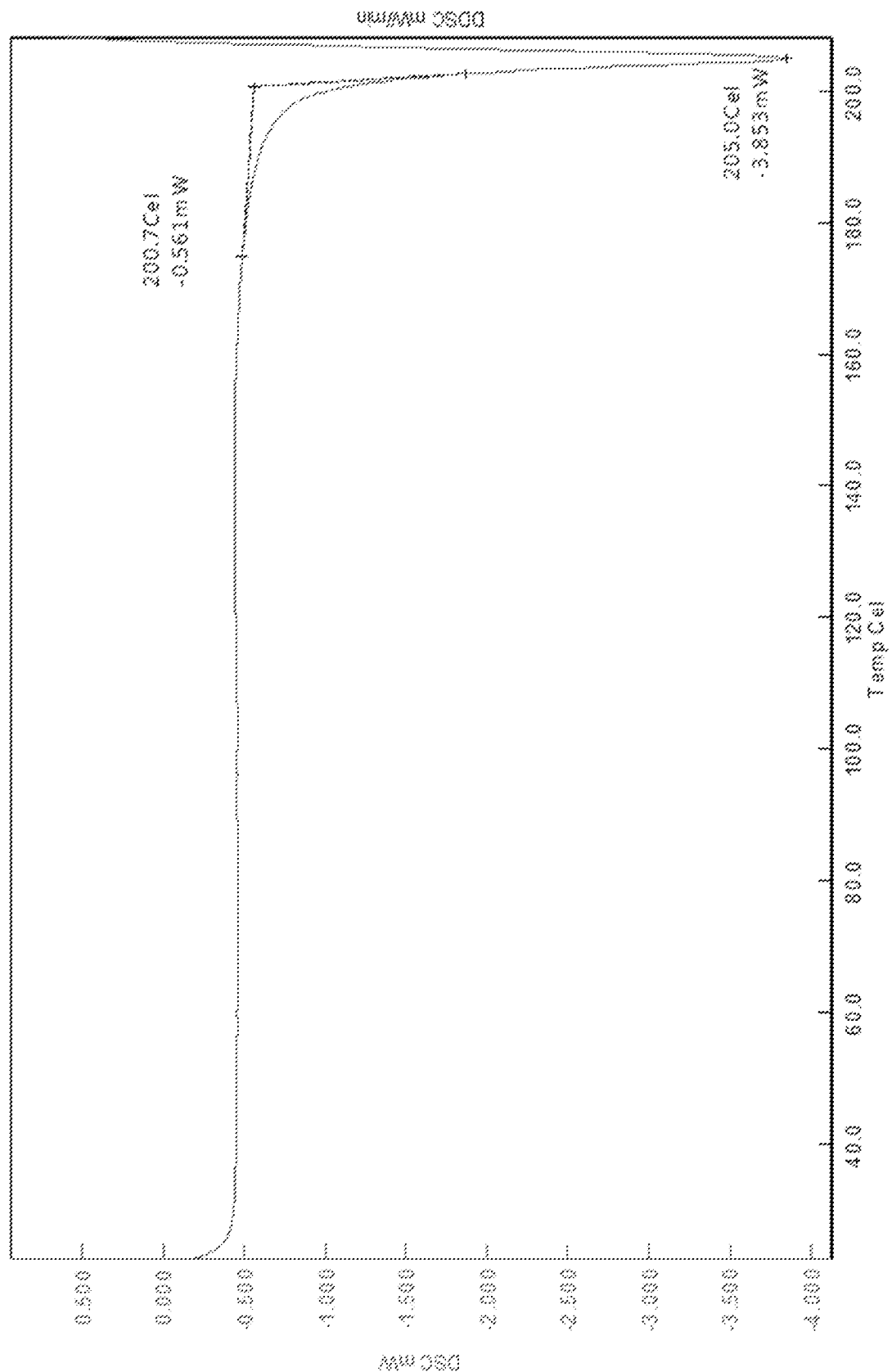
FIG. 27. Illustrates a DSC thermogram of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 2.
Figure 28:
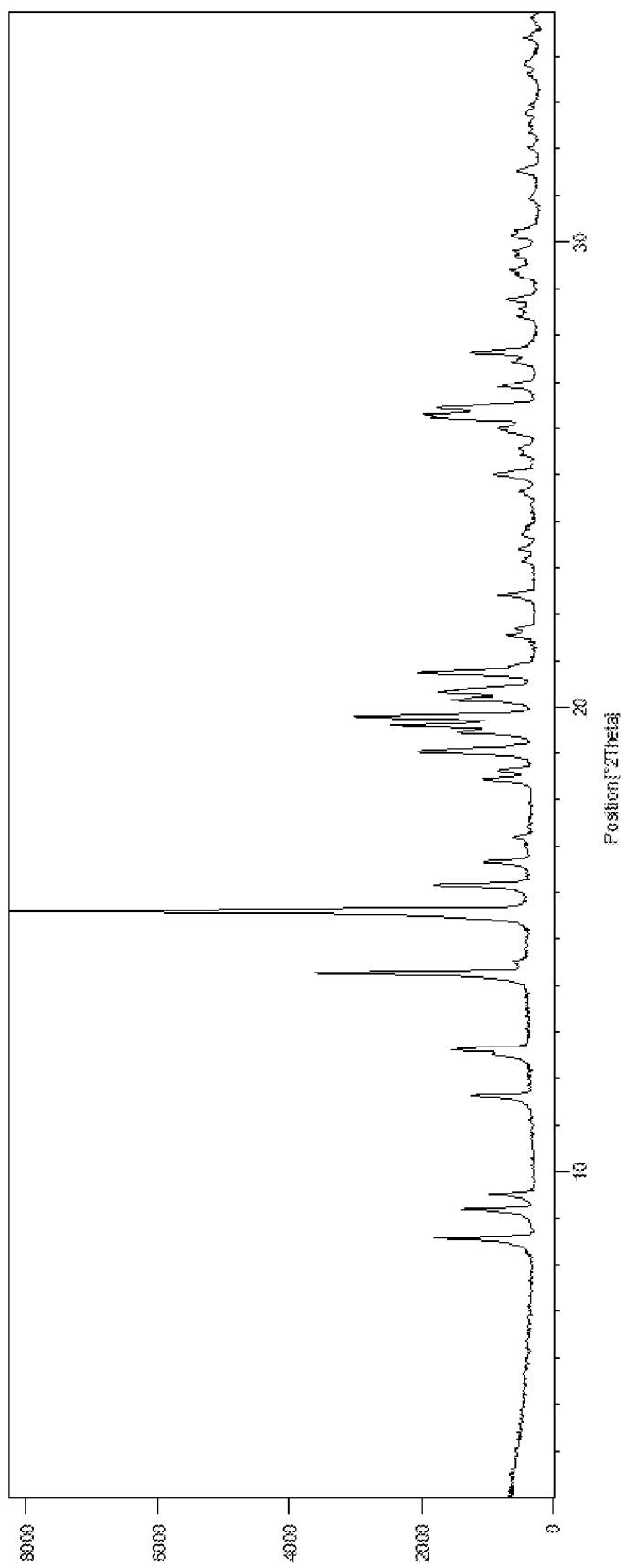
FIG. 28. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 2.
Figure 29:
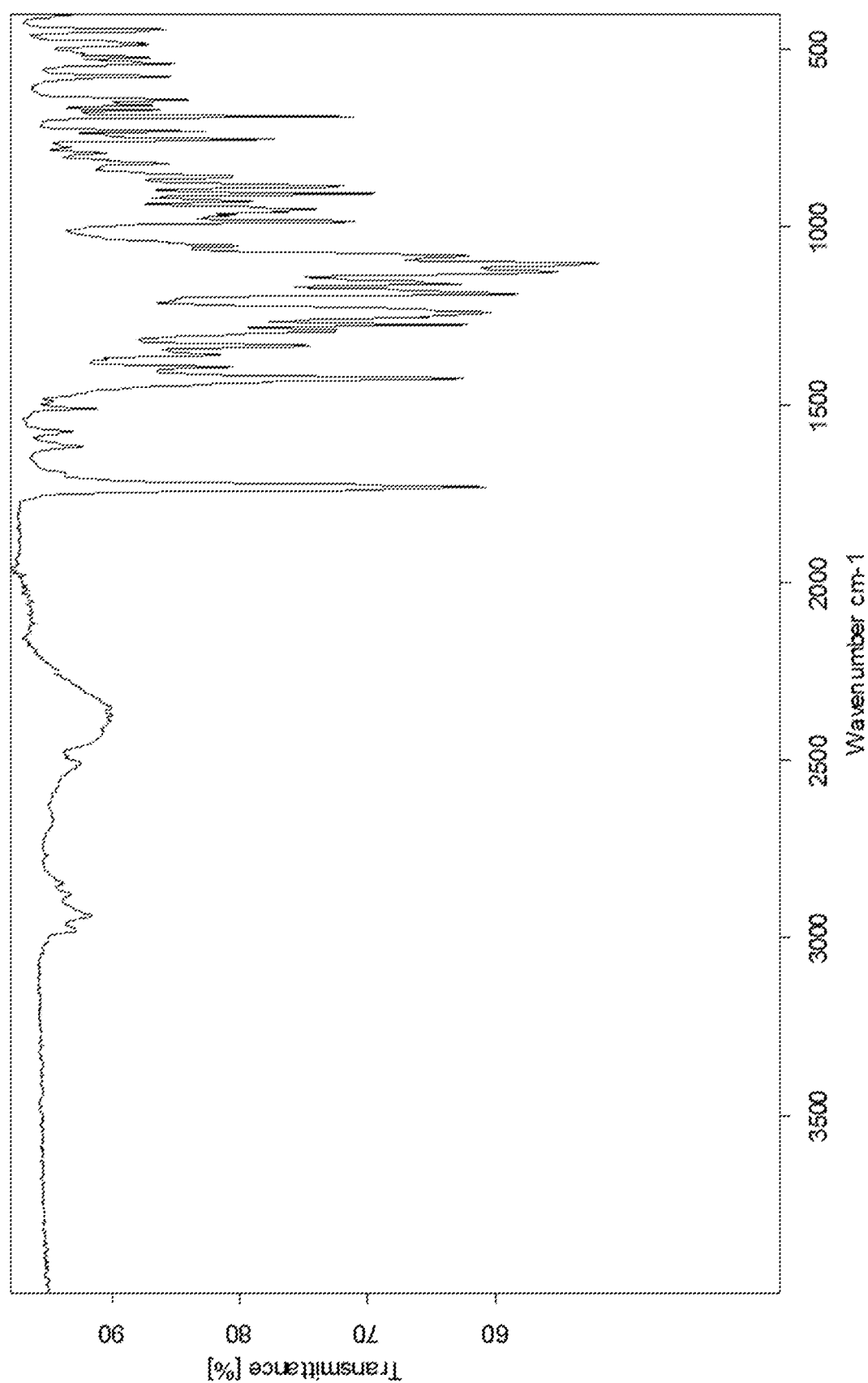
FIG. 29. Illustrates an infrared (IR) spectrum of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 2.

In some embodiments, Compound 2 is crystalline. In some embodiments, Compound 2 is crystalline Form 2. Crystalline Form 2 of Compound 2 is characterized as having at least one of the following properties:
  (a) an X-ray powder diffraction (XRPD) pattern substantially the same as shown in FIG. 28;
  (b) an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta;
  (c) a thermo-gravimetric analysis (TGA) thermogram substantially similar to the one set forth in FIG. 26;
  (d) a DSC thermogram substantially similar to the one set forth in FIG. 27;
  (e) a DSC thermogram with an endotherm having an onset at about 201° C.;
  (f) an infrared (IR) spectrum substantially similar to the one set forth in FIG. 29; (g) infrared (IR) spectrum with peaks at about 1729 cm$^{-1}$, 1426 cm$^{-1}$, 1102 cm$^{-1}$, 984 cm$^{-1}$, and 907 cm$^{-1}$;
  (h) non-hygroscopicity; or
  (i) combinations thereof.

In some embodiments, Compound 2, Form 2, is characterized as having at least two of the properties selected from (a) to (h). In some embodiments, Compound 2, Form 2, is characterized as having at least three of the properties selected from (a) to (h). In some embodiments, Compound 2, Form 2, is characterized as having at least four of the properties selected from (a) to (h). In some embodiments, Compound 2, Form 2, is characterized as having at least five of the properties selected from (a) to (h). In some embodiments, Compound 2, Form 2, is characterized as having at least six of the properties selected from (a) to (h). In some embodiments, Compound 2, Form 2, is characterized as having at least seven of the properties selected from (a) to (h). In some embodiments, Compound 2, Form 2, is characterized as having properties (a) to (h).

In some embodiments, Compound 2, Form 2, has an X-ray powder diffraction (XRPD) pattern substantially the same as shown in FIG. 28. In some embodiments, Compound 2, Form 2, has an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7°. In some embodiments, Compound 2, Form 2, has a thermo-gravimetric analysis (TGA) thermogram substantially similar to the one set forth in FIG. 26. In some embodiments, Compound 2, Form 2, has a DSC thermogram substantially similar to the one set forth in FIG. 27. In some embodiments, Compound 2, Form 2, has a DSC thermogram with an endotherm having an onset at about 201° C. In some embodiments, Compound 2, Form 2, has a DSC thermogram with an endotherm having an onset at about 201° C. and a peak at about 205° C. In some embodiments, Compound 2, Form 2, has an infrared (IR) spectrum substantially similar to the one set forth in FIG. 29. In some embodiments, Compound 2, Form 2, has an infrared (IR) spectrum with peaks at about 1729 cm$^{-1}$, 1426 cm$^{-1}$, 1102 cm$^{-1}$, 984 cm$^{-1}$, and 907 cm$^{-1}$. In some embodiments, Compound 2, Form 2, is obtained from acetone, acetonitrile, anisole, dichloromethane, diisopropyl ether, ethanol, ethyl acetate, isopropyl acetate, methanol, methylethyl ketone, methyl isobutyl ketone, tert-butylmethyl ether, 2-propanol, tetrahydrofuran, toluene, 2-ethoxyethanol, 2-methyl tetrahydrofuran, or tert-amyl alcohol. In some embodiments, Compound 2, Form 2, is solvated. In some embodiments, Compound 2, Form 2, is unsolvated. In some embodiments, Compound 2, Form 2, is anhydrous.

Compound 3, Bis-HCl Salt

Figure 17:
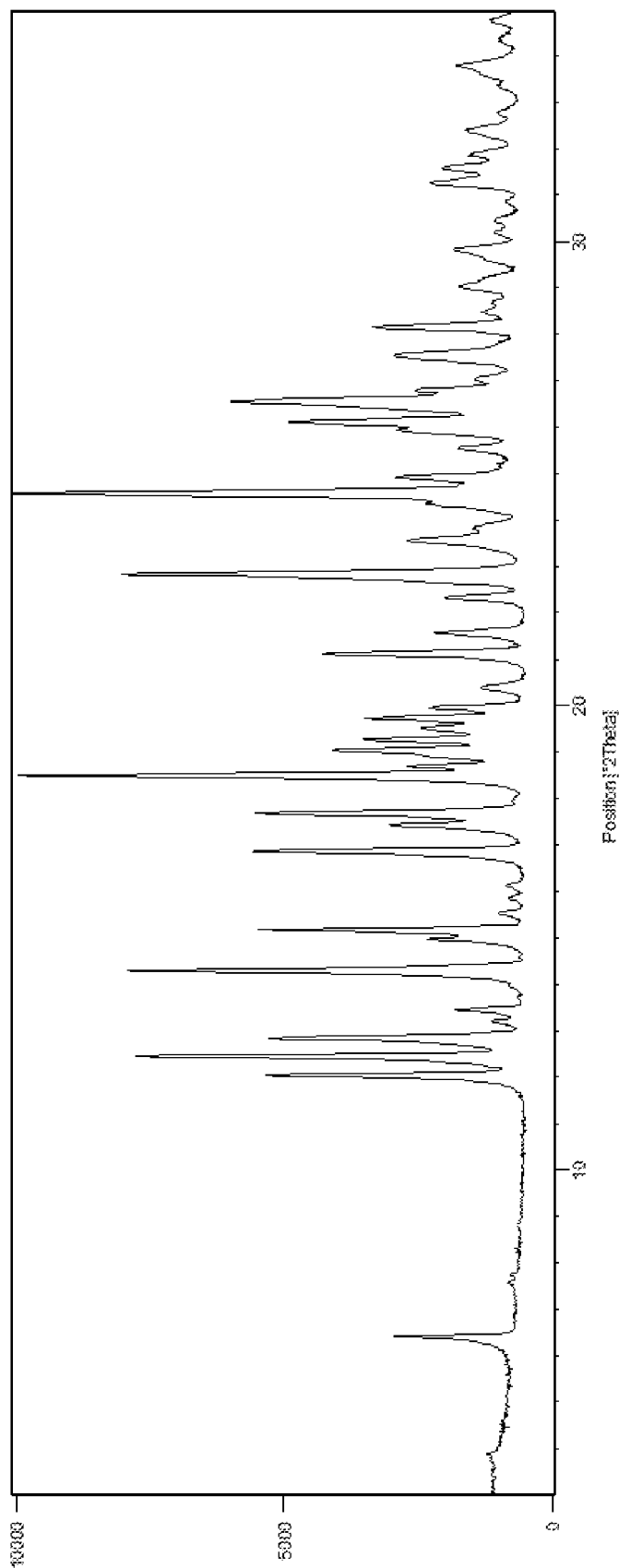
FIG. 17. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate bis-HCl salt.
Figure 18:
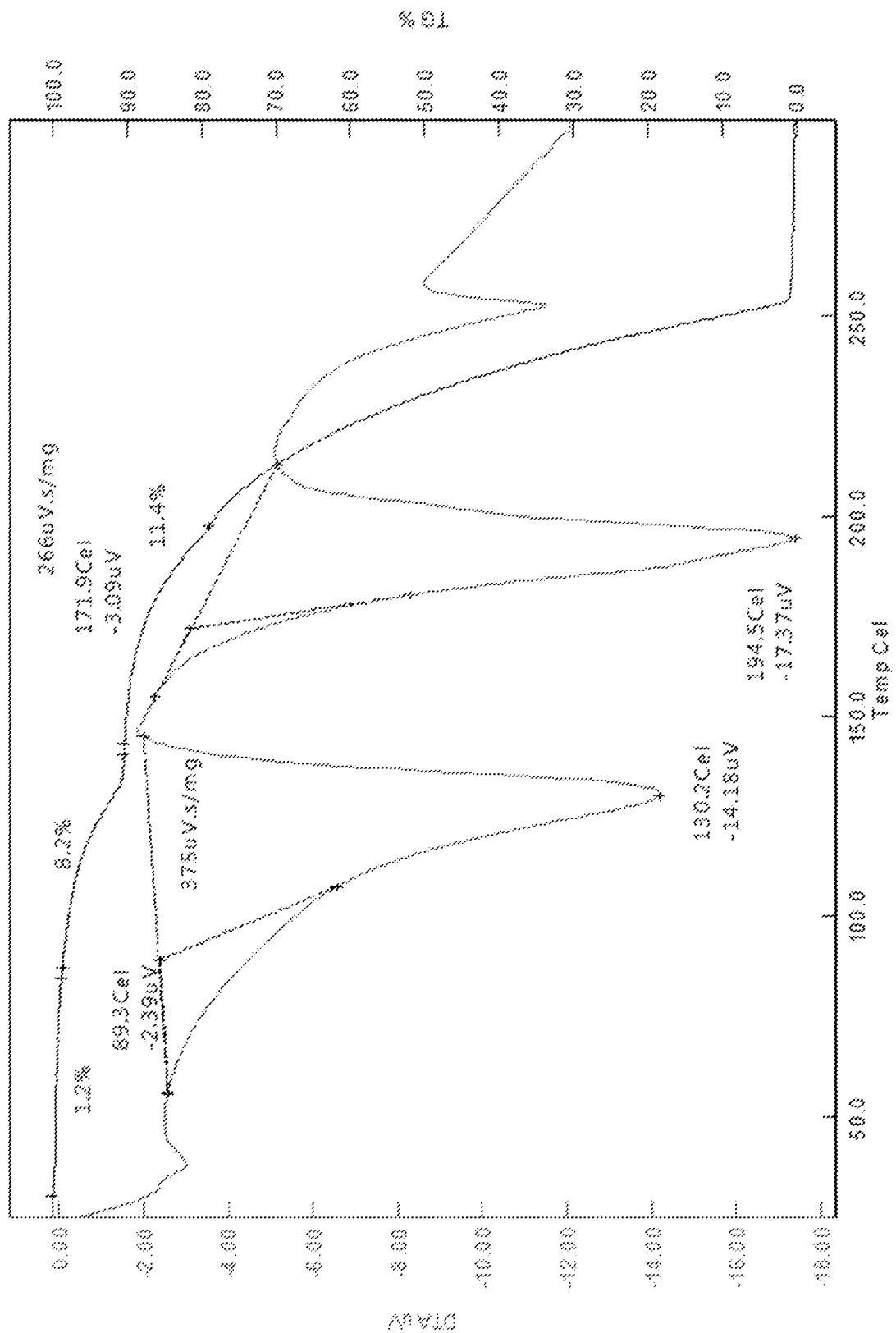
FIG. 18. Illustrates a TGA thermogram of crystalline 1,1,1,3,3,3-hexafluoropropan-2-yl 4-(2-(pyrrolidin-1-yl)-4-(trifluoromethyl)benzyl)piperazine-1-carboxylate bis-HCl salt.
Figure 19:
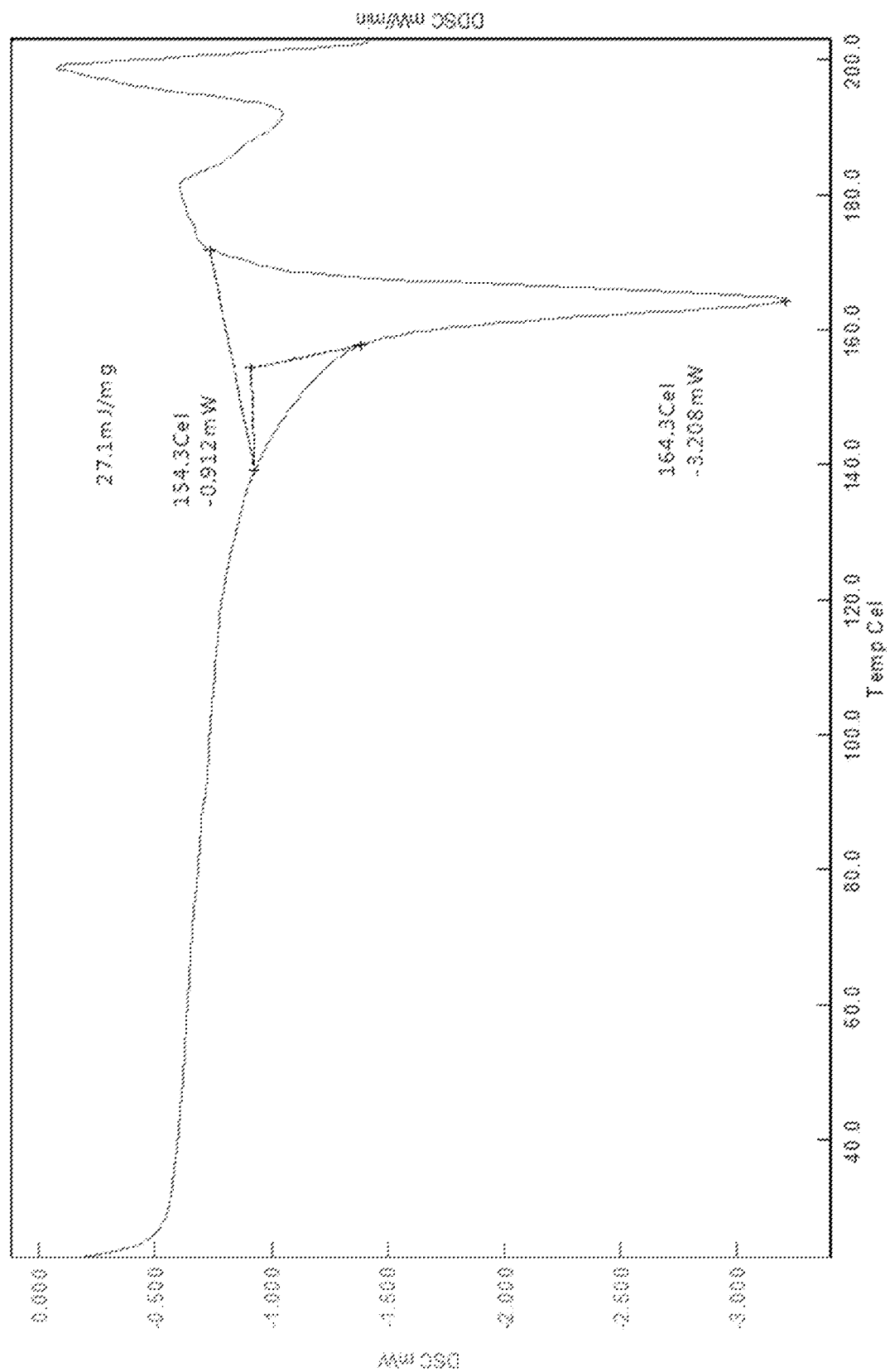
FIG. 19. Illustrates a DSC thermogram of crystalline 1,1,1,3,3,3-hexafluoropropan-2-yl 4-(2-(pyrrolidin-1-yl)-4-(trifluoromethyl)benzyl)piperazine-1-carboxylate bis-HCl salt.

Compound 3 is 1,1,1,3,3,3-hexafluoropropan-2-yl 4-(2-(pyrrolidin-1-yl)-4-(trifluoromethyl)benzyl)piperazine-1-carboxylate bis-HCl salt. In some embodiments, Compound 3 is crystalline. In some embodiments, Compound 3 is crystalline having at least one of the following properties:
  (a) an X-ray powder diffraction (XRPD) pattern substantially the same as shown in FIG. 17;
  (b) an X-ray powder diffraction (XRPD) pattern with characteristic peaks at 6.4° 2-Theta, 12.0° 2-Theta, 12.5° 2-Theta, 14.3° 2-Theta, 18.5° 2-Theta, and 22.8° 2-Theta;
  (c) a thermo-gravimetric analysis (TGA) thermogram substantially similar to the one set forth in FIG. 18;
  (d) a DSC thermogram substantially similar to the one set forth in FIG. 19;
  (e) a DSC thermogram with an endotherm having an onset at about 154° C.; or
  (f) combinations thereof.

In some embodiments, Compound 3 is characterized as having at least two of the properties selected from (a) to (e). In some embodiments, Compound 3 is characterized as having at least three of the properties selected from (a) to (e). In some embodiments, Compound 3 is characterized as having at least four of the properties selected from (a) to (e). In some embodiments, Compound 3 is characterized as having properties (a) to (e).

In some embodiments, the Compound 3 has an X-ray powder diffraction (XRPD) pattern substantially the same as shown in FIG. 17. In some embodiments, Compound 3 has an X-ray powder diffraction (XRPD) pattern with characteristic peaks at 6.4° 2-Theta, 12.0° 2-Theta, 12.5° 2-Theta, 14.3° 2-Theta, 18.5° 2-Theta, and 22.8° 2-Theta. In some embodiments, Compound 3 has a thermo-gravimetric analysis (TGA) thermogram substantially similar to the one set forth in FIG. 18. In some embodiments, the crystalline bis-hydrochloride salt has a DSC thermogram substantially similar to the one set forth in FIG. 19. In some embodiments, Compound 3 has a DSC thermogram with an endotherm having an onset at about 154° C. In some embodiments, Compound 3 has a DSC thermogram with an endotherm having an onset at about 154° C. and a peak at about 164° C. In some embodiments, Compound 3 is obtained from tert-butylmethyl ether and 5 equivalents of HCl. In some embodiments, the crystalline bis-hydrochloride salt is solvated. In some embodiments, Compound 3 is unsolvated. In some embodiments, Compound 3 is anhydrous.

Compound 4, Besylate Salt

Compound 4 is 1,1,1,3,3,3-hexafluoropropan-2-yl 4-(2-(pyrrolidin-1-yl)-4-(trifluoromethyl)benzyl)piperazine-1-carboxylate besylate salt. In some embodiments, 1,1,1,3,3,3-hexafluoropropan-2-yl 4-(2-(pyrrolidin-1-yl)-4-(trifluoromethyl)benzyl)piperazine-1-carboxylate besylate salt is crystalline Form 1. In some embodiments, 1,1,1,3,3,3-hexafluoropropan-2-yl 4-(2-(pyrrolidin-1-yl)-4-(trifluoromethyl)benzyl)piperazine-1-carboxylate besylate salt is crystalline Form 2.

Compound 4, Form 1

Figure 30:
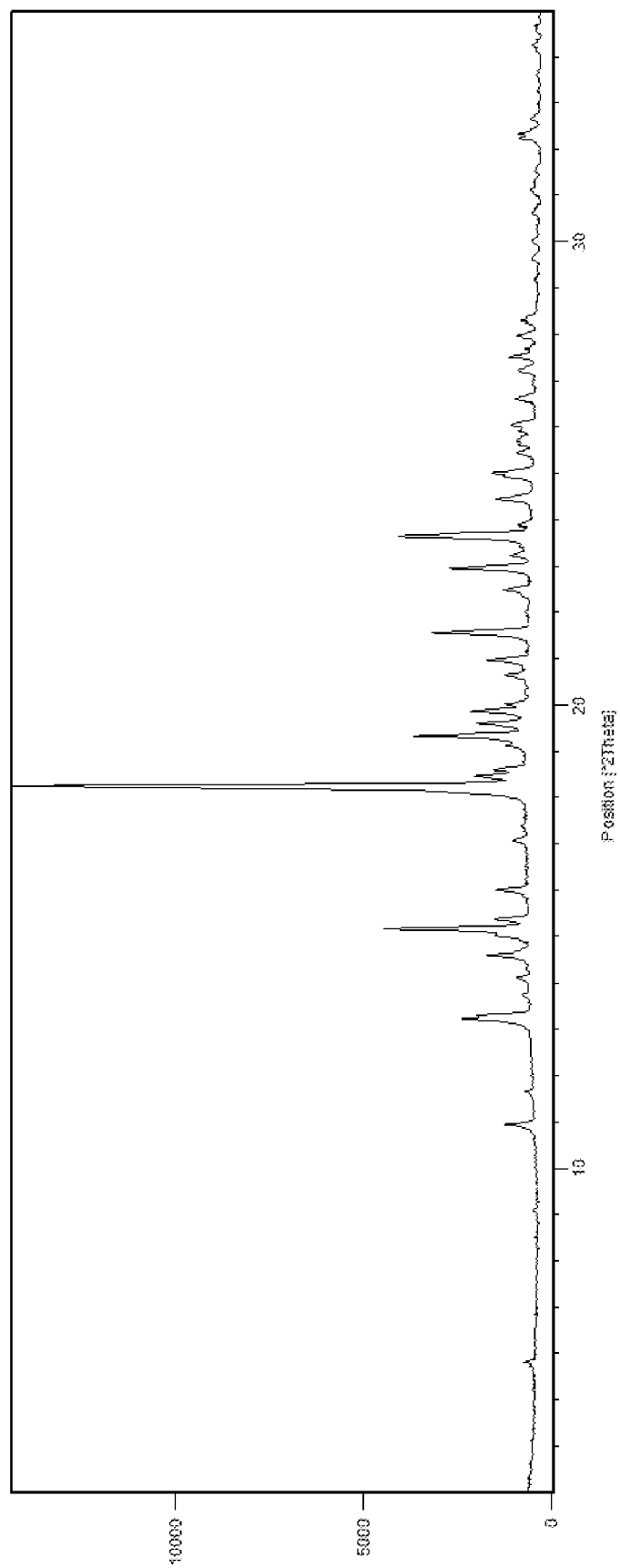
FIG. 30. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate besylate salt, Form 1.

In some embodiments, Compound 4 is crystalline. In some embodiments, Compound 4 is crystalline Form 1. In some embodiments, Compound 4, Form 1, has an X-ray powder diffraction (XRPD) pattern substantially the same as shown in FIG. 30. In some embodiments, Compound 4, Form 1, has an X-ray powder diffraction (XRPD) pattern with characteristic peaks at 13.2° 2-Theta, 15.2° 2-Theta, 18.2° 2-Theta, 19.3° 2-Theta, and 21.6° 2-Theta. In some embodiments, the Compound 4, Form 1, is obtained from acetone, acetonitrile, ethyl acetate, 2-propanol, and THF. In some embodiments, Compound 4, Form 1, is solvated. In some embodiments, Compound 4, Form 1, is unsolvated. In some embodiments, Compound 4, Form 1, is anhydrous.

Compound 4, Form 2

Figure 31:
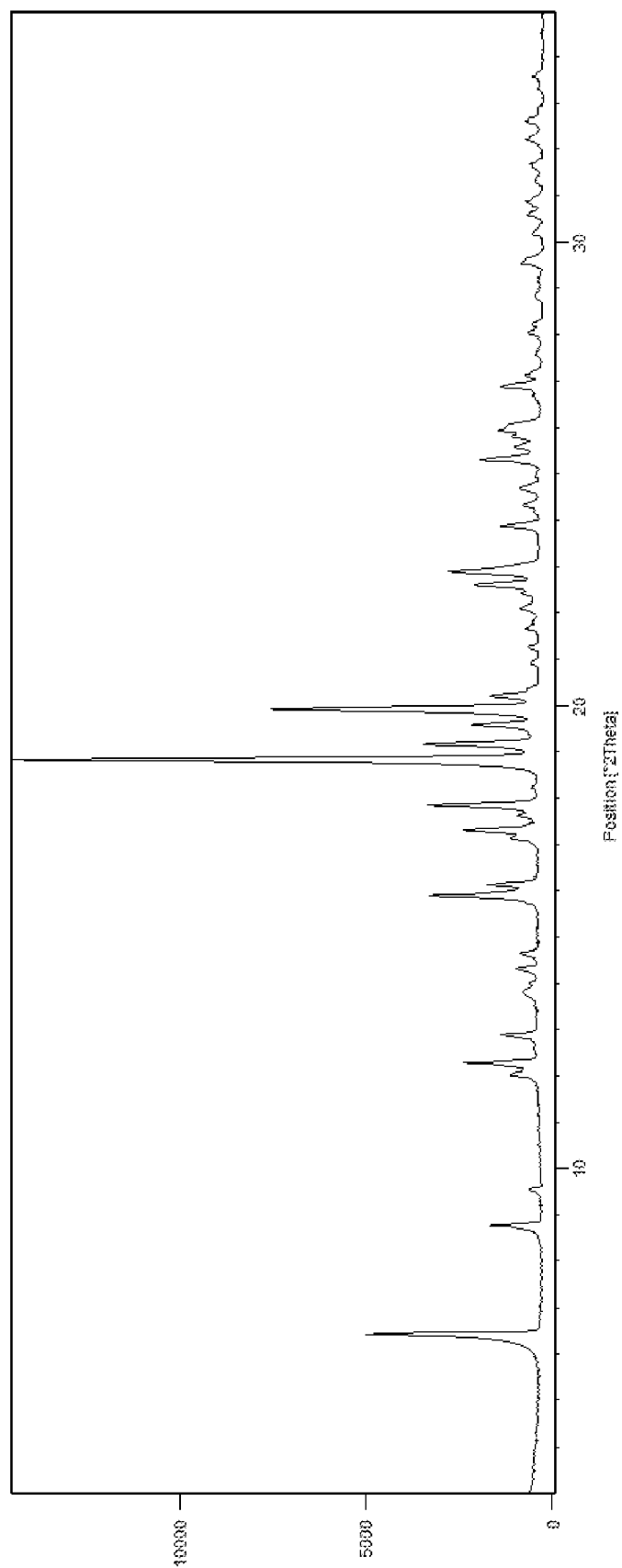
FIG. 31. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate besylate salt, Form 2.

In some embodiments, Compound 4 is crystalline. In some embodiments, Compound 4 is crystalline Form 2. Crystalline Form 2 of Compound 4 is characterized as having at least one of the following properties:
(a) an X-ray powder diffraction (XRPD) pattern substantially the same as shown in FIG. 31;
(b) an X-ray powder diffraction (XRPD) pattern with characteristic peaks at 6.4° 2-Theta, 15.9° 2-Theta, 17.8° 2-Theta, 18.8° 2-Theta, and 19.9° 2-Theta;
(c) a thermo-gravimetric analysis (TGA) thermogram substantially similar to the one set forth in FIG. 33; or
(d) combinations thereof.

In some embodiments, Compound 4, Form 2, is characterized as having at least two of the properties selected from (a) to (c). In some embodiments, Compound 4, Form 2, is characterized as having properties (a) to (c). 6.4° 2-Theta, 15.9° 2-Theta, 17.8° 2-Theta, 18.8° 2-Theta, and 19.9° 2-Theta.

In some embodiments, Compound 4, Form 2, has an X-ray powder diffraction (XRPD) pattern substantially the same as shown in FIG. 31. In some embodiments, Compound 4, Form 2, has an X-ray powder diffraction (XRPD) pattern with characteristic peaks at 6.4° 2-Theta, 15.9° 2-Theta, 17.8° 2-Theta, 18.8° 2-Theta, and 19.9° 2-Theta. In some embodiments, Compound 4, Form 2, is obtained from tert-butylmethyl ether. In some embodiments, the crystalline besylate salt, Form 2, is solvated. In some embodiments, Compound 4, Form 2, is unsolvated. In some embodiments, Compound 4, Form 2, is anhydrous.

Compound 5, Mesylate Salt

Figure 38:
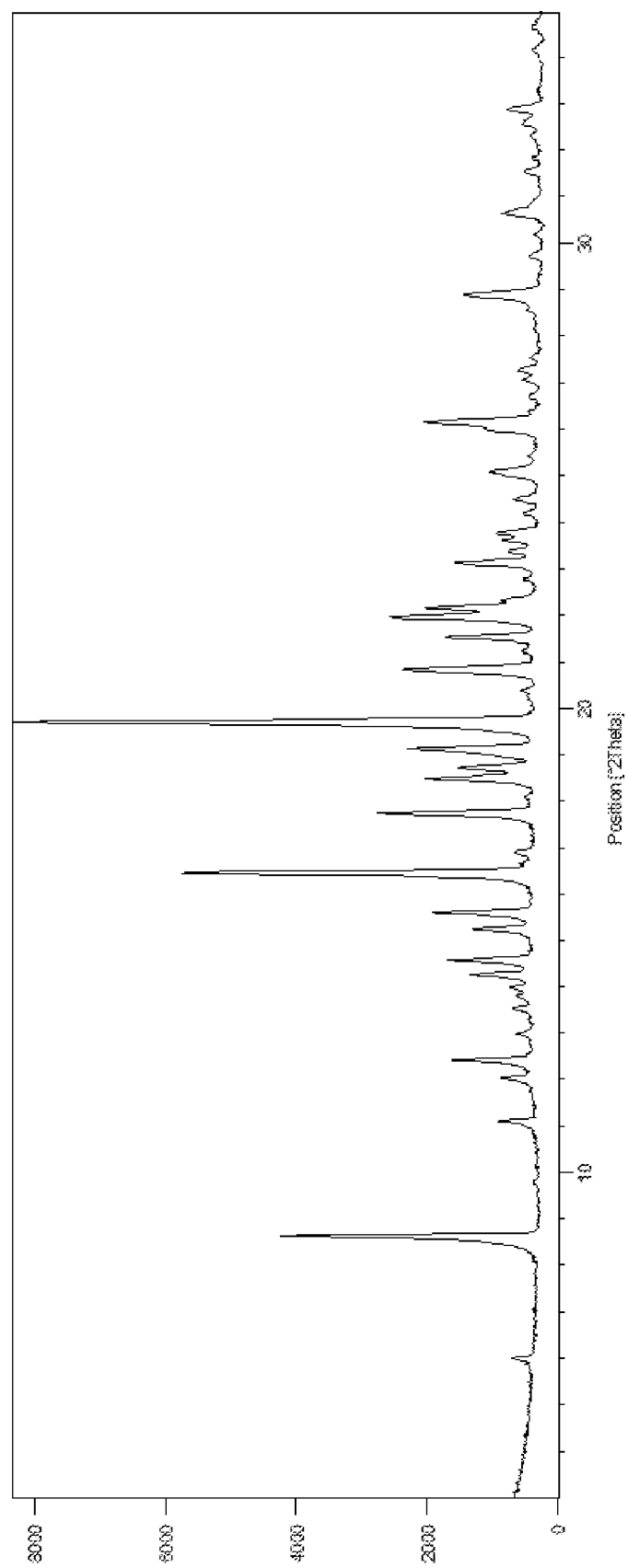
FIG. 38. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate mesylate salt.

Compound 5 is 1,1,1,3,3,3-hexafluoropropan-2-yl 4-(2-(pyrrolidin-1-yl)-4-(trifluoromethyl)benzyl)piperazine-1-carboxylate mesylate salt. In some embodiments, Compound 5 is crystalline. In some embodiments, Compound 5 is crystalline having at least one of the following properties:
(a) an X-ray powder diffraction (XRPD) pattern substantially the same as shown in FIG. 38;
(b) an X-ray powder diffraction (XRPD) pattern with characteristic peaks at 8.6° 2-Theta, 12.4° 2-Theta, 14.6° 2-Theta, 16.5° 2-Theta, 17.7° 2-Theta, and 19.7° 2-Theta;
(c) a thermo-gravimetric analysis (TGA) thermogram substantially similar to the one set forth in FIG. 40;
(d) a DSC thermogram substantially similar to the one set forth in FIG. 41;
(e) a DSC thermogram with an endotherm having an onset at about 179° C.; or
(f) combinations thereof.

In some embodiments, Compound 5 is characterized as having at least two of the properties selected from (a) to (e). In some embodiments, Compound 5 is characterized as having at least three of the properties selected from (a) to (e). In some embodiments, Compound 5 is characterized as having at least four of the properties selected from (a) to (e). In some embodiments, Compound 5 is characterized as having properties (a) to (e).

In some embodiments, Compound 5 has an X-ray powder diffraction (XRPD) pattern substantially the same as shown in FIG. 38. In some embodiments, Compound 5 has an X-ray powder diffraction (XRPD) pattern with characteristic peaks at 8.6° 2-Theta, 12.4° 2-Theta, 14.6° 2-Theta, 16.5° 2-Theta, 17.7° 2-Theta, and 19.7° 2-Theta. In some embodiments, Compound 5 has a thermo-gravimetric analysis (TGA) thermogram substantially similar to the one set forth in FIG. 40. In some embodiments, Compound 5 has a DSC thermogram substantially similar to the one set forth in FIG. 41. In some embodiments, Compound 5 has a DSC thermogram with an endotherm having an onset at about 179° C. In some embodiments, Compound 5 has a DSC thermogram with an endotherm having an onset at about 179° C. and a peak at about 182° C. In some embodiments, Compound 5 is obtained from tert-butylmethyl ether, ethyl acetate, tetrahydrofuran, water/acetone, water/acetonitrile, or water/2-propanol. In some embodiments, Compound 5 is solvated. In some embodiments, Compound 5 is unsolvated. In some embodiments, Compound 5 is anhydrous.

Compound 6, Fumarate Salt

Compound 6 is 1,1,1,3,3,3-hexafluoropropan-2-yl 4-(2-(pyrrolidin-1-yl)-4-(trifluoromethyl)benzyl)piperazine-1-carboxylate fumarate salt. In some embodiments, 1,1,1,3,3,3-hexafluoropropan-2-yl 4-(2-(pyrrolidin-1-yl)-4-(trifluoromethyl)benzyl)piperazine-1-carboxylate fumarate salt is crystalline Form 1. In some embodiments, 1,1,1,3,3,3-hexafluoropropan-2-yl 4-(2-(pyrrolidin-1-yl)-4-(trifluoromethyl)benzyl)piperazine-1-carboxylate fumarate salt is crystalline Form 2. In some embodiments, 1,1,1,3,3,3-hexafluoropropan-2-yl 4-(2-(pyrrolidin-1-yl)-4-(trifluoromethyl)benzyl)piperazine-1-carboxylate fumarate salt is crystalline Form 3.

Compound 6, Form 1

Figure 42:
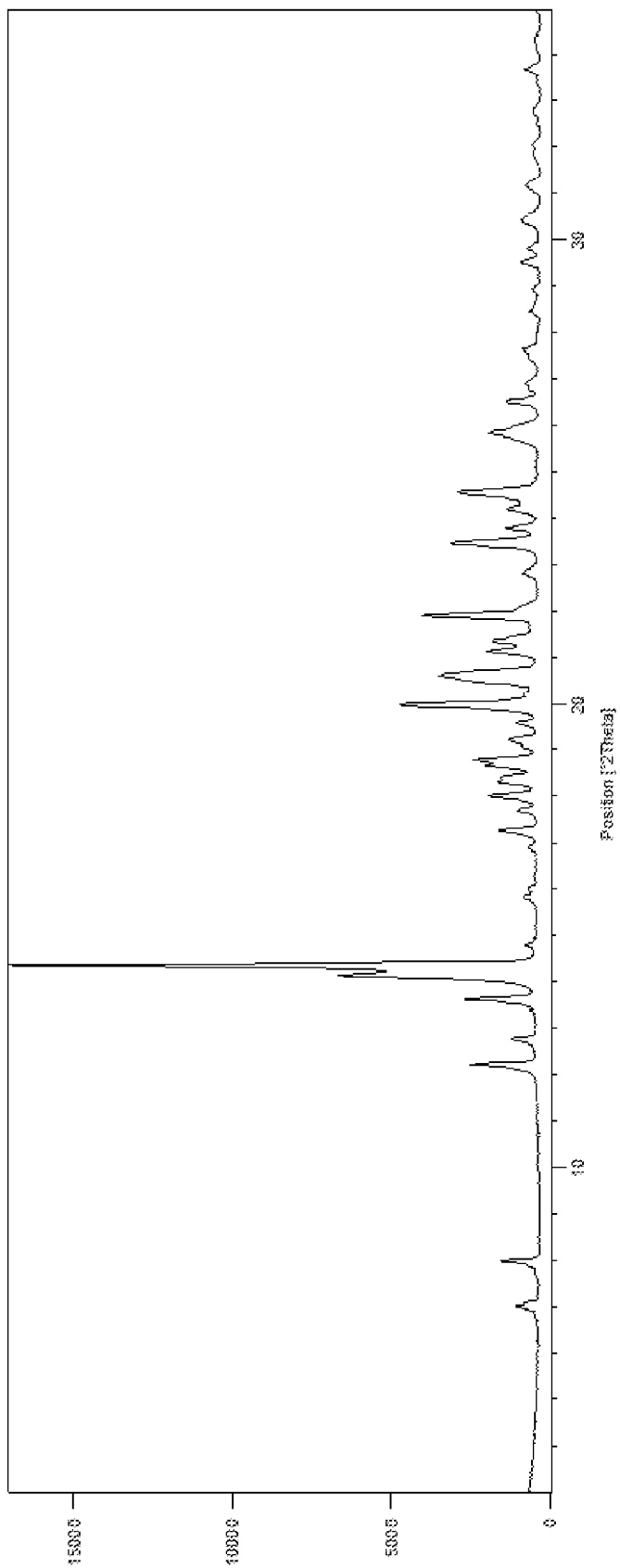
FIG. 42. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 1.

In some embodiments, Compound 6 is crystalline. In some embodiments, Compound 6 is crystalline Form 1. Crystalline Form 1 of Compound 6 is characterized as having at least one of the following properties:
(a) an X-ray powder diffraction (XRPD) pattern substantially the same as shown in FIG. 42;
(b) an X-ray powder diffraction (XRPD) pattern with characteristic peaks at 13.6° 2-Theta, 14.1° 2-Theta, 14.3° 2-Theta, 20.0° 2-Theta, and 21.9° 2-Theta;
(c) a thermo-gravimetric analysis (TGA) thermogram substantially similar to the one set forth in FIG. 44;
(d) a DSC thermogram substantially similar to the one set forth in FIG. 45;
(e) a DSC thermogram with an endotherm having an onset at about 126° C.;
(f) non-hygroscopicity; or
(g) combinations thereof.

In some embodiments, Compound 6, Form 1, is characterized as having at least two of the properties selected from (a) to (f). In some embodiments, Compound 6, Form 1, is characterized as having at least three of the properties selected from (a) to (f). In some embodiments, Compound 6, Form 1, is characterized as having at least four of the properties selected from (a) to (f). In some embodiments, Compound 6, Form 1, is characterized as having at least five of the properties selected from (a) to (f). In some embodiments, Compound 6, Form 1, is characterized as having properties (a) to (f).

In some embodiments, Compound 6, Form 1, has an X-ray powder diffraction (XRPD) pattern substantially the same as shown in FIG. 42. In some embodiments, Compound 6, Form 1, has an X-ray powder diffraction (XRPD) pattern with characteristic peaks at 13.6° 2-Theta, 14.1° 2-Theta, 14.3° 2-Theta, 20.0° 2-Theta, and 21.9° 2-Theta. In some embodiments, Compound 6, Form 1, has a thermo-gravimetric analysis (TGA) thermogram substantially similar to the one set forth in FIG. 44. In some embodiments, Compound 6, Form 1, has a DSC thermogram substantially similar to the one set forth in FIG. 45. In some embodiments, Compound 6, Form 1, has a DSC thermogram with an endotherm having an onset at about 126° C. In some embodiments, Compound 6, Form 1, has a DSC thermogram with an endotherm having an onset at about 126° C. and a peak at about 132° C. In some embodiments, Compound 6 is non-hygroscopic. In some embodiments Compound 6, Form 1, is obtained from 1-butanol, 1-propanol, 2-propanol, acetone/water mixtures, acetonitrile/water mixtures, ethanol, methyl acetate/water, methyl ethyl ketone/water, methanol/acetonitrile and 2-methoxyethanol/acetonitrile. In some embodiments, Compound 6, Form 1, is solvated. In some embodiments Compound 6, Form 1, is unsolvated. In some embodiments, Compound 6, Form 1, is anhydrous.

Compound 6, Form 2

Figure 46:
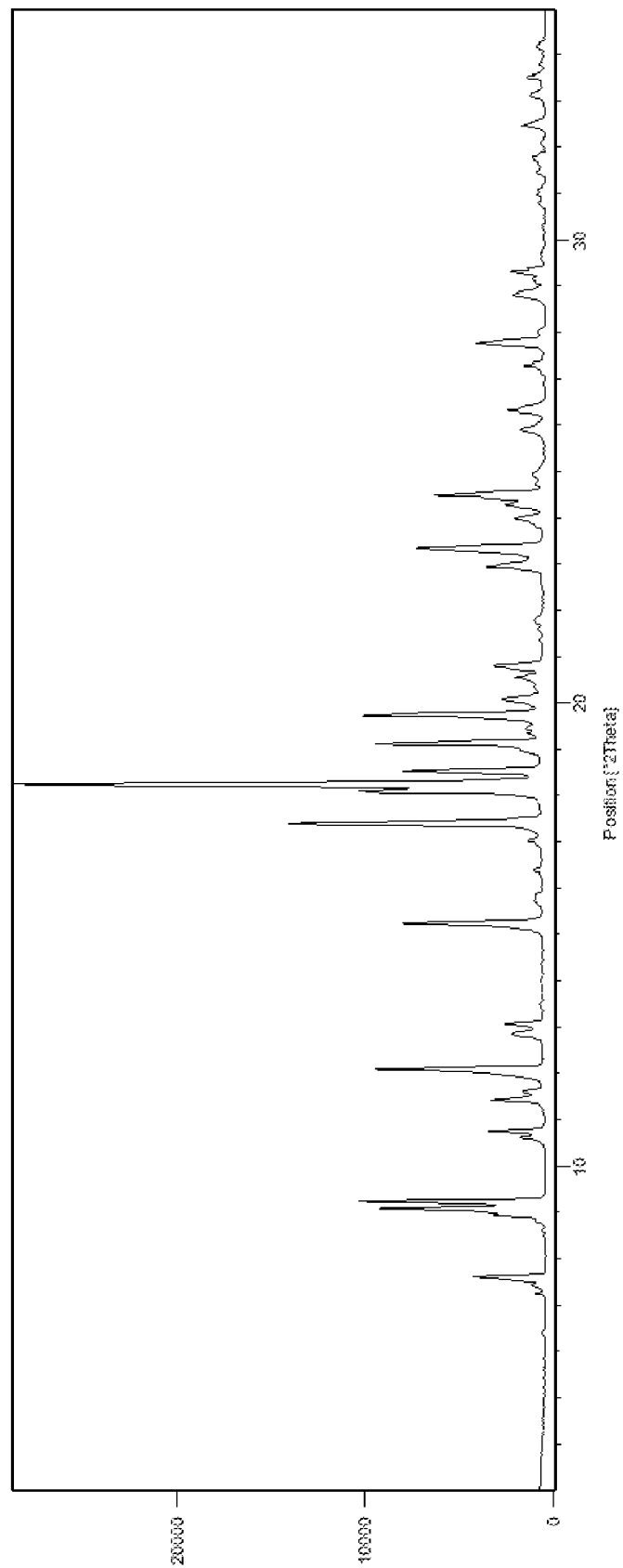
FIG. 46. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 2.
Figure 47:
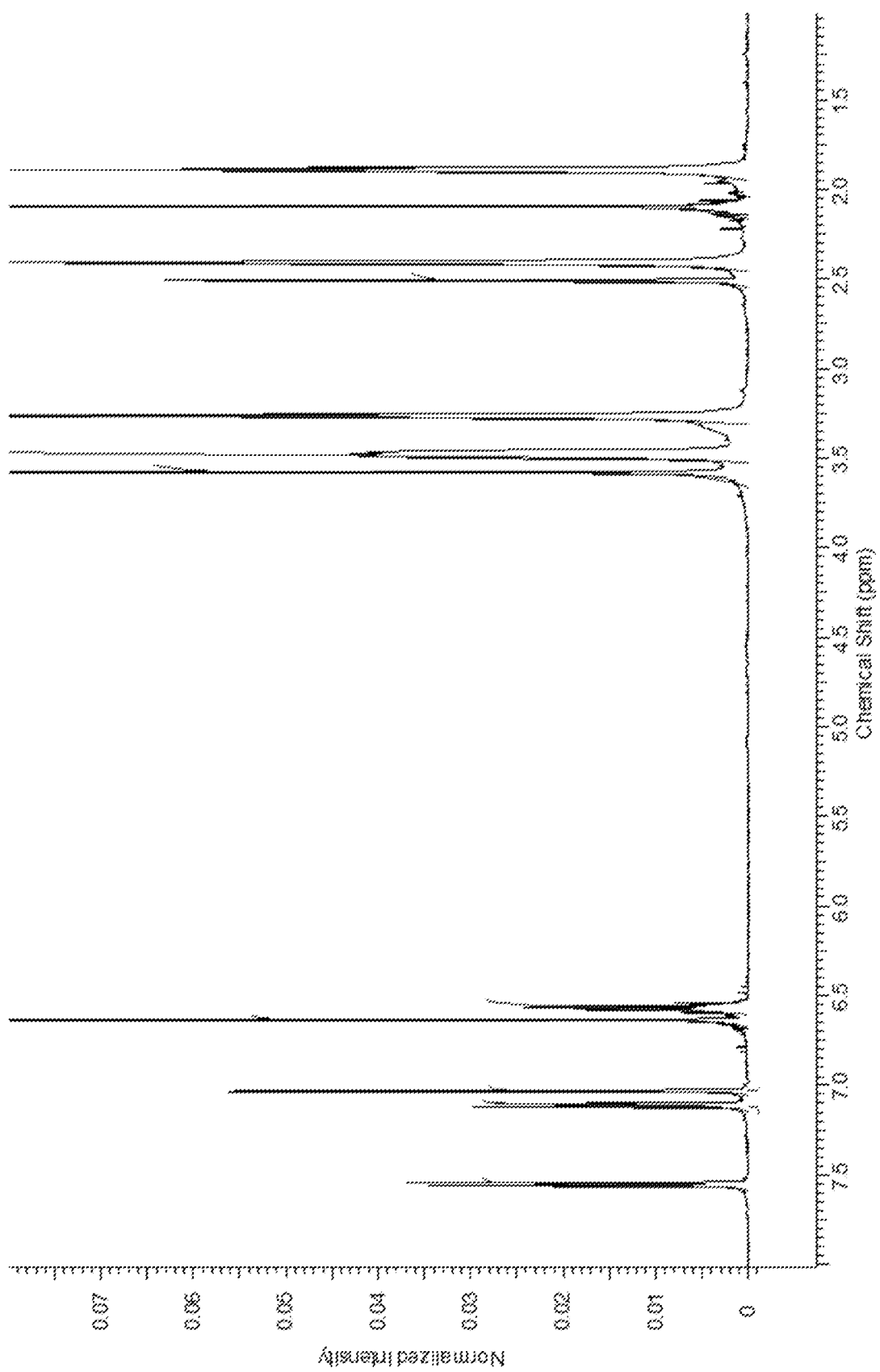
FIG. 47. Illustrates an NMR spectrum of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 2.
Figure 48:
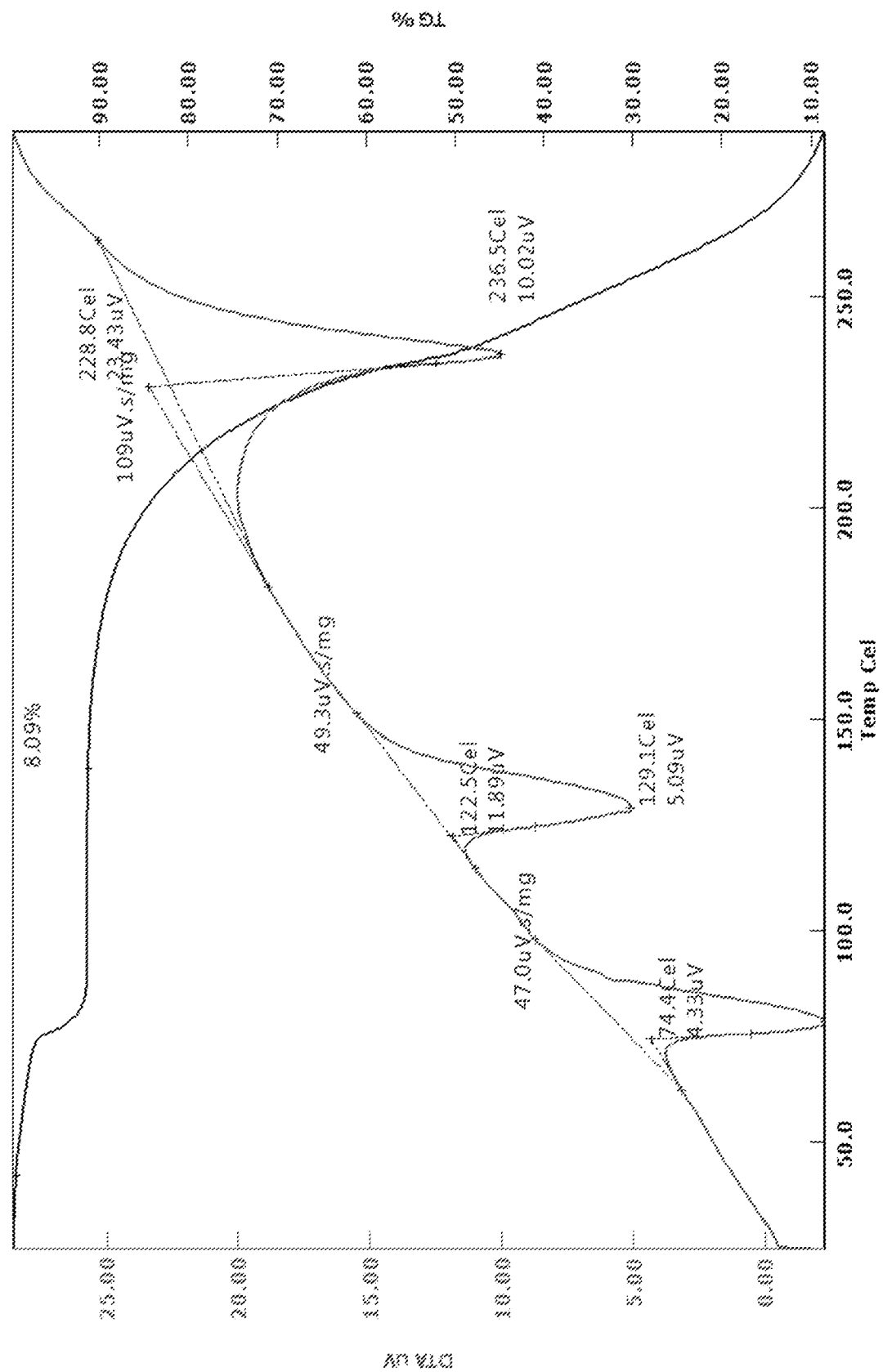
FIG. 48. Illustrates a TGA thermogram of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 2.

In some embodiments, Compound 6 is crystalline. In some embodiments, Compound 6 is crystalline Form 2. Crystalline Form 2 of Compound 6 is characterized as having at least one of the following properties:
(a) an X-ray powder diffraction (XRPD) pattern substantially the same as shown in FIG. 46;
(b) an X-ray powder diffraction (XRPD) pattern with characteristic peaks at 9.2° 2-Theta, 12.1° 2-Theta, 15.2° 2-Theta, 17.4° 2-Theta, 18.2° 2-Theta, 19.1° 2-Theta, and 19.7° 2-Theta;
(c) a thermo-gravimetric analysis (TGA) thermogram substantially similar to the one set forth in FIG. 48; or
(d) combinations thereof.

In some embodiments, Compound 6, Form 2, is characterized as having at least two of the properties selected from (a) to (c). In some embodiments, Compound 6, Form 2, is characterized as having properties (a) to (c).

In some embodiments, Compound 6, Form 2, has an X-ray powder diffraction (XRPD) pattern substantially the same as shown in FIG. 46. In some embodiments, Compound 6, Form 2, has an X-ray powder diffraction (XRPD) pattern with characteristic peaks at 9.2° 2-Theta, 12.1° 2-Theta, 15.2° 2-Theta, 17.4° 2-Theta, 18.2° 2-Theta, 19.1° 2-Theta, and 19.7° 2-Theta. In some embodiments, Compound 6, Form 2, has a thermo-gravimetric analysis (TGA) thermogram substantially similar to the one set forth in FIG. 48. In some embodiments, Compound 6, Form 2, is obtained from acetone/water.

Compound 6, Form 3

Figure 49:
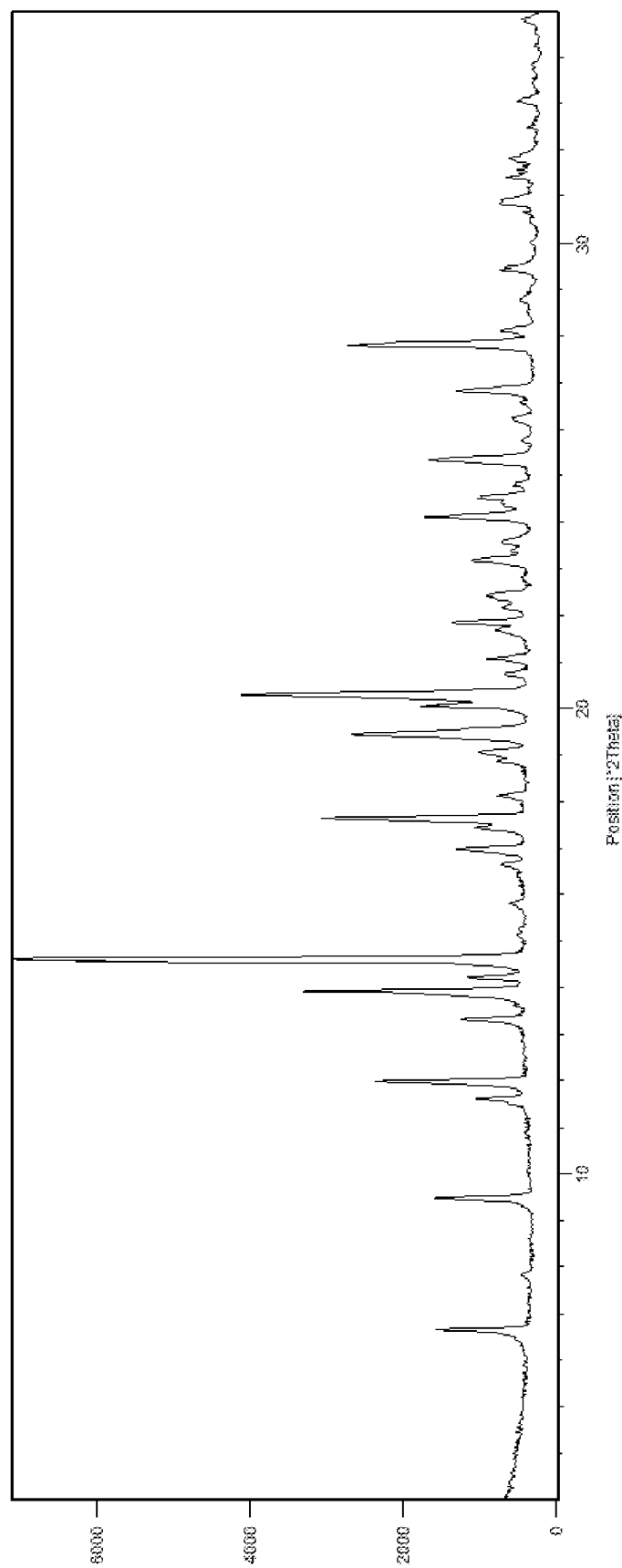
FIG. 49. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 3.
Figure 50:
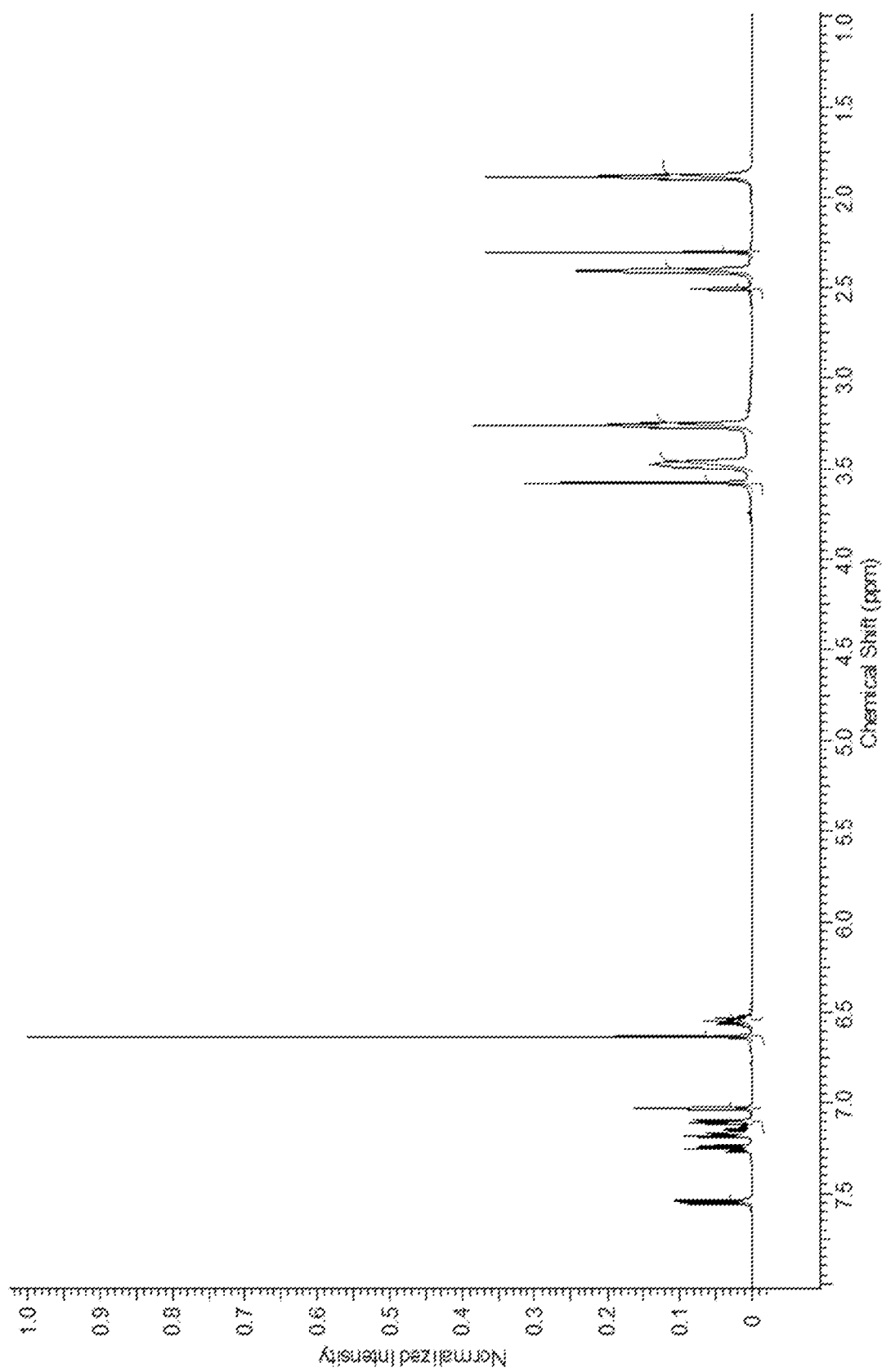
FIG. 50. Illustrates an NMR spectrum of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 3.
Figure 51:
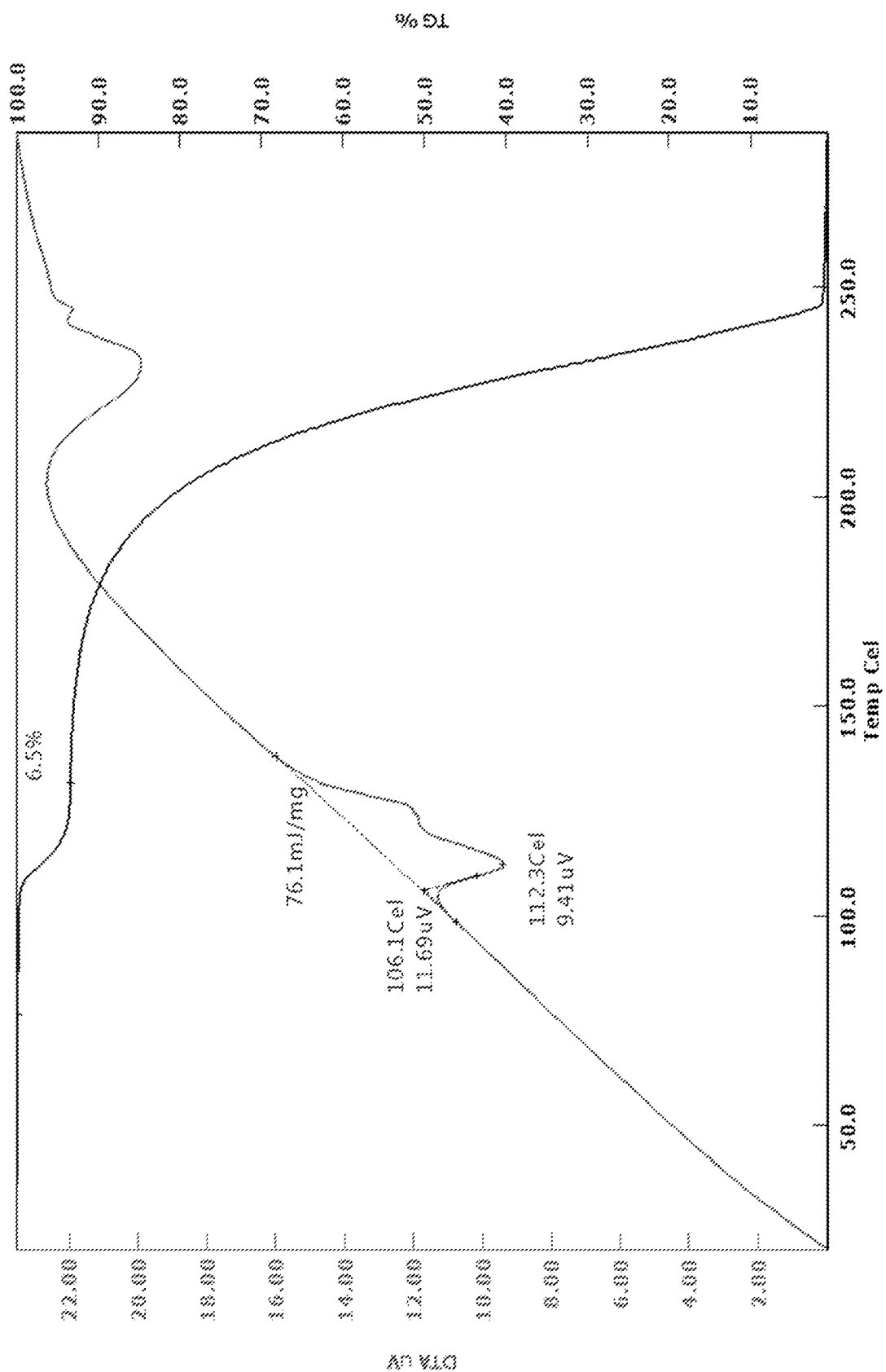
FIG. 51. Illustrates a TGA thermogram of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 3.
Figure 52:
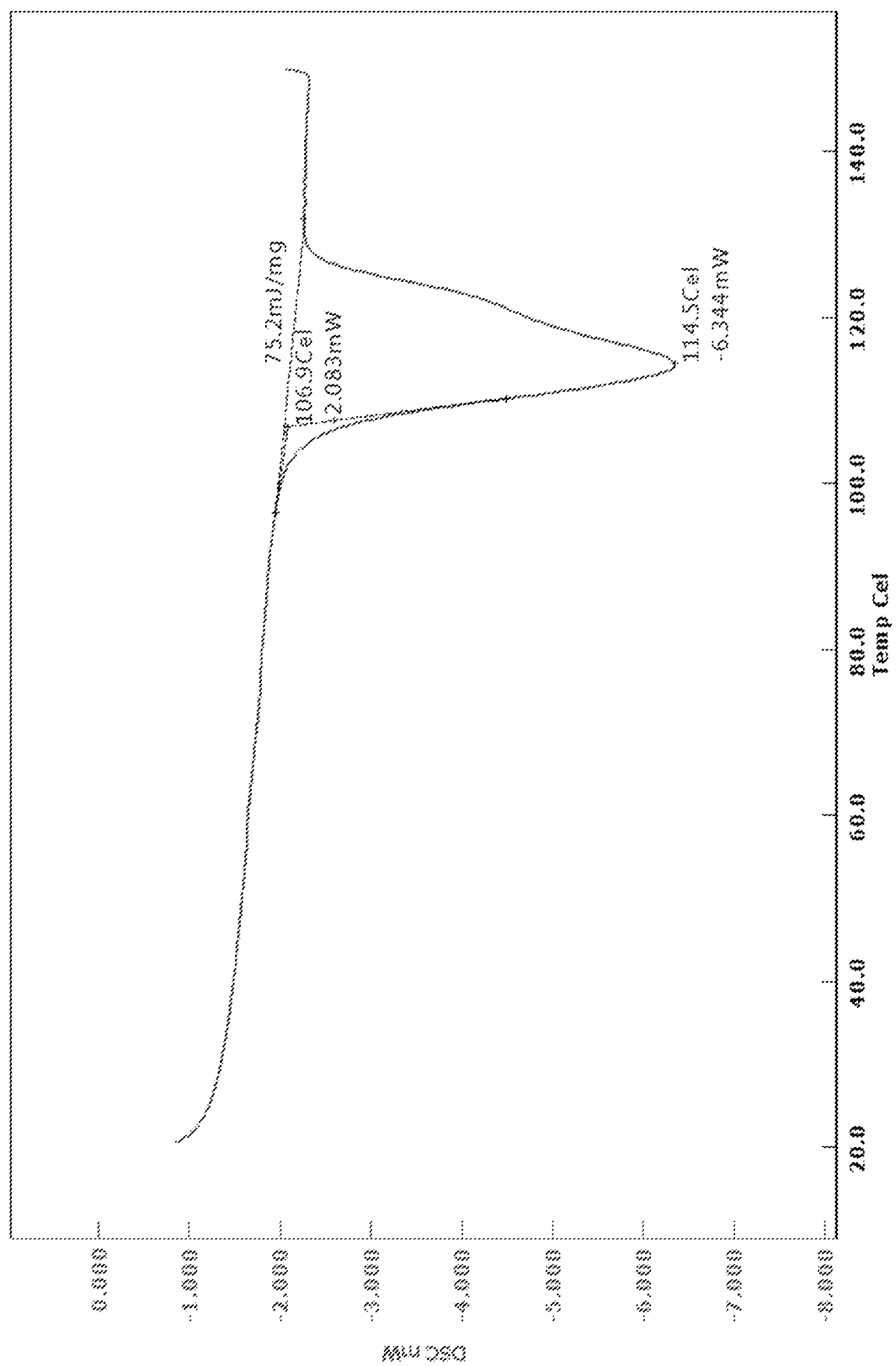
FIG. 52. Illustrates a DSC thermogram of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 3.

In some embodiments, Compound 6 is crystalline. In some embodiments, Compound 6 is crystalline Form 3. Crystalline Form 3 of Compound 6 is characterized as having at least one of the following properties:
(a) an X-ray powder diffraction (XRPD) pattern substantially the same as shown in FIG. 49;
(b) an X-ray powder diffraction (XRPD) pattern with characteristic peaks at 6.7° 2-Theta, 9.5° 2-Theta, 12.0° 2-Theta, 13.9° 2-Theta, 14.6° 2-Theta, 17.6° 2-Theta, 19.4° 2-Theta, and 20.3° 2-Theta;
(c) a thermo-gravimetric analysis (TGA) thermogram substantially similar to the one set forth in FIG. 51;
(d) a DSC thermogram substantially similar to the one set forth in FIG. 52;
(e) a DSC thermogram with an endotherm having an onset at about 107° C.; or
(f) combinations thereof.

In some embodiments, Compound 6, Form 3, is characterized as having at least two of the properties selected from (a) to (e). In some embodiments, Compound 6, Form 3, is characterized as having at least three of the properties selected from (a) to (e). In some embodiments, Compound 6, Form 3, is characterized as having at least four of the properties selected from (a) to (e). In some embodiments, Compound 6, Form 3, is characterized as having properties (a) to (e).

In some embodiments, Compound 6, Form 3, has an X-ray powder diffraction (XRPD) pattern substantially the same as shown in FIG. 49. In some embodiments, the crystalline 6.7° 2-Theta, 9.5° 2-Theta, 12.0° 2-Theta, 13.9° 2-Theta, 14.6° 2-Theta, 17.6° 2-Theta, 19.4° 2-Theta, and 20.3° 2-Theta. In some embodiments, Compound 6, Form 3, has a thermo-gravimetric analysis (TGA) thermogram substantially similar to the one set forth in FIG. 51. In some embodiments, Compound 6, Form 3, has a DSC thermogram substantially similar to the one set forth in FIG. 52. In some embodiments, Compound 6, Form 3, has a DSC thermogram with an endotherm having an onset at about 107° C. In some embodiments, Compound 6, Form 3, has a DSC thermogram with an endotherm having an onset at about 107° C. and a peak at about 115° C. In some embodiments, Compound 6, Form 3, is obtained from dioxane/water.

Preparation of Crystalline Forms

In some embodiments, crystalline forms of 1,1,1,3,3,3-hexafluoropropan-2-yl 4-(2-(pyrrolidin-1-yl)-4-(trifluoromethyl)benzyl)piperazine-1-carboxylate are prepared as outlined in the Examples. It is noted that solvents, temperatures and other reaction conditions presented herein may vary.

In certain embodiments, provided herein are methods for making a solid form of Compound 1, comprising 1) obtaining a saturated solution of Compound 1 in a solvent at a first temperature (e.g., about 60° C.); 2) adding an anti-solvent into the saturated solution at the first temperature; 3) cooling down to a second temperature (e.g., about −5° C. to about 15° C.); and 4) collecting a solid if there is precipitation, and evaporating the solvent to collect a solid if there is no precipitation; and 5) optionally drying. In certain embodiments, provided herein are methods for making a solid form of Compound 1, comprising 1) obtaining a saturated solution of Compound 1 in a solvent at about 60° C.; 2) adding an anti-solvent into the saturated solution at about 60° C.; 3) cooling down to about 5° C.; and 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the methods for making a solid form of Compound 1 are anti-solvent recrystallization experiments.

In another embodiment, crystalline Compound 1 is substantially pure. In certain embodiments, the substantially pure crystalline Compound 1 is substantially free of other solid forms, e.g., amorphous solid. In certain embodiments, the purity of the substantially pure crystalline Compound 1 is no less than about 95%, no less than about 96%, no less than about 97%, no less than about 98%, no less than about 98.5%, no less than about 99%, no less than about 99.5%, or no less than about 99.8%.

In certain embodiments, provided herein are methods for making a solid form of Compound 2, comprising 1) obtaining a saturated solution of Compound 2 in a solvent at a first temperature (e.g., about 60° C.); 2) adding an anti-solvent into the saturated solution at the first temperature; 3) cooling down to a second temperature (e.g., about −5° C. to about 15° C.); and 4) collecting a solid if there is precipitation, and evaporating the solvent to collect a solid if there is no precipitation; and 5) optionally drying. In certain embodiments, provided herein are methods for making a solid form of Compound 2, comprising 1) obtaining a saturated solution of Compound 2 in a solvent at about 60° C.; 2) adding an anti-solvent into the saturated solution at about 60° C.; 3) cooling down to about 5° C.; and 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the methods for making a solid form of Compound 2 are anti-solvent recrystallization experiments. In certain embodiments, Compound 2, Form 1 is prepared. In certain embodiments, Compound 2, Form 2 is prepared.

In another embodiment, crystalline Compound 2, Form 1 is substantially pure. In certain embodiments, the substantially pure crystalline Compound 2, Form 1 is substantially free of other solid forms, e.g., amorphous solid. In certain embodiments, the purity of the substantially pure crystalline Compound 2, Form 1 is no less than about 95%, no less than about 96%, no less than about 97%, no less than about 98%, no less than about 98.5%, no less than about 99%, no less than about 99.5%, or no less than about 99.8%.

In another embodiment, crystalline Compound 2, Form 2 is substantially pure. In certain embodiments, the substantially pure crystalline Compound 2, Form 2 is substantially free of other solid forms, e.g., amorphous solid. In certain embodiments, the purity of the substantially pure crystalline Compound 2, Form 2 is no less than about 95%, no less than about 96%, no less than about 97%, no less than about 98%, no less than about 98.5%, no less than about 99%, no less than about 99.5%, or no less than about 99.8%.

In certain embodiments, provided herein are methods for making a solid form of Compound 3, comprising 1) obtaining a saturated solution of Compound 3 in a solvent at a first temperature (e.g., about 60° C.); 2) adding an anti-solvent into the saturated solution at the first temperature; 3) cooling down to a second temperature (e.g., about −5° C. to about 15° C.); and 4) collecting a solid if there is precipitation, and evaporating the solvent to collect a solid if there is no precipitation; and 5) optionally drying. In certain embodiments, provided herein are methods for making a solid form of Compound 3, comprising 1) obtaining a saturated solution of Compound 3 in a solvent at about 60° C.; 2) adding an anti-solvent into the saturated solution at about 60° C.; 3) cooling down to about 5° C.; and 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the methods for making a solid form of Compound 3 are anti-solvent recrystallization experiments.

In another embodiment, crystalline Compound 3 is substantially pure. In certain embodiments, the substantially pure crystalline Compound 3 is substantially free of other solid forms, e.g., amorphous solid. In certain embodiments, the purity of the substantially pure crystalline Compound 3 is no less than about 95%, no less than about 96%, no less than about 97%, no less than about 98%, no less than about 98.5%, no less than about 99%, no less than about 99.5%, or no less than about 99.8%.

In certain embodiments, provided herein are methods for making a solid form of Compound 4, comprising 1) obtaining a saturated solution of Compound 4 in a solvent at a first temperature (e.g., about 60° C.); 2) adding an anti-solvent into the saturated solution at the first temperature; 3) cooling down to a second temperature (e.g., about −5° C. to about 15° C.); and 4) collecting a solid if there is precipitation, and evaporating the solvent to collect a solid if there is no precipitation; and 5) optionally drying. In certain embodiments, provided herein are methods for making a solid form of Compound 4, comprising 1) obtaining a saturated solution of Compound 4 in a solvent at about 60° C.; 2) adding an anti-solvent into the saturated solution at about 60° C.; 3) cooling down to about 5° C.; and 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the methods for making a solid form of Compound 4 are anti-solvent recrystallization experiments. In certain embodiments, Compound 4, Form 1 is prepared. In certain embodiments, Compound 4, Form 2 is prepared.

In another embodiment, crystalline Compound 4, Form 1 is substantially pure. In certain embodiments, the substantially pure crystalline Compound 4, Form 1 is substantially free of other solid forms, e.g., amorphous solid. In certain embodiments, the purity of the substantially pure crystalline Compound 4, Form 1 is no less than about 95%, no less than about 96%, no less than about 97%, no less than about 98%, no less than about 98.5%, no less than about 99%, no less than about 99.5%, or no less than about 99.8%.

In another embodiment, crystalline Compound 4, Form 2 is substantially pure. In certain embodiments, the substantially pure crystalline Compound 4, Form 2 is substantially free of other solid forms, e.g., amorphous solid. In certain embodiments, the purity of the substantially pure crystalline Compound 4, Form 2 is no less than about 95%, no less than about 96%, no less than about 97%, no less than about 98%, no less than about 98.5%, no less than about 99%, no less than about 99.5%, or no less than about 99.8%.

In certain embodiments, provided herein are methods for making a solid form of Compound 5, comprising 1) obtaining a saturated solution of Compound 5 in a solvent at a first temperature (e.g., about 60° C.); 2) adding an anti-solvent into the saturated solution at the first temperature; 3) cooling down to a second temperature (e.g., about −5° C. to about 15° C.); and 4) collecting a solid if there is precipitation, and evaporating the solvent to collect a solid if there is no precipitation; and 5) optionally drying. In certain embodiments, provided herein are methods for making a solid form of Compound 5, comprising 1) obtaining a saturated solution of Compound 5 in a solvent at about 60° C.; 2) adding an anti-solvent into the saturated solution at about 60° C.; 3) cooling down to about 5° C.; and 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the methods for making a solid form of Compound 5 are anti-solvent recrystallization experiments.

In another embodiment, crystalline Compound 5 is substantially pure. In certain embodiments, the substantially pure crystalline Compound 5 is substantially free of other solid forms, e.g., amorphous solid. In certain embodiments, the purity of the substantially pure crystalline Compound 5 is no less than about 95%, no less than about 96%, no less than about 97%, no less than about 98%, no less than about 98.5%, no less than about 99%, no less than about 99.5%, or no less than about 99.8%.

In certain embodiments, provided herein are methods for making a solid form of Compound 6, comprising 1) obtaining a saturated solution of Compound 6 in a solvent at a first temperature (e.g., about 60° C.); 2) adding an anti-solvent into the saturated solution at the first temperature; 3) cooling down to a second temperature (e.g., about −5° C. to about 15° C.); and 4) collecting a solid if there is precipitation, and evaporating the solvent to collect a solid if there is no precipitation; and 5) optionally drying. In certain embodiments, provided herein are methods for making a solid form of Compound 6, comprising 1) obtaining a saturated solution of Compound 6 in a solvent at about 60° C.; 2) adding an anti-solvent into the saturated solution at about 60° C.; 3) cooling down to about 5° C.; and 4) collecting a solid if there is precipitation, and evaporating the solvent to collect a solid if there is no precipitation; and 5) optionally air drying. In certain embodiments, the ratio by volume of solvent and anti-solvent is about 1:9. In certain embodiments, the methods for making a solid form of Compound 6 are anti-solvent recrystallization experiments. In certain embodiments, Compound 6, Form 1 is prepared. In certain embodiments, Compound 6, Form 2 is prepared. In certain embodiments, Compound 6, Form 3 is prepared.

In another embodiment, crystalline Compound 6, Form 1 is substantially pure. In certain embodiments, the substantially pure crystalline Compound 6, Form 1 is substantially free of other solid forms, e.g., amorphous solid. In certain embodiments, the purity of the substantially pure crystalline Compound 6, Form 1 is no less than about 95%, no less than about 96%, no less than about 97%, no less than about 98%, no less than about 98.5%, no less than about 99%, no less than about 99.5%, or no less than about 99.8%.

In another embodiment, crystalline Compound 6, Form 2 is substantially pure. In certain embodiments, the substantially pure crystalline Compound 6, Form 2 is substantially free of other solid forms, e.g., amorphous solid. In certain embodiments, the purity of the substantially pure crystalline Compound 6, Form 2 is no less than about 95%, no less than about 96%, no less than about 97%, no less than about 98%, no less than about 98.5%, no less than about 99%, no less than about 99.5%, or no less than about 99.8%.

In another embodiment, crystalline Compound 6, Form 3 is substantially pure. In certain embodiments, the substantially pure crystalline Compound 6, Form 3 is substantially free of other solid forms, e.g., amorphous solid. In certain embodiments, the purity of the substantially pure crystalline Compound 6, Form 3 is no less than about 95%, no less than about 96%, no less than about 97%, no less than about 98%, no less than about 98.5%, no less than about 99%, no less than about 99.5%, or no less than about 99.8%.

Suitable Solvents

Therapeutic agents that are administrable to mammals, such as humans, must be prepared by following regulatory guidelines. Such government regulated guidelines are referred to as Good Manufacturing Practice (GMP). GMP guidelines outline acceptable contamination levels of active therapeutic agents, such as, for example, the amount of residual solvent in the final product. Preferred solvents are those that are suitable for use in GMP facilities and consistent with industrial safety concerns. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005).

Solvents are categorized into three classes. Class 1 solvents are toxic and are to be avoided. Class 2 solvents are solvents to be limited in use during the manufacture of the therapeutic agent. Class 3 solvents are solvents with low toxic potential and of lower risk to human health. Data for Class 3 solvents indicate that they are less toxic in acute or short-term studies and negative in genotoxicity studies.

Class 1 solvents, which are to be avoided, include: benzene; carbon tetrachloride; 1,2-dichloroethane; 1,1-dichloroethene; and 1,1,1-trichloroethane.

Examples of Class 2 solvents are: acetonitrile, chlorobenzene, chloroform, cyclohexane, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, N-methylpyrrolidine, nitromethane, pyridine, sulfolane, tetralin, toluene, 1,1,2-trichloroethene and xylene.

Class 3 solvents, which possess low toxicity, include: acetic acid, acetone, anisole, 1-butanol, 2-butanol, butyl acetate, tert-butylmethyl ether (MTBE), cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran.

Residual solvents in active pharmaceutical ingredients (APIs) originate from the manufacture of API. In some cases, the solvents are not completely removed by practical manufacturing techniques. Appropriate selection of the solvent for the synthesis of APIs may enhance the yield, or determine characteristics such as crystal form, purity, and solubility. Therefore, the solvent is a critical parameter in the synthetic process.

In some embodiments, compositions comprising Compound 1, Compound 2, Compound 3, Compound 4, Compound 5, or Compound 6 comprise an organic solvent(s). In some embodiments, compositions comprising Compound 1, Compound 2, Compound 3, Compound 4, Compound 5, or Compound 6 comprise a residual amount of an organic solvent(s). In some embodiments, compositions comprising Compound 1, Compound 2, Compound 3, Compound 4, Compound 5, or Compound 6 comprise a residual amount of a Class 3 solvent. In some embodiments, the organic solvent is a Class 3 solvent. In some embodiments, the Class 3 solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, and tetrahydrofuran. In some embodiments, the Class 3 solvent is selected from ethyl acetate, isopropyl acetate, tert-butylmethylether, heptane, isopropanol, and ethanol.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of Compound 1, Compound 2, Compound 3, Compound 4, Compound 5, or Compound 6 dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which Compound 1, Compound 2, Compound 3, Compound 4, Compound 5, or Compound 6 is absorbed into the general circulation when the pharmaceutical composition is taken orally as compared to intravenous injection.

"Blood plasma concentration" refers to the concentration of Compound 1, Compound 2, Compound 3, Compound 4, Compound 5, or Compound 6 in the plasma component of blood of a subject. It is understood that the plasma concentration of Compound 1, Compound 2, Compound 3, Compound 4, Compound 5, or Compound 6 may vary significantly between subjects, due to variability with respect to metabolism and/or possible interactions with other therapeutic agents. In accordance with one embodiment disclosed herein, the blood plasma concentration of Compound 1, Compound 2, Compound 3, Compound 4, Compound 5, or Compound 6 may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of Compound 1, Compound 2, Compound 3, Compound 4, Compound 5, or Compound 6 may vary from subject to subject.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound 1, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The terms "inhibits", "inhibiting", or "inhibitor" of a kinase, as used herein, refer to inhibition of enzymatic activity.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of MAGL, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

Pharmaceutical Compositions/Formulations

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

A pharmaceutical composition, as used herein, refers to a mixture of Compound 1, Compound 2, Compound 3, Compound 4, Compound 5, or Compound 6 with other chemical components, such as carriers, stabilizers, diluents, dispersing agents, suspending agents, thickening agents, and/or excipients. The pharmaceutical composition facilitates administration of the compound to a mammal. In practicing the methods of treatment or use provided herein, therapeutically effective amounts of Compound 1, Compound 2, Compound 3, Compound 4, Compound 5, or Compound 6 are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The term "pharmaceutical combination" as used herein, means a product that results from the mixing or combining of more than one active ingredient and includes both fixed and non-fixed combinations of the active ingredients. The term "fixed combination" means that the active ingredients, e.g. Compound 1, Compound 2, Compound 3, Compound 4, Compound 5, or Compound 6, and a co-agent, are both administered to a patient simultaneously in the form of a single entity or dosage. The term "non-fixed combination" means that the active ingredients, e.g. Compound 1, Compound 2, Compound 3, Compound 4, Compound 5, or Compound 6, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

In some embodiments, crystalline Compound 1, Compound 2, Compound 3, Compound 4, Compound 5, or Compound 6 is incorporated into pharmaceutical compositions to provide solid oral dosage forms. In other embodiments, crystalline Compound 1, Compound 2, Compound 3, Compound 4, Compound 5, or Compound 6 is used to prepare pharmaceutical compositions other than oral solid dosage forms. The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

Dosage Forms

The pharmaceutical compositions described herein can be formulated for administration to a mammal via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include Compound 1, Compound 2, Compound 3, Compound 4, Compound 5, or Compound 6 can be formulated into any suitable dosage form, including but not limited to, solid oral dosage forms, controlled release formulations, fast melt formulations, effervescent formulations, tablets, powders, pills, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bio-erodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of Compound 1, Compound 2, Compound 3, Compound 4, Compound 5, or Compound 6 with one or more pharmaceutical excipients to form a bulk blend composition. When referring to these bulk blend compositions as homogeneous, it is meant that the particles of Compound 1, Compound 2, Compound 3, Compound 4, Compound 5, or Compound 6 are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include Compound 1, Compound 2, Compound 3, Compound 4, Compound 5, or Compound 6, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of Compound 1, Compound 2, Compound 3, Compound 4, Compound 5, or Compound 6. In one embodiment, some or all of the particles of the Compound 1, Compound 2, Compound 3, Compound 4, Compound 5, or Compound 6 are coated. In another embodiment, some or all of the particles of the Compound 1, Compound 2, Compound 3, Compound 4, Compound 5, or Compound 6 are microencapsulated. In still another embodiment, the particles of the Compound 1, Compound 2, Compound 3, Compound 4, Compound 5, or Compound 6 are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethyl cellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

In order to release the Compound 1, Compound 2, Compound 3, Compound 4, Compound 5, or Compound 6 from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel®PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like. In some embodiments provided herein, the disintegrating agent is selected from the group consisting of natural starch, a pregelatinized starch, a sodium starch, methylcrystalline cellulose, methylcellulose, croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, or a gum. In some embodiments provided herein, the disintegrating agent is croscarmellose sodium.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropyl cellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like. In some embodiments provided herein, the lubricant is selected from the group consisting of stearic acid, calcium hydroxide, talc, corn starch, sodium stearyl fumarate, stearic acid, sodium stearates, magnesium stearate, zinc stearate, and waxes. In some embodiments provided herein, the lubricant is magnesium stearate.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like. In some embodiments provided herein, the diluent is selected from the group consisting of lactose, sucrose, dextrose, dextrates, maltodextrin, mannitol, xylitol, sorbitol, cyclodextrins, calcium phosphate, calcium sulfate, starches, modified starches, microcrystalline cellulose, microcellulose, and talc. In some embodiments provided herein, the diluent is microcrystalline cellulose.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. In some embodiments provided herein, the surfactant is selected from the group consisting of sodium lauryl sulfate, sorbitan monooleate, polyoxyethylene sorbitan monooleate, polysorbates, polaxomers, bile salts, glyceryl monostearate, copolymers of ethylene oxide and propylene oxide. In some embodiments provided herein, the surfactant is sodium lauryl sulfate.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethyl cellulose, hydroxyethyl cellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of Compound 1, Compound 2, Compound 3, Compound 4, Compound 5, or Compound 6 from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of Compound 1, Compound 2, Compound 3, Compound 4, Compound 5, or Compound 6 inside of a capsule. In some embodiments, the formulations (non-aqueous suspensions and solutions) are placed in a soft gelatin capsule. In some embodiments, the formulations (non-aqueous suspensions and solutions) are placed in a hard shell gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of Compound 1, Compound 2, Compound 3, Compound 4, Compound 5, or Compound 6 and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with Compound 1, Compound 2, Compound 3, Compound 4, Compound 5, or Compound 6 which sufficiently isolate the Compound 1, Compound 2, Compound 3, Compound 4, Compound 5, or Compound 6 from other non-compatible excipients. Materials compatible with Compound 1, Compound 2, Compound 3, Compound 4, Compound 5, or Compound 6 are those that delay the release of the compounds of Compound 1, Compound 2, Compound 3, Compound 4, Compound 5, or Compound 6 in vivo.

Exemplary microencapsulation materials useful for delaying the release of the formulations including compounds described herein, include, but are not limited to, hydroxypropyl cellulose ethers (HPC) such as Klucel or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG,HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD 100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated Compound 1, Compound 2, Compound 3, Compound 4, Compound 5, or Compound 6 may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of Compound 1, Compound 2, Compound 3, Compound 4, Compound 5, or Compound 6 are microencapsulated prior to being formulated into one of the above forms. In still another embodiment, some or most of the particles are coated prior to being further formulated by using standard coating procedures, such as those described in Remington's Pharmaceutical Sciences, 20th Edition (2000).

In other embodiments, the solid dosage formulations of the Compound 1, Compound 2, Compound 3, Compound 4, Compound 5, or Compound 6 are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with Compound 1, Compound 2, Compound 3, Compound 4, Compound 5, or Compound 6 may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers.

The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles <1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include Compound 1, Compound 2, Compound 3, Compound 4, Compound 5, or Compound 6 are delivered using a pulsatile dosage form. A pulsatile dosage form is capable of providing one or more immediate release pulses at predetermined time points after a controlled lag time or at specific sites. Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, non-polymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., *Pharmaceutical Dosage Forms*, 2 Ed., Vol. 1, pp. 209-214 (1990); Singh et al., *Encyclopedia of Pharmaceutical Technology*, $2^{nd}$ Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of Compound 1, Compound 2, Compound 3, Compound 4, Compound 5, or Compound 6 at least one dispersing agent or suspending agent for oral administration to a subject. The formulations may be a powder and/or granules for suspension, and upon admixture with water, a substantially uniform suspension is obtained.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Dosing and Treatment Regimens

In some embodiments, the amount of Compound 1, Compound 2, Compound 3, Compound 4, Compound 5, or Compound 6 that is administered to a mammal is from about 0.5 mg/day to about 1000 mg/day. In some embodiments, the amount of Compound 1, Compound 2, Compound 3, Compound 4, Compound 5, or Compound 6 that is administered to a mammal is from about 1 mg/day to about 500 mg/day. In some embodiments, the amount of Compound 1, Compound 2, Compound 3, Compound 4, Compound 5, or Compound 6 that is administered to a mammal is from about 2 mg/day to about 400 mg/day. In some embodiments, the amount of Compound 1, Compound 2, Compound 3, Compound 4, Compound 5, or Compound 6 that is administered to a mammal is from about 5 mg/day to about 300 mg/day. In some embodiments, the amount of Compound 1, Compound 2, Compound 3, Compound 4, Compound 5, or Compound 6 that is administered to a mammal is from about 10 mg/day to about 160 mg/day. In some embodiments, the amount of Compound 1, Compound 2, Compound 3, Compound 4, Compound 5, or Compound 6 that is administered to a mammal is from about 5 mg/day to about 100 mg/day. In some embodiments, the amount of Compound 1, Compound 2, Compound 3, Compound 4, Compound 5, or Compound 6 that is administered to a mammal is from about 1 mg/day to about 50 mg/day. In some embodiments, the amount of Compound 1, Compound 2, Compound 3, Compound 4, Compound 5, or Compound 6 that is administered to a mammal is from about 2 mg/day to about 50 mg/day. In some embodiments, the amount of Compound 1, Compound 2, Compound 3, Compound 4, Compound 5, or Compound 6 that is administered to a mammal is from about 2 mg/day to about 30 mg/day. In some embodiments, the amount of Compound 1, Compound 2, Compound 3, Compound 4, Compound 5, or Compound 6 that is administered to a mammal is from about 1 mg/day to about 20 mg/day. In some embodiments, the amount of Compound 1, Compound 2, Compound 3, Compound 4, Compound 5, or Compound 6 that is administered to a mammal is from about 2 mg/day to about 20 mg/day. In some embodiments, the amount of Compound 1, Compound 2, Compound 3, Compound 4, Compound 5, or Compound 6 that is administered to a mammal is from about 1 mg/day to about 10 mg/day. In some embodiments, the amount of Compound 1, Compound 2, Compound 3, Compound 4, Compound 5, or Compound 6 that is administered to a mammal is from about 2 mg/day to about 10 mg/day. In some embodiments, the amount of Compound 1, Compound 2, Compound 3, Compound 4, Compound 5, or Compound 6 that is administered to a mammal is about 500 mg/day. In some embodiments, the amount of Compound 1, Compound 2, Compound 3, Compound 4, Compound 5, or Compound 6 that is administered to a mammal is about 450 mg/day. In some embodiments, the amount of Compound 1, Compound 2, Compound 3, Compound 4, Compound 5, or Compound 6 that is administered to a mammal is about 400 mg/day. In some embodiments, the amount of Compound 1, Compound 2, Compound 3, Compound 4, Compound 5, or Compound 6 that is administered to a mammal is about 350 mg/day. In some embodiments, the amount of Compound 1, Compound 2, Compound 3, Compound 4, Compound 5, or Compound 6 that is administered to a mammal is about 300 mg/day. In some embodiments, the amount of Compound 1, Compound 2, Compound 3, Compound 4, Compound 5, or Compound 6 that is administered to a mammal is about 275 mg/day. In some embodiments, the amount of Compound 1, Compound 2, Compound 3, Compound 4, Compound 5, or Compound 6 that is administered to a mammal is about 250 mg/day. In some embodiments, the amount of Compound 1, Compound 2, Compound 3, Compound 4, Compound 5, or Compound 6 that is administered to a mammal is about 225 mg/day. In some embodiments, the amount of Compound 1, Compound 2, Compound 3, Compound 4, Compound 5, or Compound 6 that is administered to a mammal is about 200 mg/day. In some embodiments, the amount of Compound 1, Compound 2, Compound 3, Compound 4, Compound 5, or Compound 6 that is administered to a mammal is about 190 mg/day. In some embodiments, the amount of Compound 1, Compound 2, Compound 3, Compound 4, Compound 5, or Compound 6 that is administered to a mammal is about 180 mg/day. In some embodiments, the amount of Compound 1, Compound 2, Compound 3, Compound 4, Compound 5, or Compound 6 that is administered to a mammal is about 170 mg/day. In some embodiments, the amount of Compound 1, Compound 2, Compound 3, Compound 4, Compound 5, or Compound 6 that is administered to a mammal is about 160 mg/day. In some embodiments, the amount of Compound 1, Compound 2, Compound 3, Compound 4, Compound 5, or Compound 6 that is administered to a mammal is about 150 mg/day. In some embodiments, the amount of Compound 1, Compound 2, Compound 3, Compound 4, Compound 5, or Compound 6 that is administered to a mammal is about 140 mg/day. In some embodiments, the amount of Compound 1, Compound 2, Compound 3, Compound 4, Compound 5, or Compound 6 that is administered to a mammal is about 130 mg/day. In some embodiments, the amount of Compound 1, Compound 2, Compound 3, Compound 4, Compound 5, or Compound 6 that is administered to a mammal is about 120 mg/day. In some embodiments, the amount of Compound 1, Compound 2, Compound 3, Compound 4, Compound 5, or Compound 6 that is administered to a mammal is about 110 mg/day. In some embodiments, the amount of Compound 1, Compound 2, Compound 3, Compound 4, Compound 5, or Compound 6 that is administered to a mammal is about 100 mg/day. In some embodiments, the amount of Compound 1, Compound 2, Compound 3, Compound 4, Compound 5, or Compound 6 that is administered to a mammal is about 95 mg/day. In some embodiments, the amount of Compound 1, Compound 2, Compound 3, Compound 4, Compound 5, or Compound 6 that is administered to a mammal is about 90 mg/day. In some embodiments, the amount of Compound 1, Compound 2, Compound 3, Compound 4, Compound 5, or Compound 6 that is administered to a mammal is about 85 mg/day. In some embodiments, the amount of Compound 1, Compound 2, Compound 3, Compound 4, Compound 5, or Compound 6 that is administered to a mammal is about 80 mg/day. In some embodiments, the amount of Compound 1, Compound 2, Compound 3, Compound 4, Compound 5, or Compound 6 that is administered to a mammal is about 75 mg/day. In some embodiments, the amount of Compound 1, Compound 2, Compound 3, Compound 4, Compound 5, or Compound 6 that is administered to a mammal is about 70 mg/day. In some embodiments, the amount of Compound 1, Compound 2, Compound 3, Compound 4, Compound 5, or Compound 6 that is administered to a mammal is about 65 mg/day. In some embodiments, the amount of Compound 1, Compound 2, Compound 3, Compound 4, Compound 5, or Compound 6 that is administered to a mammal is about 60 mg/day. In some embodiments, the amount of Compound 1, Compound 2, Compound 3, Compound 4, Compound 5, or Compound 6 that is administered to a mammal is about 55 mg/day. In some embodiments, the amount of Compound 1, Compound 2, Compound 3, Compound 4, Compound 5, or Compound 6 that is administered to a mammal is about 50 mg/day. In some embodiments, the amount of Compound 1, Compound 2, Compound 3, Compound 4, Compound 5, or Compound 6 that is administered to a mammal is about 45 mg/day. In some embodiments, the amount of Compound 1, Compound 2, Compound 3, Compound 4, Compound 5, or Compound 6 that is administered to a mammal is about 40 mg/day. In some embodiments, the amount of Compound 1, Compound 2, Compound 3, Compound 4, Compound 5, or Compound 6 that is administered to a mammal is about 35 mg/day. In some embodiments, the amount of Compound 1, Compound 2, Compound 3, Compound 4, Compound 5, or Compound 6 that is administered to a mammal is about 30 mg/day. In some embodiments, the amount of Compound 1, Compound 2, Compound 3, Compound 4, Compound 5, or Compound 6 that is administered to a mammal is about 25 mg/day. In some embodiments, the amount of Compound 1, Compound 2, Compound 3, Compound 4, Compound 5, or Compound 6 that is administered to a mammal is about 20 mg/day. In some embodiments, the amount of Compound 1, Compound 2, Compound 3, Compound 4, Compound 5, or Compound 6 that is administered to a mammal is about 15 mg/day. In some embodiments, the amount of Compound 1, Compound 2, Compound 3, Compound 4, Compound 5, or Compound 6 that is administered to a mammal is about 10 mg/day. In some embodiments, the amount of Compound 1, Compound 2, Compound 3, Compound 4, Compound 5, or Compound 6 that is administered to a mammal is about 5 mg/day. In some embodiments, the amount of Compound 1, Compound 2, Compound 3, Compound 4, Compound 5, or Compound 6 that is administered to a mammal is about 2 mg/day. In some embodiments, the amount of Compound 1, Compound 2, Compound 3, Compound 4, Compound 5, or Compound 6 that is administered to a mammal is about 1 mg/day. In some embodiments, Compound 1, Compound 2, Compound 3, Compound 4, Compound 5, or Compound 6 is administered orally. In some embodiments, Compound 1, Compound 2, Compound 3, Compound 4, Compound 5, or Compound 6 is administered once per day, twice per day, or three times per day. In some embodiments, Compound 1, Compound 2, Compound 3, Compound 4, Compound 5, or Compound 6 is administered daily. In some embodiments, Compound 1, Compound 2, Compound 3, Compound 4, Compound 5, or Compound 6 is administered once daily. In some embodiments, Compound 1, Compound 2, Compound 3, Compound 4, Compound 5, or Compound 6 is administered every other day. In some embodiments, the Compound 1, Compound 2, Compound 3, Compound 4, Compound 5, or Compound 6 is a maintenance therapy.

Compound 1, Compound 2, Compound 3, Compound 4, Compound 5, or Compound 6 can be used in the preparation of medicaments for the inhibition of MAGL or for the treatment of diseases or conditions that would benefit, at least in part, from inhibition of MAGL including in the treatment of inflammation or neuropathic pain. In addition, a method for treating any of the diseases or conditions described herein in a subject in need of such treatment, involves administration of pharmaceutical compositions containing Compound 1, Compound 2, Compound 3, Compound 4, Compound 5, or Compound 6, or pharmaceutically acceptable solvate thereof, in therapeutically effective amounts to said subject.

The compositions containing Compound 1, Compound 2, Compound 3, Compound 4, Compound 5, or Compound 6 are administered for prophylactic, therapeutic, or maintenance treatment. In some embodiments, compositions containing Compound 1, Compound 2, Compound 3, Compound 4, Compound 5, or Compound 6 are administered for therapeutic applications. In some embodiments, compositions containing Compound 1, Compound 2, Compound 3, Compound 4, Compound 5, or Compound 6 are administered for prophylactic applications.

In some embodiments, Compound 1, Compound 2, Compound 3, Compound 4, Compound 5, or Compound 6 is administered daily. In some embodiments, Compound 1, Compound 2, Compound 3, Compound 4, Compound 5, or Compound 6 is administered every other day.

In some embodiments, Compound 1, Compound 2, Compound 3, Compound 4, Compound 5, or Compound 6 is administered once per day. In some embodiments, Compound 1, Compound 2, Compound 3, Compound 4, Compound 5, or Compound 6 is administered twice per day. In some embodiments, Compound 1, Compound 2, Compound 3, Compound 4, Compound 5, or Compound 6 is administered three times per day. In some embodiments, Compound 1, Compound 2, Compound 3, Compound 4, Compound 5, or Compound 6 is administered four times per day.

In some embodiments, Compound 1, Compound 2, Compound 3, Compound 4, Compound 5, or Compound 6 is administered until disease progression, unacceptable toxicity, or individual choice. In some embodiments, Compound 1, Compound 2, Compound 3, Compound 4, Compound 5, or Compound 6 is administered daily until disease progression, unacceptable toxicity, or individual choice. In some embodiments, Compound 1, Compound 2, Compound 3, Compound 4, Compound 5, or Compound 6 is administered every other day until disease progression, unacceptable toxicity, or individual choice.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, the severity of the disease, the identity (e.g., weight) of the subject or host in need of treatment, but can nevertheless be routinely determined in a manner known in the art according to the particular circumstances surrounding the case, including, e.g., the specific agent being administered, the route of administration, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Methods

In some embodiments disclosed herein are methods of modulating the activity of MAGL.

Contemplated methods, for example, comprise exposing said enzyme to a compound described herein. The ability of compounds described herein to modulate or inhibit MAGL is evaluated by procedures known in the art and/or described herein. Another aspect of this disclosure provides methods of treating a disease associated with expression or activity of MAGL in a patient.

Also disclosed herein are methods of treating and/or preventing in a patient in need thereof a disorder such as one or more of acute or chronic pain and neuropathy. Disclosed methods include administering a pharmaceutically effective amount of a compound described herein.

Neuropathic Pain and Inflammation

MAGL inhibitors are efficacious in several rodent models of pain including models of neuropathic pain. MAGL inhibitors also reduce disease and inflammation in multiple preclinical models. In the mouse experimental autoimmune encephalomyelitis model of multiple sclerosis, MAGL inhibition reduced disease severity, prevented demyelination and reduced inflammation. In some embodiments is a method of treating pain in a patient in need thereof, comprising administering to the patient a therapeutically effective amount of Compound 1, Compound 2, Compound 3, Compound 4, Compound 5, or Compound 6 described herein. In another embodiment is a method of treating neuropathic pain in a patient in need thereof, comprising administering to the patient a therapeutically effective amount of Compound 1, Compound 2, Compound 3, Compound 4, Compound 5, or Compound 6 described herein. In another embodiment is a method of treating inflammatory pain in a patient in need thereof, comprising administering to the patient a therapeutically effective amount of Compound 1, Compound 2, Compound 3, Compound 4, Compound 5, or Compound 6 described herein. In another embodiment is a method of treating inflammation in a patient in need thereof, comprising administering to the patient a therapeutically effective amount of Compound 1, Compound 2, Compound 3, Compound 4, Compound 5, or Compound 6 described herein.

Acute Pain, Inflammatory Pain, Cancer Pain, and Pain Caused by Peripheral Neuropathy MAGL inhibitors have shown efficacy in several rodent models of pain including models of acute pain, inflammatory pain, cancer pain, and pain caused by chemotherapy-induced peripheral neuropathy.

In some embodiments, disclosed herein is a method of treating acute pain in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating inflammatory pain in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating cancer pain in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating pain caused by peripheral neuropathy in a patient in need thereof, comprising administering to the patient a therapeutically effective amount of Compound 1, Compound 2, Compound 3, Compound 4, Compound 5, or Compound 6 described herein.

Central Pain

Central pain is neuropathic pain caused by lesion or dysfunction of the central nervous system, for example, post-stroke, multiple sclerosis, neuromyelitis optica, idiopathic inflammatory transverse myelitis, spinal cord injury, brachial-radial pain syndrome, and central craniofacial pain. Exocannabinoids have demonstrated activity in central pain associated with multiple sclerosis. For example, a third-party 4-week randomized double-blind placebo-controlled parallel group trial with MS and central pain using an oromucosal spray, THC/CBD, containing the CB1 agonist delta-9-tetrahydrocannabinol and cannabidiol (another *Cannabis*-derived alcohol) showed that the active agent was superior to placebo in reducing the mean intensity of pain (NRS-11) and of sleep disturbance. The same THC/CBD preparation was studied in a larger group of MS patients with central neuropathic pain utilizing a two-stage design; in the second phase of this study, the time to treatment failure (primary endpoint) statistically favored THC/CBD, as did an improvement in the Pain NRS-11 and sleep quality. Several other third-party studies of exocannabinoids in central pain have indicated activity.

In some embodiments, MAGL inhibitors described herein have efficacy in treatment of central pain. In some embodiments, disclosed herein is a method of treating central pain in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating post-stroke pain in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating pain associated with multiple sclerosis in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating neuromyelitis optica in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating idiopathic inflammatory transverse myelitis in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating pain associated with a spinal cord injury in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating brachial-radial pain syndrome in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating central craniofacial pain in a patient in need thereof, comprising administering to the patient a therapeutically effective amount of Compound 1, Compound 2, Compound 3, Compound 4, Compound 5, or Compound 6 described herein.

Fibromyalgia

Fibromyalgia (FM) is a common, chronic, idiopathic condition characterized by diffuse body pain and the presence of pressure allodynia. Several third-party studies of exocannabinoids in FM have indicated activity. For example, measures of pain (e.g., NRS-11, Pain VAS) and the Fibromyalgia Impact Questionnaire (FIQ), which measures limitations in several activities of daily living impacted by FM, have demonstrated activity of drugs in FM clinical trials. In an 8-week, 40-patient study, compared with placebo an exocannabinoid improved pain measured on a 10 cm VAS, and improved the FIQ domain of anxiety and the FIQ total score.

In some embodiments, MAGL inhibitors described herein have efficacy in treatment of FM. In some embodiments, disclosed herein is a method of treating fibromyalgia in a patient in need thereof, comprising administering to the patient a therapeutically effective amount of Compound 1, Compound 2, Compound 3, Compound 4, Compound 5, or Compound 6 described herein.

Migraine

Migraine is a common episodic disorder of head and facial pain. Migraine attacks can be acutely treated with NSAIDs, acetaminophen, a variety of triptans (e.g., sumatriptan), and antiemetics, but some migraine sufferers have pain unresponsive to existing treatment options. Third party data suggests that endocannabinoid pathways may be relevant in migraine. In patients with chronic migraine and probable analgesic-overuse headache, CSF samples showed higher levels of the endocannabinoid palmitoylethanolamide and lower levels of anandamide compared with healthy controls. In addition, patients with a primary diagnosis of migraine headaches found a decrease in the frequency of migraine headaches after initiating marijuana therapy.

In some embodiments, MAGL inhibitors described herein have efficacy in treatment of migraine. In some embodiments, disclosed herein is a method of treating migraine in a patient in need thereof, comprising administering to the patient a therapeutically effective amount of Compound 1, Compound 2, Compound 3, Compound 4, Compound 5, or Compound 6 described herein.

Vasoocclusive Painful Crisis in Sickle Cell Disease

Vasoocclusive painful crisis is believed to be the result of altered rheology of red blood cells (RBC) with occlusion of microcapillaries and ischemic pain in patients with sickle cell disease (SCD), a hereditary condition due to mutations in the adult hemoglobin beta gene. Third party data demonstrates pain-related behaviors and neurochemical alterations in mice expressing human sickle hemoglobin are markedly improved by treating mice with a cannabinoid receptor agonist.

In some embodiments, MAGL inhibitors described herein have efficacy in treatment of vasoocclusive painful crisis in SCD. In some embodiments, disclosed herein is a method of treating vasoocclusive painful crisis in sickle cell disease in a patient in need thereof, comprising administering to the patient a therapeutically effective amount of Compound 1, Compound 2, Compound 3, Compound 4, Compound 5, or Compound 6 described herein.

Multiple Sclerosis Symptomatic Treatment

Nearly all multiple sclerosis (MS) patients of all subtypes have one or more symptoms of spasticity, pain, disturbed sleep, bladder dysfunction, and fatigue. Disease modifying therapies do not improve symptoms. Spasticity affects over 80% of MS patients; 34% have moderate, severe, or total spasticity. Severe spasticity is related to cost and level of care, and is independently related to quality of life in MS. Third party data supports the use of exocannabinoids for the treatment of MS spasticity and pain.

In some embodiments, MAGL inhibitors described herein have efficacy in treatment of spasticity, pain, disturbed sleep, or bladder dysfunction associated with multiple sclerosis. In some embodiments, disclosed herein is a method of treating spasticity, pain, disturbed sleep, or bladder dysfunction associated with multiple sclerosis in a patient in need thereof, comprising administering to the patient a therapeutically effective amount of Compound 1, Compound 2, Compound 3, Compound 4, Compound 5, or Compound 6 described herein.

Functional Chest Pain

Functional chest pain, sometimes called non-GERD, non-cardiac chest pain, is a functional gastrointestinal disorder where discomfort of upper GI structures is perceived in the chest. In addition to consuming medical resources to rule out other treatable conditions, functional chest pain causes distress for patients. It may be treated with tricyclic antidepressants or serotonin norepinephrine reuptake inhibitors, but not all patients respond. In patients with functional chest pain, a syndrome ascribed to GI hypersensitivity, third party data showed an exocannabinoid improved chest pain symptoms and raised sensory threshold for balloon distension of the esophagus in a placebo-controlled 4 week study.

In some embodiments, MAGL inhibitors described herein have efficacy in treatment of functional chest pain. In some embodiments, disclosed herein is a method of treating functional chest pain in a patient in need thereof, comprising administering to the patient a therapeutically effective amount of Compound 1, Compound 2, Compound 3, Compound 4, Compound 5, or Compound 6 described herein.

Rheumatoid Arthritis and Osteoarthritis

Third party data found CB1 and CB2 receptors to be present in the synovia of rheumatoid arthritis (RA) and osteoarthritis (OA) patients. The endocannabinoids anandamide and 2-AG were identified in synovial fluid of RA and OA patients, but not in normal volunteers. In addition, a small RA patient trial with nabiximols (THC/CBD oromucosal spray) showed improved pain on movement at rest, improved sleep, and an improvement in the standard RA Disease Activity Score in 28 joints.

In some embodiments, MAGL inhibitors described herein have efficacy in treatment of pain and inflammation in RA and OA. In some embodiments, disclosed herein is a method of treating rheumatoid arthritis or osteoarthritis in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating rheumatoid arthritis pain or osteoarthritis pain in a patient in need thereof, comprising administering to the patient a therapeutically effective amount of Compound 1, Compound 2, Compound 3, Compound 4, Compound 5, or Compound 6 described herein.

Alzheimer's Disease

Alzheimer's disease (AD) is the most common cause of dementia, affecting ~5.3 million people in the US. Agitation and aggression are risk factors for institutionalization of patients with dementia. Third party data showed that exocannabinoid improved anorexia and decreased agitation in AD patients and reduced nighttime agitation. This data suggests that a MAGL inhibitor would be efficacious in AD patients with dementia and agitation.

In some embodiments, MAGL inhibitors described herein have efficacy in treatment of Alzheimer's disease. In some embodiments, disclosed herein is a method of treating agitation or aggression associated with Alzheimer's disease in a patient in need thereof, comprising administering to the patient a therapeutically effective amount of Compound 1, Compound 2, Compound 3, Compound 4, Compound 5, or Compound 6 described herein.

Functional Dyspepsia

Functional dyspepsia (FD) is one of the most common gastrointestinal disorders encountered in clinical practice. Several pathophysiological mechanisms have been proposed to underlie symptom generation in FD, including visceral hypersensitivity due to central or peripheral sensitization, low-grade inflammatory states, altered secretion of gastrointestinal hormones, genetic predisposition, and abnormal gastric emptying or accommodation. Third party data supports the hypothesis that the function of the endocannabinoid system is altered in FD patients.

In some embodiments, MAGL inhibitors described herein have efficacy in treatment of functional dyspepsia. In some embodiments, disclosed herein is a method of treating functional dyspepsia in a patient in need thereof, comprising administering to the patient a therapeutically effective amount of Compound 1, Compound 2, Compound 3, Compound 4, Compound 5, or Compound 6 described herein.

Inflammatory Bowel Disease

Inflammatory bowel disease (IBD) involves chronic inflammation of all or part of the digestive tract. IBD primarily includes ulcerative colitis and Crohn's disease. Both usually involve severe diarrhea, pain, fatigue and weight loss. IBD can be debilitating and sometimes leads to life-threatening complications. Third party data showed that MAGL inhibition was protective in a mouse model of IBD.

In some embodiments, MAGL inhibitors described herein have efficacy in treatment of inflammatory bowel disease. In some embodiments, disclosed herein is a method of treating inflammatory bowel disease in a patient in need thereof, comprising administering to the patient a therapeutically effective amount of Compound 1, Compound 2, Compound 3, Compound 4, Compound 5, or Compound 6 described herein.

Skeletal Muscle Contusion

Skeletal muscle contusion indicates a direct, blunt, compressive force to a muscle. Contusions are one of the most common sports-related injuries. The severity of contusions ranges from simple skin contusions to muscle and bone contusions to internal organ contusions. In third party data, MAGL inhibition demonstrated anti-inflammatory effects in a rat skeletal muscle contusion model.

In some embodiments, MAGL inhibitors described herein have efficacy in treatment of skeletal muscle contusion. In some embodiments, disclosed herein is a method of treating a skeletal muscle contusion in a patient in need thereof, comprising administering to the patient a therapeutically effective amount of Compound 1, Compound 2, Compound 3, Compound 4, Compound 5, or Compound 6 described herein.

In another embodiment is a method of treating a disease or disorder in a patient comprising administering to the patient in need thereof a therapeutically effective amount of Compound 1, Compound 2, Compound 3, Compound 4, Compound 5, or Compound 6 described herein, wherein the disease or disorder is selected from the group consisting of epilepsy/seizure disorder, multiple sclerosis, neuromyelitis optica (NMO), Tourette syndrome, Alzheimer's disease, and abdominal pain associated with irritable bowel syndrome. In another embodiment is a method of treating epilepsy/seizure disorder in a patient comprising administering to the patient in need thereof a therapeutically effective amount of Compound 1, Compound 2, Compound 3, Compound 4, Compound 5, or Compound 6 described herein. In another embodiment is a method of treating multiple sclerosis in a patient comprising administering to the patient in need thereof a therapeutically effective amount of Compound 1, Compound 2, Compound 3, Compound 4, Compound 5, or Compound 6 described herein. In another embodiment is a method of treating neuromyelitis optica (NMO) in a patient comprising administering to the patient in need thereof a therapeutically effective amount of Compound 1, Compound 2, Compound 3, Compound 4, Compound 5, or Compound 6 described herein. In another embodiment is a method of treating Tourette syndrome in a patient comprising administering to the patient in need thereof a therapeutically effective amount of Compound 1, Compound 2, Compound 3, Compound 4, Compound 5, or Compound 6 described herein. In another embodiment is a method of treating Alzheimer's disease in a patient comprising administering to the patient in need thereof a therapeutically effective amount of Compound 1, Compound 2, Compound 3, Compound 4, Compound 5, or Compound 6 described herein. In another embodiment is a method of treating abdominal pain associated with irritable bowel syndrome in a patient comprising administering to the patient in need thereof a therapeutically effective amount of Compound 1, Compound 2, Compound 3, Compound 4, Compound 5, or Compound 6 described herein.

In another embodiment is a method of treating acute pain, inflammatory pain, cancer pain, pain caused by peripheral neuropathy, central pain, fibromyalgia, migraine, vasoocclusive painful crises in sickle cell disease, functional chest pain, rheumatoid arthritis, osteoarthritis, functional dyspepsia, or spasticity, pain, sleep disturbance, or bladder dysfunction associated with multiple sclerosis, in a patient in need thereof comprising administering to the patient a therapeutically effective amount of Compound 1, Compound 2, Compound 3, Compound 4, Compound 5, or Compound 6 described herein.

Tourette Syndrome and Chronic Motor or Vocal Tic Disorders

Tourette syndrome (TS) is a neurodevelopmental condition characterized by chronic motor and vocal tics with an onset before 18 years of age. Tics are rapid, recurrent, purposeless movements or vocalizations. Persistent Motor or Vocal Tic Disorder are two recognized syndromes characterized by isolated motor or vocal tics, respectively. In other aspects, the conditions of Persistent Motor or Vocal Tic Disorder are similar to TS.

TS is largely considered to be a disease of childhood, with onset around 5 years of age. Tics typically increase in severity until mid-teens and then decline in late adolescence and early adult life. An objective re-examination of the persistency of tics into adulthood indicated that 90% of adults diagnosed as children with TS still had tics.

TS is highly heritable with variable expression. Males are more commonly affected than females, with the male-to-female ratio between three and four to one. TS frequently occurs together with attention deficit hyperactivity disorder (ADHD) and obsessive-compulsive disorder (OCD). The impact of TS is substantial, with a decreased quality of life often associated with unemployment, underachievement, increased tic severity, the presence of co-morbidities such as OCD, ADHD, anxiety and depression.

Third-party quantitative imaging studies in TS have shown a reduction in the volume of the caudate nucleus and thinning of sensorimotor cortices across children and adults. These observations suggest that cortical motor regions and basal ganglia dysfunction are causally related to TS. This hypothesis is supported by the involvement of basal ganglia in selecting or suppressing motor behaviors including routine behaviors or habits. The caudate is heavily innervated by dopaminergic projections from the substantia nigra, which may relate to the clinical utility of dopaminergic antagonists in reducing tic severity in TS. The involvement of the endocannabinoid (eCB) system in suppressing basal ganglia dopaminergic transmission suggests a rationale for manipulation of this receptor system for therapeutic gain in TS. Several third-party studies describe improvement in tic symptoms with *cannabis* or THC administration.

In some embodiments, MAGL inhibitors described herein have efficacy in treatment of Tourette Syndrome, Persistent Motor Tic Disorder, and Persistent Vocal Tic Disorder. In some embodiments, disclosed herein is a method of treating Tourette Syndrome in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating Tourette Syndrome in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating Persistent Motor Tic Disorder in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating Persistent Motor Tic Disorder in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating Persistent Vocal Tic Disorder in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating Persistent Vocal Tic Disorder in a patient in need thereof, comprising administering to the patient a therapeutically effective amount of Compound 1, Compound 2, Compound 3, Compound 4, Compound 5, or Compound 6 described herein.

Attention Deficit and Hyperactivity Disorder (ADHD)

ADHD is a chronic mental health condition with inattention, hyperactivity and impulsive behavior that occur in multiple settings and affect function in academic, social or occupational activities. Symptoms start in childhood and may persist into adulthood. It is estimated that from 8 to 11% of US school age children have ADHD and 4% of US adults have adult ADHD. Diagnosis can be made according to criteria in the Diagnostic and Statistical Manual of Mental Disorders, Version 5. Target symptoms can be monitored through ADHD-specific rating scales.

Adults with ADHD often report an improvement in symptoms when using *cannabis* with some reporting a preference towards *cannabis* over their ADHD stimulant medication. A third-party study of ADHD patients resistant to numerous pharmacological treatments describe improvement in ADHD symptoms with smoked *cannabis*, particularly an improvement in concentration, impulsivity and sleep. Another third-party study noted improvement attention associated with driving after oral administration of THC. In addition, patients with Tourette Syndrome frequently have ADHD as a comorbid condition.

In some embodiments, MAGL inhibitors described herein have efficacy in treatment of attention deficit and hyperactivity disorder. In some embodiments, disclosed herein is a method of treating attention deficit and hyperactivity disorder in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating attention deficit and hyperactivity disorder in a patient in need thereof, comprising administering to the patient a therapeutically effective amount of Compound 1, Compound 2, Compound 3, Compound 4, Compound 5, or Compound 6 described herein.

Obsessive-Compulsive Disorder (OCD)

Obsessive-compulsive disorder (OCD) is a chronic mental health condition characterized by recurrent intrusive thoughts, images, or urges (obsessions) that typically cause anxiety or distress, and by repetitive mental or behavioral acts (compulsions) that the individual feels driven to perform. OCD typically starts in adolescence, persists throughout a person's life, and produces substantial impairment in functioning due to the severe and chronic nature of the illness. A lifetime prevalence of 2% is estimated in the US. Diagnosis can be made according to criteria in the Diagnostic and Statistical Manual of Mental Disorders, Version 5. Target symptoms can be monitored through OCD-specific rating scales. Numerous lines of evidence suggest the cortico-striato-thalamo-cortical circuits to the pathophysiology of OCD. Patients with OCD frequently have the diagnoses of an anxiety disorder. Treatments targeted towards anxiety are often considered for OCD treatment.

A rodent model of repetitive behavior pertinent to anxiety disorders identified that both THC and an MAGL inhibitor decreased repetitive behavior, but only the MAGL inhibitor showed no decrease in locomotor behavior. The effects were mediated by the CB1 receptor. In addition, third-party case reports of adults with refractive obsessive compulsive disorder have described benefit with oral THC. A controlled trial of oral THC in adults with Tourette Syndrome, often accompanied by comorbid OCD, identified improvements in obsessive compulsive behavior.

In some embodiments, MAGL inhibitors described herein have efficacy in treatment of obsessive-compulsive disorder. In some embodiments, disclosed herein is a method of treating obsessive-compulsive disorder in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating obsessive-compulsive disorder in a patient in need thereof, comprising administering to the patient a therapeutically effective amount of Compound 1, Compound 2, Compound 3, Compound 4, Compound 5, or Compound 6 described herein.

Trichtillomania

Trichtillomania is characterized by repetitive pulling out of one's hair leading to hair loss and functional impairment. This hair pulling disorder is relatively common and is associated with social disruption. Overlap with Tourette's syndrome has been suggested as both diagnostic groups are characterized by motor impulses that are difficult to suppress. In a third-party study, oral THC reduced symptoms of trichotillomania in an open label clinical study, indicating involvement of the endocannabinoid pathway.

In some embodiments, MAGL inhibitors described herein have efficacy in treatment of trichotillomania. In some embodiments, disclosed herein is a method of treating trichotillomania in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating trichotillomania in a patient in need thereof, comprising administering to the patient a therapeutically effective amount of Compound 1, Compound 2, Compound 3, Compound 4, Compound 5, or Compound 6 described herein.

Trigeminal Neuralgia and Glossopharyngeal Neuralgia

An uncommon form of chronic neuropathic pain is trigeminal neuralgia or glossopharyngeal neuralgia. Trigeminal neuralgia (TN) or tic douloureux is characterized by recurrent, brief episodes of unilateral pains in the distribution of one or more divisions of the fifth cranial (trigeminal) nerve or ninth or tenth cranial (glossopharyngeal) nerve. Many cases are caused by vascular compression of the nerve leading to symptoms. Other causes may be infection (e.g. herpes zoster), after trauma, or due to a tumor. Demyelination lesions, such as those found in multiple sclerosis, may also cause trigeminal neuralgia by establishing ectopic nerve impulse generation in the brainstem.

TG is considered one of the most painful afflictions of man. Third party data suggests that refractory trigeminal neuralgia is responsive to *cannabis* based medicine.

In some embodiments, MAGL inhibitors described herein have efficacy in treatment of trigeminal neuralgia or glossopharyngeal neuralgia. In some embodiments, disclosed herein is a method of treating trigeminal neuralgia in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating trigeminal neuralgia in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating glossopharyngeal neuralgia in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating glossophyryngeal neuralgia in a patient in need thereof, comprising administering to the patient a therapeutically effective amount of Compound 1, Compound 2, Compound 3, Compound 4, Compound 5, or Compound 6 described herein.

Traumatic Brain Injury (TBI)

Traumatic brain injury (TBI) is a leading cause of death in North America for younger than 45. Survivors may live with significant disabilities, resulting in major socioeconomic burden.

The pathophysiology of TBI-related brain injury is divided into two separate concepts of primary brain injury and secondary brain injury. The acute brain damage after traumatic brain injury TBI results from primary injury, which is the result of the external mechanical force leading to contusion, laceration, and coagulopathy.

Secondary brain injury immediately follows the primary injury, which is mediated with a complex cascade of molecular, cellular and immune responses, resulting in neuroinflammation, excitotoxicity, oxidative stress, disruption of calcium homeostasis, mitochondrial dysfunction, neuronal injury, and neuronal death. Repetitive bouts of mild TBI are found in military combatants and sporting events, and can lead to chronic traumatic encephalopathy or 'dementia pugilistica'. Chronic traumatic encephalopathy (CTE) is clinically marked by memory impairment, emotional lability, personality changes and may eventually progress to dementia. Pathologically, these changes are characterized by atrophy, deposits of abnormal proteins composed of beta-amyloid, phosphorylated tau and transactivation response DNA-binding protein 43 (TDP-43). Similar pathological changes may be seen years after a single episode of TBI. Interruption of the process of secondary brain injury has been the focus of neuroprotective treatments to prevent the consequences of TBI.

In the responses to secondary damage, the inflammatory response associated with other processes likely plays a key role in causing neuropathology following TBI. Inflammation has been recognized to be one of the important hallmarks in TBI. Proinflammatory markers such as cytokines interleukin (IL)-1$\beta$, IL-6, and tumor necrosis factor alpha (TNF$\alpha$), and chemokines released from activated astroglial cells and infiltrated leukocytes in the brain and cerebrospinal fluid are robustly elevated after TBI, and may be correlated with the outcome. Histological changes found in the chronic state demonstrate neurofibrillary tangles and aggregates of tau protein. Chronic traumatic encephalopathy is now considered a 'tauopathy', with histological similarity to features observed in other degenerating diseases with aggregates of tau protein. Appropriate and timely intervention during this critical window following the primary injury after TBI may significantly reduce secondary brain damage and eventually prevent occurrence of CTE.

Third-party data showed that MAGL inhibition reduced widespread neuroinflammation in several animal models of AD. The action of an MAGL inhibitor was tested in valid mouse model of repeated mild closed head injury. This model showed impairment in neurological function of the animals, including tests of special learning and memory. In other third-party data, a MAGL inhibitor also improved cognitive function, and reduced neuroinflammation, neurodegeneration, phospho-tau accumulation and TDP-43 aggregates in diverse brain regions.

In some embodiments, MAGL inhibitors described herein have efficacy in treatment of traumatic brain injury. In some embodiments, disclosed herein is a method of treating traumatic brain injury in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating traumatic brain injury in a patient in need thereof, comprising administering to the patient a therapeutically effective amount of Compound 1, Compound 2, Compound 3, Compound 4, Compound 5, or Compound 6 described herein.

Alzheimer's Disease

Alzheimer's Disease (AD) is often categorized as a secondary tauopathy along with chronic traumatic encephalopathy caused by traumatic brain injury. The pathological hallmark of neurofibrillary tangles in AD are composed of hyperphosphorylated tau protein which inhibits microtubule function. Extracts of mutant tau protein into mice lead to spread of tau pathology to other regions of the brain. There are multiple approaches to control tau hyperphosphorylation in clinical trial for AD. These include passive and active immunization against phospho-tau, inhibitors of tau kinases, inhibition of O-glcNAcation and small molecules that can disaggregate tau filaments and tangles.

Third-party data has shown MAGL inhibition to reduce microglial activation, neurodegeneration and behavioral abnormalities in these mice. Similar benefits of MAGL inhibition were observed in a distinct genetic mouse model of AD (PS 1/APP⁺).

In some embodiments, MAGL inhibitors described herein have efficacy in treatment of cognitive decline associated with Alzheimer's Disease. In some embodiments, disclosed herein is a method of treating cognitive decline associated with Alzheimer's Disease in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating cognitive decline associated with Alzheimer's Disease in a patient in need thereof, comprising administering to the patient a therapeutically effective amount of Compound 1, Compound 2, Compound 3, Compound 4, Compound 5, or Compound 6 described herein.

Primary Tauopathies

Primary tauopathies include progressive supranuclear palsy (PSP), corticobasal degeneration and frontotemporal dementia (FTD). Secondary tauopathies include chronic traumatic encephalopathy and Alzheimer's Disease.

Frontotemporal dementia (FTD) is a clinically and neuropathologically diverse disorder characterized by disturbances in behavior personality and language. In patients younger than 65, it is an equally common cause of dementia as Alzheimer's Disease. Degeneration of the frontal and temporal lobes occurs, and correlates relatively well with the clinical syndrome, but not the pathological subtype. FTD is an umbrella term including a clinical spectrum includes behavioral variant FTD (bvFTD) compromising 50% of cases, and three forms of primary progressive aphasia distinguished by the type of language impairment.

Frontotemporal lobar degeneration (FTLD) is the pathological diagnosis associated with the clinical spectrum. Atrophy and neuronal loss, myelin loss and gliosis are seen in the frontal and temporal lobes. The characteristic pathological feature in FTLD the presence of abnormal intraneuronal and glial protein inclusions consisting of aggregates of hyperphosphorylated tau or the transactivation response DNA binding protein, TDP-43, or FUS proteinopathy.

Progressive Supranuclear Palsy (PSP) is an uncommon neurodegenerative motor syndrome that has some features of parkinsonism (bradykinesia, rigidity and postural instability). PSP consists of motor and cognitive changes. The motor aspects include dysphagia, rigidity, axial dystonia, a characteristic gait and falls. One unique motor feature is a supranuclear ophthalmoplegia (weakness in vertical conjugate eye movements) that manifests as a characteristic facial appearance of constant surprise. Cognitive changes similar to that of bvFTD occur in PSP. The pathological features are neuronal loss and gliosis in the basal ganglia, cerebellum, brainstem and to lesser extent, the cortex. In third-party imaging studies, PSP patients demonstrate marked midbrain atrophy. Numerous neurochemical abnormalities have been described including reduction in acetylcholine neurons and a decrease in dopaminergic neurons projecting to the striatum. GABAergic neurons are reduced. Ultrastructural changes show phosphorylated tau aggregation in neurons (globose neurofibrillary tangles which are single straight filaments), oligodendrocytes (coiled bodies) and astrocytes (tufted astrocytes). These changes appear to damage neurons expressing several neurotransmitters. Tau protein is found at lower levels in CSF. Disease progression is rapid with patients become dependent in 3-4 years with death at 6-12 years after presentation.

In some embodiments, MAGL inhibitors described herein have efficacy in treatment of primary tauopathies. In some embodiments, MAGL inhibitors described herein have efficacy in treatment of progressive supranuclear palsym, corticobasal degeneration, or frontotemporal dementia. In some embodiments, disclosed herein is a method of treating progressive supranuclear palsy in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating progressive supranuclear palsy in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating corticobasal degeneration in a patient in need thereof, comprising administering to the patient a therapeutically effective amount of 1,1,1,3,3, 3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating corticobasal degeneration in a patient in need thereof, comprising administering to the patient a therapeutically effective amount of Compound 1, Compound 2, Compound 3, Compound 4, Compound 5, or Compound 6 described herein. In some embodiments, disclosed herein is a method of treating frontotemporal dementia in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating frontotemporal dementia in a patient in need thereof, comprising administering to the patient a therapeutically effective amount of Compound 1, Compound 2, Compound 3, Compound 4, Compound 5, or Compound 6 described herein.

Stroke

Stroke causes neuronal death when the blood supply to a portion of the brain is blocked. Ischemic stroke is more common than hemorrhagic stroke, and atherosclerosis is the most common cause of local disease within the arteries that supply the brain. Like Traumatic Brain Injury, the pathophysiology of stroke is conceptually divided into two areas, a primary area strictly dependent on the interrupted blood supply, and a secondary area of brain at risk due to the elaboration of factors due to dying neurons, activated glial and astrocytic cells, and inflammatory cellular influx.

Third-party data showed that pretreatment with an MAGL inhibitor protected hypoxic ischemic brain injury in neonatal rats. Another model of neuroprotection is to examine the effects of toxic insults to retinal ganglia cells in the eye. Retinal ganglia cells are neurons that are highly sensitive to ischemia. MAGL inhibitors elevate the endocannabinoid 2-AG which acts as an agonist on CB1 and CB2 receptors. Agonists of the CB1 receptor prevent the death of retinal ganglia cells. The physiological role of cannabinoids is to serve as a feedback mechanism of excessive neurotransmission, limiting excitatory neurotoxicity in the brain.

In some embodiments, MAGL inhibitors described herein have efficacy in improving functional outcome following stroke. In some embodiments, disclosed herein is a method of improving functional outcome following stroke in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of improving functional outcome following stroke in a patient in need thereof, comprising administering to the patient a therapeutically effective amount of Compound 1, Compound 2, Compound 3, Compound 4, Compound 5, or Compound 6 described herein.

Amyotrophic Lateral Sclerosis

Amyotrophic Lateral Sclerosis (ALS), also known as Lou Gehrig's disease, is a rapidly progressive, neurodegenerative disorder characterized by the selective loss of motor neurons in the brain and spinal cord, leading to complete paralysis and death usually within 3-5 years from diagnosis. While the majority of ALS cases are sporadic, a growing number of familial forms of the disease (~10% of total cases) are recognized, including those caused my mutations to the genes encoding superoxide dismutase-1 (SOD-1), TAR-DNA binding protein-43 (TDP-43), or FUS (fused in sarcoma) protein, as well as by a hexanucleotide repeat expansion in the non-coding region of the gene C90RF72. The disease still lacks an effective treatment for symptoms and/or disease progression. In the (G93A) SOD-1 mouse model of ALS, treatment with the exocannabinoids A9-THC, cannabinol, WIN55,212-2, or AM1241, as well as increasing endogenous cannabinoids through the genetic ablation of the endocannabinoid degrading enzyme FAAH, have all shown to significantly delay disease progression. Third-party studies of ALS patients self-medicating with *cannabis* have reported alleviation of ALS-related symptoms, including pain, cramps, spasticity and excessive drooling. Disease modifying potential in ALS has also been shown in a randomized clinical study using endpoints of death or time to tracheostomy.

In some embodiments, MAGL inhibitors described herein have efficacy in treating Amyotrophic Lateral Sclerosis (ALS) or ALS-related symptoms. In some embodiments, disclosed herein is a method of treating Amyotrophic Lateral Sclerosis (ALS) or ALS-related symptoms in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating Amyotrophic Lateral Sclerosis (ALS) or ALS-related symptoms in a patient in need thereof, comprising administering to the patient a therapeutically effective amount of Compound 1, Compound 2, Compound 3, Compound 4, Compound 5, or Compound 6 described herein.

Huntington's Disease

Huntington's Disease (HD) is a genetic, fatal, progressive neurodegenerative disorder characterized by cognitive, psychiatric, and motor disturbances. HD is caused by a polymorphic trinucleotide CAG repeat expansion in the huntingtin gene and is inherited in an autosomal dominant manner. There are approximately 30,000 people in the US presenting with the disease, with another 200,000 at risk of inheriting it. Medications for symptomatic relieve in HD are currently available but limited, and no treatment can prevent the decline associated with the disease. Third-party data has shown exogenous cannabinoids such as cannabidiol and CB1/CB2 pharmacological agonists provide neuroprotection in a variety of animal models of HD (e.g. R6/2 mice, quinolinate-lesioned mice, 3-nitropropionate- or malonate-lesioned rats).

In some embodiments, MAGL inhibitors described herein have efficacy in treating Huntington's Disease. In some embodiments, disclosed herein is a method of treating Huntington's Disease in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating Huntington's Disease in a patient in need thereof, comprising administering to the patient a therapeutically effective amount of Compound 1, Compound 2, Compound 3, Compound 4, Compound 5, or Compound 6 described herein.

Glaucoma

Glaucoma is a group of optic neuropathies characterized by selective loss of retinal ganglion cells (RGCs) and progressive optic nerve damage leading to irreversible visual field loss and blindness. Elevated intraocular eye pressure (IOP) constitutes a major risk factor for optic nerve damage in glaucoma. All currently approved glaucoma treatments work by modulating IOP without directly preventing RGC loss. Third-part data has demonstrated the IOP lowering effects of systemic and topical cannabinoid receptor agonists in humans, non-human primates, and rodents.

Increases in the endogenous cannabinoid 2-arachidonoylglycerol (2-AG) following MAGL inhibition have also been shown to similarly lower IOP in mice.

In some embodiments, MAGL inhibitors described herein have efficacy in treating glaucoma. In some embodiments, disclosed herein is a method of treating glaucoma in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating glaucoma in a patient in need thereof, comprising administering to the patient a therapeutically effective amount of Compound 1, Compound 2, Compound 3, Compound 4, Compound 5, or Compound 6 described herein.

Atopic Dermatitis

Atopic Dermatitis (AD), also known as eczema, is a common chronic inflammatory skin disorder associated with dysfunction of the body's immune system. AD affects up to 20% of children but can extend to adulthood affecting up to 3% of adults. In AD the skin becomes extremely itchy. Excessive scratching leads to redness, swelling, cracking, "weeping" clear fluid and crusting of the skin. A functional endocannabinoid signaling system is present in the skin and mediates multiple aspects of skin biology. Third-party studies indicate that CB1 and CB2 receptors are upregulated in atopic dermatitis and that the endocannabinoid system exerts a protective effect in models of skin allergy. In addition, it has been demonstrated that MAGL inhibitors can decrease MAGL activity and increase levels of 2-AG in rodent skin.

In some embodiments, MAGL inhibitors described herein have efficacy in treating atopic dermatitis. In some embodiments, disclosed herein is a method of treating atopic dermatitis in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating atopic dermatitis in a patient in need thereof, comprising administering to the patient a therapeutically effective amount of Compound 1, Compound 2, Compound 3, Compound 4, Compound 5, or Compound 6 described herein.

Pruritus

Pruritus, or itch, is an unpleasant sensation causing the desire to scratch. Pruritus is a common and troublesome symptom of many skin disorders (e.g. atopic dermatitis), but is also associated with many systemic (e.g. liver and kidney diseases), neurogenic (e.g. herpetic neuralgia, surgery, stroke) and pharmacological (opioid-induced pruritus) origins. Despite a variety of causes, pruritus is mediated by a common sensory pathway in the nervous system that is believed to be regulated by the endocannabinoid system. In third-party human studies, topical application of a potent mixed CB1 and CB2 agonist reduced histamine-induced itching. Furthermore, CB1 antagonists have been shown to promote scratching in rodents, whereas, agonists reduce pruritus in rodent models.

In some embodiments, MAGL inhibitors described herein have efficacy in treating pruritus. In some embodiments, disclosed herein is a method of treating pruritus in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating pruritus in a patient in need thereof, comprising administering to the patient a therapeutically effective amount of Compound 1, Compound 2, Compound 3, Compound 4, Compound 5, or Compound 6 described herein.

Parkinson's Disease

Parkinson's Disease (PD) is a progressive neurodegenerative disorder that affects the basal ganglia. Characteristic motor symptoms of PD include tremor, rigidity, bradykinesia and muscle stiffness. The motor symptoms of PD are caused predominantly by alterations in the substantia nigra, including death of nigral dopaminergic neurons. Current treatment of PD, such as dopamine replacement therapies, serve to alleviate symptoms, but no disease-modifying therapies are available. Exogenous cannabinoids have been found to have beneficial effects on PD symptoms. For example, in a third-party open-label observational study, smoked *cannabis* was found to impart a significant improvement in tremor, rigidity, and bradykinesia in patients with severe PD-related pain and tremor that was insufficiently controlled by current anti-Parkinson medications. Significant improvement was also observed after *cannabis* consumption on pain and sleep scores. Preclinically, exogenous cannabinoids and MAGL inhibitors produce disease-modifying protective effects in parkinsonian rodent models.

In some embodiments, MAGL inhibitors described herein have efficacy in treating Parkinson's Disease. In some embodiments, disclosed herein is a method of treating Parkinson's Disease in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of Parkinson's Disease in a patient in need thereof, comprising administering to the patient a therapeutically effective amount of Compound 1, Compound 2, Compound 3, Compound 4, Compound 5, or Compound 6 described herein.

Autism

Autism spectrum disorder (ASD) is a group of common neurodevelopmental disorders characterized by repetitive behaviors and impairments with social interaction and communication. Autism affects approximately 22 million people worldwide and approximately 1.5% of children in the United States. Symptoms vary greatly between individuals but begin in early childhood and affect daily functioning. Autism has a strong genetic link and numerous genes have been associated with the disorder, including more than 30 mutations in genes for neuroligin 1-4, which are postsynaptic cell-adhesion molecules that control synaptic properties. In third-party data of mice bearing autism-associated mutations in neuroligin-3, tonic endocannabinoid signaling is dramatically impaired leading to excessive inhibitory synaptic activity.

In some embodiments, MAGL inhibitors described herein have efficacy in treating autism. In some embodiments, disclosed herein is a method of treating autism in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating autism in a patient in need thereof, comprising administering to the patient a therapeutically effective amount of Compound 1, Compound 2, Compound 3, Compound 4, Compound 5, or Compound 6 described herein.

Opioid-Sparin in Pain

The clinical use of opioid analgesics for the treatment of pain is associated with serious clinical liabilities including constipation, respiratory depression, pruritis, tolerance, abuse and addiction. Abuse of prescription opioids is considered a public health crisis with an estimated 2.1 million people in the United States suffering from substance use disorders related to prescription opioid pain relievers. One strategy for reducing the negative side effects of opioids is to reduce the dose of opioid necessary to adequately control pain by combining with another antinociceptive agent.

MAGL inhibitors are efficacious as monotherapy in multiple models of pain, including models of acute, neuropathic, inflammatory and cancer pain. MAGL inhibition has also been shown to produce opioid-sparing effects preclinical pain models. In the chronic constrictive injury (CCI) neuropathic pain model in mice, combined treatment with a MAGL inhibitor and the opioid morphine resulted in synergistic improvements in efficacy compared to treatment of either compound alone. The combination of MAGL inhibition and morphine did not produce opioid-like reductions in gastric motility, produce cannabimimetic effects in the drug discrimination assay or undergo tolerance following repeat dosing.

In the formalin acute pain model in rats, MAGL inhibition synergistically potentiated the activity of the opioid morphine. In this study, doses of the MAGL inhibitor and morphine that were ineffective as monotherapy, produced significant antinociceptive effects in combination, suggesting that MAGL inhibitors allow for adequate pain relief in patients with substantially reduced opioid drug burden. Since the side effects of opioid drugs are dose dependent, in some embodiments this opioid-sparing effect reduces the acute side-effects associated with opioid analgesics, such as constipation, dizziness, constipation, sedation, and dry mouth, and reduces the potential for the emergence of the negative consequences of long-term opioid use including dependence, withdrawal and overdose death.

In some embodiments, MAGL inhibitors described herein synergistically potentiate the activity of an opioid analgesic. In some embodiments, MAGL inhibitors described herein reduce the acute side-effects associated with an opioid analgesic. In some embodiments, disclosed herein is a method of synergistically potentiating the activity of an opioid analgesic in a patient being treated with an opioid analgesic, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of synergistically potentiating the activity of an opioid analgesic in a patient being treated with an opioid analgesic, comprising administering to the patient a therapeutically effective amount of Compound 1, Compound 2, Compound 3, Compound 4, Compound 5, or Compound 6 described herein. In some embodiments, disclosed herein is a method of reducing the acute side-effects associated with an opioid analgesic in a patient being treated with an opioid analgesic, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of reducing the acute side-effects associated with an opioid analgesic in a patient being treated with an opioid analgesic, comprising administering to the patient a therapeutically effective amount of Compound 1, Compound 2, Compound 3, Compound 4, Compound 5, or Compound 6 described herein.

Dystonias

Dystonias are a heterogeneous group of movement disorders, conceptually recharacterized in the late 1980s by purported involvement of the basal ganglia and clinically characterized by sustained or intermittent muscle contractions causing abnormal, often repetitive, movements, postures, or both. Dystonic movements are typically patterned, twisting, and may be tremulous. Dystonia is often initiated or worsened by voluntary action and associated with overflow muscle activation.

Dystonias may be classified based on clinical characteristics (age at onset, body distribution, temporal pattern, coexistence of other movement disorders, and other neurologic manifestations) and etiologic characteristics (other nervous system pathology and the pattern of inheritance). Primary dystonias in children, are often systemic, and may be accompanied by other clinical features, such as spasticity or encephalopathy, and may have a genetic basis. Primary dystonias in adults are usually isolated, related to practiced activities, and more common than those of children, and are idiopathic and not progressive. Example primary isolated dystonias are blepharospasm, cervical dystonia (torticollis), and writer's cramp. There is unmet need in dystonias for oral medications that improve function.

In some embodiments, MAGL inhibitors described herein have efficacy in treating dystonia. In some embodiments, disclosed herein is a method of treating dystonia in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In some embodiments, disclosed herein is a method of treating dystonia in a patient in need thereof, comprising administering to the patient a therapeutically effective amount of Compound 1, Compound 2, Compound 3, Compound 4, Compound 5, or Compound 6 described herein.

In another embodiment is a method of treating Down's syndrome in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In another embodiment is a method of treating Down's syndrome in a patient in need thereof, comprising administering to the patient a therapeutically effective amount of Compound 1, Compound 2, Compound 3, Compound 4, Compound 5, or Compound 6 described herein.

In another embodiment is a method of lowering intraocular eye pressure (IOP) in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In another embodiment is a method of lowering intraocular eye pressure (IOP) in a patient in need thereof, comprising administering to the patient a therapeutically effective amount of Compound 1, Compound 2, Compound 3, Compound 4, Compound 5, or Compound 6 described herein. In another embodiment is a method of treating glaucoma in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In another embodiment is a method of treating glaucoma in a patient in need thereof, comprising administering to the patient a therapeutically effective amount of Compound 1, Compound 2, Compound 3, Compound 4, Compound 5, or Compound 6 described herein.

In another embodiment is a method of treating complex regional pain syndrome in a patient in need thereof, comprising administering to the patient a therapeutically effective amount of 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof. In another embodiment is a method of treating complex regional pain syndrome in a patient in need thereof, comprising administering to the patient a therapeutically effective amount of Compound 1, Compound 2, Compound 3, Compound 4, Compound 5, or Compound 6 described herein.

In certain embodiments, a disclosed compound utilized by one or more of the foregoing methods is one of the generic, subgeneric, or specific compounds described herein, such as Compound 1, Compound 2, Compound 3, Compound 4, Compound 5, or Compound 6.

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Combination Therapies

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as, conventional oral dosage forms, that are administered either simultaneously or sequentially.

For example, e.g., for contemplated treatment of pain, a disclosed compound is co-administered with another therapeutic for pain such as an opioid, a cannabinoid receptor (CB1 or CB2) modulator, a COX-2 inhibitor, acetaminophen, and/or a non-steroidal anti-inflammatory agent. Additional therapeutics e.g., for the treatment of pain that are co-administered, include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a tricyclic antidepressant, such as imipramine, amitriptyline, or desipramine. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a serotonin-norepinephrine reuptake inhibitor, such as duloxetine, milnacipran, venlafaxine, or clomipramine. In some embodiments, 1,1,1,3,3,3-hexafluoropropan-2-yl 4-(2-

(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with an alpha-2-delta inhibitor, such as gabapentin or pregabalin. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with an antiepileptic drug, such as topiramate, lamotrigine, levetiracetam, valproate, clonazepam, oxcarbazine, or carbamazepine.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with an opioid, such as morphine, codeine, oxycodone, oxymorphone, tramadol, tapentadol, methadone, or fentanyl.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with acetaminophen. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a nonsteroidal anti-inflammatory drug, such as ibuprofen, naproxen, celecoxib, or diclofenac. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a disease-modifying antirheumatic drug, such as tofacitinib, leflunomide, or methotrexate.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with exo-cannabinoids, such as oral delta-9-THC and nabiximols (Sativex).

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a muscle relaxant such as baclofen and tizanidine. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with diazepam.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a prokinetic agent, such as metoclopramide, domperidone, or itopride. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a 5-HT4 agonist, such as tegaserod or mosapride. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with buspirone.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a neuroleptic, such as pimozide, olanzapine, risperidone, or quetiapine.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a cholinesterase inhibitor, such as donepezil, rivastigmine, or galantamine. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a NMDA antagonist, such as memantine.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with dopamine replacement therapy, such as levodopa or carbidopa-levodopa. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a catechol-O-methyl transferase (COMT) inhibitor, such as tolcapone or entacapone. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a dopamine agonist, such as bromocriptine, pramipexole, or ropinirole. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a monamine oxidase (MAO) B inhibitor, such as selegiline or rasagiline. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with an anticholinergic agent, such as benztropine, trihexyphenidyl, or procyclidine.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a dopamine antagonist, such as haloperidol, pimozide, or fluphenazine. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a VMAT2 inhibitor which depletes dopamine, such as tetrabenazine. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with an alpha adrenergic agonist, such as clonidine or guanfacine.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a selective serotonin reuptake inhibitors (SSRI), such as fluoxetine, sertraline, paroxetine, citalopram or escitalopram.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a stimulant, such as methylphenidate, dextroamphetamine, or lisdexamfetamine. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with an antidepressant, such as bupropion or atomoxetine.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a serotonin 1b/1d agonist. In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a triptan, such as sumatriptan or zolmitriptan.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with a glutamate inhibitor, such as riluzole.

In some embodiments, 1,1,1,3,3,3-hexafluoropropan-2-yl 4-(2-(pyrrolidin-1-yl)-4-(trifluoromethyl)benzyl)piperazine-1-carboxylate, or a pharmaceutically acceptable salt or solvate thereof, such as Compound 1, Compound 2, Compound 3, Compound 4, Compound 5, or Compound 6 is co-administered with an H1 antihistamine, such as diphenhydramine, hydroxyzine, cetirizine, loratadine, or desloratadine.

Kits/Articles of Manufacture

For use in the therapeutic methods of use described herein, kits and articles of manufacture are also described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Packaging materials for use in packaging pharmaceutical products include, e.g., U.S. Pat. No. 5,323,907. Examples of pharmaceutical packaging materials include, but are not limited to, blister packs, bottles, tubes, bags, containers, bottles, and any packaging material suitable for a selected formulation and intended mode of administration and treatment.

In some embodiments, the compounds or compositions described herein, are presented in a package or dispenser device which may contain one or more unit dosage forms containing the active ingredient. The compound or composition described herein is packaged alone, or packaged with another compound or another ingredient or additive. In some embodiments, the package contains one or more containers filled with one or more of the ingredients of the pharmaceutical compositions. In some embodiments, the package comprises metal or plastic foil, such as a blister pack. In some embodiments, the package or dispenser device is accompanied by instructions for administration, such as instructions for administering the compounds or compositions for treating a neoplastic disease. In some embodiments, the package or dispenser is accompanied with a notice associated with the container in form prescribed by a governmental agency regulating the manufacture, use, or sale of pharmaceuticals, which notice is reflective of approval by the agency of the form of the drug for human or veterinary administration. In some embodiments, such notice, for example, is the labeling approved by the U.S. Food and Drug Administration for prescription drugs, or the approved product insert. In some embodiments, compositions include a compound described herein formulated in a compatible pharmaceutical carrier are prepared, placed in an appropriate container, and labeled for treatment of an indicated condition.

For example, the container(s) include Compound 1, Compound 2, Compound 3, Compound 4, Compound 5, or Compound 6, optionally in a composition or in combination with another agent as disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In one embodiment, compositions containing a compound provided herein formulated in a compatible pharmaceutical carrier are also prepared, placed in an appropriate container, and labeled for treatment of an indicated condition.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
t-Bu tert-butyl
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
$Et_2O$ diethyl ether
EtOH ethanol
EtOAc ethyl acetate
HPLC high performance liquid chromatography
Me methyl
MeOH methanol
MS mass spectroscopy
NMR nuclear magnetic resonance
RP-HPLC reverse phase-high pressure liquid chromatography
TFA trifluoroacetic acid
THF tetrahydrofuran
TLC thin layer chromatography

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1. Preparation of Compound 1 (Form 1)
[[Free Base]]

The preparation of Compound 1 is disclosed in WO 2013/103973, the content of which is incorporated by reference in its entirety.

Example 2. Preparation of Compound 2 (Form 1)
[[Mono-HCl]]

To Compound 1 (20.0 g) in 9 v/w of tert-butylmethyl ether was added conc. HCl (1.06 eq) at 35° C. The suspension was cooled to room temperature and the solid was collected by filtration and washed with tert-butylmethyl ether. The solid was dried to give Compound 2 (19.3 g, 90%).

Example 3. Preparation of Compound 3 (Form 1)
[[Bis-HCl]]

Compound 3 was made in a similar manner as described for Compound 2 in Example 2 except 5 equivalents of HCl were used in the procedure.

II. Characterization of Compounds

Example 1: X-ray Powder Diffraction (XRPD)

XRPD analysis was carried out on a PANalytical X'pert pro, scanning the samples between 3 and 35° 2θ. The material was gently compressed into a multi well plate with Kapton or Mylar polymer film to support the sample. The multi well plate was then loaded into a PANalytical diffractometer running in transmission mode and analyzed, using the following experimental conditions:

Raw Data Origin: XRD measurement (*.XRDML)
Scan Axis: Gonio
Start Position [° 2θ]: 3.0066
End Position [° 2θ]: 34.9866
Step Size [° 2θ]: 0.0130
Scan Step Time [s]: 18.8700
Scan Type: Continuous
PSD Mode: Scanning
PSD Length [° 2θ]: 3.35
Offset [° 2θ]: 0.0000
Divergence Slit Type: Fixed
Divergence Slit Size [° ]: 1.0000
Measurement Temperature [° C.]: 25.00
Anode Material: Cu
K-Alpha1 [Å]: 1.54060
K-Alpha2 [Å]: 1.54443
K-Beta [Å]: 1.39225
K-A2/K-A1 Ratio: 0.50000
Generator Settings: 40 mA, 40 kV
Goniometer Radius [mm]: 240.00
Dist. Focus-Diverg. Slit [mm]: 91.00
Incident Beam Monochromator: No
Spinning: No XRPD analysis (FIG. 1) of Form 1 of Compound 1 showed the free base to be crystalline.

XRPD analysis (FIG. 9) of Form 1 of Compound 2 showed this form of the mono-hydrochloride to be crystalline.

XRPD analysis (FIG. 28) of Form 2 of Compound 2 showed this form of the mono-hydrochloride to be crystalline.

XRPD analysis (FIG. 17) of Form 1 of Compound 3 showed this form of the bis-hydrochloride to be crystalline.

XRPD analysis (FIG. 30) of Form 1 of Compound 4 showed this form of the besylate to be crystalline.

XRPD analysis (FIG. 31) of Form 2 of Compound 4 showed this form of the besylate to be crystalline.

XRPD analysis (FIG. 38) of Form 1 of Compound 5 showed this form of the mesylate to be crystalline.

XRPD analysis (FIG. 42) of Form 1 of Compound 6 showed this form of the fumarate to be crystalline.

XRPD analysis (FIG. 46) of Form 2 of Compound 6 showed this form of the fumarate to be crystalline.

XRPD analysis (FIG. 49) of Form 3 of Compound 6 showed this form of the fumarate to be crystalline.

Example 2: Polarized Light Microscopy (PLM)

The presence of crystallinity (birefringence) was determined using an Olympus BX50 polarising microscope, equipped with a Motic camera and image capture software (Motic Images Plus 2.0). All images were recorded using the 20× objective lens, unless otherwise stated.

PLM analysis of Form 1 of Compound 1 showed birefringent particles of plate-like morphology.

PLM analysis of Form 1 of Compound 2 showed birefringent particles of needle/lath-like morphology.

PLM analysis of Form 2 of Compound 2 showed birefringent particles of plate-like morphology.

PLM analysis of Form 1 of Compound 3 showed birefringent particles of rod-like morphology.

PLM analysis of Form 1 of Compound 6 showed birefringent particles of plate-like morphology.

PLM analysis of Form 2 of Compound 6 showed birefringent particles of plate-like morphology.

PLM analysis of Form 3 of Compound 6 showed birefringent particles of plate-like morphology.

Example 3: Thermo-Gravimetric Analysis (TGA)

Approximately 5 mg of material was weighed into an open aluminium pan and loaded into a simultaneous thermogravimetric/differential thermal analyser (TG/DTA) and held at room temperature. The sample was then heated at a rate of 10° C./min from 25° C. to 300° C. or 20 OC to 300° C. during which time the change in sample weight was recorded along with any differential thermal events (DTA). Nitrogen was used as the purge gas, at a flow rate of 100 or 300 mL/min.

TGA (FIG. 2) of Form 1 of Compound 1 showed a very small mass loss of 0.1% up to ca. 140° C. prior to degradation. DTA showed a single endotherm with onset temperature at ca. 81.4° C.

TG/DTA (FIG. 10) of Form 1 of Compound 2 showed a small weight loss of 0.3% likely owing to residual solvent (water) loss, followed by a loss of 8.3% prior to degradation. DTA showed a broad endotherm with onset at ca. 159.4° C. The onset corresponded with the received DSC data in Example 4.

TGA (FIG. 18) of Form 1 of Compound 3 showed a loss of 1.2% (likely residual solvent/water) followed by a loss of 8.2% associated with first endotherm. DTA showed a broad endotherm, with onset at ca. 89.3° C. and a further endotherm with onset at ca. 171.9° C. 3.2% would be required for a mono-hydrate and 6.0% for loss of HCl.

TG/DTA (FIG. 44) of Form 1 of Compound 6 showed a sharp endotherm with onset at 128.1° C. and peak at 133.4° C.

TG/DTA (FIG. 48) of Form 2 of Compound 6 showed a broad thermal event with an onset at around 75° C. which corresponds to a mass loss of 8.1%.

TG/DTA (FIG. 51) of Form 3 of Compound 6 showed a broad thermal event with an onset at 106° C. which corresponds to a mass loss of 6.5%. A thermal event is seen at around 200° C. which corresponds to the sublimation of the solid resulting in complete mass loss.

Example 4: Differential Scanning Calorimetry (DSC)

Approximately 5 mg of material was weighed into an aluminium DSC pan and sealed non-hermetically with a pierced aluminium lid. The sample pan was then loaded into a Seiko DSC6200 (equipped with a cooler) cooled and held at 25° C. Once a stable heat-flow response was obtained, the sample and reference were heated to 160° C. or 175° C. or 200° C. or 205° C. or 215° C. or 220° C. at scan rate of 10° C./min and the resulting heat flow response monitored.

For Compound 1, the sample was analyzed for 1.5 cycles. Nitrogen was used as the purge gas, at a flow rate of 50 mL/min. DSC analysis (FIG. 3) of Form 1 of Compound 1 showed a sharp endotherm with onset temperature at 80.3° C.

DSC analysis (FIG. 11) of Form 1 of Compound 2 showed a sharp endotherm with an onset temperature of 181.6° C. followed by a peak at 192.6° C. This occurred at a higher temperature than by DTA and could be due to the different preparations: DSC analysis was conducted in closed pan with pin-hole (non-hermetically), while TG/DTA was carried out in an open pan environment.

Figure 12:
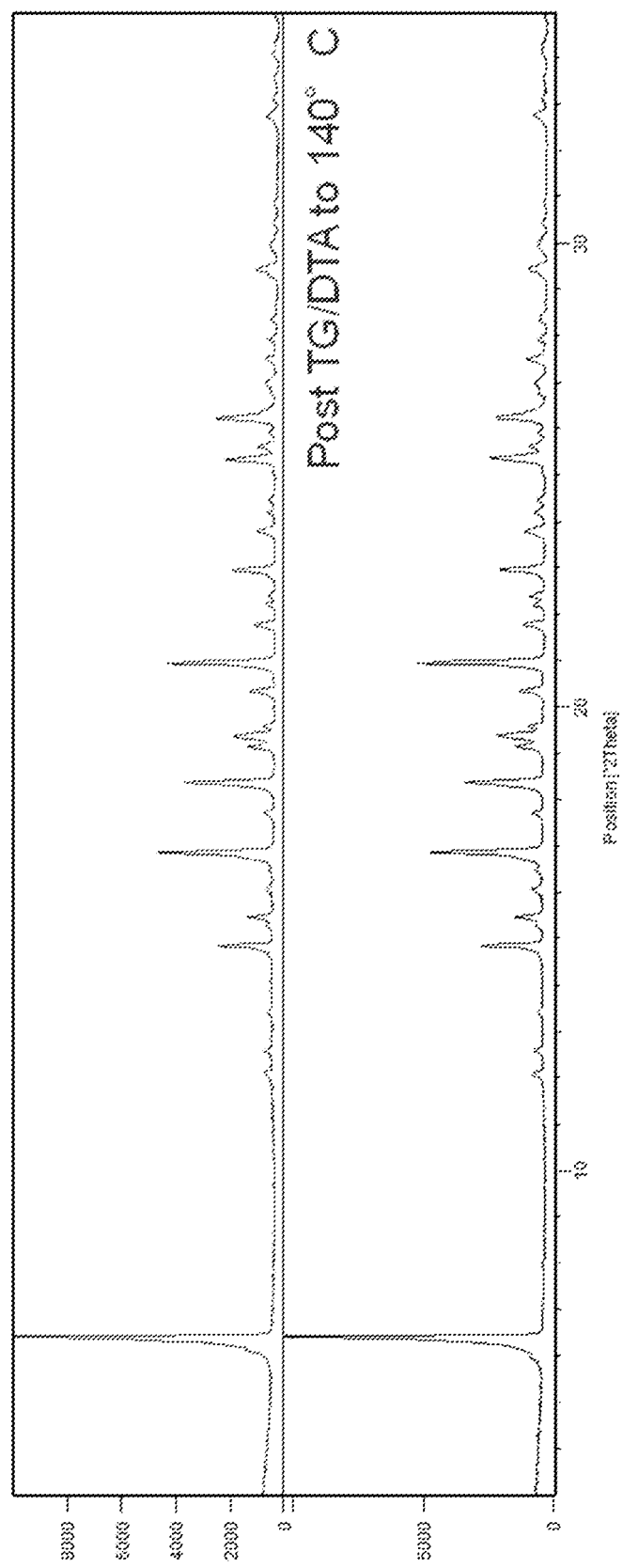
FIG. 12. Illustrates an X-ray powder diffraction (XRPD) pattern of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 1, after heating to 140° C. and cooling.

Material from Compound 2 (Form 1) was also heated to 140° C. and allowed to cool. The material was analysed by XRPD (FIG. 12), to determine any form change, which could be consistent with a solid-solid transition. The material was shown to remain unchanged.

DSC analysis (FIG. 19) of Form 1 of Compound 3 showed an endotherm with onset at 154.3° C. The data received shows values of 168.23° C. and 170.69° C. The higher events in the DSC analysis may reflect the different preparations: DSC analysis was conducted in a closed pan with pin-hole (non hermetically), while TGA was carried out in open pan.

DSC analysis (FIG. 45) of Form 1 of Compound 6 showed an endotherm with onset at 126.4° C. DSC analysis was conducted in a closed pan with pin-hole (non hermetically), while TGA was carried out in open pan.

DSC analysis (FIG. 52) of Form 3 of Compound 6 showed an endotherm with onset at 106.9° C. DSC analysis was conducted in a closed pan with pin-hole (non hermetically), while TGA was carried out in open pan.

Example 5: Gravimetric Vapor Sorption (GVS)

Approximately 10 mg of sample was placed into a mesh vapour sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion). After completion of the sorption cycle, the sample was dried using the same procedure to 0% RH, and finally taken back to the starting point of 40% RH.

The weight change during the sorption/desorption cycles were plotted, allowing for the hygroscopic nature of the sample to be determined.

Figure 4:
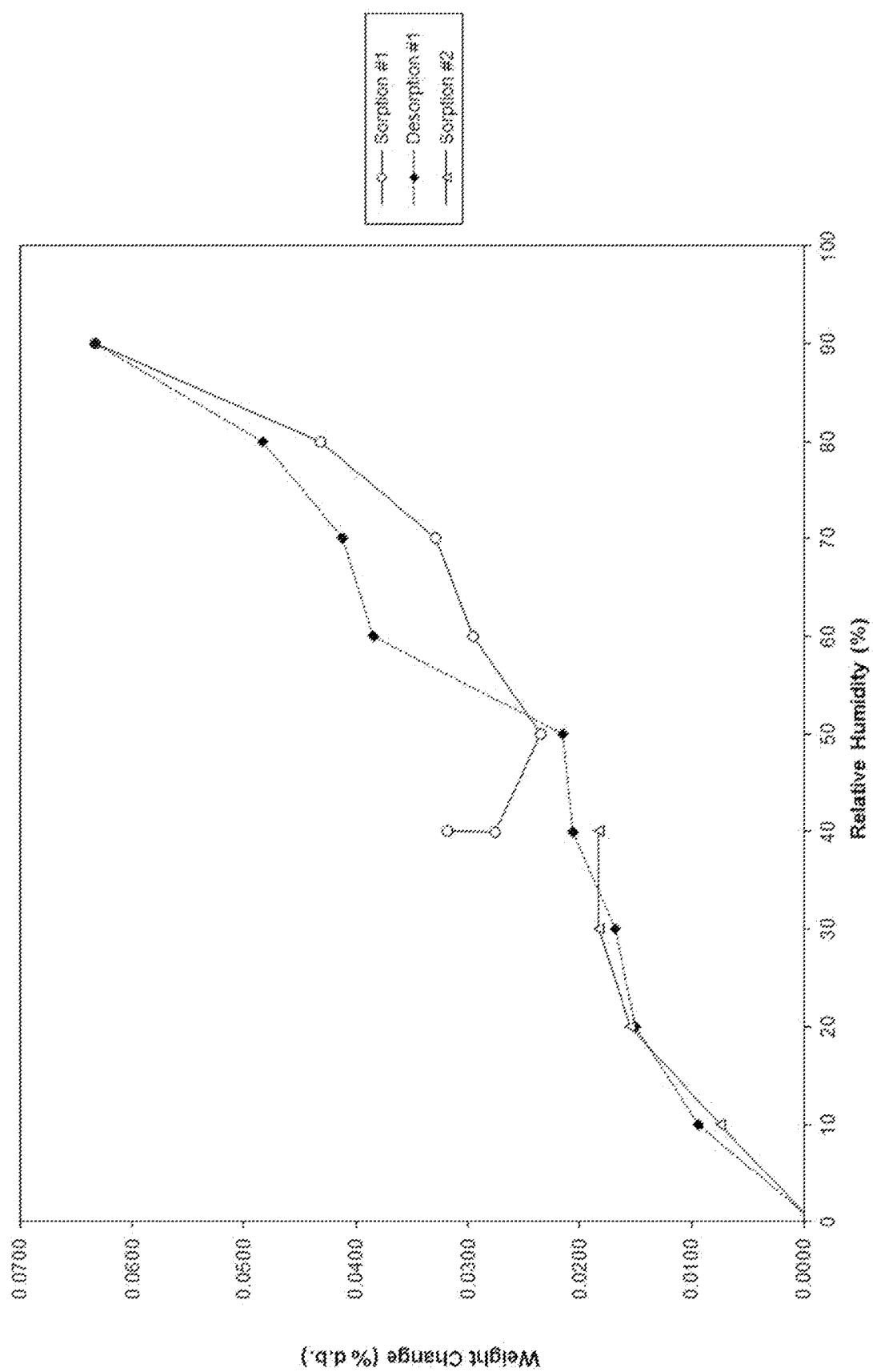
FIG. 4. Illustrates a gravimetric vapor sorption (GVS) analysis of crystalline 1,1,1,3,3,3-hexafluoropropan-2-yl 4-(2-(pyrrolidin-1-yl)-4-(trifluoromethyl)benzyl)piperazine-1-carboxylate free base.
Figure 5:
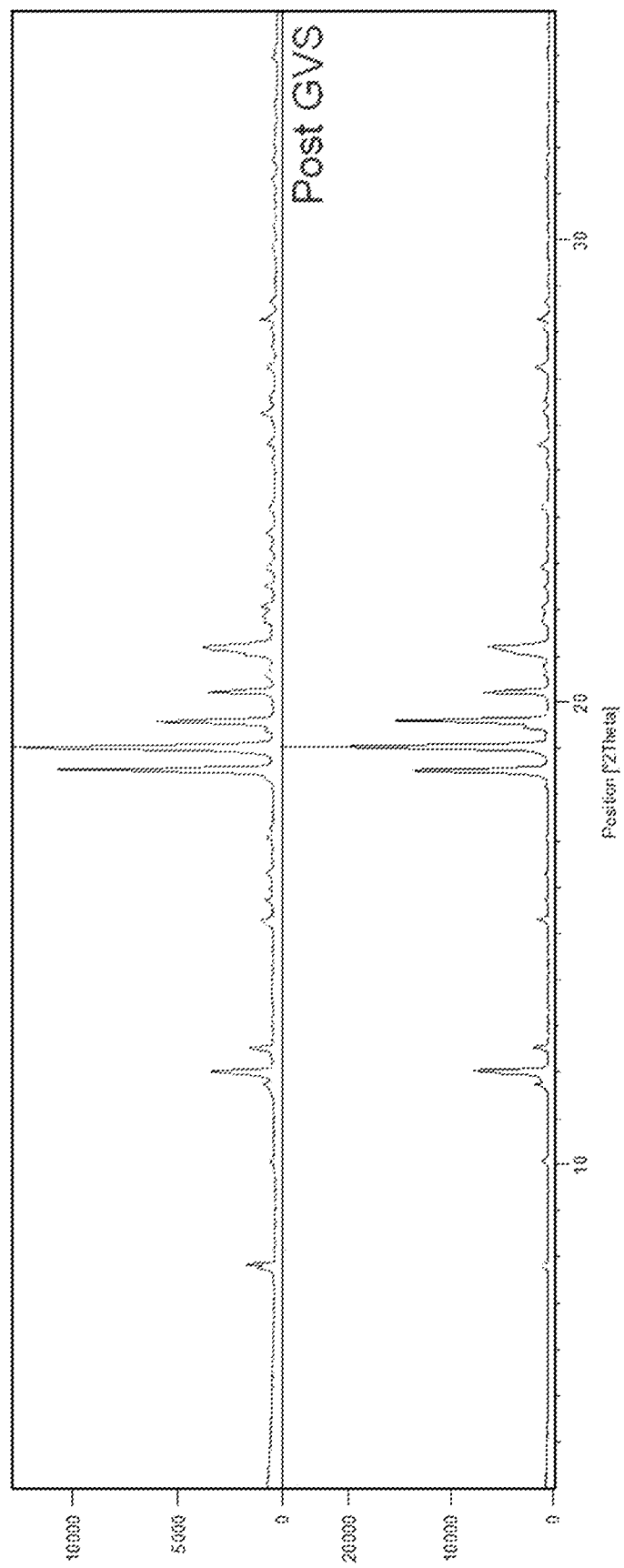
FIG. 5. Illustrates an X-ray powder diffraction (XRPD) pattern of crystalline 1,1,1,3,3,3-hexafluoropropan-2-yl 4-(2-(pyrrolidin-1-yl)-4-(trifluoromethyl)benzyl)piperazine-1-carboxylate free base pre-GVS and post-GVS.

GVS analysis (FIG. 4) of Form 1 of Compound 1 showed the free base to be very non-hygroscopic with <0.07% weight uptake at 90% RH. Post-GVS analysis by XRPD (FIG. 5) showed the material to remain unchanged, indicating high stability of this form towards extreme humidities.

Figure 13:
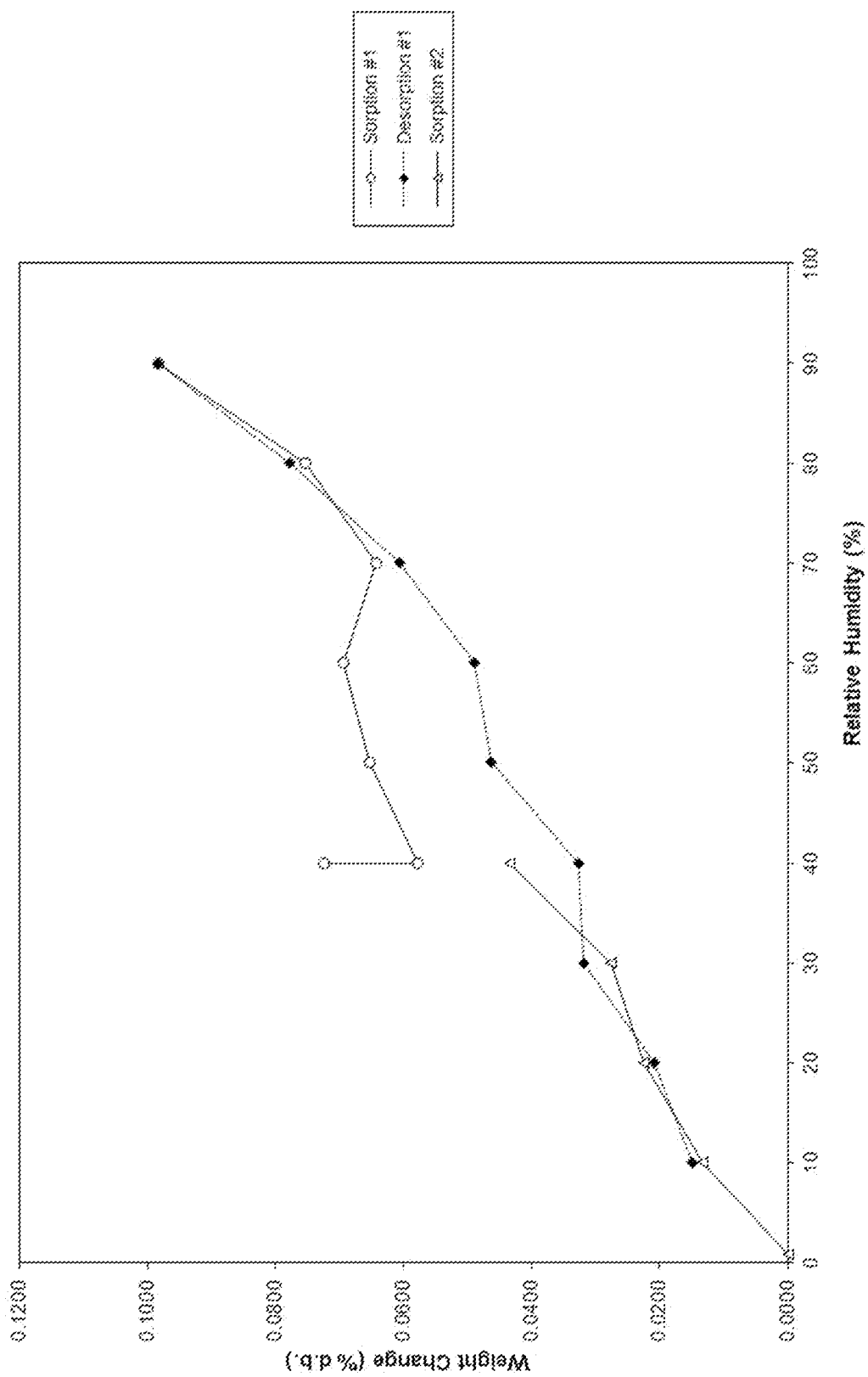
FIG. 13. Illustrates a gravimetric vapor sorption (GVS) analysis of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 1.
Figure 14:
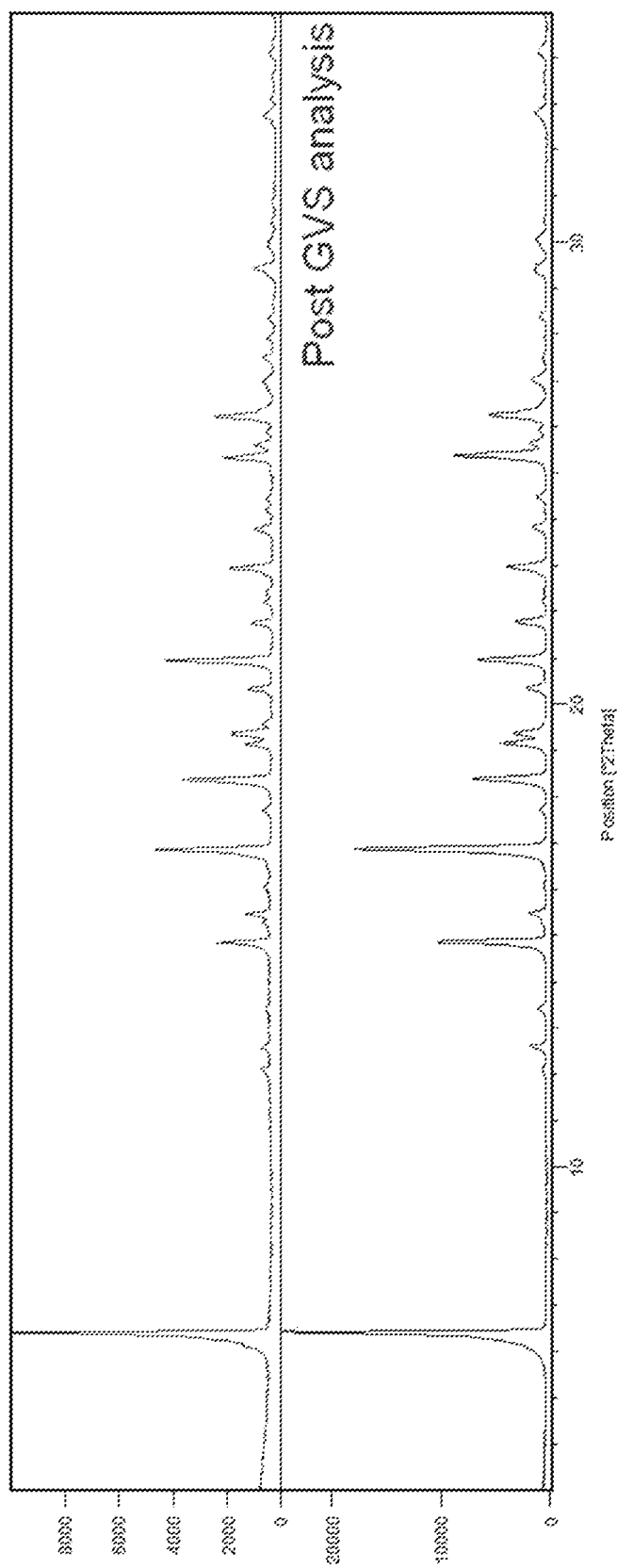
FIG. 14. Illustrates an X-ray powder diffraction (XRPD) pattern of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 1, post-GVS.

GVS analysis (FIG. 13) of Form 1 of Compound 2 showed the material to be very non-hygroscopic with <0.1% uptake at 90% RH. Post-GVS analysis by XRPD (FIG. 14) showed the material to remain unchanged, indicating high stability of this form towards extreme humidities.

Figure 20:
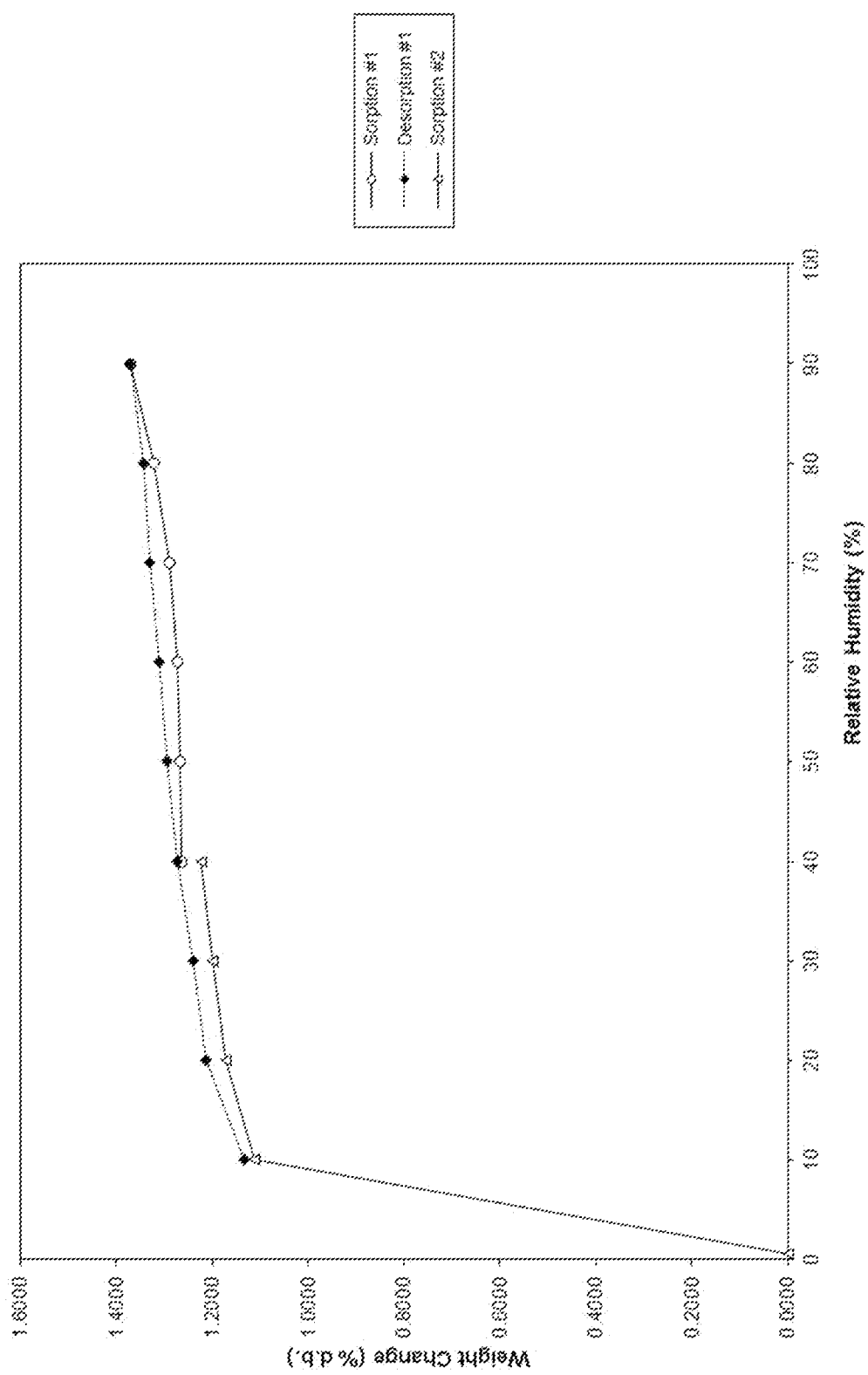
FIG. 20. Illustrates a GVS analysis of crystalline 1,1,1,3,3,3-hexafluoropropan-2-yl 4-(2-(pyrrolidin-1-yl)-4-(trifluoromethyl)benzyl)piperazine-1-carboxylate bis-HCl salt.
Figure 21:
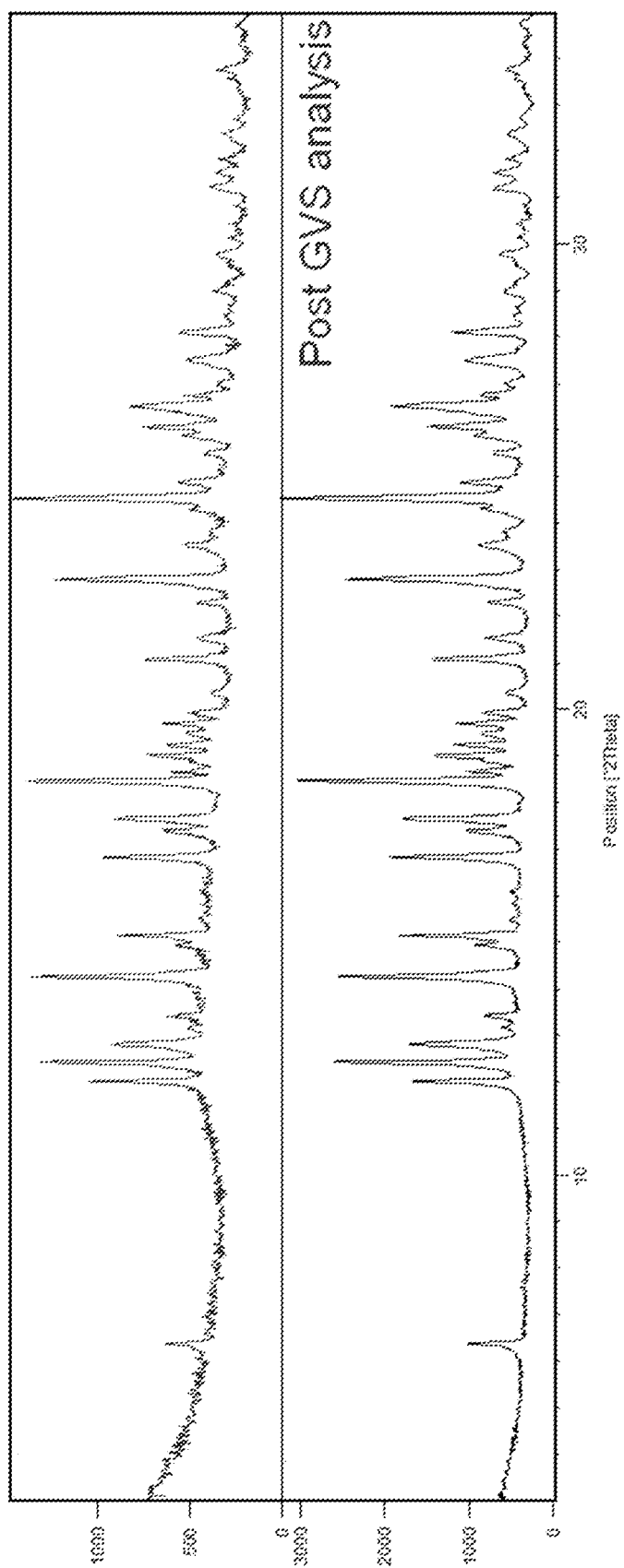
FIG. 21. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate bis-HCl salt post-GVS.

GVS analysis (FIG. 20) of Form 1 of Compound 3 showed the material to be slightly hygroscopic with 1.4% uptake at 90% RH. The large step between 0-10% RH suggests that the material could be hydrated. Post-GVS analysis by XRPD (FIG. 21) showed the material to remain unchanged.

Figure 53:
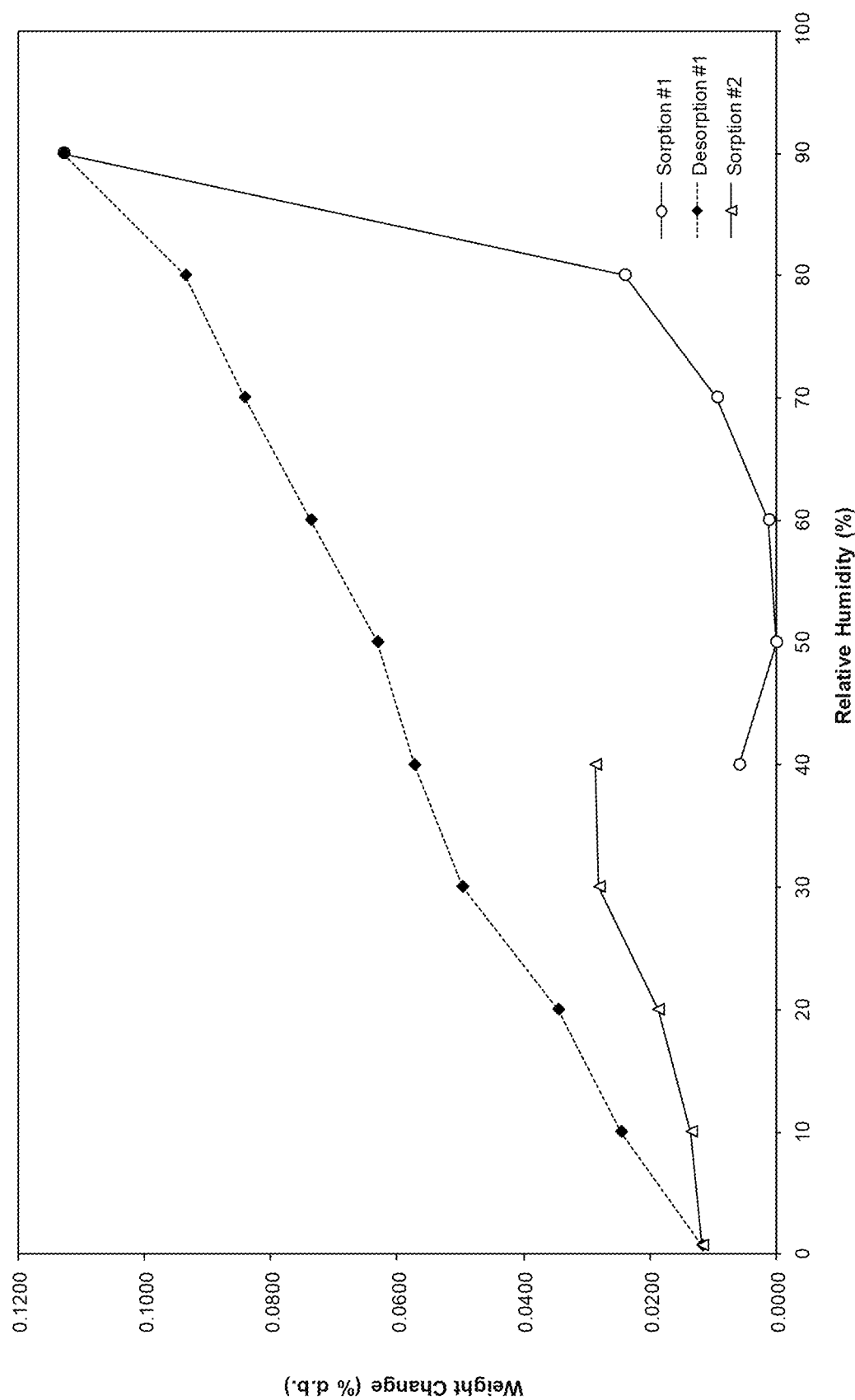
FIG. 53. Illustrates a gravimetric vapor sorption (GVS) analysis of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 1.
Figure 55:
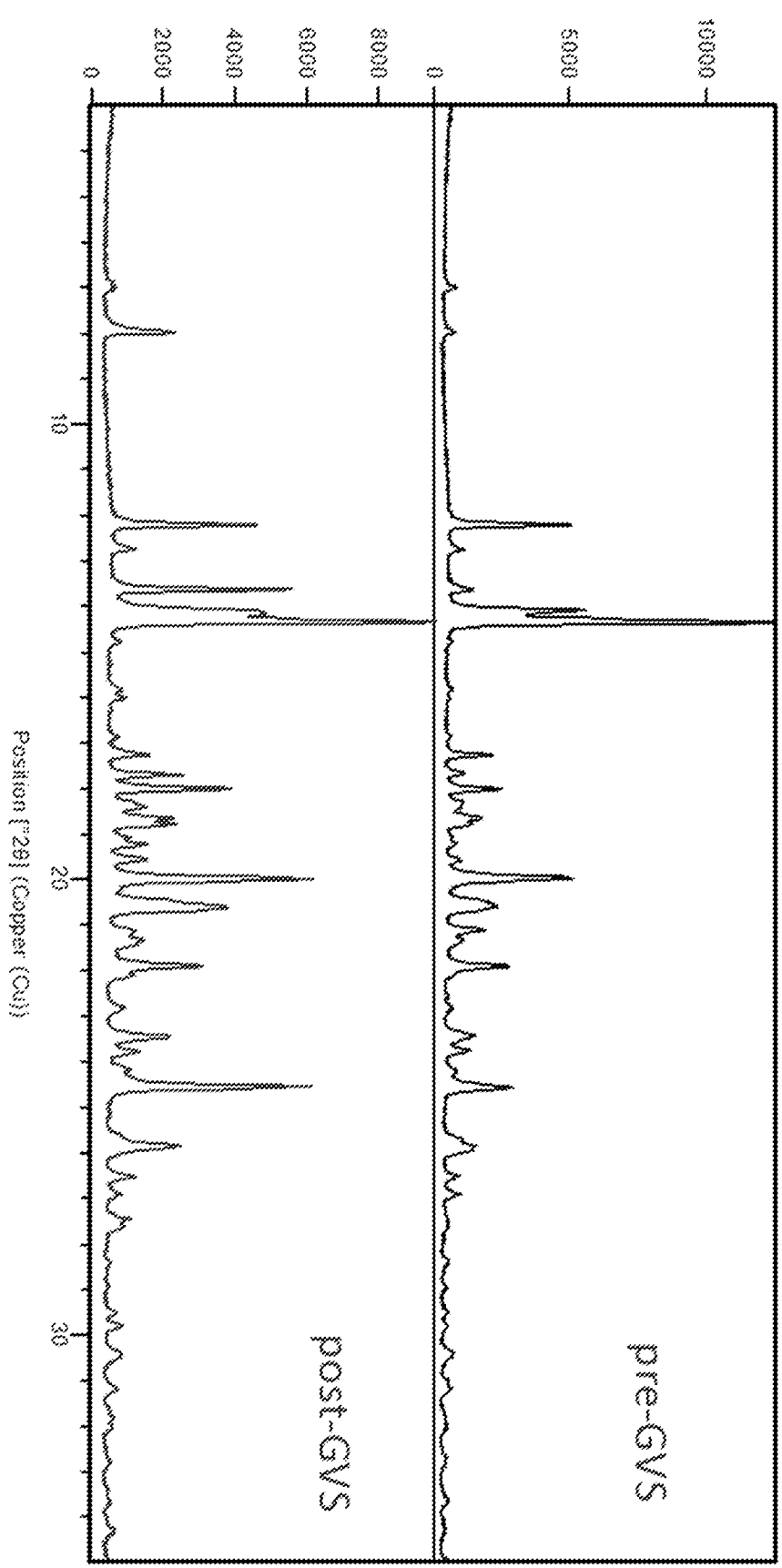
FIG. 55. Illustrates an XRPD pattern of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 1, pre-GVS and post-GVS.

GVS analysis (FIG. 53) of Form 1 of Compound 6 showed the material to non-hygroscopic with 0.11% uptake at 90% RH. Post-GVS analysis by XRPD (FIG. 55) showed the material to remain unchanged.

Figure 54:
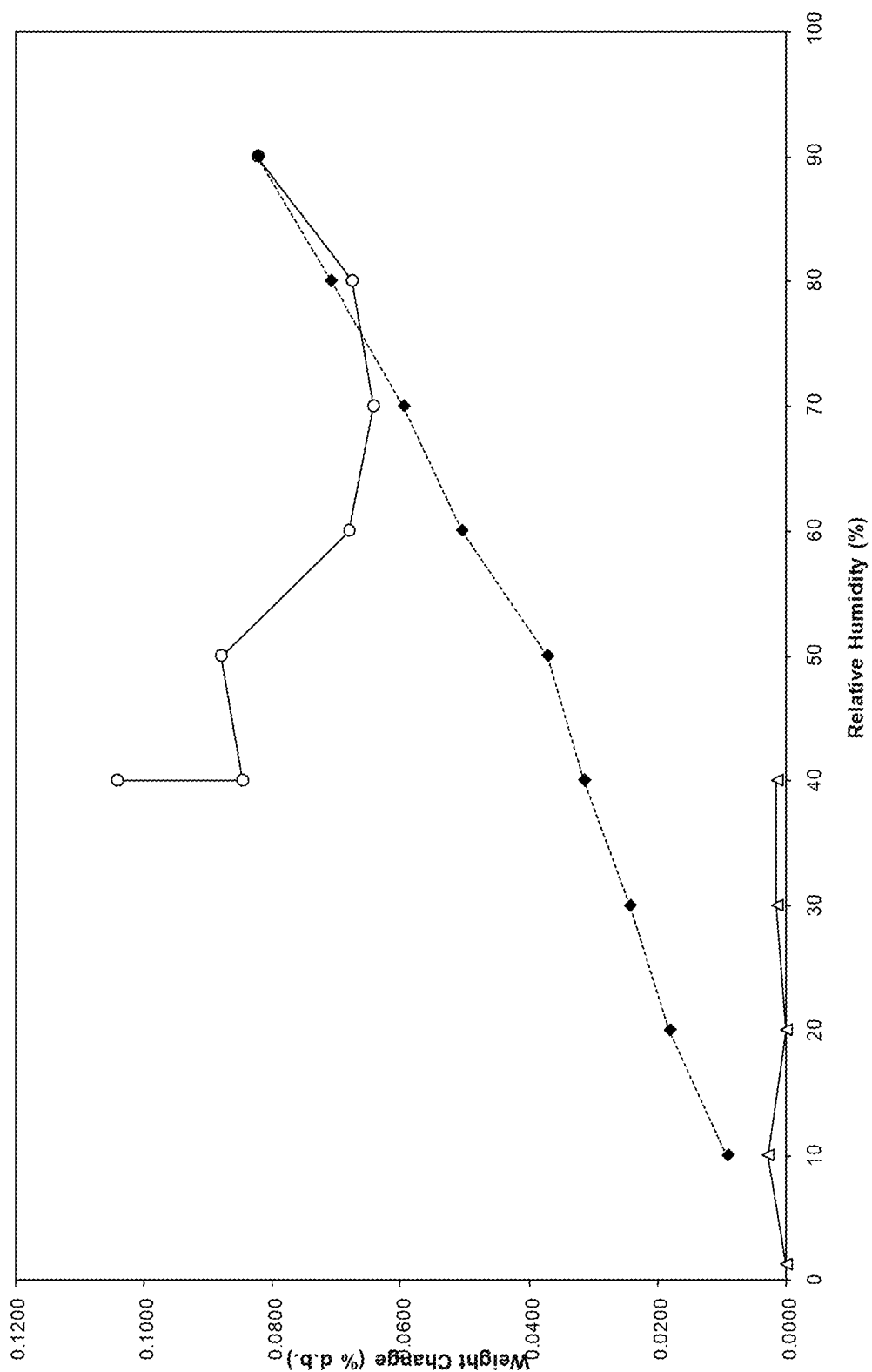
FIG. 54. Illustrates a gravimetric vapor sorption (GVS) analysis of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 3.

GVS analysis (FIG. 54) of Form 3 of Compound 6 showed the material to be non-hygroscopic with 0.08% uptake at 90% RH. Post-GVS analysis by XRPD showed minor changes, indicating the crystal form could have changed during the GVS experiment. When Form 3 was stressed at high humidity for 1 week it converted to Form 1 of Compound 6.

Example 6: Dynamic Vapor Sorption (DVS)

Approximately 10 mg of sample was placed into a mesh vapour sorption balance pan and loaded into a DVS-1 dynamic vapour sorption balance by Surface Measurement Systems. The sample was subjected to a ramping profile from 40-90% relative humidity (RH) at 10% increments, maintaining the sample at each step until a stable weight had been achieved (99.5% step completion). After completion of the sorption cycle, the sample was dried using the same procedure to 0% RH and then a second sorption cycle back to 40% RH. The weight changes during the sorption/desorption cycles were plotted, allowing for the hygroscopic nature of the sample to be determined. XRPD analysis was then carried out on any solid retained.

Example 7: Karl Fischer Coulometric Titration (KF)

Approximately 10-15 mg of solid material was accurately weighed into a vial. The solid was then manually introduced into the titration cell of a Mettler Toledo C30 Compact Titrator. The vial was back-weighed after the addition of the solid and the weight of the added solid entered on the instrument. Titration was initiated once the sample had fully dissolved in the cell. The water content was calculated automatically by the instrument as a percentage and the data printed.

KF analysis of Form 1 of Compound 2, which was carried out to compare with Form 3, calculated 1.4% water. A mono hydrate would require 3.1%. Up to ca. 0.5% can be due to introduction of the sample to the cell. This calculated value is higher than expected from TG/DTA and GVS analysis, although there is no suggestion of lattice bound water.

KF analysis of Form 1 of Compound 3 calculated 3.2% water. A mono hydrate requires 3.1%.

Example 8: Infrared Spectroscopy (IR)

Figure 6:
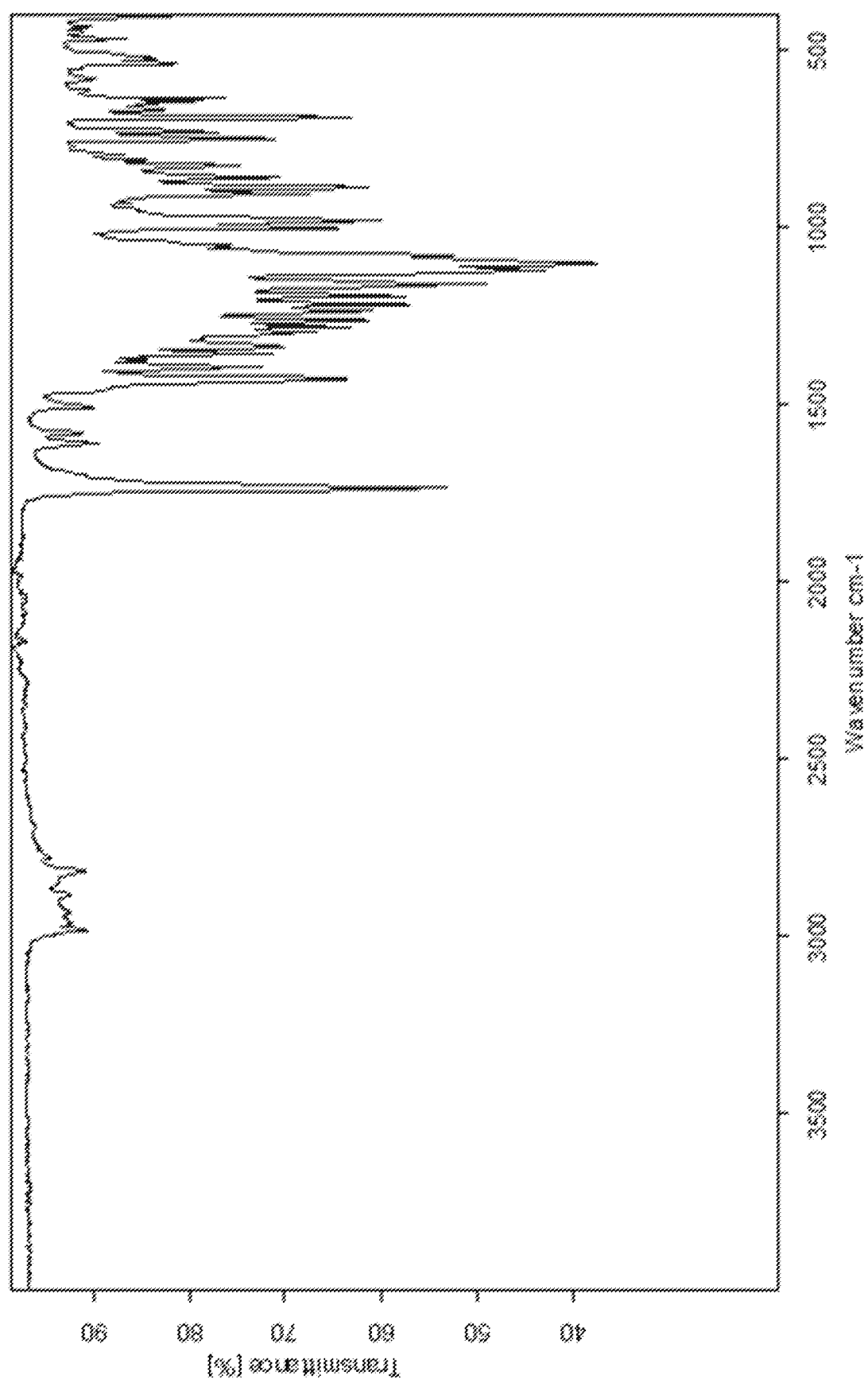
FIG. 6. Illustrates an infrared (IR) spectrum of crystalline 1,1,1,3,3,3-hexafluoropropan-2-yl 4-(2-(pyrrolidin-1-yl)-4-(trifluoromethyl)benzyl)piperazine-1-carboxylate free base.

Infrared spectroscopy was carried out on a Bruker ALPHA P spectrometer. Sufficient material was placed onto the centre of the plate of the spectrometer and the spectra were obtained using the following parameters:
Resolution: 4 $cm^{-1}$
Background Scan Time: 16 scans
Sample Scan Time: 16 scans
Data Collection: 4000 to 400 $cm^{-1}$
Result Spectrum: Transmittance
IR analysis of Compound 1 is shown in FIG. 6.

Example 9: $^1$H Nuclear Magnetic Resonance ($^1$H-NMR)

$^1$H-NMR experiments were performed on a Bruker AVA500 (frequency: 500 MHz). Experiments were performed in deuterated DMSO and each sample was prepared to ca. 10 mM concentration.

Figure 7:
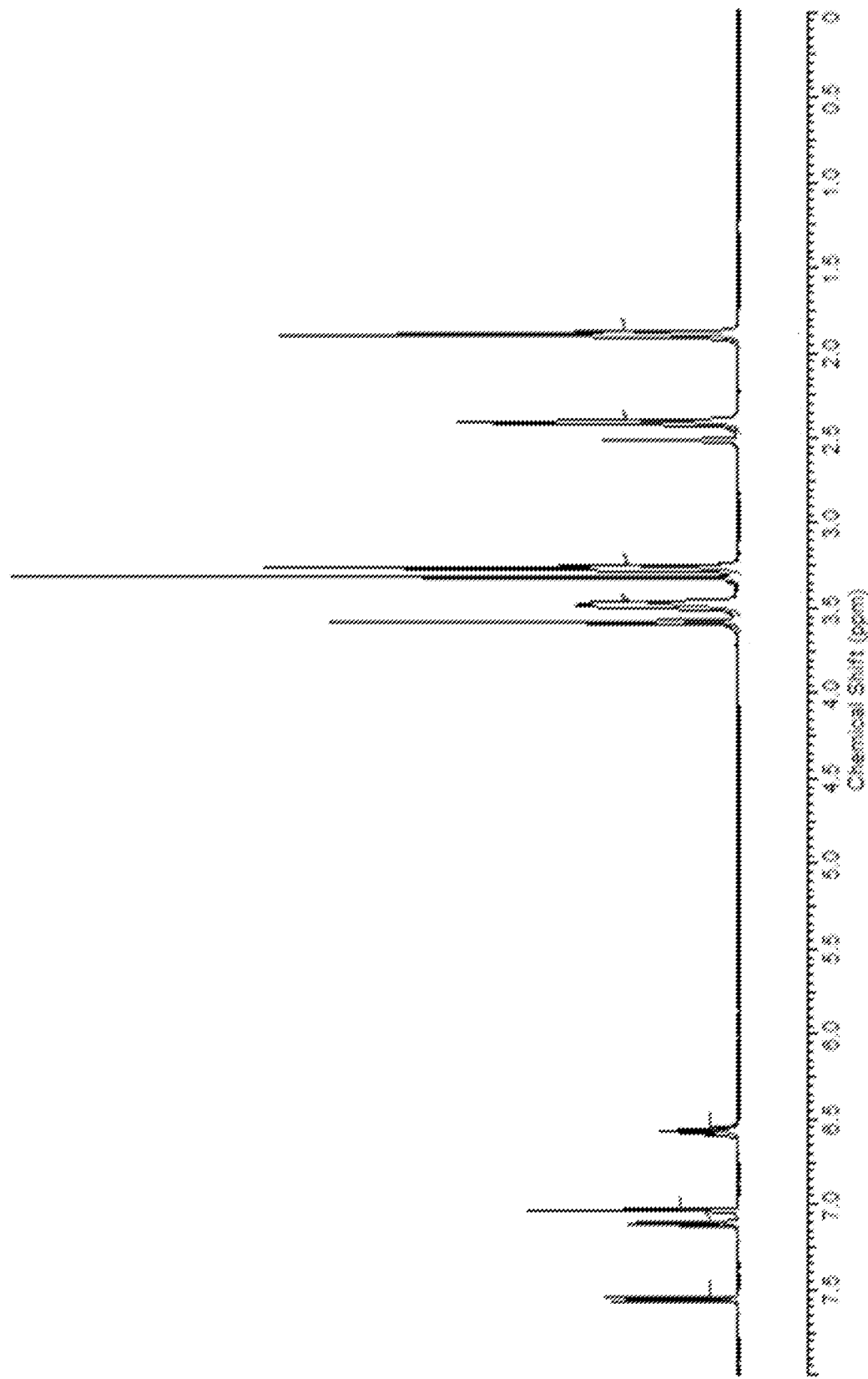
FIG. 7. Illustrates an NMR spectrum of crystalline 1,1,1,3,3,3-hexafluoropropan-2-yl 4-(2-(pyrrolidin-1-yl)-4-(trifluoromethyl)benzyl)piperazine-1-carboxylate free base.

$^1$H-NMR spectrum of Compound 1 is shown in FIG. 7. Purity is shown in Example 10. IR analysis is shown in Example 8. Further characterization by XRPD, PLM, TG/DTA, DSC, and GVS in Examples 1-5 show this sample to be Form 1 of Compound 1.

Figure 15:
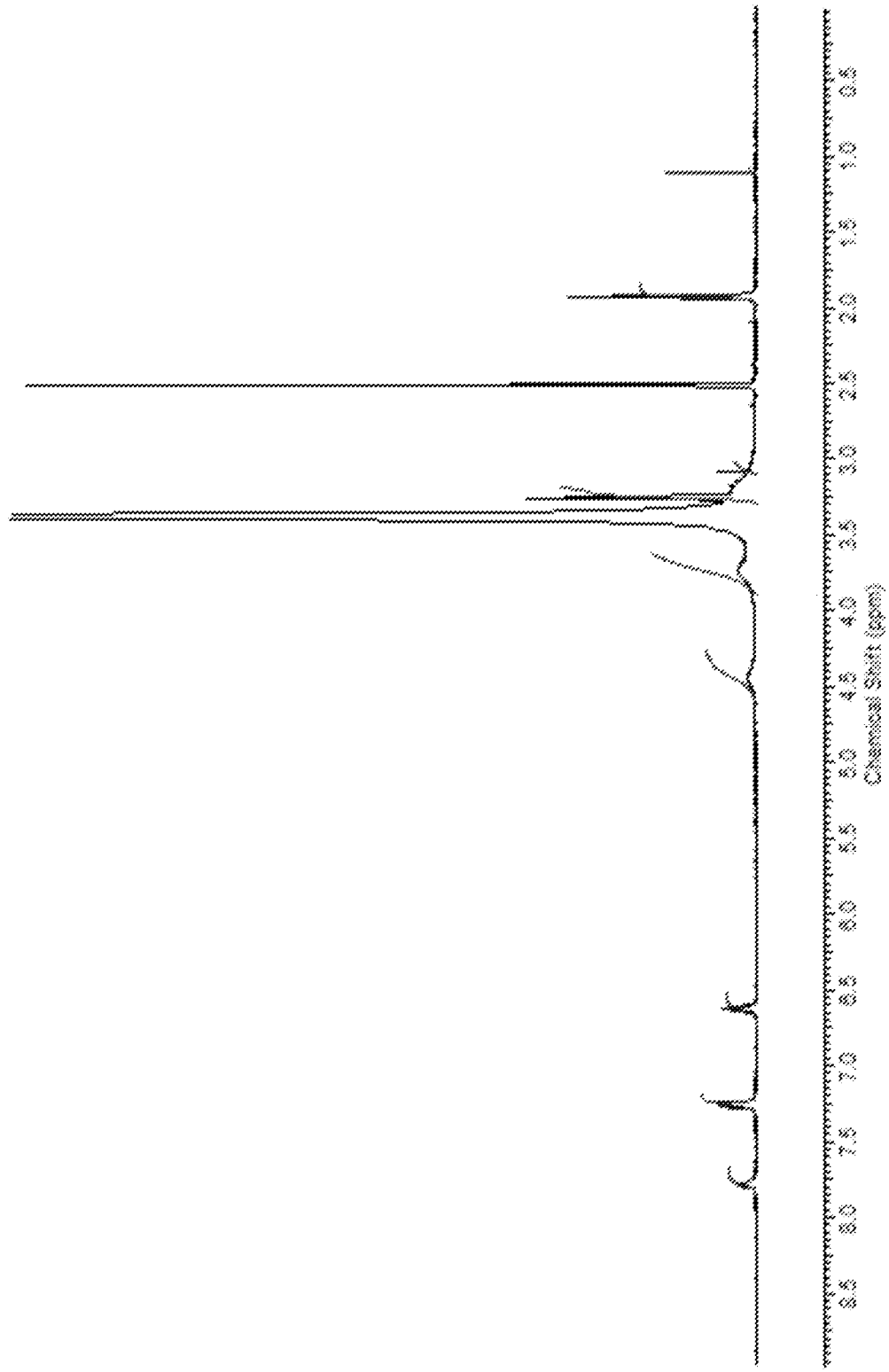
FIG. 15. Illustrates an NMR spectrum of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 1.

$^1$H-NMR spectrum of Compound 2 is shown in FIG. 15. Purity is shown in Example 10. Further characterization by XRPD, PLM, TG/DTA, DSC, GVS, KF, and IC in Examples 1-5, 7, and 11 show this sample to be Form 1 of Compound 2.

Figure 22:
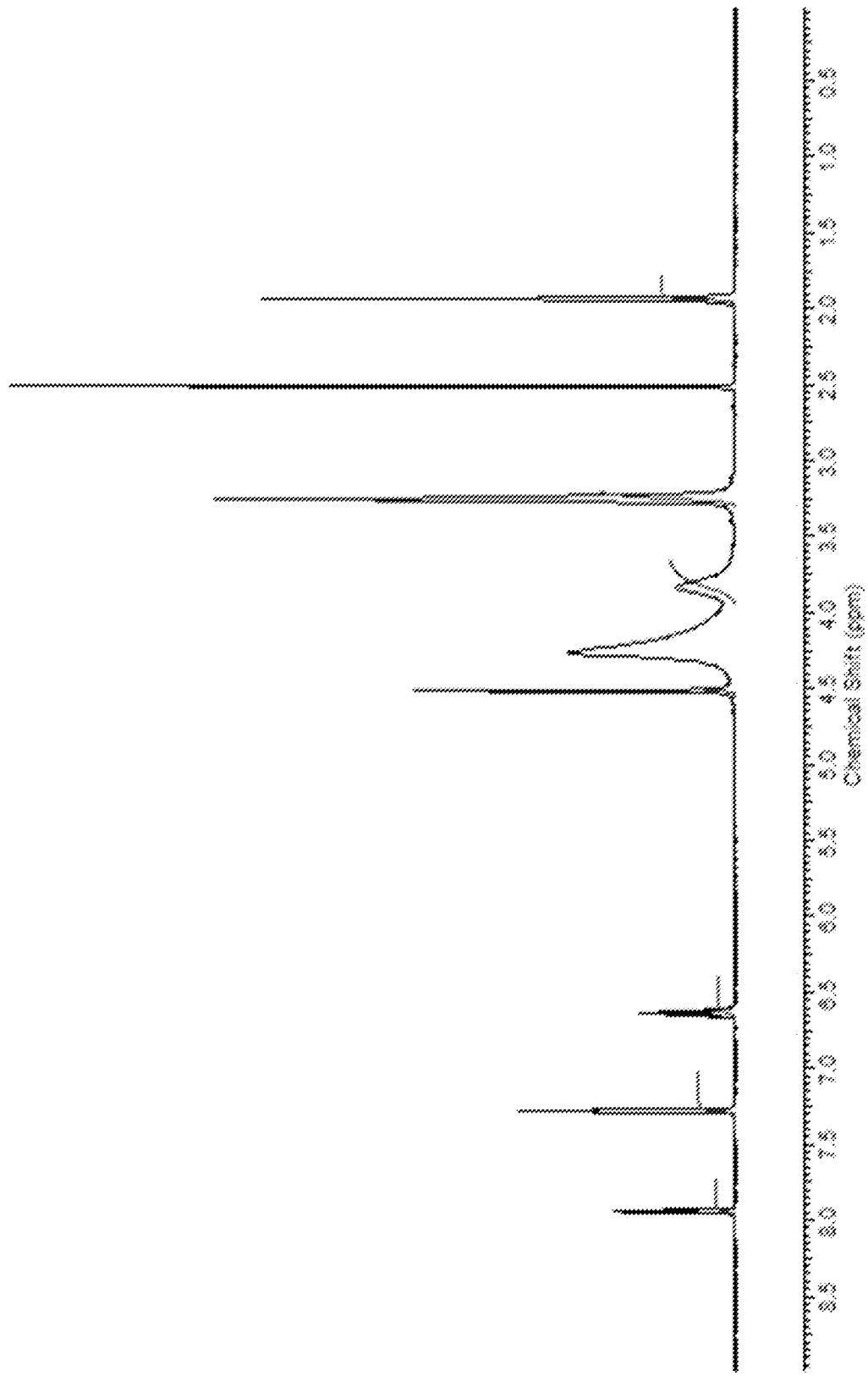
FIG. 22. Illustrates an NMR spectrum of crystalline 1,1,1,3,3,3-hexafluoropropan-2-yl 4-(2-(pyrrolidin-1-yl)-4-(trifluoromethyl)benzyl)piperazine-1-carboxylate bis-HCl salt.

$^1$H-NMR spectrum of Compound 3 is shown in FIG. 22. Purity is shown in Example 10. Further characterization by XRPD, PLM, TG/DTA, DSC, GVS, KF, and IC in Examples 1-5, 7, and 11 show this sample to be Form 1 of Compound 3.

Figure 56:
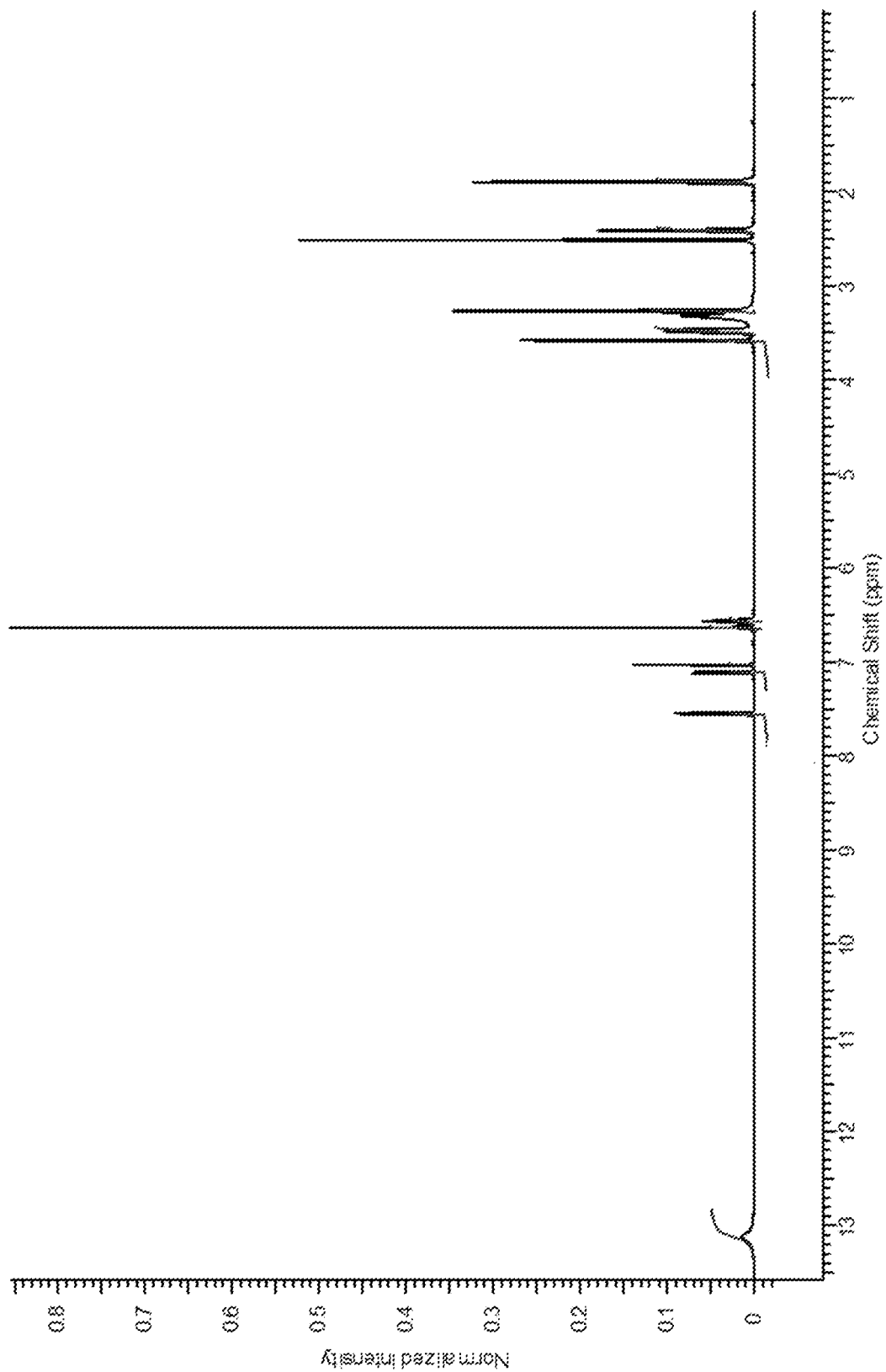
FIG. 56. Illustrates an NMR spectrum of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 1.

$^1$H-NMR spectrum of Compound 6 is shown in FIG. 56. Purity is shown in Example 10. Further characterization by XRPD, PLM, TG/DTA, DSC, and GVS in Examples 1-5 show this sample to be Form 1 of Compound 6.

Example 10: High Performance Liquid Chromatography-Ultraviolet Detection (HPLC-UV)

HPLC-UV was carried out using the following parameters:
Instrument: HPLC—Agilent 1100 with UV detector
Column: Waters XBridge C18 3.5 μm 150×4.6 mm
Column Temperature: 40° C.
UV wavelength: 265 nm
Injection Volume: 25 μL
Flow Rate: 1.0 mL/min
Mobile Phase A: Aqueous 10 mM pH 8.5 ammonium acetate
Mobile Phase B: Acetonitrile
Gradient Program

| Time (minutes) | Solvent B [%] |
| --- | --- |
| 0 | 60 |
| 1 | 60 |
| 30 | 90 |
| 38 | 90 |

| Time (minutes) | Solvent B [%] |
|---|---|
| 39 | 60 |
| 45 | 60 |

Figure 8:
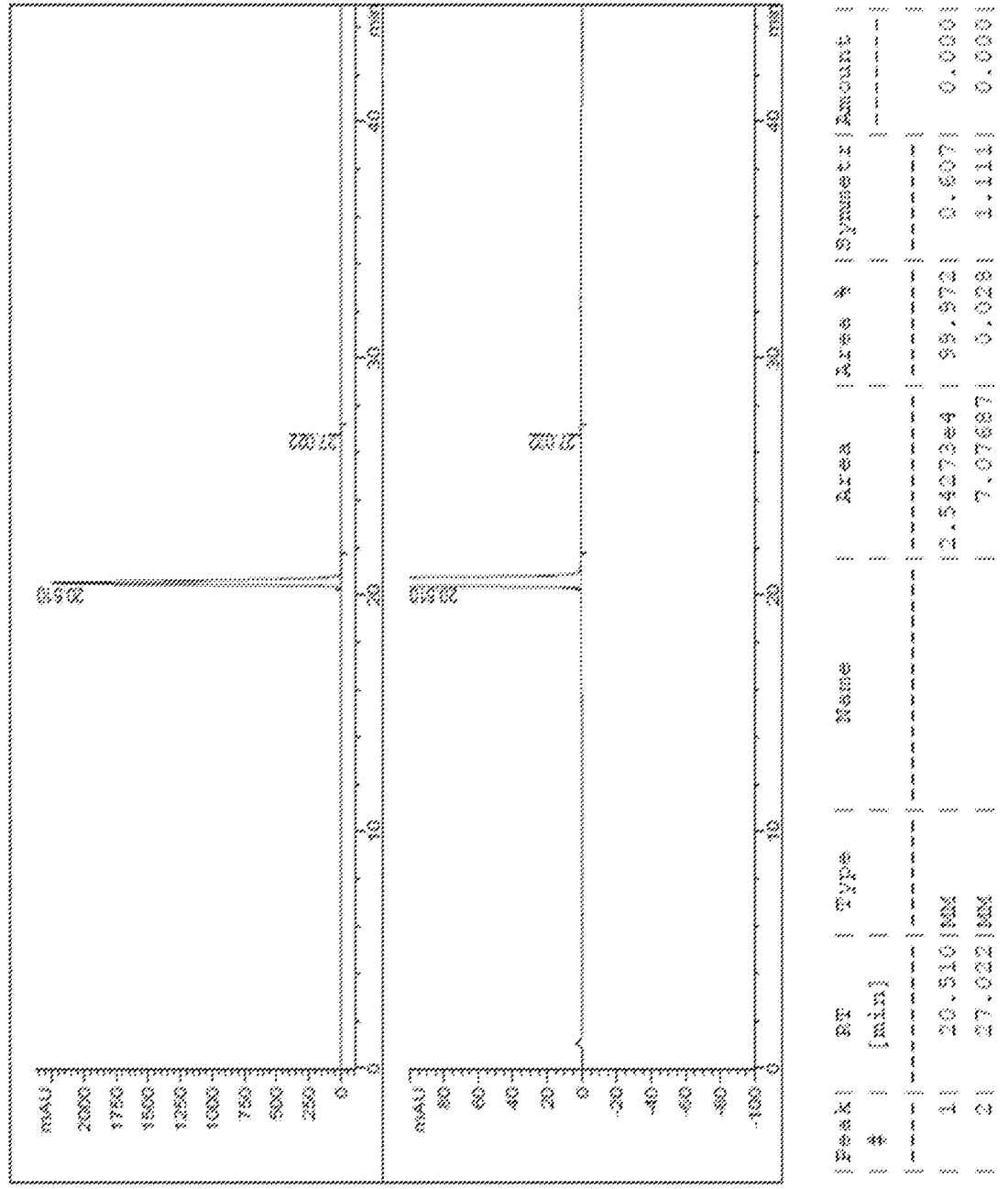
FIG. 8. Illustrates the HPLC purity of crystalline 1,1,1,3,3,3-hexafluoropropan-2-yl 4-(2-(pyrrolidin-1-yl)-4-(trifluoromethyl)benzyl)piperazine-1-carboxylate free base.

HPLC purity of Compound 1 was measured to be >99.9% (see FIG. 8).

Figure 16:
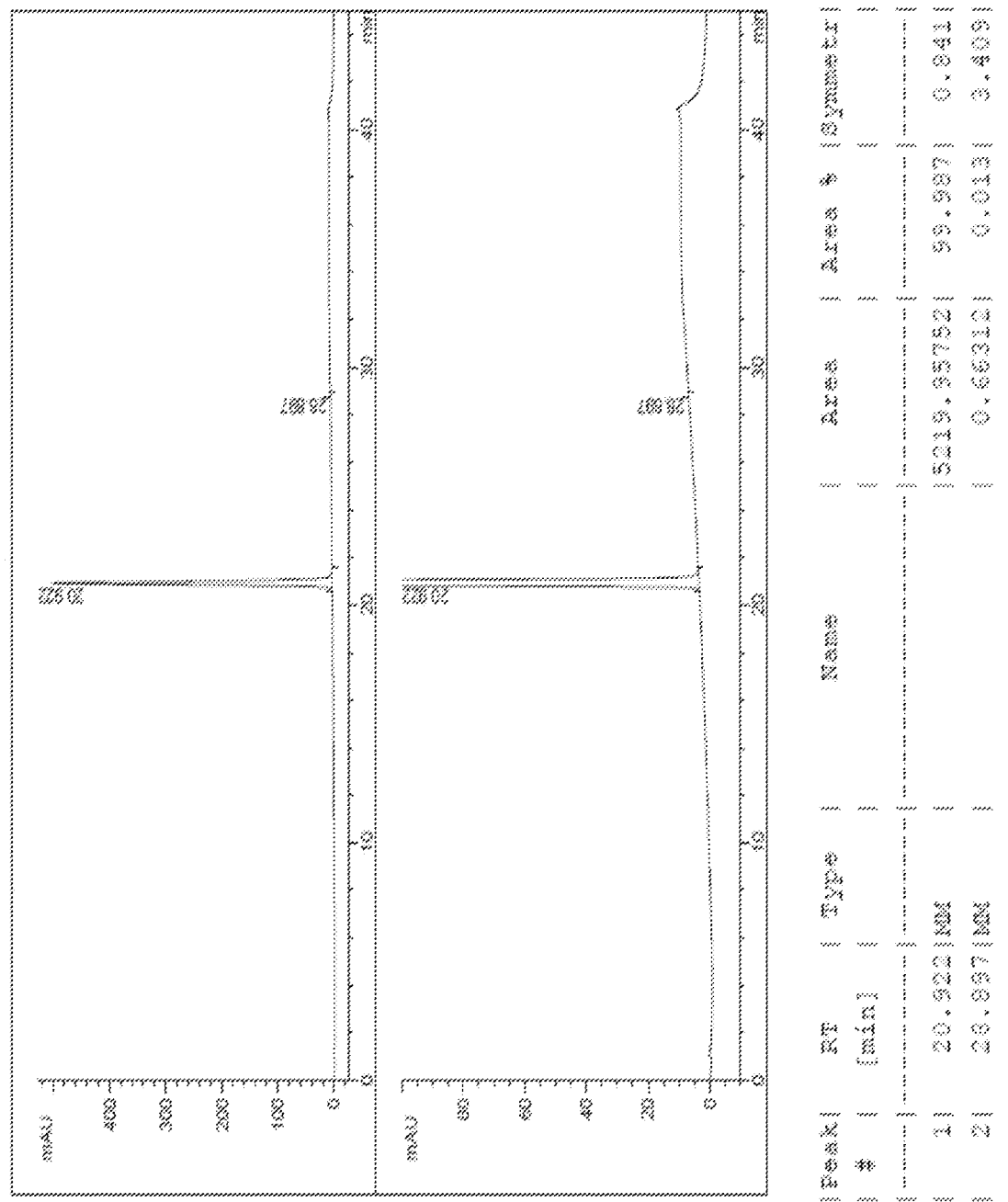
FIG. 16. Illustrates the HPLC purity of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 1.

HPLC purity of Compound 2 was measured to be >99.9% (see FIG. 16).

Figure 23:
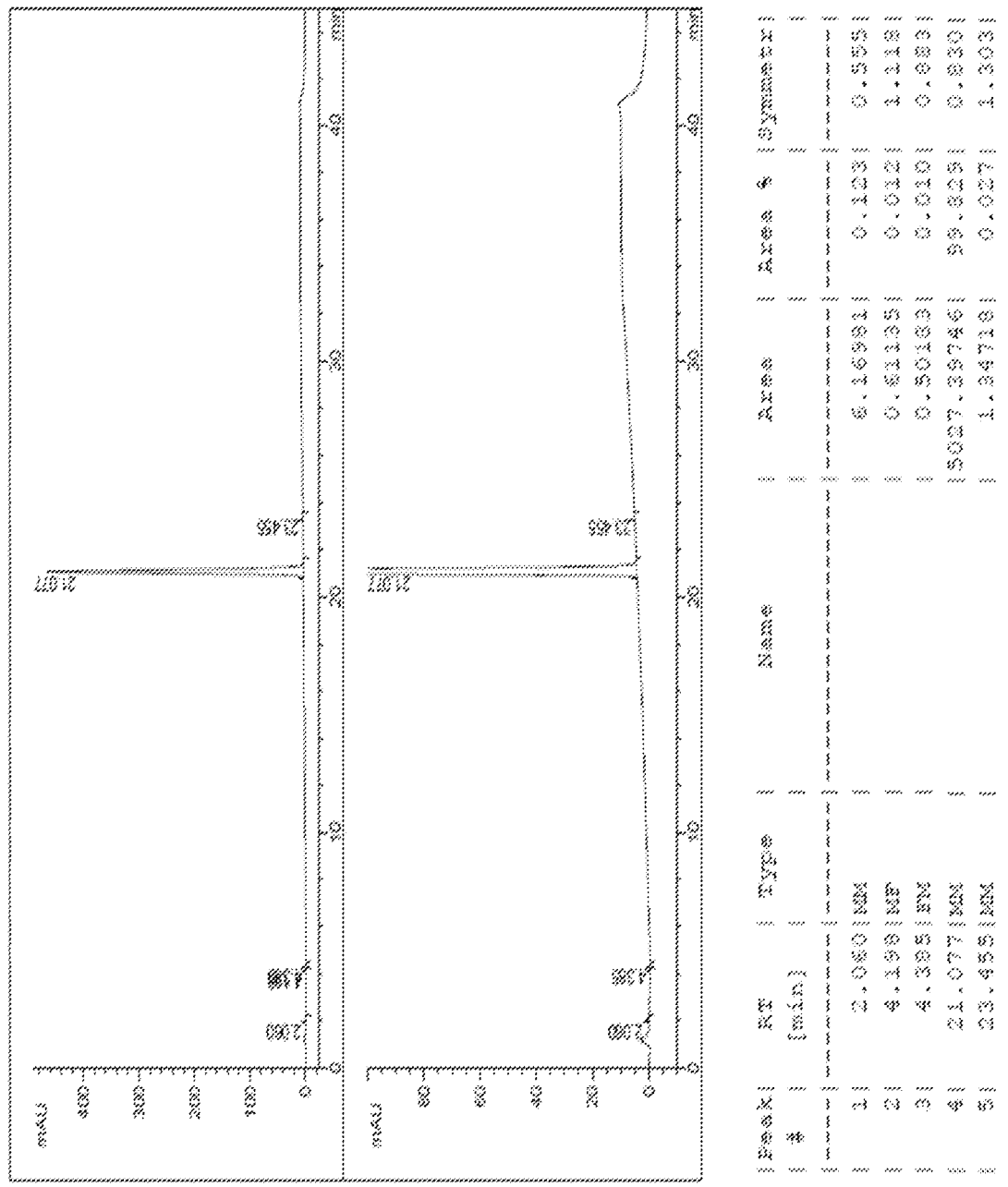
FIG. 23. Illustrates the HPLC purity of crystalline 1,1,1,3,3,3-hexafluoropropan-2-yl 4-(2-(pyrrolidin-1-yl)-4-(trifluoromethyl)benzyl)piperazine-1-carboxylate bis-HCl salt.
Figure 24A:
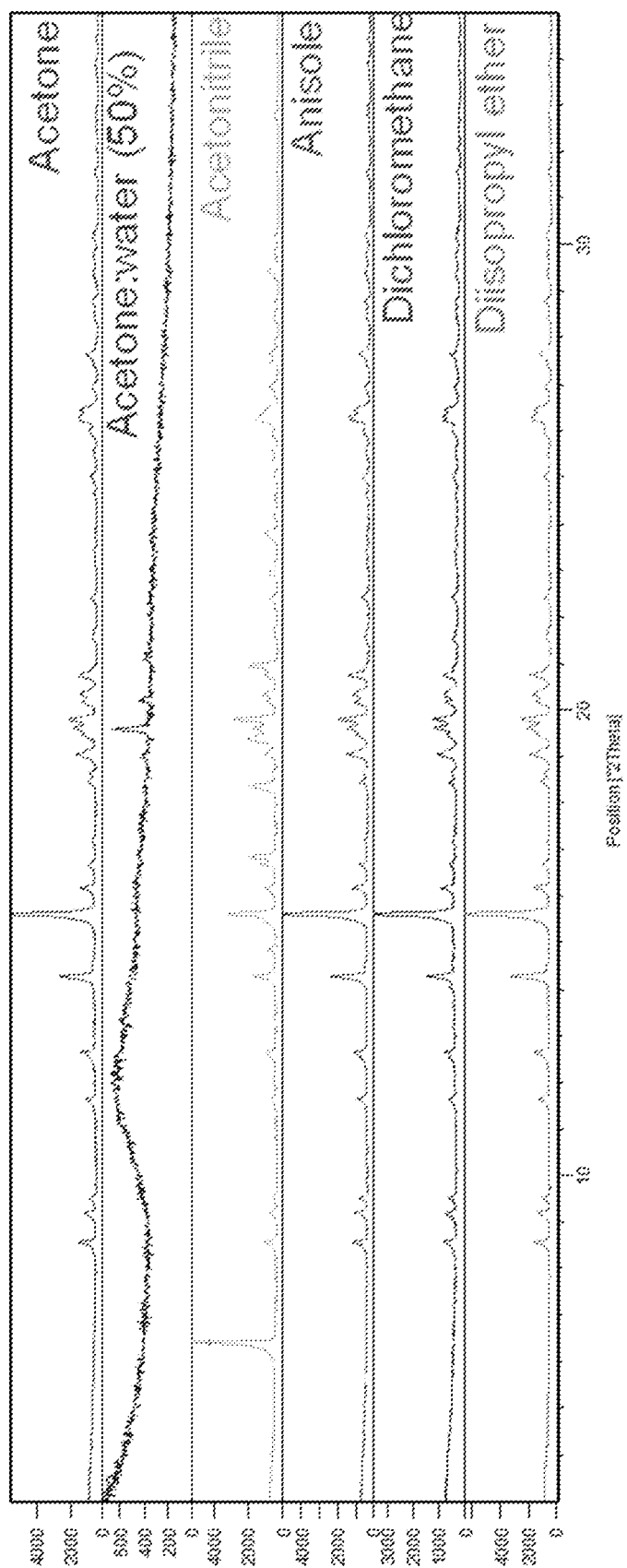
FIGS. 24A-D. Illustrates an XRPD analysis of results obtained from the solvent solubility screen.
Figure 24B:
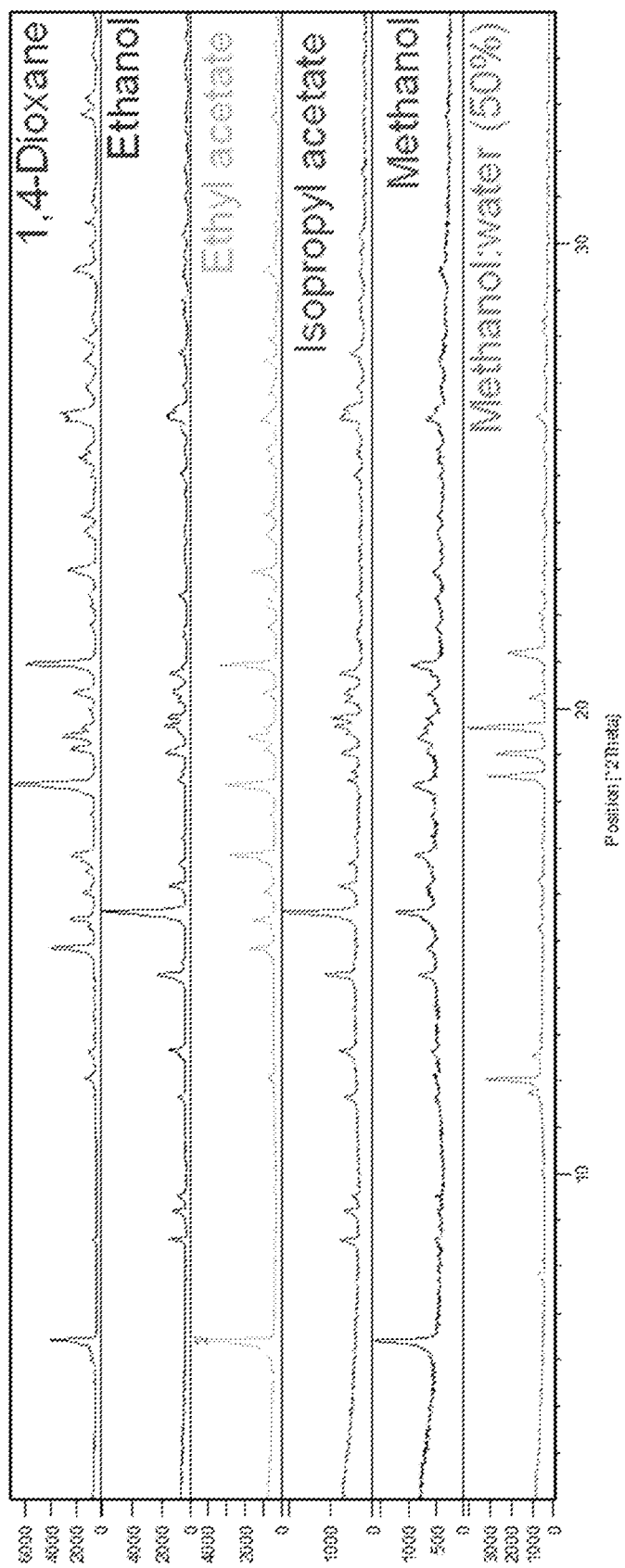
Figure 24C:
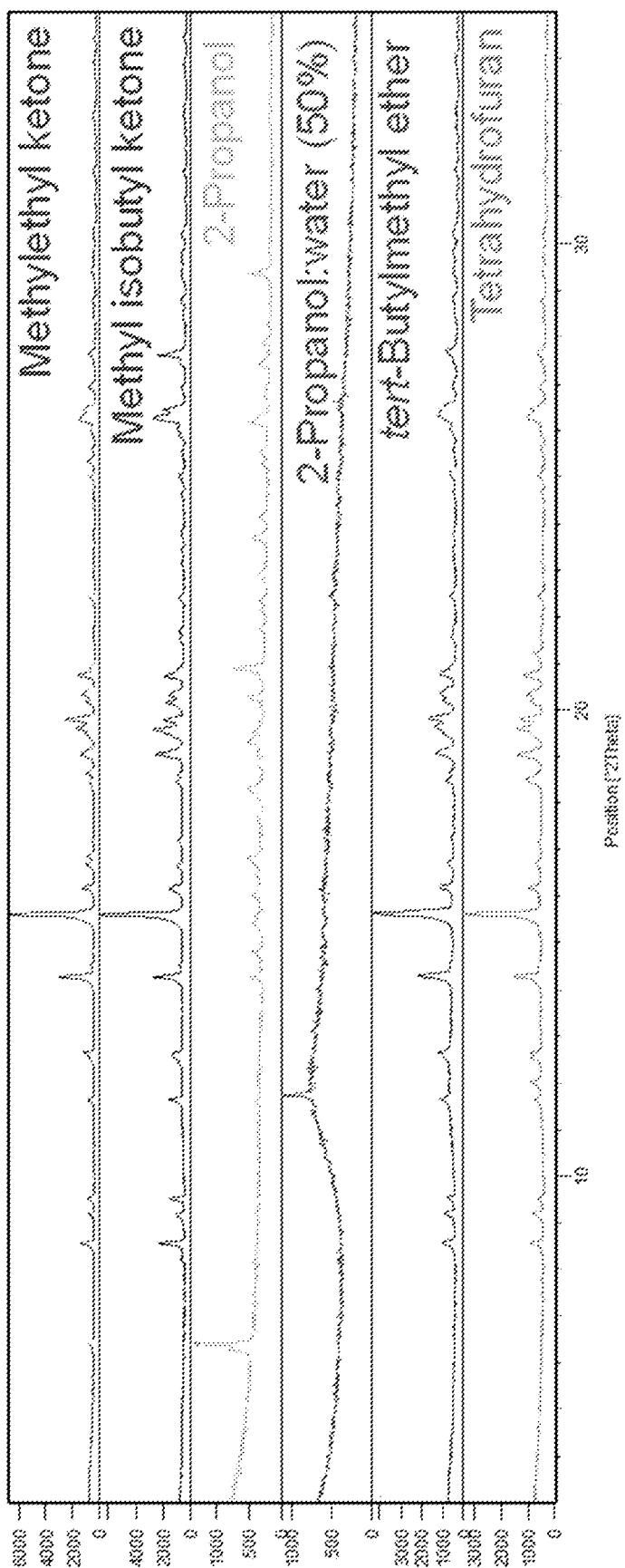
Figure 24D:
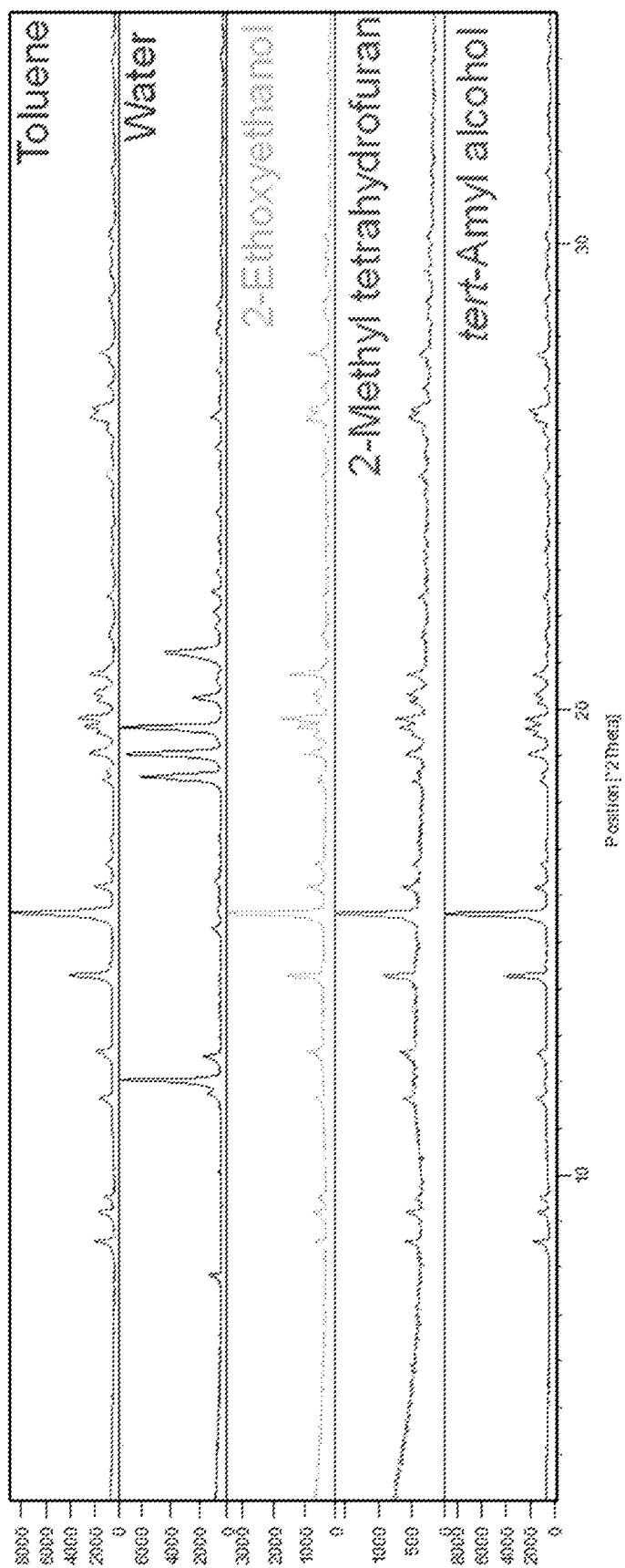

HPLC purity of Compound 3 was measured to be 99.8% (see FIG. 23).

Figure 57:
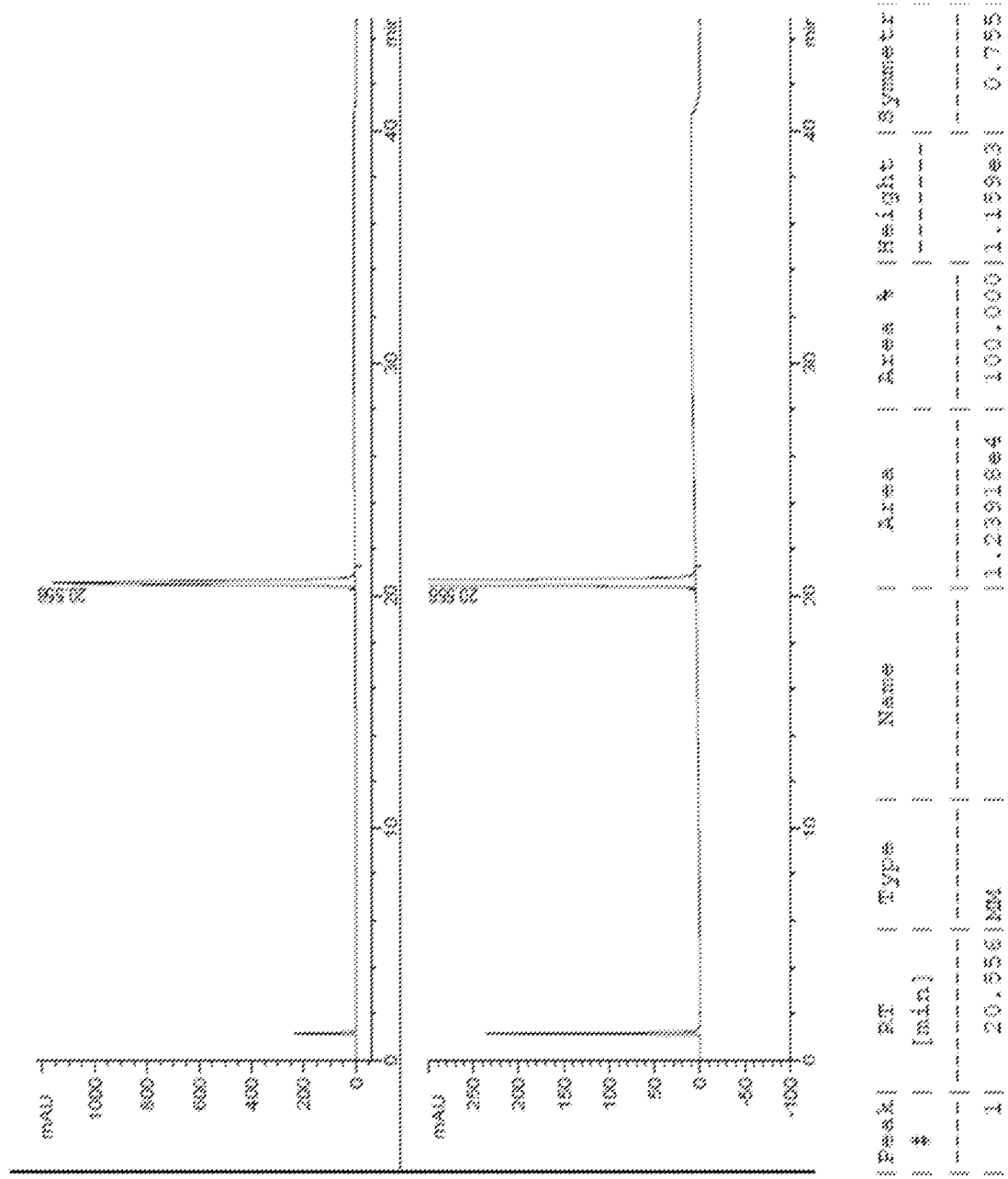
FIG. 57. Illustrates the HPLC purity of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 1.

HPLC purity of Compound 6 was measured to be >99.9% (see FIG. 57).

Example 11: Ion Chromatography (IC)

Ion chromatography was carried out using the following parameters:
Column: Dionex IonPac AS14A-5 μm, 3×150 mm
Guard Column: Dionex IonPac AG14A-5 μm, 3×30 mm
Mobile Phase: 8 mM Na2CO3/1 mM NaHCO$_3$
Flow Rate: 0.5 mL/min
Runtime: 15 minutes
Detector suppression: 50 mA, water regenerant as required
Column Temperature: 30° C.
Injection Volume: 25 μL IC analysis of Compound 2 (sample preparation using water: 2-propanol (20% solvent)) calculated 5.9% w/w HCl which equates to 0.86 moles HCl:free base. Repeat analysis (sample preparation using water: methanol (50% solvent)) calculated 6.4% w/w HCl which equates to 0.95 moles HCl:free base. The methanol preparation resulted in improved concordant results (2 injections for each sample).

Initial IC analysis of Compound 3 (sample preparation using water:2-propanol (20% solvent)) calculated 11.2% w/w HCl which equates to 1.95 moles HCl:free base. Repeat analysis sample preparation using water:methanol (50% solvent) calculated 11.1% w/w HCl which equates to 1.94 moles HCl:free base.

Example 12: Solvent Solubility Screen for Compound 1

Ca. 100 mg of free base was dissolved in 1.1 mL of dichloromethane and concentrated in vacuo to produce a clear gum, which converted to a white static solid upon standing. The sample was analyzed by XRPD to confirm crystallinity. PLM analysis was also conducted as preferred orientation was observed by XRPD.

Ca. 100 mg of free base was dissolved in 1 mL of acetone and concentrated in vacuo to produce a clear gum which converted to a white solid upon scratching with a spatula. The sample was analyzed by XRPD to confirm crystallinity. PLM analysis was also conducted as preferred orientation was observed by XRPD.

Ca. 200 mg of free base was milled in a ball mill at 50 Hz for 6 hours and the resulting solid was found to be static.

Ca. 100 mg of free base was dissolved in 1 mL of acetone and 1 mL of DCM. Both solutions were syringe filtered to remove any "seeds" and allowed to evaporate at ambient temperature in new vials.

Compound 1 which was concentrated in vacuo from both DCM and acetone was found to remain as Form 1. In addition, both evaporation experiments from DCM and acetone and 6 hours milling experiments were found to return crystalline Form 1 material.

Because attempts to prepare amorphous Compound 1 were unsuccessful, crystalline Form 1 material was used in the solvent solubility screen.

Ca. 10 mg of crystalline Compound 1 was placed in 32 vials and 5 volume aliquots of the appropriate solvent systems were added to the appropriate vial. Between each addition, the mixture was checked for dissolution and if no dissolution was apparent, the mixture was heated to ca. 40° C. and checked again. This procedure was continued until dissolution was observed or until 100 volumes of solvent had been added. After the addition of 100 volumes, a further 100 volumes were added to samples which had not dissolved to give a total of 200 volumes. If 200 volumes were added without dissolution, the solubility was calculated to be below this point (<5 mg/mL). Results are listed in Table 1.

TABLE 1

Solubility screen results for Compound 1

| Solvent | Approximate Solubility (mg/mL) |
|---|---|
| Acetone | >202 |
| Acetone:water (50%) | >202* |
| Acetonitrile | >196 |
| Anisole | >200 |
| Dichloromethane | >198 |
| Diisopropyl Ether | >208 |
| Dimethylacetamide | >204 |
| Dimethylformamide | >204 |
| Dimethylsulfoxide | 50 |
| 1,4-Dioxane | >206 |
| Ethanol | 67 |
| Ethyl acetate | >198 |
| Isopropyl acetate | >198 |
| Methanol | 72 |
| Methanol:water (50%) | <5 |
| Methylethyl ketone | >202 |
| Methyl isobutyl ketone | >196 |
| N-Methyl-2-pyrrolidone | >198 |
| 2-Propanol | 69** |
| 2-Propanol:water (50%) | <5 |
| tert-Butylmethyl ether | >196 |
| Tetrahydrofuran | >198 |
| Toluene | >202 |
| Water | <5 |
| 1-Butanol | 39 |
| 2-Ethoxyethanol | 103 |
| 2-Methyl tetrahydrofuran | >200 |
| Benzonitrile | >214 |
| Chlorobenzene | 69 |
| Heptane | 49 |
| Hexane | 49 |
| tert-Amyl alcohol | 69 |

*precipitated after ca. 30 minutes
**precipitated after ca. 2 days

Crystalline Compound 1 was found to completely dissolve (>5 mg/mL) in 29 out of the 32 solvent systems. In particular, there was high solubility (>196 mg/mL) in 19 of 32 examined solvent systems, moderate solubility (>39 mg/mL) in 10 of 32 examined solvent systems, and poor solubility (<5 mg/mL) in 3 of 32 examined solvent systems. The acetone:water (50%) sample was observed to have precipitated after ca. 30 minutes. The 2-propanol sample was observed to have precipitated after ca. 2 days.

XRPD analysis was carried out on all samples; samples which dissolved were allowed to evaporate. These XRPD analyses indicated observation of Form 1 of Compound 1 in all samples. Samples from dimethylformamide, ethanol, methanol, 1-butanol, 2-ethoxyethanol, and heptane which exhibited preferred orientation were further analyzed by PLM.

Example 13: Primary Polymorph Screening of Compound 1

The following experiments were conducted in 24 solvents (acetone, 50:50 acetone/water, acetonitrile, anisole, diisopropyl ether, dimethylformamide, dimethylsulfoxide, ethanol, ethyl acetate, methanol, methylethyl ketone, methyl isobutyl ketone, N-methyl-2-pyrrolidone, 2-propanol, tert-butylmethyl ether, tetrahydrofuran, toluene, 1-butanol, 2-ethoxyethanol, benzonitrile, chlorobenzene, heptane, hexane, and tert-amyl alcohol).

A. Temperature Cycling Experiments

The results obtained from the solubility approximation experiments were used to prepare slurries for temperature cycling. The slurries were temperature cycled at 40° C. in 4 hour cycles for a period of 48 hours (slurries were held at 40° C. for 4 hours followed by a hold at ambient for 4 hours, the cooling/heating rates after the 4 hour hold periods was ca. 1° C./min). After temperature cycling the majority of the samples were stored in a freezer in order to obtain solids.

B. Crash Cooling Experiments

Crash cooling experiments were performed by placing filtered saturated solutions of the material, in each of the 24 selected solvent systems, in environments of 2° C. and −18° C. Any solid material was then recovered and allowed to dry at ambient conditions prior to analysis.

C. Re-Preparation of Methanol Crash Cooling (−18° C.)

The methanol crash cooling sample at −18° C. was re-prepared to determine if the additional peaks that were observed in the initial sample were reproducible.

A slurry of Compound 1 was prepared in 200 μL of methanol, syringe filtered and stored in the freezer. Within ca. 2 hours solid had formed and was analyzed by XRPD.

D. Anti-Solvent Addition Experiments

Anti-solvent addition experiments were conducted at ambient (ca. 22° C.) by adding the selected anti-solvent to filtered saturated solutions of the material. Anti-solvent was added to each of the 24 selected solvent systems to give 50:50 solvent:anti-solvent mixtures, and stored in the refrigerator to encourage precipitation. Deionized water was used as the anti-solvent for all samples. A further aliquot of anti-solvent was added to samples that did not precipitate.

E. Evaporation Experiments

Evaporation experiments were conducted by allowing the solvents from filtered saturated solutions, in each of the 24 solvent systems, to evaporate at ambient conditions in open vials. Any solid material produced was then recovered and analyzed after the sample had evaporated to dryness.

Samples from these experiments were analyzed by XPRD. Temperature cycling results were consistent with solubility samples in Example 9. Form 1 was obtained from all experiments which had sufficient solid for analysis, suggesting a monomorphic system.

Samples that showed preferred orientation were analyzed by PLM and showed plate-like morphologies, as was observed for the initial Compound 1 material (see Example 2).

Example 14: Solvent Solubility Screen for Compound 2

Approximately 100 mg of HCl salt (Form 1, Compound 2) was ball milled at 50 Hz and analysed by XRPD after 15 and 30 minutes, to test how readily amorphous material could be obtained. After 15 minutes of milling, the HCl salt (100 mg) was poorly crystalline; however, after 30 minutes of milling, the HCl salt was found to be amorphous.

Approximately 500 mg of HCl salt (Form 1, Compound 2) was ball milled at 50 Hz and analysed by XRPD every 30 minutes until 3.5 hours. After 3 hours of milling, the HCl salt (500 mg) displayed minimal crystallinity; however, after 3.5 hours the HCl salt was found to be amorphous.

Approximately 10 mg of amorphous HCl salt (from 500 mg batch) was placed in each of 28 vials and 5 volume aliquots of the appropriate solvent systems were added to the appropriate vial. Between each addition, the mixture was checked for dissolution and if no dissolution was apparent, the mixture was heated to ca. 40 OC and checked again. This procedure was continued until dissolution was observed or 100 volumes of solvent had been added. Then a further addition of 100 volumes was added to samples which had not dissolved. If 200 volumes of solvent were added without dissolution of the material, solubility was calculated to be below this point. Results are listed in Table 2.

TABLE 2

Solubility screen results for Compound 2

| Solvent | Approximate Solubility (mg/mL) |
| --- | --- |
| Acetone | 40 |
| Acetone:water (50%) | <5* |
| Acetonitrile | 40 |
| Anisole | <5* |
| Dichloromethane | 70** |
| Diisopropyl Ether | <5 |
| Dimethylacetamide | 99 |
| Dimethylformamide | 99 |
| Dimethylsulfoxide | 66 |
| 1,4-Dioxane | 5 |
| Ethanol | 33 |
| Ethyl acetate | 5 |
| Isopropyl acetate | <5 |
| Methanol | 101 |
| Methanol:water (50%) | <5 |
| Methylethyl ketone | 28 |
| Methyl isobutyl ketone | <5* |
| N-Methyl-2-pyrrolidone | 101 |
| 2-Propanol | 5 |
| 2-Propanol:water (50%) | <5* |
| tert-Butylmethyl ether | <5 |
| Tetrahydrofuran | 25** |
| Toluene | <5 |
| Water | <5 |
| 1-Butanol | <5 |
| 2-Ethoxyethanol | 49** |
| 2-Methyl tetrahydrofuran | <5 |
| tert-Amyl alcohol | <5 |

*partial dissolution
**Precipitated overnight

Amorphous Compound 2 was found to completely dissolve (>5 mg/mL) in 15 out of the 28 solvent systems. Acetone:water (50%) sample was observed to have precipitated after ca. 2 h, dissolution was initially observed at 18 mg/mL. Dichloromethane, tetrahydrofuran, and 2-ethoxyethanol samples were observed to have precipitated overnight.

Samples which dissolved were allowed to evaporate (apart from DMA, DMF, DMSO and NMP solvents). XRPD analysis was carried out on all remaining samples in which solids were obtained. Of these samples, the solid from 14 solvent systems (acetone, anisole, dichloromethane, diisopropyl ether, ethanol, isopropyl acetate, methyl ethyl ketone, methyl isobutyl ketone, tert-butylmethyl ether, tetrahydrofuran, toluene, 2-ethoxy ethanol, 2-methyl tetrahydrofuran, and tert-amyl alcohol) was a previously unobserved form, Form 2, of Compound 2, and the solid from 3 solvent systems (1,4-dioxane, ethyl acetate, and 2-propanol) was Form 1 of Compound 2. Five solvent systems (1:1::acetone:water, 1:1::methanol:water, 1:1::2-propanol:water, water, and 1-butanol) either provided no solid or free base material (Compound 1). Two solvent systems (acetonitrile and methanol) provided a mixture of Forms 1 and 2 of Compound 2 (FIGS. 24A-24D).

Example 15: Primary Polymorph Screening of Compound 2

I. Exploration of Polymorphism by Reactive Crystallization

Eight solvent systems (acetone, dichloromethane, ethanol, ethyl acetate, methanol, 2-propanol, tert-butylmethyl ether, and tetrahydrofuran) were selected for the reactive crystallizations. Approximately 50 mg of free base was dissolved in 250 μL to 1250 μL of solvent. One equivalent of HCl from a stock solution (200 μL) in the appropriate solvent was added. The addition of acid was carried out at 40° C. with stirring, then the solution was allowed to cool. On addition of acid the tert-butylmethyl ether sample was the only sample where direct precipitation was observed. However the precipitate re-dissolved then re-precipitated upon cooling to ambient temperature. After stirring at ambient temperature for ca. 20 h, the 2-propanol sample had a very small amount of precipitate. Heptane was then added to all samples except t-BME providing 50:50 solvent:anti-solvent mixtures. The resulting methanol sample was immiscible with heptane. Precipitate was observed in the acetone, ethyl acetate, 2-propanol and THF samples. A precipitate was obtained from the DCM/heptane and ethanol/heptane mixtures after storage in the refrigerator for ca. 5 days.

Figure 25:
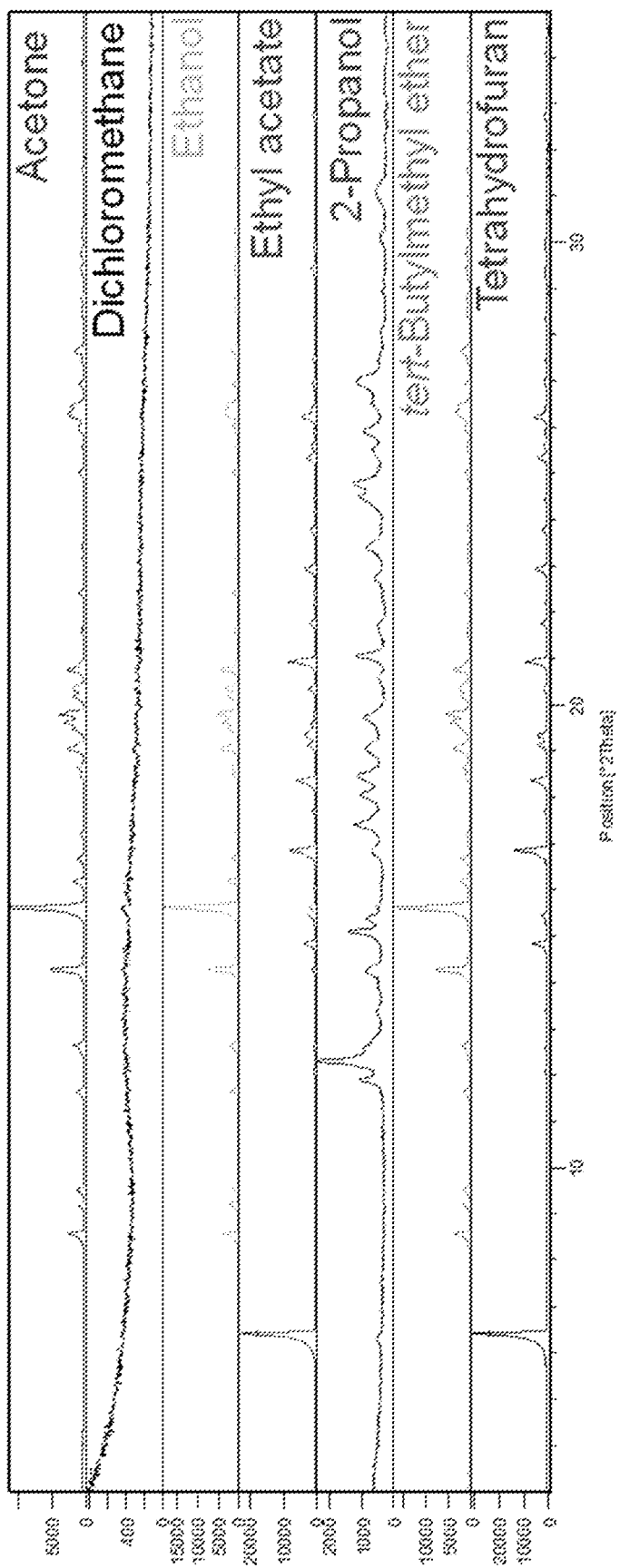
FIG. 25. Illustrates an XRPD analysis of results obtained from the primary polymorph screen.

Samples were analyzed by XRPD. Acetone, ethanol, and tert-butylmethyl ether provided Form 2 of Compound 2. Solids from dichloromethane provided weak data for Form 2 of Compound 2. Ethyl acetate and tetrahydrofuran provided Form 1 of Compound 2. 2-Propanol provided a mixture of Forms 1 and 2, and methanol provided no solids (FIG. 25).

Figure 26:
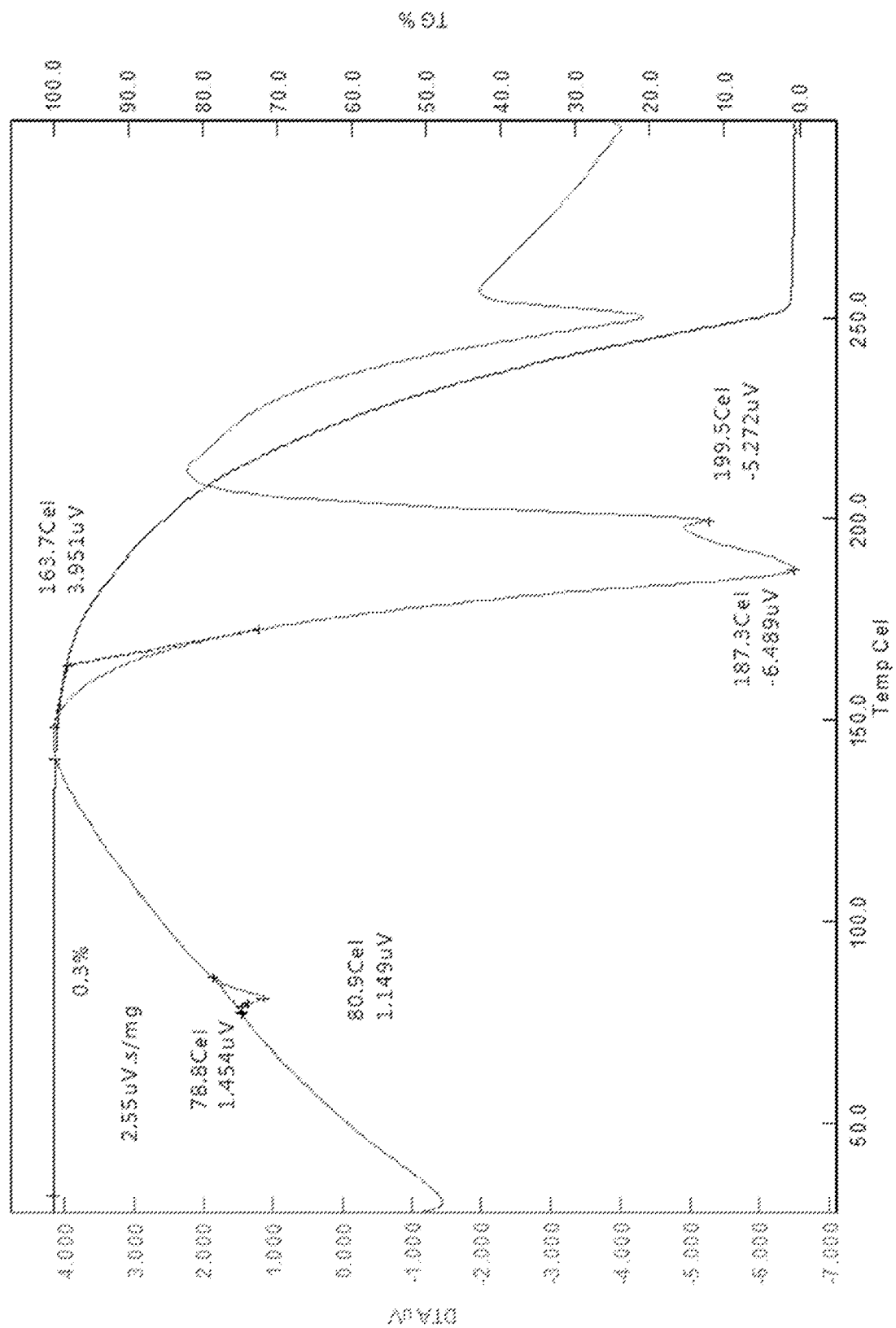
FIG. 26. Illustrates a TGA thermogram of crystalline 1,1,1,3,3,3-hexafluoropropan-2-yl 4-(2-(pyrrolidin-1-yl)-4-(trifluoromethyl)benzyl)piperazine-1-carboxylate mono-HCl salt, Form 2.

TG/DTA of Form 2 from tert-butylmethyl ether showed the material to differ from Form 1 and to be an anhydrous form. TGA showed a gradual loss of 0.3% from the outset followed by the onset of degradation. DTA showed a small endotherm with onset at ca. 78.8° C., an endotherm with onset at ca. 163.7° C. and an endotherm with peak at ca. 199.5° C. (FIG. 26).

DSC analysis of Form 2 from ethanol showed an endotherm with onset temperature of 200.4° C. (FIG. 27).

KF analysis calculated 1.6% water for Form 2 from acetone. This value is higher than expected from thermal analysis. Any water present must be non-lattice bound.

IC analysis of Form 2 from tert-butylmethyl ether (sample preparation using water:methanol (50% solvent)) calculated 6.0% w/w HCl which equates to 0.89 moles HCl:free base.

II. Use of Amorphous HCl Salt for Polymorph Screening by Crystallization of HCl Salt Approximately 1 g of HCl salt (Compound 2) was milled in a ball mill at 50 Hz and analysed by XRPD every hour for 5 hours. The HCl salt (1 g) was found to be predominantly amorphous after 5 hours milling and was shown to only decrease slightly in crystallinity between 4 and 5 hours milling.

Twenty-four solvent systems were used for this Polymorph Screening. Water and water mixtures were avoided due to the dissociation observed in the solubility assessment.

A. Temperature Cycling Experiments

The results obtained from the solubility approximation experiments were used to prepare slurries for temperature cycling. The slurries were temperature cycled at 40° C. in 4 hour cycles for a period of 24 hours (slurries were held at 40° C. for 4 hours followed by a hold at ambient temperature for 4 hours, the cooling/heating rates after the 4 hour hold periods was ca. 1° C./min).

B. Crash Cooling Experiments

Crash cooling experiments were performed by placing saturated filtered solutions of the material, in each of the 24 selected solvent systems, in environments of 2° C. and −18° C. Any solid material was then recovered and allowed to dry at ambient conditions prior to analysis.

C. Anti-solvent Addition Experiments

Anti-solvent addition experiments were conducted at ambient temperature (ca. 22° C.) by adding the selected anti-solvent to saturated, filtered solutions of the material, in each of the 24 selected solvent systems to give 50:50 solvent:anti-solvent mixtures. These samples were stored in the refrigerator to encourage precipitation. t-BME was used as the anti-solvent for all samples apart from DMSO and t-BME samples where toluene was used. A further aliquot of anti-solvent was added to samples which did not precipitate.

D. Evaporation Experiments

Evaporation experiments were conducted by allowing the solvents to evaporate from saturated, filtered solutions of the material, in each of the 24 solvent systems, at ambient conditions in open vials. Any solid material produced was then recovered and analysed after the solvent had evaporated to dryness. After ca. 17 days at ambient the anisole sample was evaporated at 50° C. to produce solid.

Samples from these experiments were analyzed by XPRD. Temperature cycling results were consistent with the solubility samples apart from:

1,4-dioxane, ethyl acetate and 2-propanol: Form 1 was obtained from solubility samples, and Form 2 was obtained from temperature cycling;

DIPE and t-BME: Form 2 was obtained from the solubility screen and Form 1 and 2 mixtures were obtained from temperature cycling;

acetonitrile and methanol: Form 1 and 2 mixtures were obtained from the solubility screen and Form 2 was obtained from temperature cycling;

MIBK: Form 2 was obtained from the solubility screen and amorphous material was obtained from temperature cycling although little solid was able to be analysed.

Form 2 was obtained from 50 different experiments and was found to consist of plate or needle-like morphologies.

"Form 3" from anisole evaporation (obtained via evaporation from hotplate at 50° C.) was shown to likely be a degradant, purity was measured to be 96.5%. Due to the small sample amount this sample was not analysed by PLM.

Additional peaks were observed at ca. 6.2 and 18.1° 2θ from MIBK Form 2 evaporation but this was not sufficient to be assigned as a different form.

Example 16: Secondary Polymorph Screen of Compound 2

Form 2 of Compound 2 was scaled up in two solvents. Material underwent 7-day stability testing and/or aqueous solubility assessment. The 7-day stability testing was conducted as follows. Material was exposed to environments of 40° C./75% RH, ambient light and 80° C. for 7 days and the resulting solids analysed by XRPD to determine if any changes had occurred, and by HPLC to determine purity. The aqueous solubility assessment was conducted as follows. A slurry was created in deionised water (5.1 mg of Form 2 and 300 μL of water) and shaken for ca. 24 hours at ambient temperature (ca. 22° C.). The initial pH and final pH were measured. The resulting mixture was then isolated by centrifuge filtration, and the solution obtained analysed by HPLC to calculate the concentration of material dissolved. Remaining solid was analysed by XRPD to determine if any changes had occurred on slurrying.

A. Scale-up of Form 2 (Compound 2) from Acetone

Approximately 300 mg of Compound 1 was dissolved in 1 mL of acetone. One equivalent of HCl was added from a stock solution in acetone (200 μL) at 40° C. with stirring. The resulting solution was then allowed to cool. On addition of acid, the sample remained a clear solution. Heptane was then added to give 50:50 solvent:anti-solvent mixture. After stirring for ca. 1 hour, a thin slurry (with insufficient solid for XRPD analysis) formed, and the sample was stored in the refrigerator for ca. 64h to provide a white slurry. Solid material was isolated by filtration and analysed by XRPD (FIG. 28). Material was then dried under vacuum for ca. 6h and re-analysed by XRPD. The yield obtained was 127 mg.

XRPD analysis showed Form 2 to be successfully scaled-up but with decreased crystallinity after drying. PLM analysis showed Form 2 to consist of birefringent particles of plate-like morphology. TG/DTA showed the material to be consistent with Form 2 from t-BME reactive crystallisation, with the artefact ca. 79° C. no longer present. TGA showed a loss of 0.5% from the outset followed by the onset of degradation. DTA showed an endotherm with onset temperature at ca. 159.1° C. DSC analysis showed an endotherm with onset temperature of 197.6° C.; this analysis was carried out with a small quantity of material due to insufficient material. DVS analysis shows Form 2 to be non-hygroscopic with <0.12% total uptake at 90% RH. The difference in the starting and ending mass at 40% RH could indicate a small amount of residual solvent present in input material. Post-DVS XRPD analysis showed the material to remain the same crystalline form. $^1$H-NMR analysis showed the material to correspond with the provided structure with no residual solvent observed. HPLC purity was measured to be 99.9%. IC analysis (sample preparation using water:methanol (50% solvent)) calculated 6.3% w/w HCl which equates to 0.95 moles HCl:free base. Material was shown to remain the same form under environments of 40° C./75% RH, ambient light and 80° C. for 7 days. HPLC purity was found to be unchanged: >99.9% purity (40° C./75% RH); >99.9% purity (ambient); 99.9% purity (80° C.). Aqueous solubility was measured to be 0.5 mg/mL. Form 2 was found to dissociate to the free base, as was previously observed in the solubility screen using amorphous material. The initial pH was measured to be 1.87 and the final pH 1.68 (pH of deionised water was measured to be 5.91).

B. Scale-Up of Form 2 (Compound 2) from Acetone (Reduced Drying)

Approximately 300 mg of free base was dissolved in 0.5 mL of acetone. One equivalent of HCl was added from a stock solution in acetone (200 μL) at 40° C. with stirring. The resulting solution was then allowed to cool. On addition of acid, the sample remained a clear solution. Heptane was then added to give 50:50 solvent:anti-solvent mixture. After stirring for ca. 1 hour, a white precipitate formed. The sample was stored in the refrigerator for ca. 3-4 days, providing a white slurry. Solid material was isolated by filtration and dried under vacuum for ca. 2h, then analysed by XRPD. The yield obtained was 90 mg.

XRPD analysis showed Form 2 to be successfully scaled-up with improved crystallinity achieved with reduced drying. GVS analysis showed Form 2 to be (very) non-hygroscopic with <0.08% total uptake at 90% RH. The difference in the starting and ending mass at 40% RH could indicate a small amount of residual solvent present in the input material. Post-GVS XRPD analysis showed that the material remained the same crystalline form.

C. Scale-Up of Form 2 (Compound 2) from Ethanol

Approximately 300 mg of free base was dissolved in 4 mL of ethanol. One equivalent of HCl was added from a stock solution in ethanol (200 μL) at 40° C. with stirring. The resulting solution was then allowed to cool. On addition of acid, the sample remained a clear solution. Heptane was then added to give 50:50 solvent:anti-solvent mixture. After stirring for ca. 1 hour, an additional 2.3 mL of heptane were added. The sample was stored in the refrigerator for ca. 3-4 days, providing a white slurry. Solid material was isolated by filtration and dried under vacuum for ca. 2h, then analysed by XRPD. The yield obtained was 154 mg.

XRPD analysis showed Form 2 to be successfully scaled-up with improved crystallinity achieved with reduced drying. KF analysis calculated 0.8% water. DSC analysis showed an endotherm with onset degradation of 200.7° C. IR analysis was carried out to obtain a reference spectrum.

This secondary screen showed Form 2 to be non-hydrated/solvated, non-hygroscopic, mono-HCl salt with no changes observed in the solid form or in chemical purity after stability testing for 1 week, but with low aqueous solubility and dissociation to the free base. Notably, Form 1 also dissociates readily to the free base in water.

Example 17: Polymorph Stability Studies of Compound 2 (Competitive Slurrying)

A. Solubility Measurement in t-BME

Solubility of Form 1 of Compound 2 was measured using the solvent addition method as described in Example 14 on 10 mg of sample. t-BME was added in 1 mL aliquots up to 10 mL, then in 5 mL and 10 mL aliquots up to a total volume of 100 mL.

Solubility of Form 1 in t-BME was measured to be <0.1 mg/mL and so this solvent was not chosen for competitive slurrying.

B. Competitive Slurrying Procedure

Four solvents (acetone, ethyl acetate, methylethyl ketone, and 2-propanol) were chosen for competitive slurrying. Saturated solutions were prepared of Form 1 in the chosen solvents and added to 20 mg of 50:50 Form 1 and 2 mixtures to create slurries. The slurries were shaken at 60° C. and ambient temperature for ca. 48 hours. Solids were then isolated by centrifuge filtration and analysed by XRPD.

XRPD analyses of solids obtained from the slurries at 60° C. and ambient temperature all indicated the presence of only Form 2. These results suggest that Form 2 is thermodynamically more stable than Form 1. MEK and acetone samples at 60° C. were observed to form orange/brown slurries but the isolated solid remained white. This could indicate chemical degradation at higher temperatures.

Example 19: Focused Salt Screen on Compound 1

A. Primary Salt Screen: Counterion Addition at 40° C.

A total of 42 experiments were set up using 7 counterions (fumaric acid, citric acid, L-tartaric acid, hippuric acid, benzene sulfonic acid, methane sulfonic acid, or HCl) in 6 different solvents (acetone, acetonitrile, ethyl acetate, 2-propanol, tert-butylmethyl ether, or THF). HCl was used for positive control experiments. Ca. 25 mg of Compound 1 (free base) was weighed into 2 mL glass vials, followed by dissolution in the appropriate solvent (500 μL) at 40° C. 1 equivalent of the counterions were weighed separately and dissolved in the allocated solvent at 40° C. to obtain 0.5 M solutions. In the vials where the counterions did not dissolve, a further 200 μL of deionised water was added to solubilize the counterion. In some cases where dissolution was not possible, a slurry of the acid was added. If the counterion was a liquid (e.g., methane sulfonic acid), it was added as a neat solution. After counterion addition, the vials were shaken at 40° C. for 1 hour. The resulting solids were analyzed by XRPD. Where enough solid was available, $^1$H NMR and TGA analysis was also carried out.

Samples that were still in solution were allowed to evaporate at ambient temperature by piercing the vial caps. Any solids were analyzed by XRPD and novel crystalline forms were also analyzed by $^1$H NMR and TGA if enough material was obtained.

Samples that were still in solution were stored in the refrigerator at 5° C. to encourage solid formation. Any solids were analyzed by XRPD.

Samples that did not produce solid materials following the refrigeration were subjected to anti-solvent addition. Any precipitate was isolated by centrifugation and analyzed by XRPD.

B. Benzene Sulfonic Acid Salt (Compound 4): Forms 1 and 2

Figure 32:
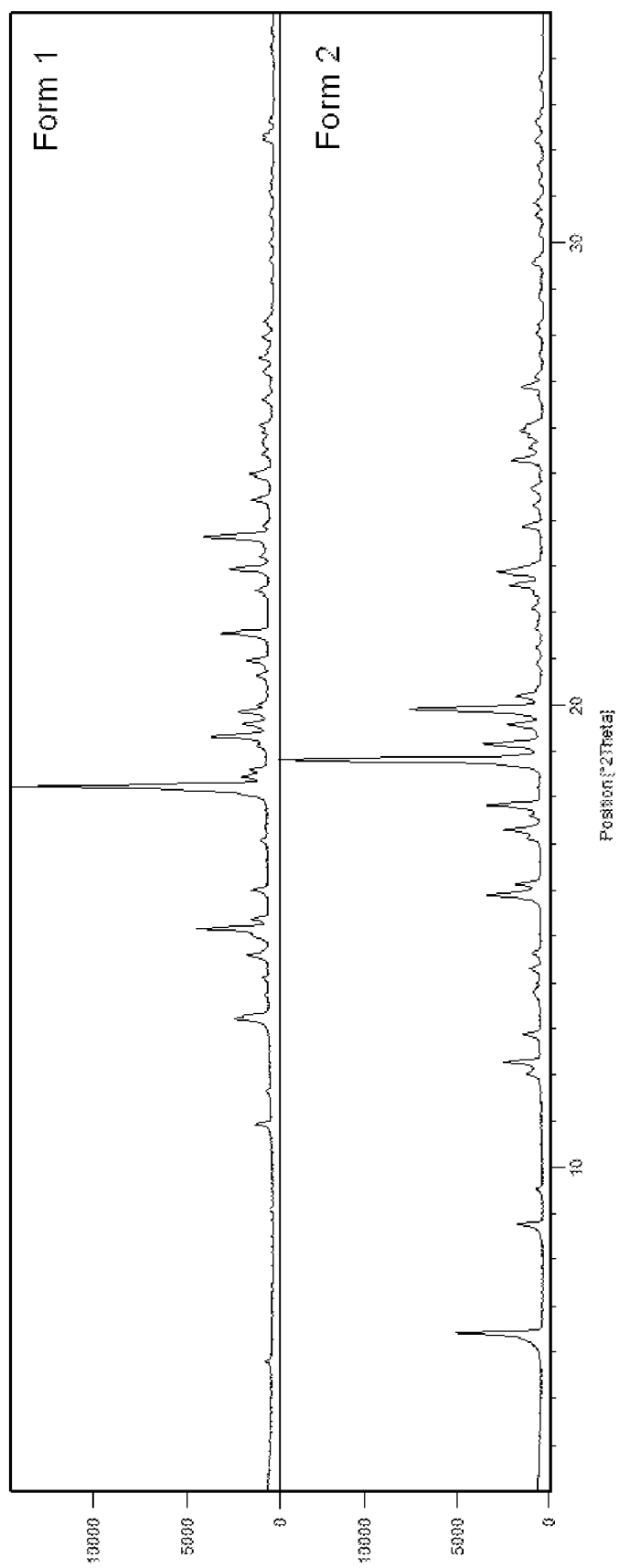
FIG. 32. Illustrates XRPD patterns of crystalline 1,1,1,3,3,3-hexafluoropropan-2-yl 4-(2-(pyrrolidin-1-yl)-4-(trifluoromethyl)benzyl)piperazine-1-carboxylate besylate salt, Forms 1 and 2.

For the counterion experiments in acetone, acetonitrile, 2-propanol and tert-butylmethyl ether, precipitation occurred by storing the vials at ambient conditions overnight. Precipitation was observed in EtOAc and THF after 5 days of cooling at 5° C. XRPD analysis identified two benzene sulfonate salt forms. Form 1 (FIG. 30) was obtained from acetone, acetonitrile, ethyl acetate, 2-propanol, and THF. Form 2 (FIG. 31) was obtained from tert-butylmethyl ether. A comparison of the XRPD patterns provided clear evidence of different crystalline forms (FIG. 32).

$^1$H NMR analysis was next carried out to confirm salt formation and check the salt stoichiometry. Due to the small amounts of benzene sulfonate Form 1 formed in each vial, the solids from the acetone and acetonitrile crystalline hits were combined for $^1$H NMR spectroscopy. The $^1$H NMR spectrum showed both API and counterion present but there were several extra peaks present. In an attempt to obtain a cleaner spectrum, samples from 2-propanol and THF were combined and a second $^1$H NMR spectrum was recorded. The same extra peaks were detected, possibly corresponding to degradation products. The NMR spectrum of benzene sulfonate Form 2 showed the material to correspond with the benzene sulfonate salt, with no impurities present. The spectra for both Forms 1 and 2 showed significant shifts and broadening in peaks, confirming salt formation.

Figure 33:
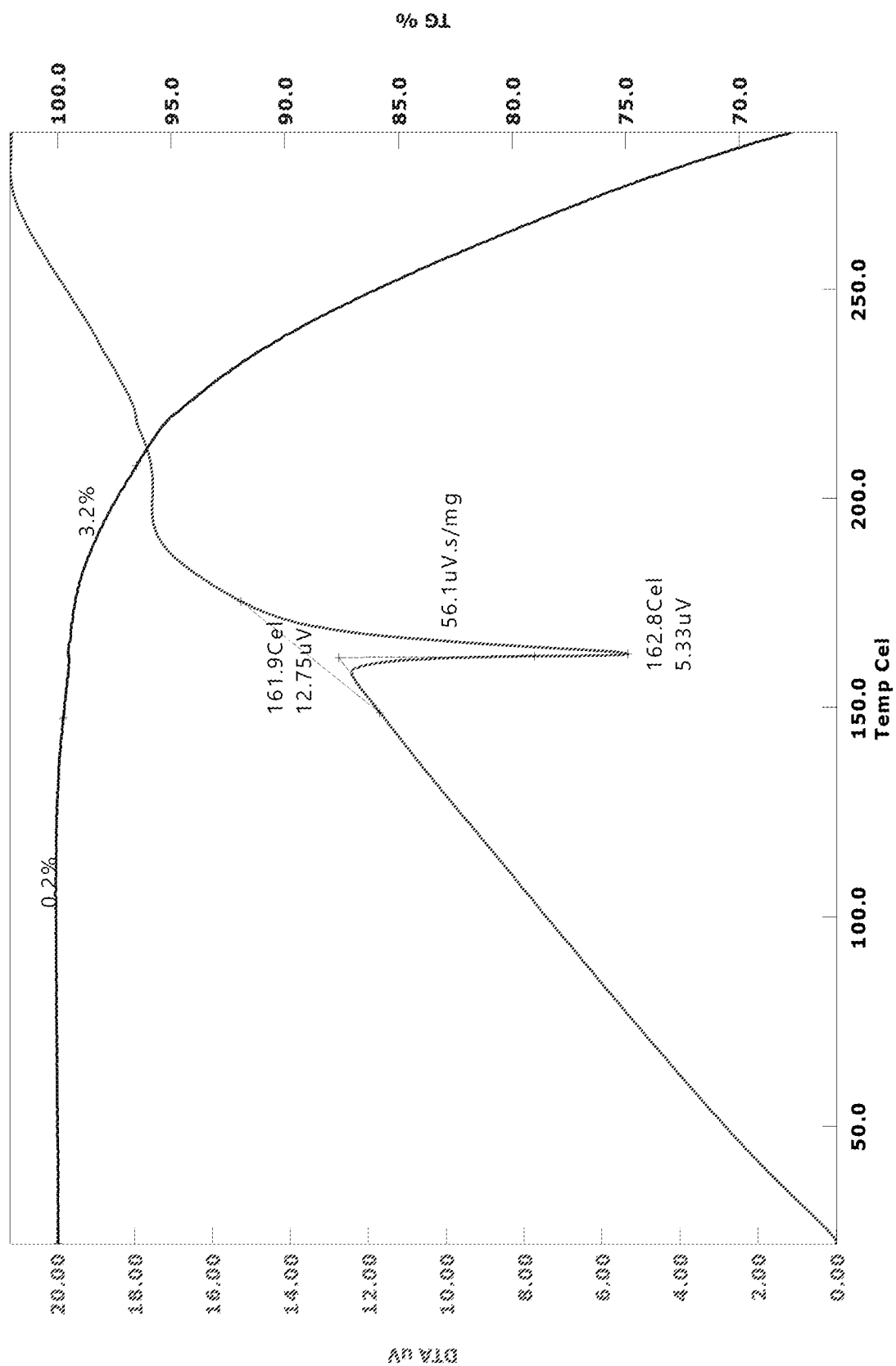
FIG. 33. Illustrates a TGA thermogram of crystalline 1,1,1,3,3,3-hexafluoropropan-2-yl 4-(2-(pyrrolidin-1-yl)-4-(trifluoromethyl)benzyl)piperazine-1-carboxylate besylate salt, Form 2.

While there was not enough sample recovered from the experiments to be able to run any thermal analysis on the benzene sulfonate Form 1, a TG/DTA experiment was run on the benzene sulfonate Form 2 obtained from tert-butylmethyl ether (FIG. 33). The material was anhydrous, with no mass loss before degradation. A sharp endothermic event was observed with onset at ca. 161.9° C. and peak at ca. 162.8° C. This was followed by a broad exotherm that was probably due to degradation of the salt.

C. Methane Sulfonic Acid Salt (Compound 5): Form 1

Figure 34:
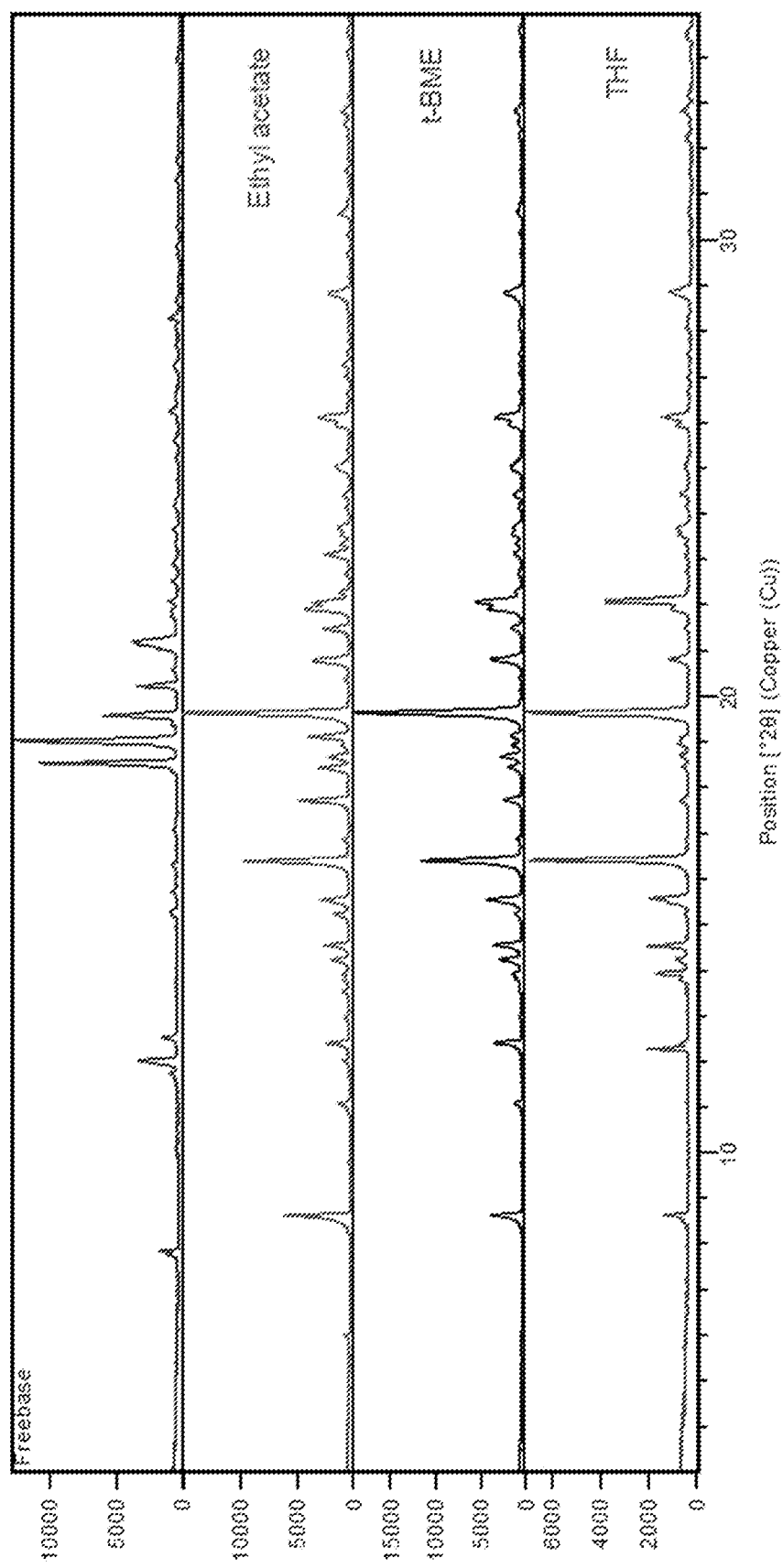
FIGS. 34 and 35. Illustrates an XRPD analysis of results obtained for 1,1,1,3,3,3-hexafluoropropan-2-yl 4-(2-(pyrrolidin-1-yl)-4-(trifluoromethyl)benzyl)piperazine-1-carboxylate mesylate salt from the focused salt screen.
Figure 35:
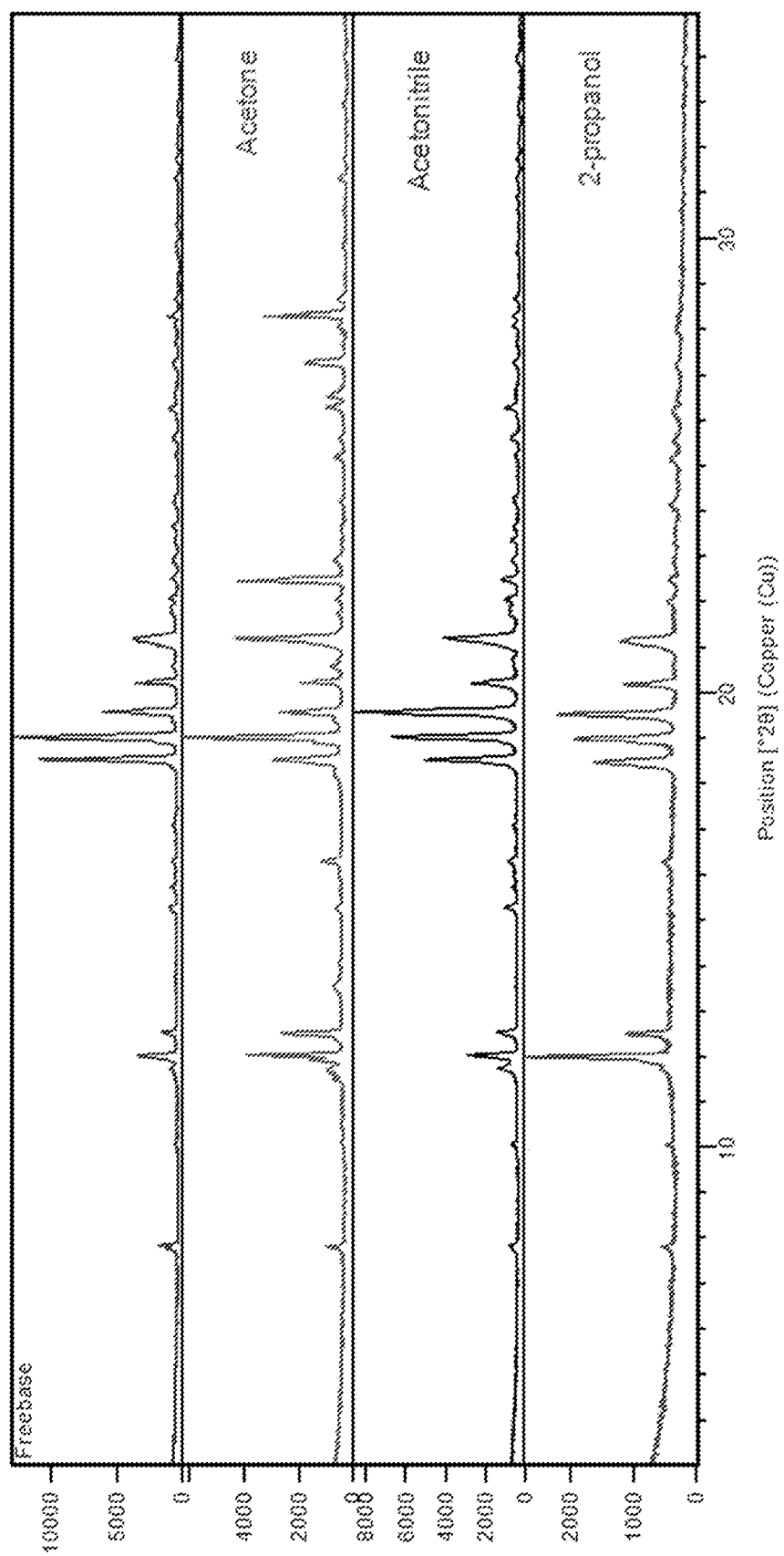

Neat methane sulfonic acid solutions were added to the free base in all solvents. In tert-butylmethyl ether, precipitation occurred after 15 minutes following counterion addition to the free base. Further solids were obtained from ethyl acetate overnight and from THF after 5 days of cooling at 5° C. Water anti-solvent addition to acetone, acetonitrile and 2-propanol led to instant solid formation. XRPD analysis identified one methane sulfonic acid salt form (FIGS. 34 and 35).

$^1$H NMR analysis was next carried out to confirm salt formation and check the salt stoichiometry. The spectrum shows both the presence of API and counterion present with significant shifts and broadening in peaks, providing clear evidence of salt formation.

A TG/DTA experiment was also run on the methane sulfonate obtained from tert-butylmethyl ether in order to explore the nature of the solid. There was a 0.4% residual solvent loss before the melting point of the compound. The trace is similar to the one obtained for benzene sulfonate but the melting point for the methane sulfonate was significantly higher than the former. A sharp endothermic event was observed with onset at ca. 180.2° C. and peak at ca. 181.5° C. This was followed by a broad exotherm that was probably due to degradation of the salt.

D. Fumaric Acid Salt (Compound 6): Form 1

Fumaric acid had low solubility in all solvents tested so 0.5 M solutions could not be prepared. A further 200 μL of water was added to the vials to aid counterion dissolution. The samples in acetone, acetonitrile, ethyl acetate and 2-propanol still did not dissolve so they were added as slurries. The samples were added to the free base in all solvents. In tert-butylmethyl ether, precipitation occurred after 15 minutes following counterion addition to the free base. Further solids were obtained from EtOAc overnight and from THF after 5 days of cooling at 5° C. Water anti-solvent addition to acetone, acetonitrile and 2-propanol led to instant solid formation.

Figure 36:
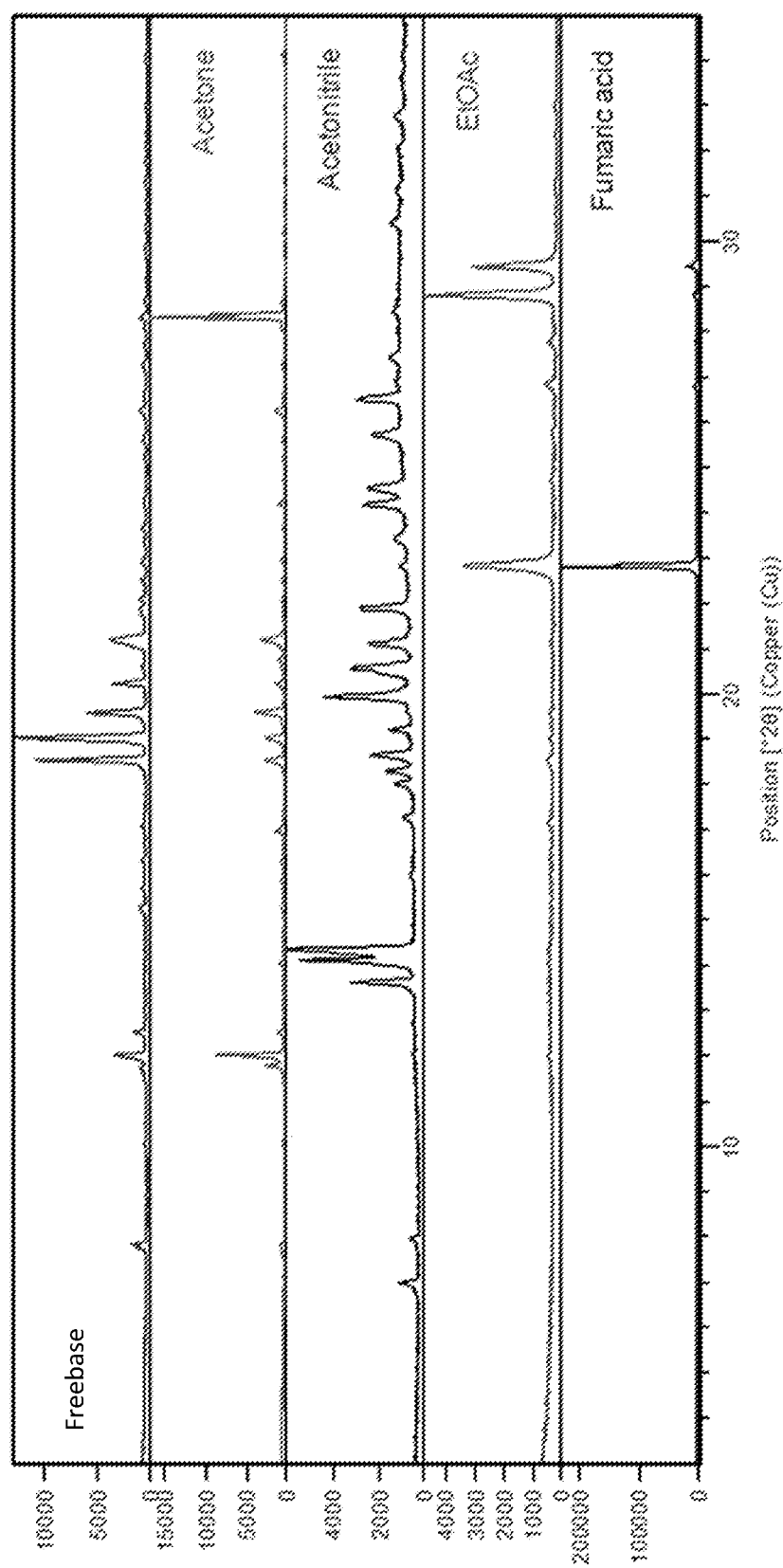
FIGS. 36 and 37. Illustrates an XRPD analysis of results obtained for 1,1,1,3,3,3-hexafluoropropan-2-yl 4-(2-(pyrrolidin-1-yl)-4-(trifluoromethyl)benzyl)piperazine-1-carboxylate fumarate salt from the focused salt screen.
Figure 37:
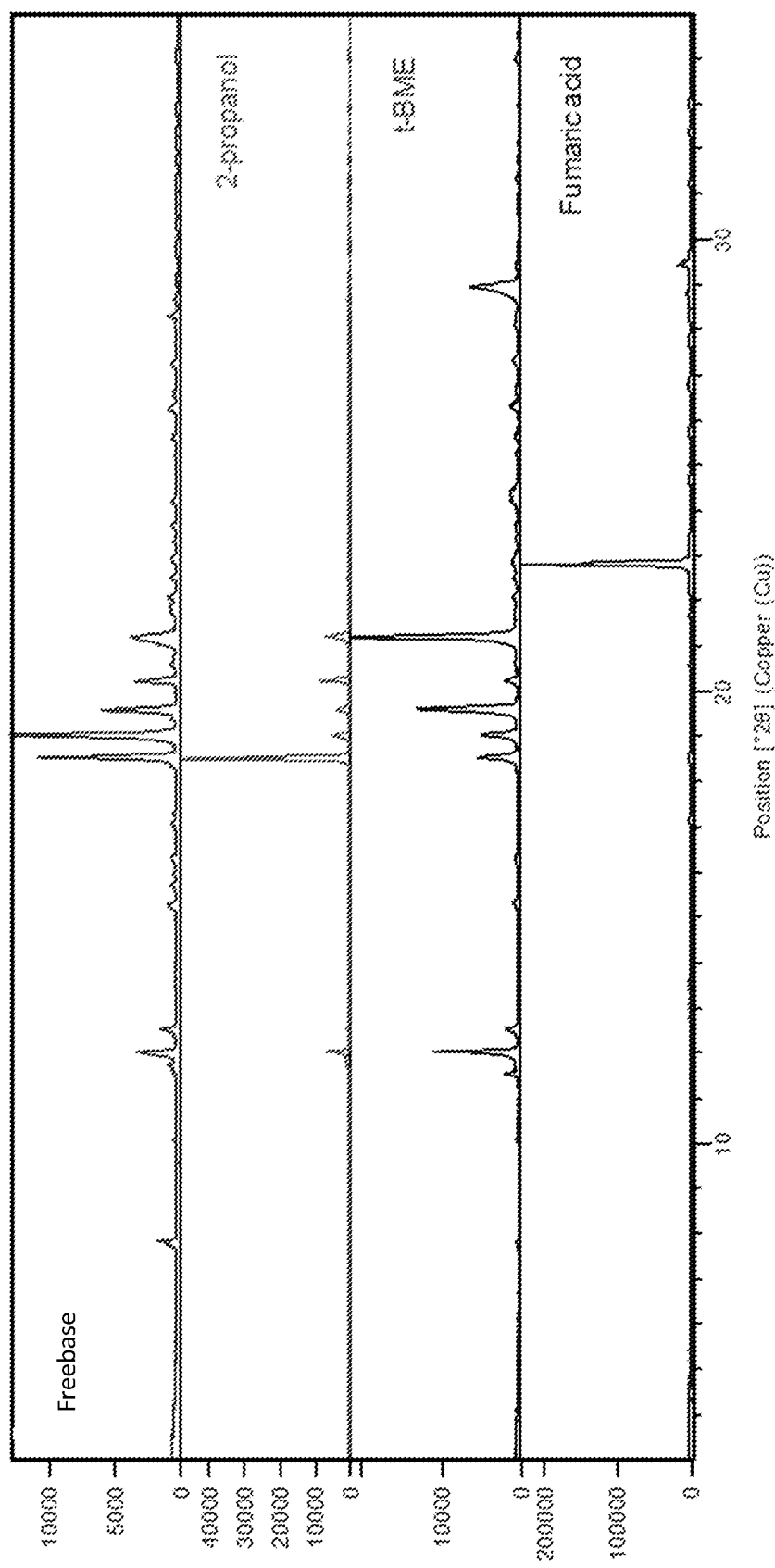

The samples obtained from all solvents apart from acetonitrile gave XRPD patterns corresponding to that of the free base, with high degrees of preferred orientation. Overnight, the sample in acetonitrile was evaporated to dryness and the XRPD of the resulting solid indicated a potential new form (FIGS. 36 and 37). To rule out that the new solid was not due to degradation, a scale-up experiment in acetonitrile was carried out using 50 mg of free base. The resulting solid was characterized by XRPD which confirmed the new form.

$^1$H NMR analysis confirmed salt formation and elucidated salt stoichiometry. The spectrum showed that both API and counterion were present. The ratio of API:fumaric acid was 1 to 0.91. The spectrum showed significant shifts in peaks, providing clear evidence of salt formation.

The TG/DTA experiment showed that there was no solvent loss before the melting point of the compound. On the DTA trace there was a very small endotherm with onset at 80.1° C. (peak at 82.9° C.), corresponding to the free base. A second, sharp endothermic event was observed with onset at ca. 133.2° C. and peak at ca. 140.2° C.

E. Citric Acid

Citric acid had low solubility in all solvents tested so 0.5 M solutions could not be prepared. A further 200 μL of water was added to the vials to obtain full counterion dissolution. In tert-butylmethyl ether, precipitation occurred after 3 days of slow evaporation following counterion addition to the free base. Further solids were obtained from acetone and 2-propanol after 5 days of cooling at 5° C. and from acetonitrile and ethyl acetate after further 2 days of slow evaporation. Water anti-solvent addition to THF did not yield solids. The majority of the solids crystallized as single crystals. After XRPD analysis of the ground crystals, it was revealed that the resulting materials displayed patterns corresponding to the pure free base.

F. L-Tartaric Acid

L-tartaric acid had low solubility in all solvents tested so 0.5 M solutions could not be prepared. A further 200 µL of water was added to the vials to obtain full counterion dissolution. In tert-butylmethyl ether, precipitation occurred after 3 days of slow evaporation following counterion addition to the free base. Further solids were obtained from 2-propanol after 5 days of cooling at 5° C. and from acetone and acetonitrile and after further 2 days of slow evaporation. Water anti-solvent addition to ethyl acetate and THF yielded solids in both cases. The majority of the solids crystallized as single crystals. After XRPD analysis, it was revealed that the resulting materials displayed patterns corresponding to either free base or a mixture of free base and counterion.

G. Hippuric Acid

Hippuric acid had low solubility in all solvents tested so 0.5 M solutions could not be prepared. A further 200 µL of water was added to the vials to obtain full counterion dissolution. The samples in acetone, acetonitrile, ethyl acetate and 2-propanol still did not dissolve so they were added as slurries. In acetonitrile, 2-propanol and tert-butylmethyl ether, solids precipitated overnight following counterion addition to the free base. Further solids were obtained from acetone, ethyl acetate and THF after 3 days of slow evaporation. After XRPD analysis, it was revealed that the resulting materials displayed patterns corresponding to either free base, counterion or a mixture of free base and counterion.

H. Secondary Salt Screen:

Following the primary screen, two salts were scaled up: the methane sulfonate (or mesylate) salt (Compound 5) and the fumarate salt (Compound 6).

Mesylate Salt (Compound 5)

300 mg of Compound 1 were weighed into a 20 mL glass scintillation vial. The solid was fully dissolved in tert-butylmethyl ether (6.0 mL) at 40° C. 1.0 equivalent of neat methane sulfonic acid (38.4 µL) was added to the free base solution. Precipitation was observed within minutes from the addition. The mixture was stirred at 40° C. for 1 hour following by cooling to room temperature. The resulting solid was isolated by centrifugation (Crop 1) and the remaining slurry from the vial was left to slowly evaporate. This yielded more solid (Crop 2). Both crops were dried in a desiccator for 3 hours and analyzed separately by XRPD and HPLC. According to XRPD analysis, Crop 1 and 2 both corresponded to the same form and had similar levels of crystallinity. Moreover, XRPD analysis confirmed that the mesylate salt obtained from the secondary screen corresponded to the form obtained in the primary screen. The combined crop yield was 85.3%. Crop 1 was used for the full characterization of the salt.

The XRPD pattern of the mesylate confirmed the new form (FIG. 38).

Figure 39:
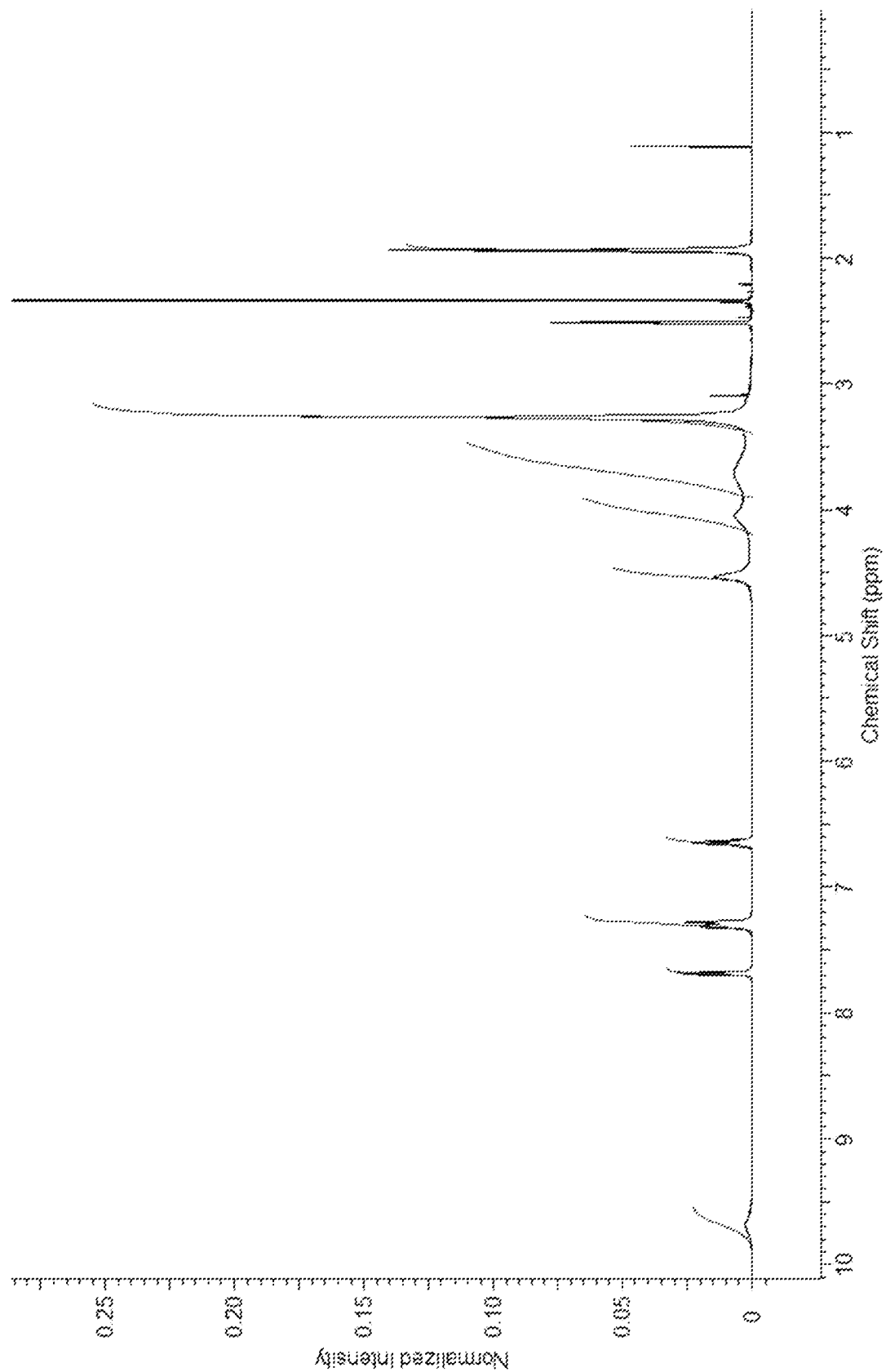
FIG. 39. Illustrates an NMR spectrum of crystalline 1,1,1,3,3,3-hexafluoropropan-2-yl 4-(2-(pyrrolidin-1-yl)-4-(trifluoromethyl)benzyl)piperazine-1-carboxylate mesylate salt.

$^1$H NMR analysis was carried out to confirm salt formation and check the salt stoichiometry. The spectrum shows both the presence of API and counterion present with significant shifts and broadening in peaks, providing clear evidence of salt formation (FIG. 39).

Figure 40:
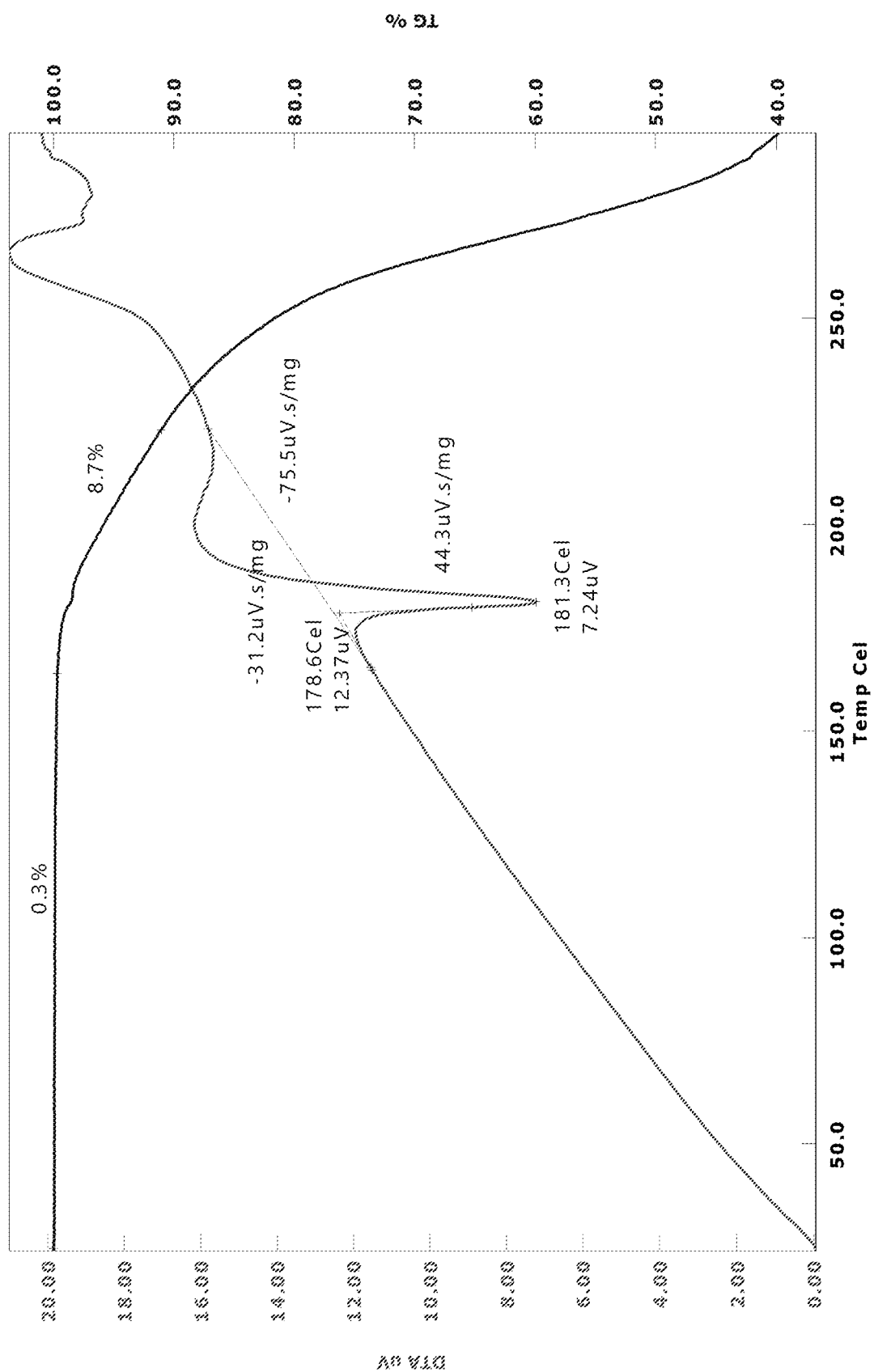
FIG. 40. Illustrates a TGA thermogram of crystalline 1,1,1,3,3,3-hexafluoropropan-2-yl 4-(2-(pyrrolidin-1-yl)-4-(trifluoromethyl)benzyl)piperazine-1-carboxylate mesylate salt.

HPLC analysis showed that Crop 1 had a purity of 99.97%. The purity levels were 99.98% following 7-day exposure to 40° C./75% RH; 99.97% following 7-day exposure to 80° C., and 99.95% following 7-day exposure at ambient conditions were observed—the changes were not believed to be significant. The purity of Crop 2 was 99.96%. TG/DTA of Crop 1 exhibited a 0.3% weight loss prior to melt. There was a single sharp endotherm with onset at 178.6° C. and peak at 181.3° C., followed by an exotherm that corresponded to sample degradation (FIG. 40).

Figure 41:
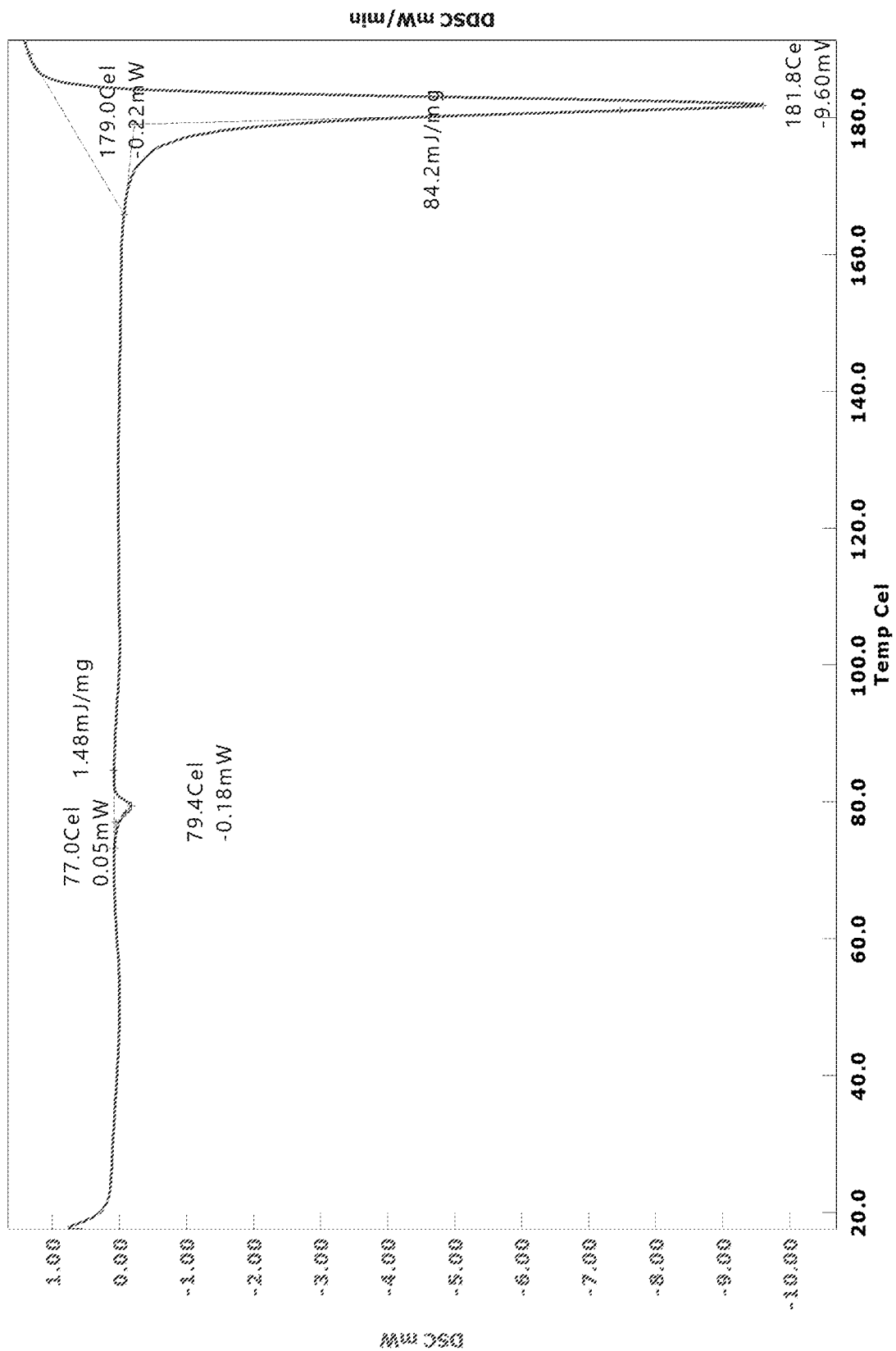
FIG. 41. Illustrates a DSC thermogram of crystalline 1,1,1,3,3,3-hexafluoropropan-2-yl 4-(2-(pyrrolidin-1-yl)-4-(trifluoromethyl)benzyl)piperazine-1-carboxylate mesylate salt.

DSC studies of the salt were consistent with TGA, confirming the presence of a sharp endotherm with an onset at 179.0° C. (peak at 181.8° C.). In addition, there was a small endotherm with onset at 77.0° C. (peak at 79.4° C.), corresponding to the melt of the free base (FIG. 41).

GVS studies show that the material was moderately hygroscopic with a gradual increase in mass with relative humidity. The weight uptake was 2.8% up to 70% humidity and 3.5% up to 90% humidity with no hysteresis between the sorption and desorption cycle. XRPD analysis of the material post-GVS showed that the sample maintained its form and crystallinity.

Fumarate Salt (Compound 6), Form 1

300 mg of Compound 1 were weighed into a 20 mL glass scintillation vial. The solid was fully dissolved in MeCN (1.5 mL) at 40° C. 1.05 equivalents of fumaric acid (72.06 mg) were weighed out in a different vial and the solid was fully dissolved in EtOH (2.4 mL) at 40° C. The fumaric acid solution was added to the free base solution and the mixture was stirred at 40° C. for 1 hour. The mixture was cooled to room temperature and the solution was subjected to slow evaporation for 2 days. Afterwards, the vial was stored at 5° C. for a further 3 days to aid precipitation. The resulting solid was isolated by centrifugation (Crop 1) and the resulting mother liquor was left to slowly evaporate. This yielded more solid (Crop 2). Both crops were dried in a desiccator for 3 hours and analyzed by XRPD and HPLC.

Crop 1 was used for the full characterization of the salt. The same form was obtained from both crops with similar levels of crystallinity.

The XRPD pattern of the fumarate salt confirmed the new form (FIG. 42).

HPLC analysis showed that the fumarate salt Crop 1 had a purity of >99.9%. The purity remained at 99.9% following 7-day exposure to 40° C./75% RH, 80° C. and ambient conditions. The changes are not believed to be significant.

Figure 43:
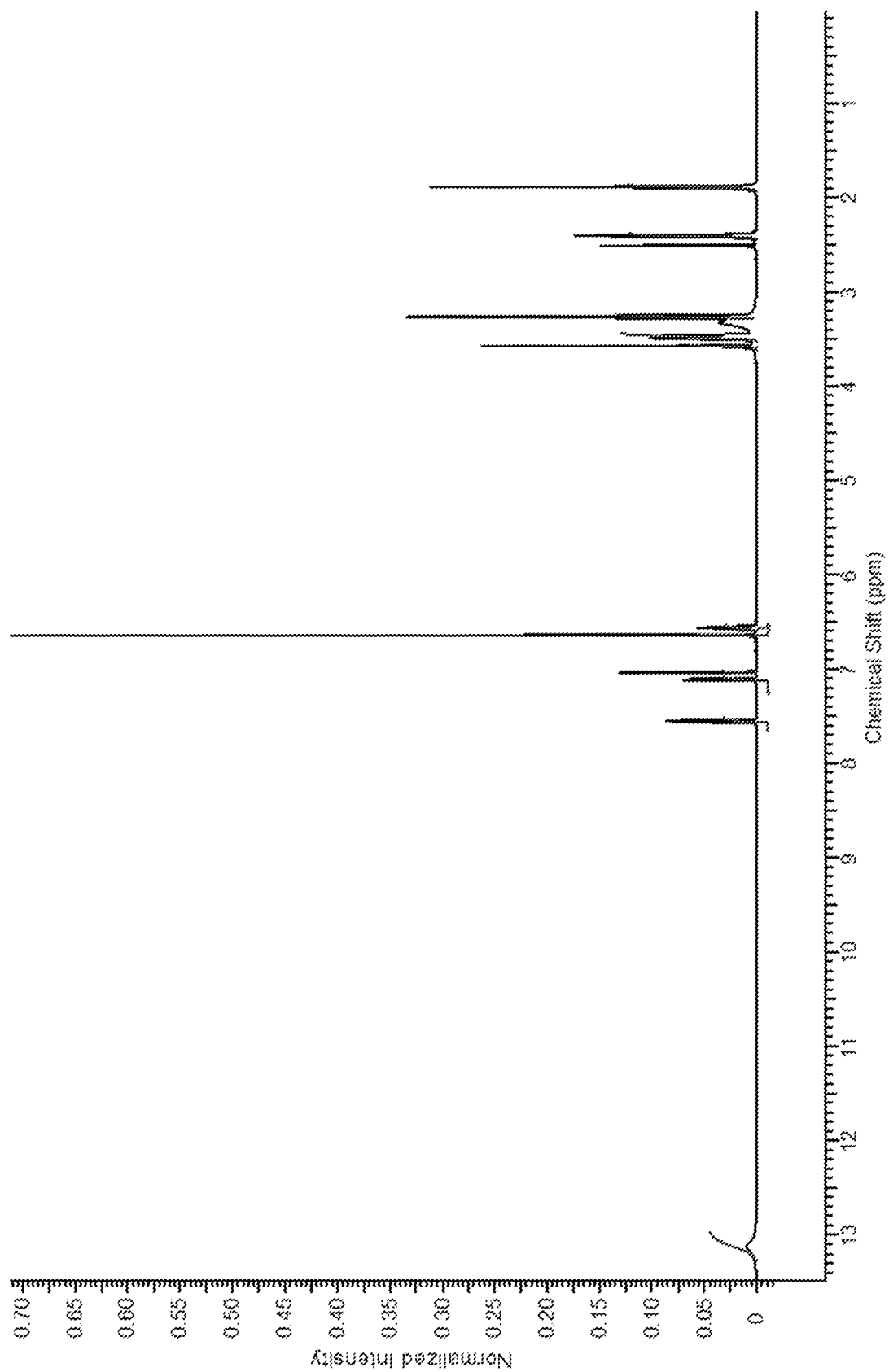
FIG. 43. Illustrates an NMR spectrum of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 1.

$^1$H NMR spectrum showed the material to correspond to the fumarate salt (FIG. 43).

Figure 44:
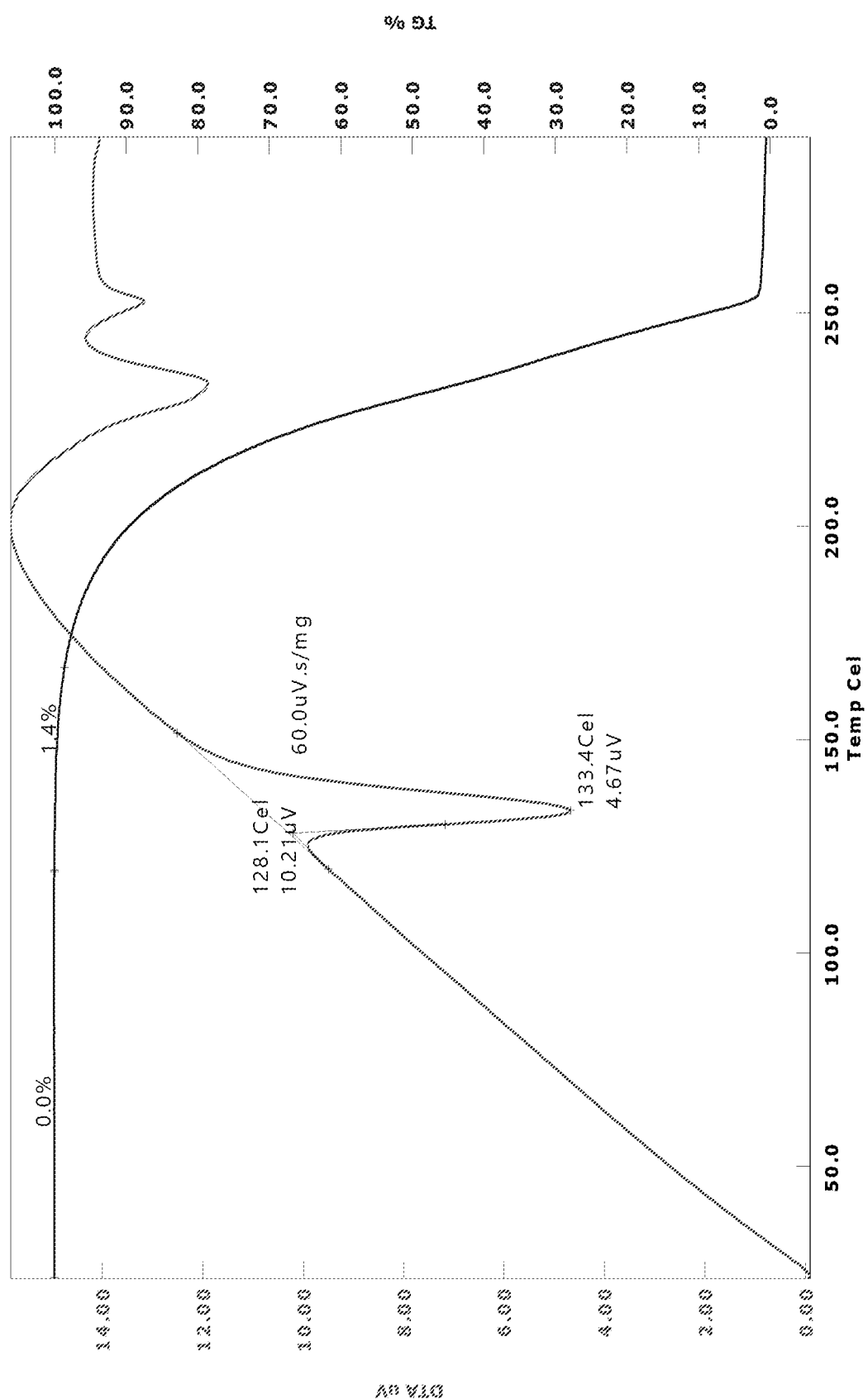
FIG. 44. Illustrates a TGA thermogram of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 1.

TG/DTA of the fumarate salt Crop 1 exhibited no weight loss prior to melt. There is a single sharp endotherm with onset at 128.1° C. and peak at 133.4° C. No endotherm corresponding to free base was seen on the scale-up material (FIG. 44).

Figure 45:
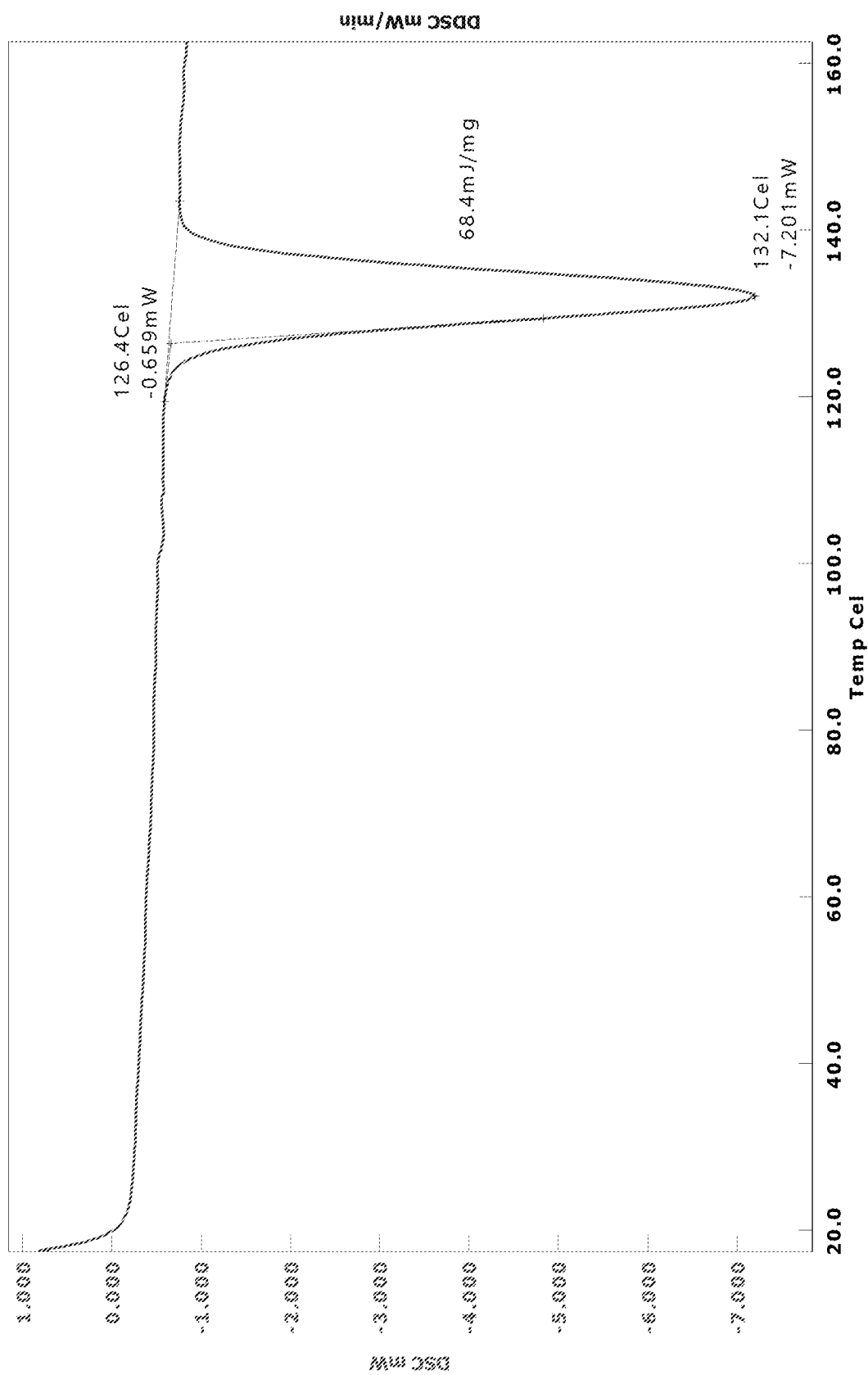
FIG. 45. Illustrates a DSC thermogram of crystalline 1,1,1,3,3,3-hexafluoropropan-2-yl 4-(2-(pyrrolidin-1-yl)-4-(trifluoromethyl)benzyl)piperazine-1-carboxylate fumarate salt, Form 1.

DSC studies of the salt were consistent with TGA, confirming the presence of a sharp endotherm with an onset at 126.4° C. and peak at 132.1° C. (FIG. 45).

GVS studies show that the material is non-hygroscopic with a very slight increase in mass above 50% relative humidity. The weight uptake is 0.11% up to 90% humidity. XRPD analysis of the material post-GVS showed that the sample maintains its form and crystallinity.

Fumarate Salt (Compound 6) Polymorph Screen, Forms 2 and 3

In a Compound 6 polymorph screen, two additional Compound 6 crystalline forms were identified. Compound 6, Form 2, was isolated from a 95/5 acetone/water slurry and Compound 6, Form 3, was isolated from in a 80/20 dioxane/ water mixture. Compound 6, Form 1 was the thermodynamically most stable form of the three Compound 6 polymorphs.

We claim:

1. A crystalline form of 1,1,1,3,3,3-hexafluoropropan-2-yl 4-(2-(pyrrolidin-1-yl)-4-(trifluoromethyl)benzyl)piperazine-1-carboxylate free base, or solvate thereof, wherein the crystalline form of 1,1,1,3,3,3-hexafluoropropan-2-yl 4-(2-(pyrrolidin-1-yl)-4-(trifluoromethyl)benzyl)piperazine-1-carboxylate free base, or solvate thereof, has an X-ray powder diffraction (XRPD) pattern with characteristic peaks at 7.8° 2-Theta, 12.0° 2-Theta, 18.5° 2-Theta, 19.0° 2-Theta, 19.6° 2-Theta and 21.2° 2-Theta.

2. A crystalline form 1 of 1,1,1,3,3,3-hexafluoropropan-2-yl 4-(2-(pyrrolidin-1-yl)-4-(trifluoromethyl)benzyl)piperazine-1-carboxylate mono-hydrochloride salt, or solvate thereof, wherein the crystalline form 1, or solvate thereof, has an X-ray powder diffraction (XRPD) pattern with characteristic peaks at 6.4° 2-Theta, 14.9° 2-Theta, 16.9° 2-Theta, 18.4° 2-Theta, and 20.9° 2-Theta.

3. A crystalline form 2 of 1,1,1,3,3,3-hexafluoropropan-2-yl 4-(2-(pyrrolidin-1-yl)-4-(trifluoromethyl)benzyl)piperazine-1-carboxylate mono-hydrochloride salt, or solvate thereof, wherein the crystalline form 2, or solvate thereof, has an X-ray powder diffraction (XRPD) pattern with characteristic peaks at 8.6° 2-Theta, 14.3° 2-Theta, 15.6° 2-Theta, 19.0° 2-Theta, 19.8° 2-Theta, and 20.7° 2-Theta.

4. A crystalline form of 1,1,1,3,3,3-hexafluoropropan-2-yl 4-(2-(pyrrolidin-1-yl)-4-(trifluoromethyl)benzyl)piperazine-1-carboxylate bis-hydrochloride salt, or solvate thereof, wherein the crystalline form of 1,1,1,3,3,3-hexafluoropropan-2-yl 4-(2-(pyrrolidin-1-yl)-4-(trifluoromethyl)benzyl)piperazine-1-carboxylate bis-hydrochloride salt, or solvate thereof, has an X-ray powder diffraction (XRPD) pattern with characteristic peaks at 6.4° 2-Theta, 12.0° 2-Theta, 12.5° 2-Theta, 14.3° 2-Theta, 18.5° 2-Theta, and 22.8° 2-Theta.

5. A crystalline form of 1,1,1,3,3,3-hexafluoropropan-2-yl 4-(2-(pyrrolidin-1-yl)-4-(trifluoromethyl)benzyl)piperazine-1-carboxyl ate fumarate salt, or solvate thereof, wherein the crystalline form of 1,1,1,3,3,3-hexafluoropropan-2-yl 4-(2-(pyrrolidin-1-yl)-4-(trifluoromethyl)benzyl)piperazine-1-carboxylate fumarate salt, or solvate thereof, has an X-ray powder diffraction (XRPD) pattern with characteristic peaks at 13.6° 2-Theta, 14.1° 2-Theta, 14.3° 2-Theta, 20.0° 2-Theta, and 21.9° 2-Theta.

6. A crystalline form of 1,1,1,3,3,3-hexafluoropropan-2-yl 4-(2-(pyrrolidin-1-yl)-4-(trifluoromethyl)benzyl)piperazine-1-carboxylate mesylate salt, or solvate thereof, wherein the crystalline form of 1,1,1,3,3,3-hexafluoropropan-2-yl 4-(2-(pyrrolidin-1-yl)-4-(trifluoromethyl)benzyl)piperazine-1-carboxylate mesylate salt, or solvate thereof, has an X-ray powder diffraction (XRPD) pattern with characteristic peaks at 8.6° 2-Theta, 12.4° 2-Theta, 14.6° 2-Theta, 16.5° 2-Theta, 17.7° 2-Theta, and 19.7° 2-Theta.

7. A pharmaceutical composition comprising the crystalline form of claim 1, or solvate thereof, and at least one inactive ingredient selected from pharmaceutically acceptable carriers, diluents, and excipients.

8. A pharmaceutical composition comprising the crystalline form 1 of claim 2, or solvate thereof, and at least one inactive ingredient selected from pharmaceutically acceptable carriers, diluents, and excipients.

9. A pharmaceutical composition comprising the crystalline form 2 of claim 3, or solvate thereof, and at least one inactive ingredient selected from pharmaceutically acceptable carriers, diluents, and excipients.

10. A pharmaceutical composition comprising the crystalline form of claim 4, or solvate thereof, and at least one inactive ingredient selected from pharmaceutically acceptable carriers, diluents, and excipients.

11. A pharmaceutical composition comprising the crystalline form of claim 5, or solvate thereof, and at least one inactive ingredient selected from pharmaceutically acceptable carriers, diluents, and excipients.

12. A pharmaceutical composition comprising the crystalline form of claim 6, or solvate thereof, and at least one inactive ingredient selected from pharmaceutically acceptable carriers, diluents, and excipients.

13. A method of therapeutically treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient in need thereof a therapeutically effective amount of a crystalline form of claim 1.

14. A method of therapeutically treating fibromyalgia in a patient in need thereof, comprising administering to the patient in need thereof a therapeutically effective amount of a crystalline form of claim 1.

15. A method of therapeutically treating spasticity, pain, disturbed sleep, bladder dysfunction, or fatigue associated with multiple sclerosis in a patient in need thereof, comprising administering to the patient in need thereof a therapeutically effective amount of a crystalline form of claim 1.

* * * * *